(12) United States Patent
Barvian et al.

(10) Patent No.: US 7,939,528 B2
(45) Date of Patent: May 10, 2011

(54) HETEROCYCLE COMPOUNDS

(75) Inventors: Kevin Karl Barvian, Durham, NC (US); Jason Daniel Speake, Durham, NC (US); David John Cowan, Durham, NC (US); Andrew Lamont Larkin, Durham, NC (US); Jerzy Ryszard Szewczyk, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 341 days.

(21) Appl. No.: 12/089,606

(22) PCT Filed: Oct. 12, 2006

(86) PCT No.: PCT/US2006/039955
§ 371 (c)(1),
(2), (4) Date: Apr. 9, 2008

(87) PCT Pub. No.: WO2007/047397
PCT Pub. Date: Apr. 26, 2007

(65) Prior Publication Data
US 2009/0054431 A1 Feb. 26, 2009

Related U.S. Application Data

(60) Provisional application No. 60/726,366, filed on Oct. 13, 2005.

(51) Int. Cl.
*A61K 31/5377* (2006.01)
*A61K 31/4184* (2006.01)
*A61K 31/416* (2006.01)
*A61P 3/00* (2006.01)
*C07D 235/04* (2006.01)
*C07D 231/56* (2006.01)
*C07D 401/02* (2006.01)
*C07D 211/06* (2006.01)
*C07D 413/02* (2006.01)

(52) U.S. Cl. ............ 514/234.5; 514/362; 514/364; 514/367; 514/375; 514/379; 514/393; 514/405; 514/412; 514/443; 514/464; 548/126; 548/127; 548/131; 548/152; 548/207; 548/217; 548/241; 548/257; 548/302.7; 548/452; 549/32; 549/462

(58) Field of Classification Search .......... 548/126, 548/127, 131, 152, 207, 217, 241, 257, 302.7, 548/360.1, 452; 549/32, 462; 514/362, 364, 514/367, 375, 379, 393, 405, 412, 443, 464
See application file for complete search history.

(56) References Cited

U.S. PATENT DOCUMENTS

| | | |
|---|---|---|
| 2002/0055651 A1 | 5/2002 | Moran et al. |
| 2004/0122237 A1 | 6/2004 | Amiri et al. |
| 2004/0180896 A1 | 9/2004 | Munson et al. |
| 2004/0192653 A1 | 9/2004 | Munson et al. |

FOREIGN PATENT DOCUMENTS

| | | |
|---|---|---|
| EP | 0 684 235 | 11/1995 |
| EP | 1 167 366 | 1/2002 |
| EP | 1 486 503 | 12/2004 |
| GB | 1111037 | 4/1968 |
| WO | WO 97/37990 | 10/1997 |
| WO | WO 98/55479 | 12/1998 |
| WO | WO 99/11255 | 3/1999 |
| WO | WO 99/26614 | 6/1999 |
| WO | WO 01/57020 | 8/2001 |
| WO | WO 02/18333 | 3/2002 |
| WO | WO 02/100833 | 12/2002 |
| WO | WO 03/082272 | 10/2003 |
| WO | WO 2004/026305 | 4/2004 |
| WO | WO 2004/080996 | 9/2004 |
| WO | WO 2005/032548 | 4/2005 |
| WO | 2005/066164 | 7/2005 |
| WO | WO 2005/066164 | 7/2005 |

OTHER PUBLICATIONS

Chen, et al., *Multivariate Analysis and Quantitative Structure-Activity Relationships. Inhibition of Dihydrofolate Reductase and Thymidylate Synthetase by Quinazolines*, J. Med. Chem., vol. 22, No. 5 (1979).

*Primary Examiner* — Kamal A Saeed
(74) *Attorney, Agent, or Firm* — Bonnie Deppenbrock

(57) ABSTRACT

The present invention relates to novel compounds which are antagonist or inverse agonists at an opioid receptor. Such compounds are useful in the treatment of obesity and related diseases and/or conditions in mammals, particularly humans. Methods of making and using such compounds are also disclosed.

13 Claims, No Drawings

HETEROCYCLE COMPOUNDS

This application is filed pursuant to 35 U.S.C. §371 as a United States National Phase Application of International Application No. PCT/US2006/039955 filed Oct. 12, 2006, which claims priority from U.S. 60/726,366 filed Oct. 13, 2005.

FIELD OF THE INVENTION

This invention relates to novel heterocycles which are antagonists or inverse agonists at one or more of the opioid receptors, to pharmaceutical compositions containing them, to processes for their preparation, and to their use in therapy.

BACKGROUND OF THE INVENTION

Obesity is a medical condition that is reaching epidemic proportions among humans in countries throughout the world. It is a condition that is associated with other diseases or conditions that disrupt life and lifestyles. Obesity is recognized as a serious risk factor for other diseases and/or conditions such as diabetes, hypertension, and arteriosclerosis. It is also known that increased body weight due to obesity can place a burden on joints, such as knee joints, causing arthritis, pain, and stiffness.

Because overeating and obesity have become such a problem, many individuals are interested in weight reduction and/or maintaining a healthy body weight.

Antagonists or inverse agonists of the opioid receptors have been shown to reduce body weight in obese rats. And the ability to bind antagonistically to opioid receptors has been suggested to be useful for treatment of many other diseases or conditions not related to obesity including drug and/or substance addiction, depression, opiate overdose, irritable bowel syndrome, septic shock, nausea, vomiting, and stroke. There is, therefore, an ongoing need for new opioid antagonists for the treatment of obesity, diseases and/or conditions associated with obesity, as well as the above-mentioned non-obesity related diseases and/or conditions.

SUMMARY OF THE INVENTION

The present invention provides a compound of Formula 1 comprising

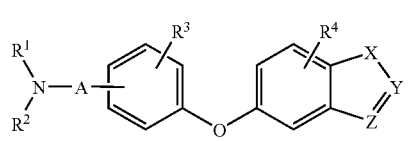

Formula 1 wherein $R^1$ is selected from the group consisting of hydrogen, $C_{1-12}$ alkyl, $C_{3-10}$ cycloalkyl, arylalkyl, heterocyclyl, heterocycloalkyl, heteroarylalkyl, cycloalkenyl, $C_{2-12}$ fluoroalkyl, $C_{3-10}$ alkoxy, and heteroalkyl;

$R^2$ is selected from the group consisting of $C_{3-12}$ alkyl, $C_{3-10}$ cycloalkyl, arylalkyl, heterocyclyl, heterocycloalkyl, heteroarylalkyl, cycloalkenyl, $C_{3-12}$ fluoroalkyl, $C_{3-10}$ alkoxy, and heteroalkyl;

$R^1$ and $R^2$ may optionally be joined to form a ring;

A is attached in the meta or para position with respect to the diarylether linker (said diarylether linker is shown as "—O—" in Formula 1) and is selected from the group consisting of $C_{1-3}$ alkylene, and $C_{2-3}$ alkoxy;

$R^3$ and $R^4$ are each independently selected from the group consisting of —H, —F, —Cl, —Br, —OH, —$OC_{1-3}$ alkyl, —$C_{1-3}$ fluoroalkyl and —$C_{1-3}$ alkyl;

X, Y, and Z are each independently selected from the group consisting of —N, —NH, —CH, —O, —S, —$NR^5$, and —$CR^6$, wherein $R^5$ and $R^6$ are each independently a $C_{1-6}$ alkyl or fluoroalkyl; and pharmaceutically acceptable salts, solvates, or physiological functional derivatives thereof.

In a preferred embodiment the carbon atoms (of $R^1$ and $R^2$) that are attached to the nitrogen are not aromatic or a carbonyl.

In one embodiment, A is a methylene attached in the para position with respect to the diarylether linker; $R^1$ is hydrogen; $R^2$ is selected from the group consisting of arylethyl, arylmethyl, $C_{4-10}$ alkyl, cycloalkenyl, cycloalkyl, heterocyclylmethyl, and heterocyclylethyl; $R^3$ and $R^4$ are each independently selected from the group consisting of —H and —F; either X or Z is —NH with the other being —CH or —N; and Y is —CH or —N.

There is provided a pharmaceutical composition comprising (i) a compound of Formula 1, a pharmaceutically acceptable salt, solvate, or physiological functional derivative thereof and (ii) at least one carrier (also referred to as an excipient or diluent), preferably a pharmaceutically acceptable carrier.

Further, there is provided a method of treatment (including prophylaxis) comprising the administering to a mammal, especially a human, a pharmaceutical composition comprising (i) a compound of Formula 1, a pharmaceutically acceptable salt, solvate, or physiological functional derivative thereof and (ii) at least one carrier (excipient or diluent). There also is provided a method of treatment (including prophylaxis) comprising the administering to a mammal, especially a human, a compound of Formula 1, a pharmaceutically acceptable salt, solvate, or physiological functional derivative thereof.

One aspect of the present invention includes a compound (or salt, solvate, or functional derivative thereof) of the present invention for use as an active therapeutic substance.

Another aspect of the present invention includes a compound of Formula 1 (or salt, solvate, or functional derivative thereof) for use in the treatment (including prophylaxis) of obesity, diabetes, hypertension, depression (major and/or bipolar), anxiety, drug addiction, and/or substance addiction. Of these conditions/diseases, obesity is the preferred one to treat.

Still another aspect of the present invention includes the use of a compound of Formula 1 (or salt, solvate, or functional derivative thereof) in the manufacture of a medicament for use in the treatment (including prophylaxis) of obesity, diabetes, hypertension, depression (major and/or bipolar), anxiety, drug addiction, and/or substance addiction. Of these conditions/diseases, obesity is the preferred one to treat.

DETAILED DESCRIPTION OF THE INVENTION

Terms are used within their accepted meanings. The following definitions are meant to clarify, but not limit, the terms defined.

As used herein, "a compound of the invention" or "a compound of Formula 1" means a compound of Formula 1 or a pharmaceutically acceptable salt, solvate, or physiologically functional derivative (such as, e.g., a prodrug), thereof.

As used herein, the term "alkyl" refers to a straight or branched chain hydrocarbon, preferably having from one to twelve carbon atoms, which may be optionally substituted, with multiple degrees of substitution included within the present invention. Examples of "alkyl" as used herein include, but are not limited to, methyl, ethyl, propyl, isopropyl, isobutyl, n-butyl, isopentyl, n-pentyl, and the like, as well as substituted versions thereof.

As used throughout this specification, the preferred number of atoms, such as carbon atoms, will be represented by, for example, the phrase "$C_{x-y}$alkyl," which refers to an alkyl group, as herein defined, containing the specified number of carbon atoms. Similar terminology will apply for other preferred terms and ranges as well.

As used herein, the term "alkenyl" refers to a straight or branched chain aliphatic hydrocarbon containing one or more carbon-to-carbon double bonds that may be optionally substituted, with multiple degrees of substitution included within the present invention. Examples include, but are not limited to, vinyl, allyl, and the like, as well as substituted versions thereof.

As used herein, the term "alkynyl" refers to a straight or branched chain aliphatic hydrocarbon containing one or more carbon-to-carbon triple bonds that may be optionally substituted, with multiple degrees of substitution included within the present invention. Examples include, but are not limited to, ethynyl, and the like, as well as substituted versions thereof.

As used herein, the term "alkylene" refers to a straight or branched chain divalent hydrocarbon radical, preferably having from one to ten carbon atoms. Alkylene groups as defined herein may optionally be substituted, with multiple degrees of substitution included within the present invention. Examples of "alkylene" as used herein include, but are not limited to, methylene, ethylene, n-propylene, n-butylene, and the like, as well as substituted versions thereof.

As used herein, the term "alkenylene" refers to a straight or branched chain divalent hydrocarbon radical, preferably having from one to ten carbon atoms, containing one or more carbon-to-carbon double bonds that may be optionally substituted, with multiple degrees of substitution included within the present invention. Examples include, but are not limited to, vinylene, allylene, 2-propenylene, and the like, as well as substituted versions thereof.

As used herein, the term "alkynylene" refers to a straight or branched chain divalent hydrocarbon radical, preferably having from one to ten carbon atoms, containing one or more carbon-to-carbon triple bonds that may be optionally substituted, with multiple degrees of substitution included within the present invention. Examples include, but are not limited to, ethynylene, and the like, as well as substituted versions thereof.

As used herein, the term "cycloalkyl" refers to an optionally substituted non-aromatic cyclic hydrocarbon ring, which optionally includes an alkylene linker through which the cycloalkyl may be attached, with multiple degrees of substitution included within the present invention. Exemplary "cycloalkyl" groups include, but are not limited to, cyclopropyl, cyclobutyl, cyclopentyl, cyclohexyl, cycloheptyl, and the like, as well as substituted versions thereof. As used herein, the term "cycloalkyl" includes an optionally substituted fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane.

As used herein, the term "cycloalkenyl" refers to an optionally substituted non-aromatic cyclic hydrocarbon ring containing one or more carbon-to-carbon double bonds which optionally includes an alkylene linker through which the cycloalkenyl may be attached, with multiple degrees of substitution included within the present invention. Exemplary "cycloalkenyl" groups include, but are not limited to, cyclopropenyl, cyclobutenyl, cyclopentenyl, cyclohexenyl, cycloheptenyl, and the like, as well as substituted versions thereof.

As used herein, the term "cycloalkylene" refers to a divalent, optionally substituted non-aromatic cyclic hydrocarbon ring, with multiple degrees of substitution included within the present invention. Exemplary "cycloalkylene" groups include, but are not limited to, cyclopropylene, cyclobutylene, cyclopentylene, cyclohexylene, cycloheptylene, and the like, as well as substituted versions thereof.

As used herein, the term "cycloalkenylene" refers to a divalent optionally substituted non-aromatic cyclic hydrocarbon ring containing one or more carbon-to-carbon double bonds, with multiple degrees of substitution included within the present invention. Exemplary "cycloalkenylene" groups include, but are not limited to, cyclopropenylene, cyclobutenylene, cyclopentenylene, cyclohexenylene, cycloheptenylene, and the like, as well as substituted versions thereof.

As used herein, the term "heterocycle" or "heterocyclyl" refers to an optionally substituted mono- or polycyclic ring system optionally containing one or more degrees of unsaturation and also containing one or more heteroatoms. Preferred heteroatoms include N, O, and/or S, including N-oxides, sulfur oxides, and dioxides. Preferably the ring is three to twelve-membered and is either fully saturated or has one or more degrees of unsaturation. Multiple degrees of substitution are included within the present definition. Such rings may be optionally fused to one or more of another "heterocyclic" ring(s) or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term heterocyclylalkyl refers to a heterocycle, as defined herein, bonded to an alkyl group, as defined herein.

As used herein, the term arylalkyl refers to an aryl group, as defined herein, bonded to an alkyl group, as defined herein.

As used herein, the term heteroalkyl refers to an alkyl group, as defined herein, wherein one or more of the atoms of the alkyl group is a heteroatom. Preferred heteroatoms include N, O, and/or S, including N-oxides, sulfur oxides, and dioxides.

As used herein, the term "aryl" refers to an optionally substituted benzene ring or to an optionally substituted fused benzene ring system, for example anthracene, phenanthrene, or naphthalene ring systems. Multiple degrees of substitution are included within the present definition. Examples of "aryl" groups include, but are not limited to, phenyl, 2-naphthyl, 1-naphthyl, and the like, as well as substituted derivatives thereof.

As used herein, the term "heteroaryl" refers to an optionally substituted monocyclic five to seven membered aromatic ring, or to an optionally substituted fused bicyclic aromatic ring system comprising two of such aromatic rings. These heteroaryl rings contain one or more heteroatoms such as nitrogen, sulfur, and/or oxygen atoms, where N-oxides, sulfur oxides, and dioxides are permissible heteroatom substitutions. Multiple degrees of substitution are included within the present definition. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizolyl, imidazopyridinyl, pyrazolopyridinyl, pyrazolopyrimidinyl, and the like, as well as substituted versions thereof.

As used herein, the term "heteroarylalkyl" refers to a heteroaryl as defined herein bonded to an alkyl as defined herein.

As used herein, the term "halogen" refers to fluorine (or fluoro), chlorine (or chloro), bromine (or bromo), or iodine (or iodo). Preferably, each halogen when present is individually either fluorine or chlorine.

As used herein, the term "fluoroalkyl" refers to an alkyl group, as defined herein, that is substituted with at least one fluorine atom. Examples of branched or straight chained "fluoroalkyl" groups useful in the present invention include, but are not limited to, methyl, ethyl, propyl, isopropyl, n-butyl, and t-butyl substituted independently with one or more fluorine. The term "fluoroalkyl" should be interpreted to include such substituents as perfluoroalkyl groups and the like.

As used herein, the term "alkoxy" refers to the group —$OR^a$, where $R^a$ is alkyl as defined above.

As used herein, the term "alkoxycarbonyl" refers to groups such as:

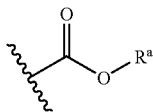

where the $R^a$ represents an alkyl group as herein defined.

As used herein, the term "aryloxycarbonyl" refers to groups such as:

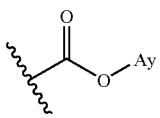

where the Ay represents an aryl group as herein defined.

As used herein, the term "heteroaryloxycarbonyl" refers to groups such as:

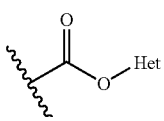

where the Het represents a heteroaryl group as herein defined.

As used herein, the term "nitro" refers to the group —$NO_2$.

As used herein, the term "cyano" refers to the group —CN.

As used herein, the term "azido" refers to the group —$N_3$.

As used herein, the term "acyl" refers to the group $R^bC(O)$—, where $R^b$ is alkyl, aryl, heteroaryl, or heterocyclyl, as each is defined herein.

As used herein, the term "oxo" refers to the group =O.

The terms "members" (and variants thereof, e.g., "membered") in the context of heterocyclic, heteroaryl, heteroaromatic, aryl, and aromatic groups refers to the total atoms, carbons and heteroatoms (e.g., N, O, and S) which form the ring. Thus, an example of a 6-membered heterocyclic ring is piperidine; an example of a 6-membered heteroaryl is pyridine; and an example of a 6-membered aryl ring is benzene.

As used herein, the term "optionally" means that the subsequently described event(s) may or may not occur, and includes both event(s) that occur and event(s) that do not occur.

Also, as used herein throughout the present specification, the phrase "optionally substituted" or variations thereof denote an optional substitution, including multiple degrees of substitution, with one or more substituent group. The phrase should not be interpreted as duplicative of the substitutions herein described and depicted. Exemplary optional substituent groups include acyl; alkyl; alkenyl; alkynyl; alkylsulfonyl; alkoxy; alkoxycarbonyl; cyano; halogen; haloalkyl; hydroxy; nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; arylsulfonyl, which may be further substituted with acyl, alkoxy, alkyl, alkenyl, alkynyl, alkylsulfonyl, cyano, halogen, haloalkyl, hydroxy, or nitro; heteroarylsulfonyl, which may be further substituted with acyl, alkoxy, alkyl, alkenyl, alkynyl, alkylsulfonyl, cyano, halogen, haloalkyl, hydroxy, or nitro; aryloxy, which may be further substituted with acyl, alkoxy, alkyl, alkenyl, alkynyl, alkylsulfonyl, cyano, halogen, haloalkyl, hydroxy, or nitro; heteroaryloxy, which may be further substituted with acyl, alkoxy, alkyl, alkenyl, alkynyl, alkylsulfonyl, cyano, halogen, haloalkyl, hydroxy, or nitro; aryloxycarbonyl, which may be further substituted with acyl, alkoxy, alkyl, alkenyl, alkynyl, alkylsulfonyl, cyano, halogen, haloalkyl, hydroxy, or nitro; heteroaryloxycarbonyl, which may be further substituted with acyl, alkoxy, alkyl, alkenyl, alkynyl, alkylsulfonyl, cyano, halogen, haloalkyl, hydroxy, or nitro; or —$N(R^*)_2$; where for each occurrence $R^*$ is independently selected from hydrogen, alkyl, alkenyl, alkynyl, cycloalkyl, heterocyclyl, aryl, aralkyl, heteroaryl, heteroaralkyl, alkylsulfonyl, arylsulfonyl, or heteroarylsulfonyl, where each occurrence of such aryl or heteroaryl may be substituted with one or more acyl, alkoxy, alkyl, alkenyl, alkylsulfonyl, cyano, halogen, haloalkyl, hydroxy, or nitro, or the two R*s may combine to form a ring, optionally having additional heteroatoms (e.g., N, O, S, etc.), optionally having one or more degrees of unsaturation, and optionally being further substituted with acyl, alkoxy, alkyl, alkenyl, alkynyl, alkylsulfonyl, cyano, halogen, haloalkyl, hydroxy, or nitro.

The compounds of Formula 1 may crystallize in more than one form, a characteristic known as polymorphism, and such polymorphic forms ("polymorphs") are within the scope of Formula 1. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain compounds of Formula 1 may exist in stereoisomeric forms (e.g., they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by Formula 1 as mixtures with isomers thereof in which one or more chiral centers are inverted. Certain compounds of Formula 1 may be prepared as regioisomers. The present invention covers both the mixture of regioisomers as well as individual compounds. Likewise, it is understood that compounds of Formula 1 may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are the individual isomers of the compounds represented by Formula 1, as well as any wholly or partially equilibrated mixtures thereof. The present invention also includes the individual isomers of the compounds represented by the formula as well as mixtures with isomers thereof in which one or more chiral centers are inverted.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. In general, the salts are formed from pharmaceutically acceptable inorganic and organic acids, or bases, as well as quaternary ammonium salts. More specific examples of suitable acid salts include maleic, hydrochloric, hydrobromic, sulphuric, phosphoric, nitric, perchloric, fumic, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthaliene-2-sulfonic, benzenesulfonic, hydroxynaphthoic, hydroiodic, malic, teroic, tannic, and the like.

Other representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts.

Other salts, which are not pharmaceutically acceptable, may be useful in the preparation of compounds of this invention and these should be considered to form a further aspect of the invention. These salts, such as oxalic, while not in themselves pharmaceutically acceptable, may be useful in the preparation of salts useful as intermediates in obtaining the compounds of the invention and their pharmaceutically acceptable salts.

More specific examples of suitable basic salts include sodium, lithium, potassium, magnesium aluminium, calcium, zinc, N,N'-dibenzylethylenediamine, chloroprocaine, chlorine, diethanolamine, ethylenediamine, n-methylglucamine, and procaine salts.

As used herein, the term "solvate" refers to a complex of variable stoichiometry formed by a solute (in this invention, a compound of Formula 1, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, $5^{th}$ Edition, Vol 1: Principles and Practice, which is incorporated herein by reference to the extent that it teaches physiologically functional derivatives.

Processes for preparing pharmaceutically acceptable salts, solvates, and physiologically functional derivatives of the compounds of Formula 1 are conventional in the art. See, for example, *Burger's Medicinal Chemistry and Drug Discovery*, $5^{th}$ Edition, Volume 1: Principles and Practice.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula 1, as well as salts, solvates, and physiological functional derivatives thereof, may be administered as the raw chemical. Additionally, the active ingredient may be presented as a pharmaceutical composition.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject.

Accordingly, the invention further provides pharmaceutical compositions (also referred to herein as "pharmaceutical formulations") that include effective amounts of compounds of the Formula 1 salts, solvates, or physiological functional derivatives thereof, and one or more pharmaceutically acceptable excipients (including carriers and/or diluents). The compounds of Formula 1, salts, solvates, or physiologically functional derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the Formula 1 a salt, solvate, or physiological functional derivative thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of Formula 1 for the treatment of humans suffering from frailty, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of Formula 1 per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the Formula 1, depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). In the present invention oral routes are preferred.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, solvates, and physiologically functional derivatives thereof, may be employed alone or in combination with other therapeutic agents. The compound(s) of Formula 1 and the other pharmaceutically active agent(s) may be administered together or separately and, when administered separately, administration may occur simultaneously or sequentially, in any order. The amounts of the compound(s) of Formula 1 and the other pharmaceutically active agent(s) and the relative timings of administration will be selected in order to achieve the desired combined therapeutic effect. The administration in combination of a compound of Formula 1 salts, solvates, or physiologically functional derivatives thereof with other treatment compounds or agent may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of the present invention may be used in the treatment of a variety of disorders and conditions and, as such, the compounds of the present invention may be used in combination with a variety of other suitable therapeutic agents useful in the treatment (including prophylaxis) of obesity and/or associated diseases, disorders, or conditions. More specifically, the present invention includes the treatment (including prophylaxis) of obesity. Other disorders, conditions, and/or diseases associated with obesity can include diabetes, depression (major and bipolar), anxiety, hypertension, drug and substance addiction, and arteriosclerosis.

One aspect of the present invention comprises a compound of Formula 1 (a salt, solvate, or physiological functional derivative thereof) in combination with at least one other species selected from the group consisting of at least one agent or drug for treating obesity, diabetes, hypertension, and arteriosclerosis. In particular, a compound of Formula 1 (a salt, solvate, or physiological functional derivative thereof) may be combined with at least one species for the treatment of obesity selected from the group of human ciliary neurotropic factor, a CB-1 antagonist or inverse agonist (such as rimonabant), a neurotransmitter reuptake inhibitor (such as sibutramine, bupropion, or bupropion HCl, radafaxine), a lipase inhibitor (such as orlistat), an MC4R agonist, a 5-HT2c agonist, a ghrelin receptor antagonist, a CCK-A receptor agonist, an NPY Y1 antagonist, $PYY^3_{-36}$ and a PPAR activator.

The compounds of this invention may be made by a variety of methods, including well-known standard synthetic methods. Illustrative general synthetic methods are set out below and then specific compounds of the invention are prepared in the working examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, *Stereochemistry of Organic Com-*

*pounds* by E. L. Eliel, S. H. Wilen, and L. N. Mander (Wiley-Interscience, 1994), incorporated by reference with regard to stereochemistry.

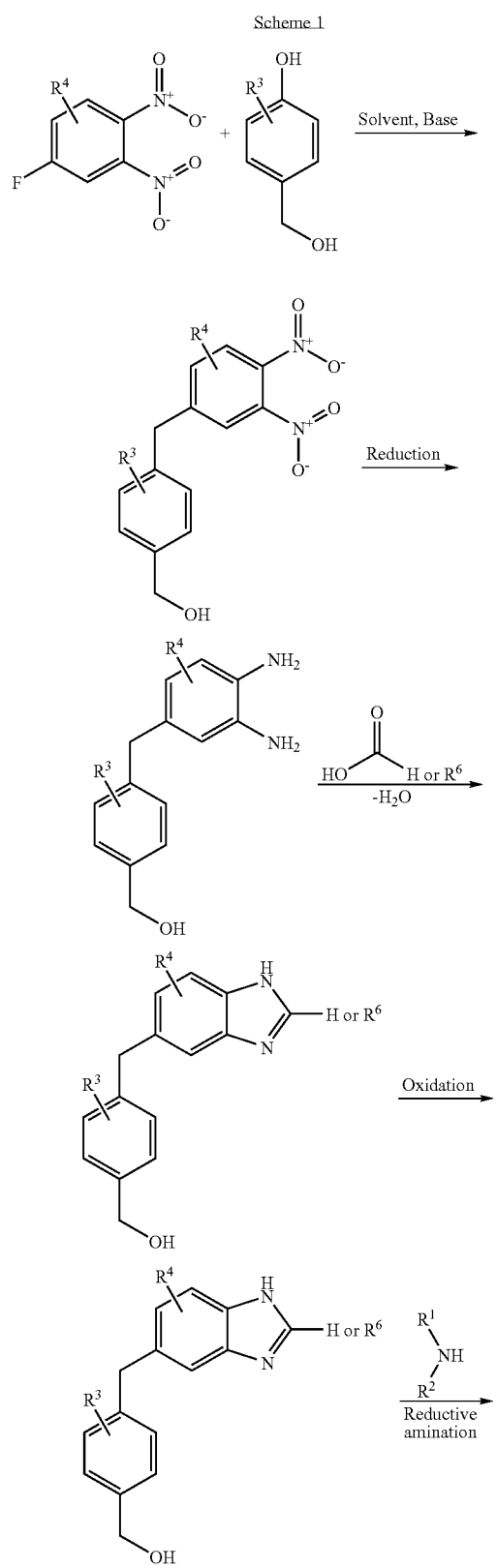

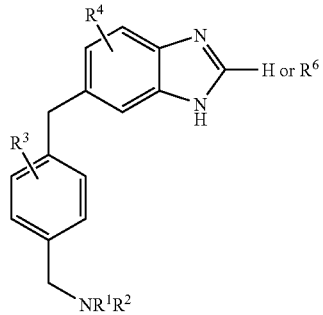

Formula 1 compounds of the invention in which either X or Z is NH, with the other being N, and in which Y is CH or $CR^2$ can be prepared in accordance with Scheme 1, wherein A is $CH_2$.

The preparation involves nucleophilic aromatic substitution of a halodinitroaromatic compound with an appropriately substituted phenol. Typical reaction conditions involve use of a base such as potassium carbonate ($K_2CO_3$) and a solvent such as dimethylformamide at a temperature from 20-100 degrees Centigrade. The dinitro is reduced under standard conditions, which may include the use of a catalyst such as palladium on carbon and hydrogen, or other methods such as the use of stannous chloride, iron, sodium sulfide or one of many other known methods. See, for example, *Reductions in Organic Chemistry*, Second Edition, Milos Hudlicky, ACS Monograph (1988).

The resulting dianiline is condensed with an appropriately substituted carboxylic acid. This typically involves heating the dianiline in the presence of the acid and may involve azeotropic removal of water in some cases. Saponification of the ester under standard conditions such as treatment with 10% aqueous lithium hydroxide (LiOH) in tetrahydrofuran provides the alcohol.

Elaboration to the aldehyde by oxidation using standard methods such as manganese dioxide, swern oxidation, or one of many other known methods such as those discussed, for example, in *Transformations in Organic Chemistry*, Second Edition, Richard C. LaRock (John Wiley and Sons: 1999), and reductive amination under standard conditions such as treatment with the desired amine and sodium cyanoborohydride in methanol with acetic acid, or one of the many other known methods for this transformation such as those discussed, for example, in *Transformations in Organic Chemistry*, Second Edition, Richard C. LaRock, (John Wiley and Sons, 1999), yield the desired compounds.

Scheme 2

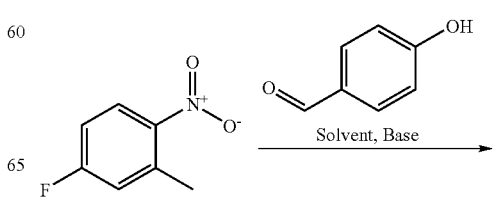

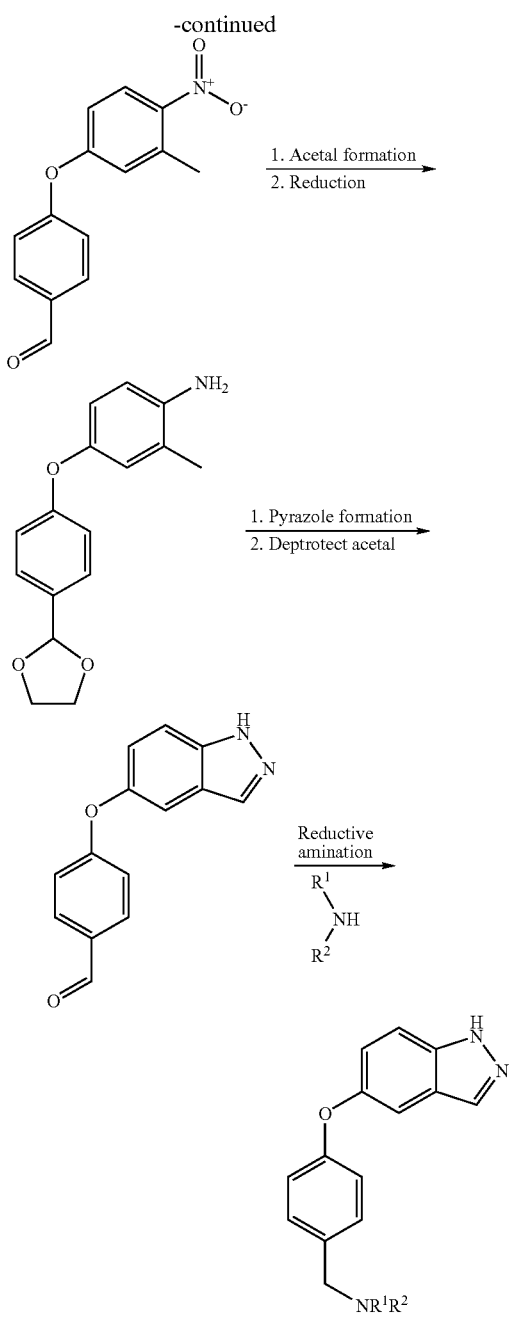

Compounds wherein X is NH, Y is N, and Z is CH can be prepared analogously to Scheme 2, wherein A is CH$_2$. The preparation involves nucleophilic aromatic substitution of a halogenated aryl nitro compound with an appropriately substituted phenol. Typical reaction conditions involve use of a base such as K$_2$CO$_3$ and a solvent such as dimethylformamide at a temperature from 20-100° C. Protection of the aldehyde group as an acetal under standard conditions, (See, for example, *Transformations in Organic Chemistry*, Second Edition, Richard C. LaRock, John Wiley and Sons: 1999), followed by reduction of the nitro under standard conditions affords the aniline intermediate. Formation of the indazole is accomplished under known conditions, such as treatment with sodium acetate and acetic anhydride, followed by isoamylnitrite in a solvent such as tetrahydrofuran, dioxane or other appropriate solvent at a temperature from 20-100 degrees Centigrade. Quenching of this reaction, or a later reaction, such as the final step in the sequence, under aqueous basic conditions to cleave the N-Acetyl group is advised. Alternatively, a separate step may be performed to remove the acetate group under standard conditions such as treatment with 10% aqueous LiOH in tetrahydrofuran. Unmasking of the aldehyde under standard conditions, such as polymer supported tosic acid and acetone, followed by reductive amination under standard conditions such as treatment with the desired amine and sodium cyanoborohydride in methanol with acetic acid, or one of the many other known methods for this transformation, (See, for example, *Transformations in Organic Chemistry*, Second Edition, Richard C. LaRock, (John Wiley and Sons: 1999)), yield the desired compounds.

Method of Testing Compounds of the Invention

Materials

LEADSeeker WGA™ beads and GTPgS35 were purchased from Amersham Bioscience (Piscataway, N.J.). GDP, Saponin™, DAMGO™, Met-Enkephalin, Dynorphin A, NaCl and HEPES™ were purchased from SIGMA (St Louis, Mo.). MgCl$_2$ was purchased from J. T. Baker (Phillipsburg, N.J.). Opioid membranes, hOPRD, hOPRK and hOPRM were prepared at GlaxoSmithkline (Harlow, UK).

Assay buffer; 20 mM HEPES, 10 mM MgCL$_2$, and 100 mM NaCl dissolved in labgrade water, pH 7.4 with KOH.

[$^{35}$S]GTPgammaS Binding Assay Measured by LEADseeker SPA (384 well)

Dilute GTPgS$^{35}$ 1:900 in assay buffer in half of required final assay volume (volume A). Add the corresponding standard agonist, Met-Enkephalin (hOPRD), Dynorphin A (hOPRK) or DAMGO (hOPRM) to give a solution concentration of 8×[EC$_{50}$], for a final assay concentration of 4×[EC$_{50}$] to volume A. Resuspend LEADSeeker beads in assay buffer in order to generate a 40 mg/mL stock solution. GDP is dissolved in assay buffer at 1 mM. Add beads (100 microgram/well final) to assay buffer containing saponin (60 microgram/mL) in half of final assay volume (volume B). Mix well by vortexing. Add opioid membranes to each respective volume B, for a final assay concentration of 1.5 microgram/well (hOPRD), 1.0 microgram/well (hOPRK), and 1.5 microgram/well (hOPRM). Continuously mix the bead/membrane solution (volume B) for 30 min prior to adding to the GTPgS$^{35}$ solution (volume A) in a 1:1 ratio using a stir plate. Just prior to adding bead/membrane solution to the GTPgS$^{35}$ solution, add GDP to volume B at 20 microMolar (10 microMolar final assay concentration). Add the bead/membrane solution to the GTPgS$^{35}$ solution in a 1:1 ratio. Add 10 microLiters of the bead/membrane/GTPgS$^{35}$ mix to the assay plate using a Multidrop (Titertek™). Agitation of the solution is needed to prevent the beads/membrane from settling at the bottom. Plates are sealed, spun at 1000 rpm for 2 mins, tapped on side to agitate and incubated at room temperature for 5 hours. Plates are then imaged using a Viewlux Plus™ Imager (Perkin Elmer).

EXPERIMENTAL SECTION

Preparative HPLC General Information: Compounds were purified by preparative HPLC at flow rate of 20 ml/min through a guard column (YMC Combiguard ODS-A 10×10 mm ID, 15/30 μm, 120 angstrom pore size) and preparative column (YMC Combiprep ODS-A, 30×50 mm ID, 5 μm, 120 angstrom pore size). The eluent was a linear gradient of acetonitrile and water, with both solvents containing 0.05% trifluoroacetic acid.

General Method 1

Preparation of Benzimidazole Compounds, where A is CH$_2$.

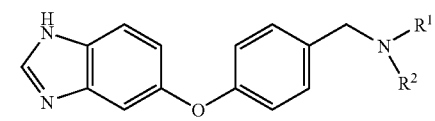

Step 1: {4-[(3,4-dinitrophenyl)oxy]phenyl}methanol Preparation

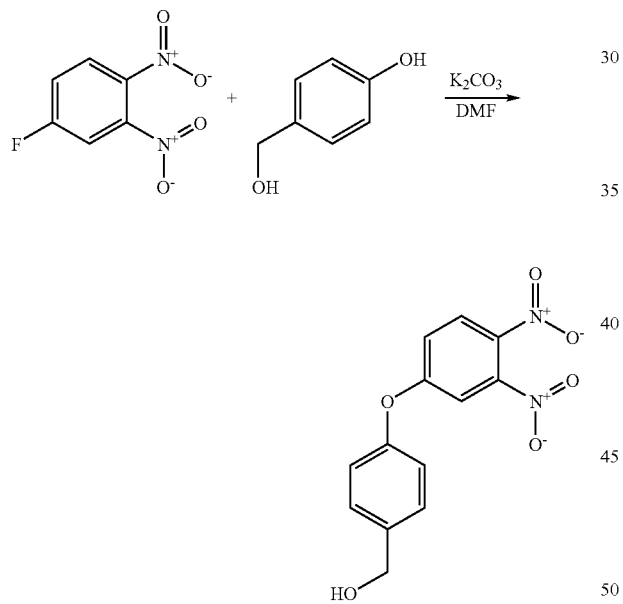

4-fluoro-1,2-dinitrobenzene (20.0 g, 107.5 mmol), 4-(hydroxymethyl)phenol (14.7 g, 118.2 mmol) and potassium carbonate (17.8 g, 129.0 mmol) were stirred in 250 ml of dimethylformamide at room temperature for approximately 17 hours. The reaction was heated at 35 degree Centigrade for 1.5 hours. Cesium carbonate (2 g, 6.14 mmol) was added and the reaction was heated at 45 deg. C. for approximately 22 hours. The solids were filtered away and washed with ethyl acetate. The filtrate was diluted with water and extracted 4 times with ethyl acetate. The ethyl acetate layers were washed with a water/brine mixture 5 times. The aqueous wash layers were back extracted with ethyl acetate twice. The organic layers were combined, dried over magnesium sulfate and concentrated under reduced pressure. The residue was purified by silica gel column chromatography (0 to 100% ethyl acetate in hexane) to give 14.1 g of {4-[(3,4-dinitrophenyl)oxy]phenyl}methanol.

$^1$H NMR (400 MHz, DMSO-d$_6$) delta ppm 4.51 (d, J=5.9 Hz, 2 H) 5.27 (t, J=5.6 Hz, 1 H) 7.20 (d, J=8.5 Hz, 2 H) 7.27 (dd, J=9.0, 2.7 Hz, 1 H) 7.43 (d, J=8.8 Hz, 2 H) 7.76 (d, J=2.7 Hz, 1 H) 8.25 (d, J=9.0 Hz, 1 H) (M-H$_2$O) 273.1, 2.28 min (LC/MS method A)

Step 2: {4-[(3,4-diaminophenyl)oxy]phenyl}methanol Preparation

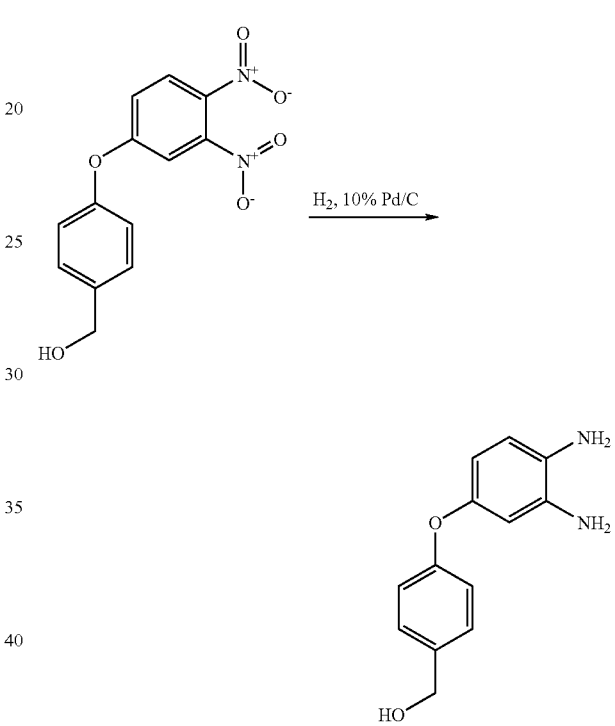

{4-[(3,4-dinitrophenyl)oxy]phenyl}methanol (3.73 g, 12.9 mmol) was hydrogenated in approximately 100 ml of ethyl acetate under a balloon of hydrogen over 1.2 g of 10% Pd on carbon (wet, degussa type) for 2.5 hours. An additional 600 mg of 10% Pd on carbon (wet, degussa type) was added and the reaction was hydrogenated under a balloon of hydrogen for 14.5 hours. The catalyst was filtered away and the filtrate was concentrated. The residue was dissolved in 1:1 ethanol:ethyl acetate and hydrogenated under a balloon of hydrogen over 1.2 g of 10% Pd on carbon (wet, degussa type) for 23.5 hours to consume remaining reaction intermediates. The catalyst was filtered away and the filtrate was concentrated to give 3.21 g of crude {4-[(3,4-diaminophenyl)oxy]phenyl}methanol, which was used without further purification.

$^1$H NMR (400 MHz, DMSO-d$_6$) delta ppm 4.39 (d, J=5.6 Hz, 2 H) 5.05 (t, J=5.9 Hz, 1 H) 6.04 (dd, J=8.3, 2.7 Hz, 1 H) 6.19 (d, J=2.7 Hz, 1 H) 6.46 (d, J=8.3 Hz, 1 H) 6.79 (d, J=8.8 Hz, 2 H) 7.19 (d, J=8.8 Hz, 2 H), (M+1) 231.2, 0.92 min (LC/MS method A)

Step 3: [4-(1H-benzimidazol-5-yloxy)phenyl]methanol Preparation

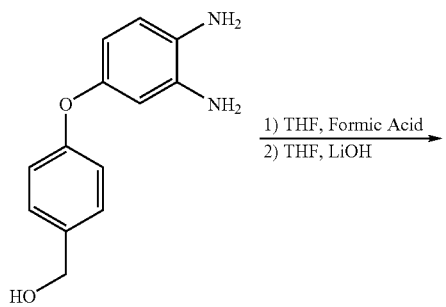

Step 4: 4-(1H-benzimidazol-5-yloxy)benzaldehyde Preparation

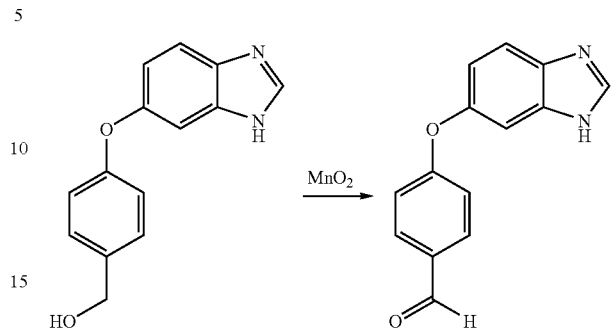

[4-(1H-benzimidazol-5-yloxy)phenyl]methanol (1.26 g) was dissolved in 70 ml of ethanol and 70 ml of chloroform and heated with $MnO_2$ (4.56 g, 52.5 mmol) in a 75 degrees Centigrade oil bath for 14 hrs. An additional 1 g of $MNO_2$ was added and the reaction continued heating for 3 hours. The reaction mixture was filtered through celite and concentrated under reduced pressure to afford 1.26 g of 4-(1H-benzimidazol-5-yloxy)benzaldehyde.

$^1$H NMR (400 MHz, DMSO-$d_6$) delta ppm 3.30 (s, 2 H) 6.99 (dd, J=8.8, 2.4 Hz, 1 H) 7.06 (d, J=8.8 Hz, 2 H) 7.35 (m, 1 H) 7.64 (d, J=8.5 Hz, 1 H) 7.87 (d, J=8.8 Hz, 2 H) 8.25 (s, 1 H) 9.88 (s, 1 H) 12.54 (s, 1 H), (M+1) 239.2, 1.42 min (LC/MS method B)

Step 5: Reductive Amination to Form Final Compounds of Formula 1

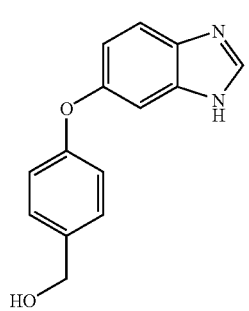

{4-[(3,4-diaminophenyl)oxy]phenyl}methanol (3.21 g of crude material) was dissolved in 20 ml THF and 10 ml of formic acid. The reaction was heated in a 100 degree Centigrade oil bath for approximately 22 hours. The reaction was concentrated under reduced pressure. The residue was dissolved in ethyl acetate and washed 5 times with saturated aqueous $NaHCO_3$. The organic layer was dried over $MgSO_4$ and concentrated under reduced pressure. The residue was dissolved in 30 ml of THF and 10 ml of 10% aqueous LiOH and heated at 100 degrees Centigrade for 30 minutes. The reaction was diluted with water and ethyl acetate. The organic layer was washed with brine three times, dried over $MgSO_4$, and concentrated under reduced pressure onto basic alumina. The compound was purified by silica gel column chromatography (100% dichloromethane to 10% (2M $NH_3$ in methanol) in dichloromethane gradient) to give 1.26 g of [4-(1H-benzimidazol-5-yloxy)phenyl]methanol.

$^1$H NMR (400 MHz, DMSO-$d_6$) delta ppm 4.43 (d, J=5.4 Hz, 2 H) 5.11 (m, 1 H) 6.90 (m, 3 H) 7.13 (m, 1 H) 7.27 (m, 2 H) 7.55 (m, 1 H) 8.18 (m, 1 H) 12.41 (m, 1 H)

$^1$H NMR (400 MHz, DMSO-D6+1 drop 30% w/w NaOD in $D_2O$) delta ppm 4.41 (s, 2 H) 6.79 (m, 1 H) 6.88 (d, J=8.5 Hz, 2 H) 7.09 (m, 1 H) 7.25 (d, J=8.1 Hz; 2 H) 7.50 (m, 1 H) 8.07 (m, 1 H), (M+1) 241.1, 1.26 min (LC/MS method B)

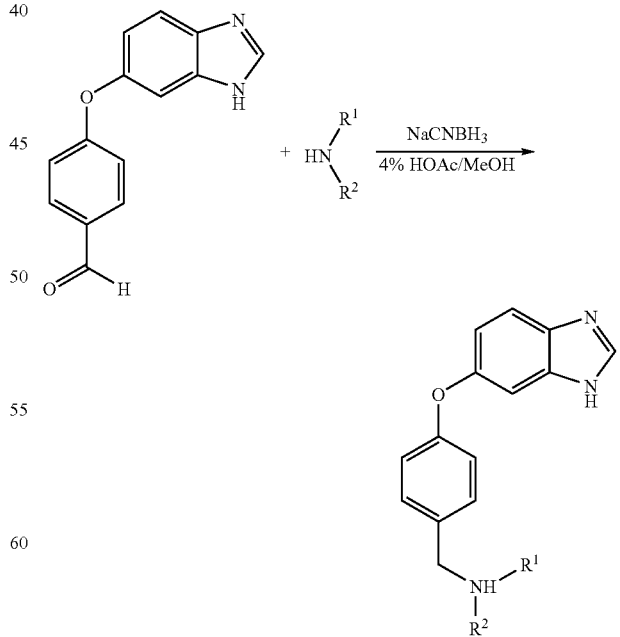

4-(1H-benzimidazol-5-yloxy)benzaldehyde (50 mg, 0.21 mmol), a primary or secondary amine (0.42 mmol), (1 equivalent of triethylamine was also added if the amine was an acid salt), and sodium cyanoborohydride (26 mg, 0.42 mmol) were stirred in 4 ml of 4% acetic acid in methanol for approximately 18 hours. The reaction was quenched with approximately 0.5 ml of water and concentrated under a stream of nitrogen. The residue was dissolved in 1 ml of 1M NaOH and approximately 3 ml ethyl acetate. The mixture was stirred vigorously using a vortex genie stirrer. The organic layer was added to a Varian Chem Elute 1001 column which was rinsed with 4-6 ml of ethyl acetate (gravity filtration) to elute the crude product. The eluent was concentrated. The residue was dissolved in 1.5-2 ml of methanol and approximately 150 µl of trifluoroacetic acid and purified using preparative HPLC.

General Method 2

Preparation of Indazole Compounds, where A is CH$_2$, X is NH, Y is N, and Z is CH.

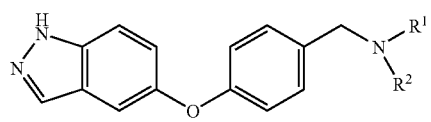

Step 1:
4-[(3-methyl-4-nitrophenyl)oxy]benzaldehyde Preparation

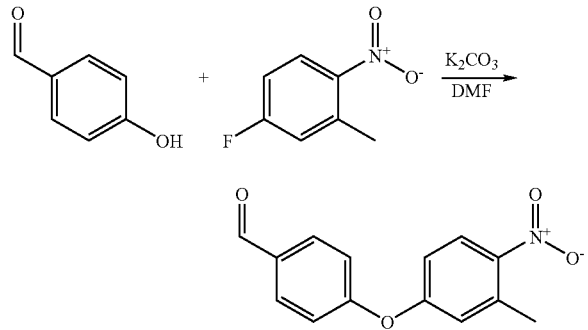

4-Hydroxybenzaldehyde (945 mg, 7.7 mmol), 4-fluoro-2-methyl-1-nitrobenzene (1.0 g, 6.4 mmol), and K$_2$CO$_3$ (1.77 g, 12.8 mmol) were stirred in 55 mL dimethylformamide at 100 degrees Centigrade for 18 hours. The reaction was cooled to room temperature, diluted with ethylacetate, extracted two times with 1N NaOH, and rinsed with brine. The organic layer was dried over MgSO$_4$, filtered and concentrated to afford 1.72 g crude 4-[(3-methyl-4-nitrophenyl)oxy]benzaldehyde, which was used without further purification.

1H NMR (400 MHz, DMSO-d$_6$) delta ppm 2.52 (s, 3 H) 7.10 (dd, J=9.0, 2.7 Hz, 1 H) 7.22 (d, J=2.7 Hz, 1 H) 7.28 (d, J=8.8 Hz, 2 H) 7.97 (d, J=8.8 Hz, 2 H) 8.09 (d, J=9.0 Hz, 1 H) 9.96 (s, 1 H), (M+1) 258.2, 1.42 min (LC/MS method A)

Step 2: 2-{4-[(3-methyl-4-nitrophenyl)oxy]phenyl}-1,3-dioxolane Preparation

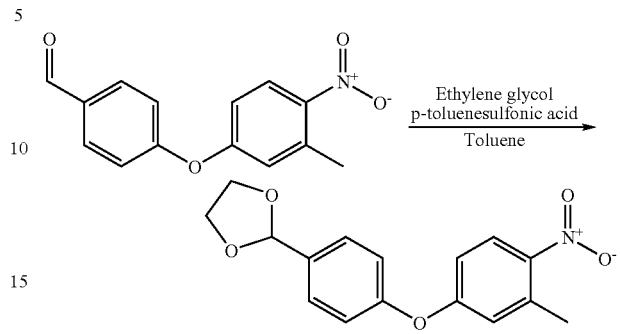

4-[(3-Methyl-4-nitrophenyl)oxy]benzaldehyde (1.72 g, 6.4 mmol), p-toluenesulfonic acid (120 mg, 0.64 mmol), and ethylene glycol (1.7 mL, 32 mmol) were heated to reflux in 70 mL toluene for 16 hours in a round bottom flask equipped with a Dean-Stark trap. The reaction mixture was cooled to room temperature, diluted with ethylacetate and extracted with 1N NaOH. The organic layer was dried over MgSO$_4$, filtered and concentrated to afford 1.89 g crude 2-{4-[(3-methyl-4-nitrophenyl)oxy]phenyl}-1,3-dioxolane, which was used without further purification.

1H NMR (400 MHz, DMSO-d$_6$) delta ppm 2.50 (s, 3 H) 3.89-3.98 (m, 2 H) 3.99-4.08 (m, 2 H) 5.73 (s, 1 H) 6.93 (dd, J=9.0, 2.9 Hz, 1 H) 7.07 (d, J=2.9 Hz, 1 H) 7.14 (d, J=8.5 Hz, 2 H) 7.50 (d, J=8.5 Hz, 2 H) 8.05 (d, J=9.0 Hz, 1 H), (M+1) 302.1, 2.69 min (LC/MS method A)

Step 3: 4-{[4-(1,3-dioxolan-2-yl)phenyl]oxy}-2-methylaniline Preparation

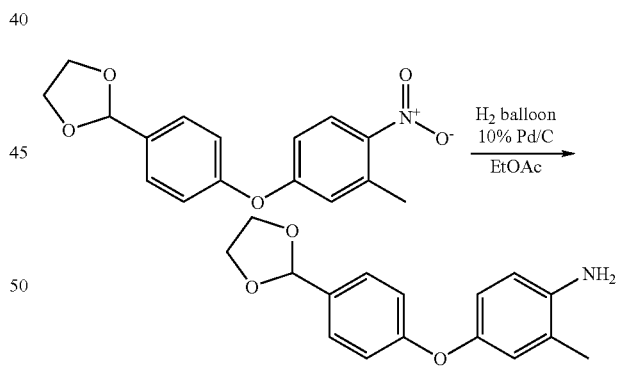

A 500 mL round bottom flask containing 2-{4-[(3-methyl-4-nitrophenyl)oxy]phenyl}-1,3-dioxolane (1.89 g, 6.27 mmol) in 60 mL ethylacetate was purged with nitrogen gas and treated with 10% palladium on carbon (650 mg, 0.63 mmol). A balloon with H$_2$ gas was attached and gas was allowed to bubble through the solution while allowing gas to escape the flask via needle. The needle was removed, and the reaction stirred under H$_2$ atmosphere for 2 days. The reaction was filtered through Celite, concentrated and purified via silica gel column chromatography (0% to 100% ethylacetate/hexane gradient) to provide 1.24 g 4-{[4-(1,3-dioxolan-2-yl)phenyl]oxy}-2-methylaniline.

1H NMR (400 MHz, DMSO-d$_6$) delta ppm 2.01 (m, 3 H) 3.86-3.93 (m, 2 H) 3.95-4.03 (m, 2 H) 4.73 (s, 2 H) 5.62 (s, 1 H) 6.58-6.64 (m, 2 H) 6.65-6.68 (m, 1 H) 6.81 (d, J=8.5 Hz, 2 H) 7.32 (d, J=8.8 Hz, 2 H), (M+1) 272.1, 1.58 min (LC/MS method A)

Step 4: 1-acetyl-5-{[4-(1,3-dioxolan-2-yl)phenyl]oxy}-1H-indazole Preparation

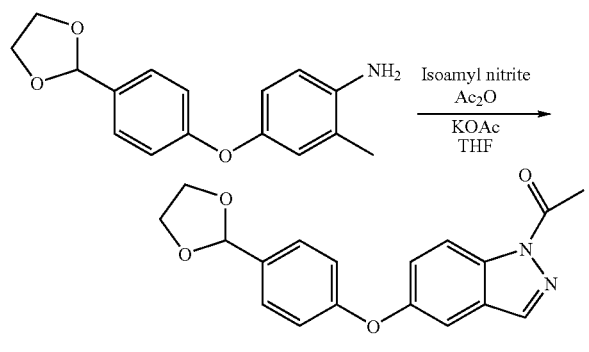

4-{[4-(1,3-dioxolan-2-yl)phenyl]oxy}-2-methylaniline (1.24 g, 4.55 mmol) in 40 mL tetrahydrofuran at room temperature was treated with potassium acetate (490 mg, 5 mmol) followed by acetic anhydride (1.42 mL, 15 mmol). After 10 minutes, the reaction was treated with isoamylnitrite (0.915 mL, 6.8 mmol) and heated to reflux for 3 hours. Catalytic 18-crown-6 was added and the reaction was refluxed for 4 days. Upon cooling to room temperature, the reaction mixture was poured into saturated aqueous NaHCO$_3$ and extracted with ethylacetate. The organic was rinsed with brine, dried over MgSO$_4$, and concentrated. The crude material was purified via silica gel column chromatography (0% to 100% ethyl acetate in hexane gradient) to provide 0.835 g 1-acetyl-5-{[4-(1,3-dioxolan-2-yl)phenyl]oxy}-1H-indazole.

1H NMR (400 MHz, DMSO-d$_6$) delta ppm 2.69 (s, 3 H) 3.90-3.96 (m, 2 H) 3.98-4.05 (m, 2 H) 5.69 (s, 1 H) 7.01 (d, J=8.8 Hz, 2 H) 7.37 (dd, J=9.0, 2.4 Hz, 1 H) 7.43 (d, J=8.8 Hz, 2 H) 7.48 (d, J=2.2 Hz, 1 H) 8.30 (d, J=9.0 Hz, 1H) 8.39 (s, 1 H), (M+1) 325.1, 2.62 min (LC/MS method A)

Step 5: 4-[(1-acetyl-1H-indazol-5-yl)oxy]benzaldehyde Preparation

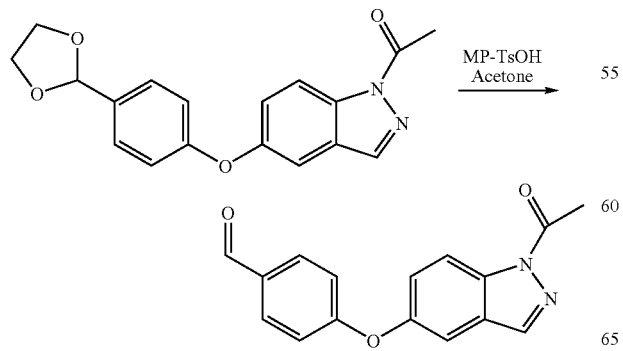

1-Acetyl-5-{[4-(1,3-dioxolan-2-yl)phenyl]oxy}-1H-indazole (835 mg, 2.57 mmol) in 25 mL acetone was treated with MP-TsOH (Argonaut, macroporous polymer supported tosic acid, approximately 200 mg, 0.28 mmol) and stirred for 16 hours. The reaction was filtered and concentrated to provide 4-[(1-acetyl-1H-indazol-5-yl)oxy]benzaldehyde quantitatively, which was used without further purification.

1H NMR (400 MHz, DMSO-d$_6$) delta ppm 2.71 (s, 3 H) 7.13 (d, J=8.8 Hz, 2 H) 7.44 (dd, J=9.0, 2.4 Hz, 1 H) 7.67 (d, J=2.4 Hz, 1 H) 7.91 (d, J=8.5 Hz, 2 H) 8.36 (d, J=8.8 Hz, 1 H) 8.44 (s, 1 H) 9.91 (s, 1 H), (M+1) 281.1, 2.53 min (LC/MS method A)

Step 6: Reductive Amination to Form Final Compounds

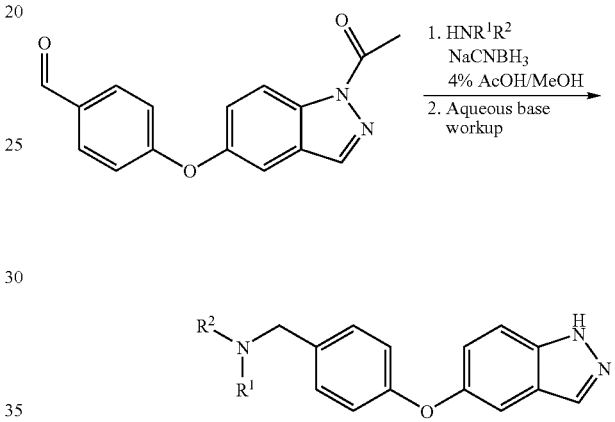

4-[(1-Acetyl-1H-indazol-5-yl)oxy]benzaldehyde (240 mg, 0.86 mmol) in 10 mL 4% acetic acid in methanol was treated with a primary or secondary amine (1.72 mmol) followed by sodiumcyanoborohydride (108 mg, 1.72 mmol). The reaction was stirred until the starting aldehyde was consumed, and the reaction was diluted with 1 N sodium hydroxide, allowing to stir until the intermediate acetate group was cleaved as indicated by LC/MS method A. This mixture was extracted with ethylacetate, and the organic rinsed with brine, dried over MgSO$_4$, and filtered. Treatment with 4 N hydrochloric acid in dioxane, followed by dilution with ethyl ether typically caused the pure desired product to precipitate. Alternatively, purification was accomplished by preparative HPLC.

General Method 3

Preparation of Benzimidazole Compounds Where A is CH$_2$ and Containing a R$^3$ Substitution

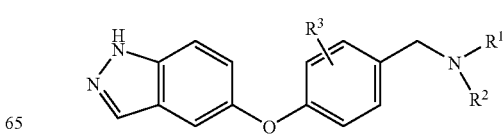

Representative Example

Preparation of N-{[4-(1H-benzimidazol-5-yloxy)-3-(methyloxy)phenyl]methyl}-2,3-dihydro-1H-inden-2-amine bis(trifluoroacetate) (Example No. 86 herein)

Step 1: (4-Hydroxy-2-nitrophenyl)formamide Preparation

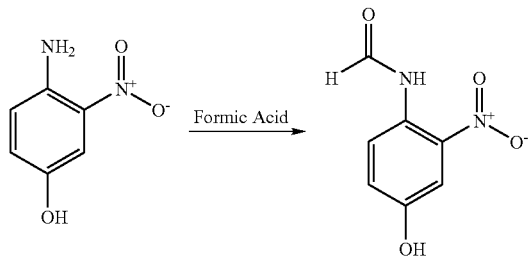

4-Amino-3-nitrophenol (36 g, 234 mmol) was split into 3 batches, approximately 12 g each. Each batch was dissolved in 150 mL of tetrahydrofuran and heated with 10 mL of 96% formic acid at 95 degrees Centigrade for 4 hours. The 3 batches were combined and concentrated. As the reactions had only proceeded ~10% to completion, the reaction mixture was dissolved in 100 mL of 96% formic acid and heated at 110 degrees Centigrade. After 30 minutes, a precipitate began to form and 150 mL of tetrahydrofuran was added to ensure good stirring. The reaction was heated at 110 degrees Centigrade for 15 hours. The reaction was concentrated and the residue was diluted with water. The resulting solid was collected by filtration. The solid was washed three times with water and then dried in a vacuum oven at 110 degrees Centigrade for approximately 18 hours to give 40.4 g of (4-hydroxy-2-nitrophenyl)formamide. (M-1) 181.0, 1.48 min (LC/MS method B)

Step 2: 4-(Formylamino)-3-nitrophenyl acetate Preparation

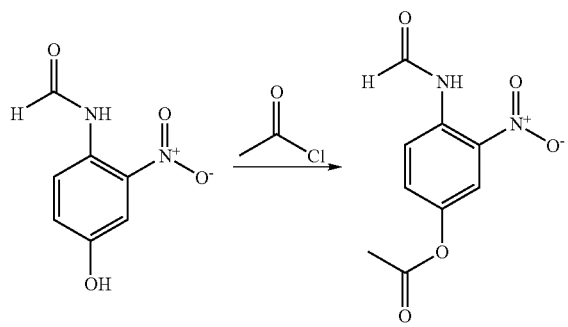

4-Hydroxy-2-nitrophenyl)formamide (36.19 g, 198.8 mmol) and triethylamine (46 ml, 328 mmol) were dissolved in tetrahydrofuran and the reaction flask was cooled in an ice bath. Acetyl chloride (15.6 ml, 218.7 mmol) was added via dropping funnel over 10 minutes. The reaction was allowed to warm to room temperature, stirred until completed (as judged by LC-MS) and was concentrated. The residue was diluted with water. The resulting solid was collected by filtration. The solid was washed twice with water and then dried in a vacuum oven at 110 degrees Centigrade for approximately 18 hours to give 23.5 g of 4-(formylamino)-3-nitrophenyl acetate. (M-1) 224.0, 1.98 min (LC/MS method B)

Step 3: 3-Amino-4-(formylamino)phenyl acetate Preparation

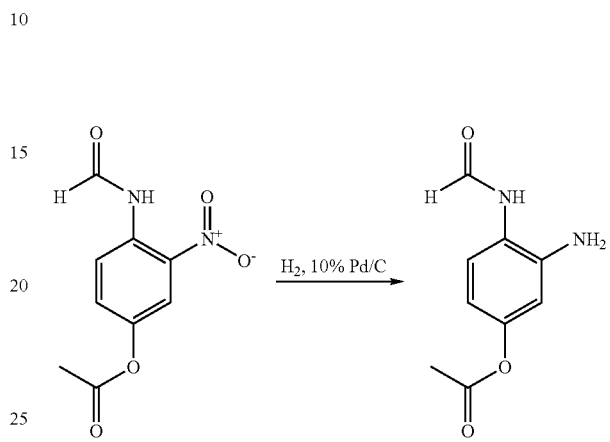

4-(Formylamino)-3-nitrophenyl acetate (13.5 g, 60.3 mmol, split into 1 g, 5 g, and 7.5 g batches) was dissolved in a minimal amount of ethyl acetate. The solution was hydrogenated over 10% Pd on carbon (wet, degussa type) on a Parr hydrogenator at 40 PSI of $H_2$ for 1 hour. The catalyst was removed by filtering the reaction through Celite. The filtrate was concentrated to give 10.3 g of 3-amino-4-(formylamino)phenyl acetate. (M+1) 195.1, 1.31 min (LC/MS method A)

Step 4: 1H-Benzimidazol-5-yl acetate Preparation

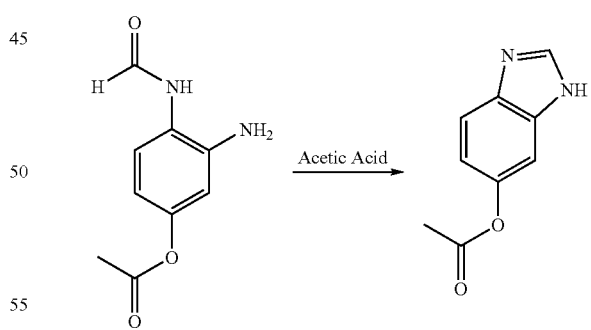

3-Amino-4-(formylamino)phenyl acetate (10.3 g, 53.1 mmol) was dissolved in ~100 mL of glacial acetic acid and heated at 65 degrees centigrade for approximately 18 hours. The reaction was concentrated and dried under vacuum. The residue was dissolved in ethyl acetate and washed three times with saturated $NaHCO_3$. The organic layer was dried over $MgSO_4$ and concentrated to give 6.89 g of 1H-benzimidazol-5-yl acetate. (M+1) 177.1, 1.02 min (LC/MS method B)

Step 5: A mixture of 1-(Triphenylmethyl)-1H-benzimidazol-5-ol and 1-(Triphenylmethyl)-1H-benzimidazol-6-ol Step 6: 4-(1H-benzimidazol-5-yloxy)-3-(methyloxy)benzaldehyde

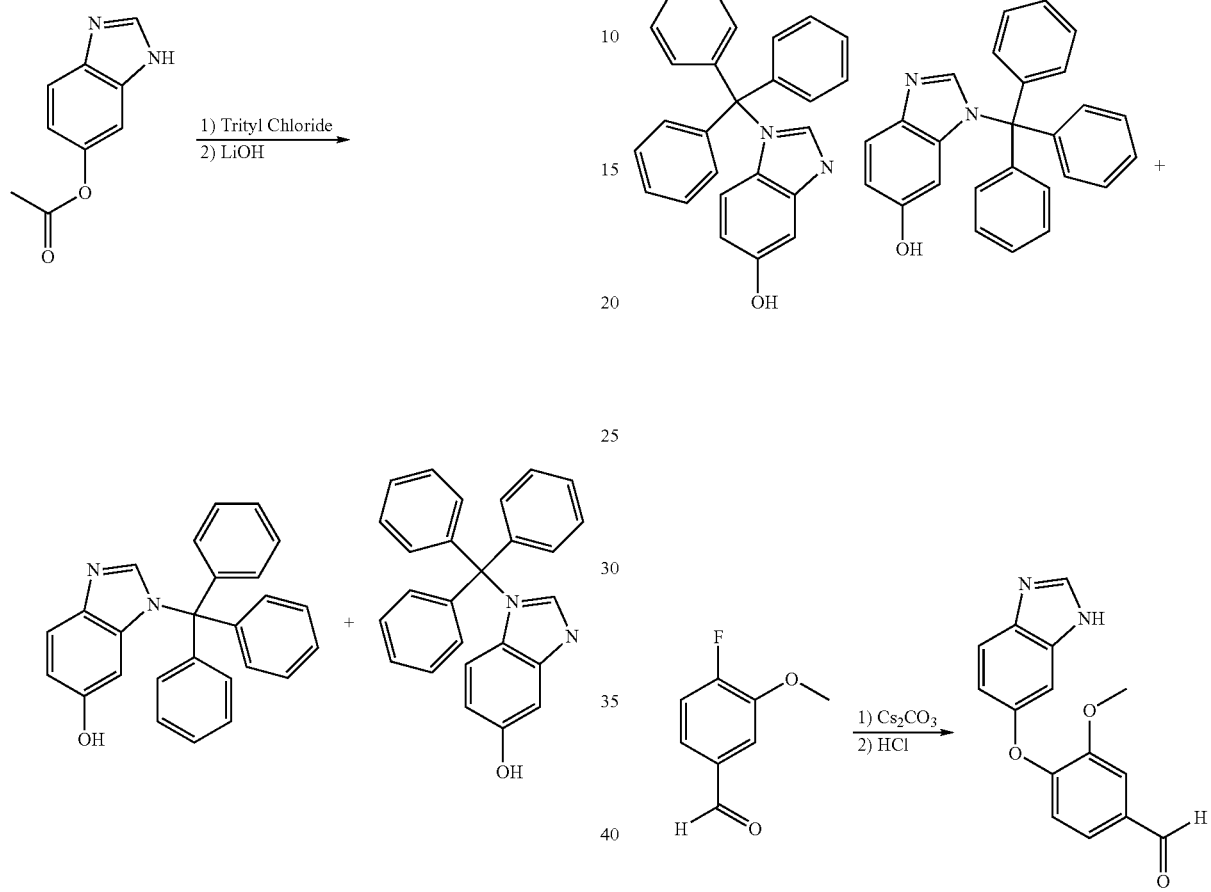

1H-Benzimidazol-5-yl acetate (6.89 g, 39.1 mmol), trityl chloride (9.82 g, 43.1 mmol) and triethylamine (11 ml, 78 mmol) were stirred in 200 mL of tetrahydrofuran for 3 days. 40 mL of aqueous 10% LiOH was added and the reaction was heated at 85 degrees Centigrade for 2 hours. The reaction was cooled to room temperature and diluted with water and ethyl acetate. The pH was adjusted to approximately pH=3 with 1N HCl. A small amount of a fine solid was filtered away, and the filtrate was extracted three times with ethyl acetate. The organic layers were combined and washed with brine. The organic layer was dried over MgSO$_4$ and concentrated. The residue was dissolved in minimal dichloromethane and partially added to an alumina column for chromatography when a precipitate formed. The alumina was washed with copious ethyl acetate and methanol. The filtrate and remainder of the crude product was concentrated together. The crude product was triturated with diethyl ether causing a solid to precipitate. The solid was collected by filtration and washed with ether to give a mixture of 1-(triphenylmethyl)-1H-benzimidazol-6-ol and 1-(triphenylmethyl)-1H-benzimidazol-5-ol. (M-H) 377.2, 2.58 min, and its isomer at 2.66 min (LC/MS method B).

A mixture of 1-(triphenylmethyl)-1H-benzimidazol-5-ol and 1-(triphenylmethyl)-1H-benzimidazol-6-ol (750 mg, 2.0 mmol), 4-fluoro-3-(methyloxy)benzaldehyde (461 mg, 3.0 mmol) and cesium carbonate (972 mg, 3.0 mmol) were heated in dimethylformamide at 80 degrees centigrade for 2 hours. The reaction was diluted with water and extracted twice with ethyl acetate. The organic layers were washed with brine, dried over MgSO$_4$, concentrated and dried under vacuum for approximately 18 hours. The residue was dissolved in 15 mL of tetrahydrofuran and stirred with 5 mL or 4N HCl in dioxane for 4 days. The reaction was concentrated and purified by preparative HPLC. Pure fractions were diluted with 1N NaOH to make basic and then extracted twice with ethyl acetate. The organic layers were dried over MgSO$_4$ and concentrated to give 4-(1H-benzimidazol-5-yloxy)-3-(methyloxy)benzaldehyde. (M+1) 269.0, 1.34 min (LC/MS method B)

Step 7: N-{[4-(1H-benzimidazol-5-yloxy)-3-(methyloxy)phenyl]methyl}-2,3-dihydro-1H-inden-2-amine bis(trifluoroacetate) (Example No. 86)

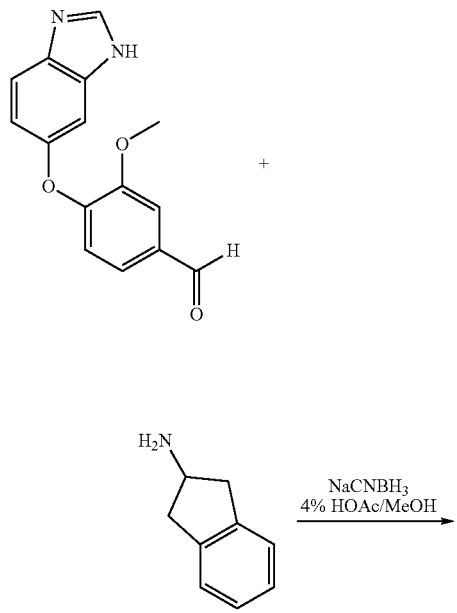

Final compounds were prepared using the appropriate aldehyde and amine using the procedure of General method 1, step 5.

General Method 4

Preparation of Benzimidazole Compounds, where A is CH$_2$

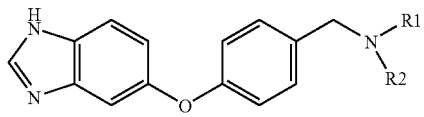

Representative Example

N-{[4-(1H-benzimidazol-5-yloxy)phenyl]methyl}-2,3-dihydro-1H-inden-2-amine dihydrochloride. (Example No. 26)

Step 1: 4-[(4-amino-3-nitrophenyl)oxy]benzaldehyde Preparation

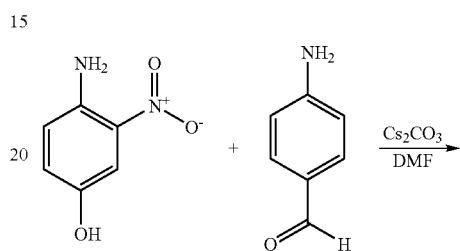

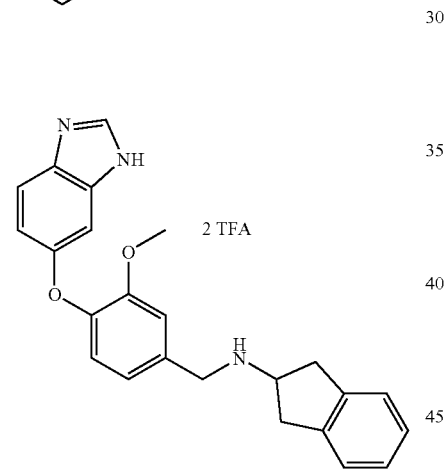

4-amino-3-nitrophenol (25 g, 162 mmol), 4-fluorobenzaldehyde (19.1 g, 154 mmol) and cesium carbonate (58 g, 178 mmol) were stirred in dimethylformamide at 85 degrees centigrade for 20 minutes and then 45 degrees Centigrade for approximately 18 hours. The reaction was allowed to cool to room temperature then filtered through celite and eluted with ethyl acetate. Water, brine and ethyl acetate were added to the filtrate which was then filtered through a glass wool packed Alltech 75 mL Extract-Clean™ filter column. The filtrate was separated into two portions and each was extracted with ethyl acetate then washed with brine four times. The organic layers were combined, dried over magnesium sulfate, concentrated onto basic alumina and purified by silica gel column chromatography (0 to 100% ethyl acetate in hexanes to give 23 g of 4-[(4-amino-3-nitrophenyl)oxy]benzaldehyde. (M+1) 259.0, 2.39 min (LC/MS method A)

Step 2: {4-[(4-Formylphenyl)oxy]-2-nitrophenyl}formamide Preparation

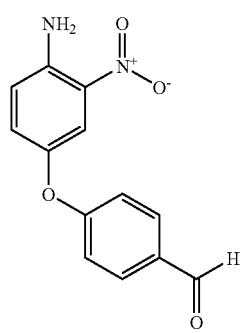

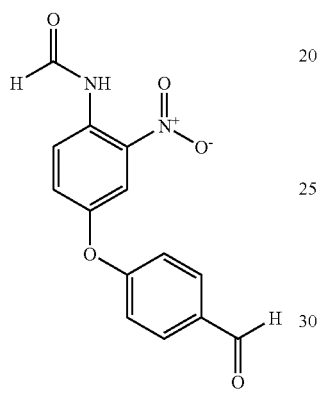

4-[(4-amino-3-nitrophenyl)oxy]benzaldehyde (1.4 g, 5.4 mmol), 10 mL of 96% formic acid and 25 mL of tetrahydrofuran were heated at reflux for approximately 18 hours. The reaction was concentrated and the residue was heated to reflux in 96% formic acid for six hours. The reaction mixture was concentrated to give {4-[(4-formylphenyl)oxy]-2-nitrophenyl}formamide. (M-1) 285.1, 2.22 min (LC/MS method A)

Step 3: 1,1-dimethylethyl 2,3-dihydro-1H-inden-2-yl [(4-{[4-({[(1,1-dimethylethyl)oxy]carbonyl}amino)-3-nitrophenyl]oxy}phenyl)methyl]carbamate Preparation

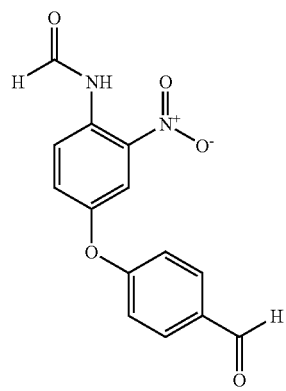

+

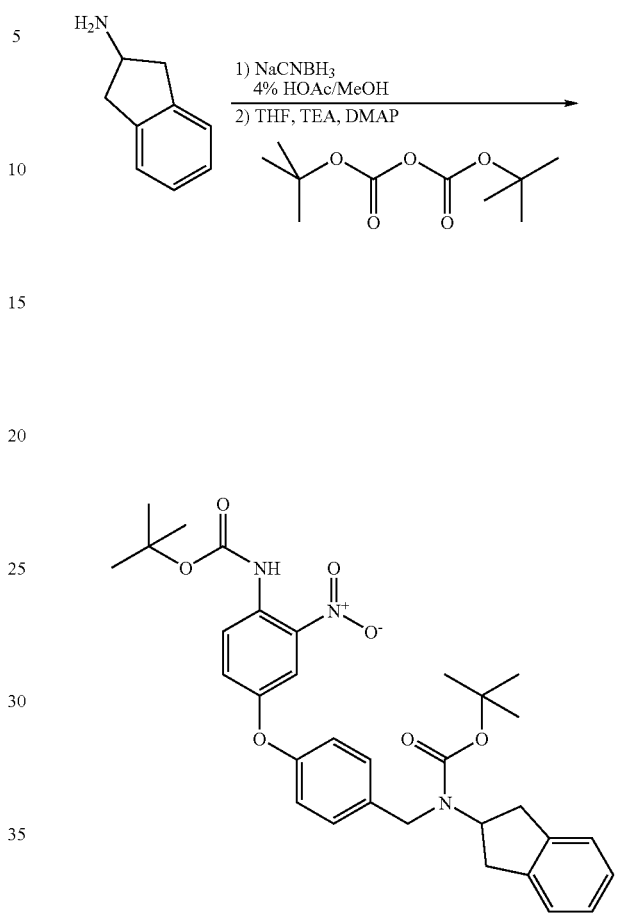

{4-[(4-formylphenyl)oxy]-2-nitrophenyl}formamide (530 mg, 1.85 mmol), amine (in this case 2-aminoindane, 300 microliters, 2.3 mmol) and sodium cyanoborohydride (151 mg, 1.4 mmol) were stirred in 25 mL of 4% acetic acid in methanol and 5 mL ethyl acetate for 67.5 hours. The reaction mixture was concentrated. The residue was dissolved in 5 mL of 1M NaOH and approximately 5 mL ethyl acetate. The mixture was stirred vigorously using a vortex genie stirrer. The organic layer was added to a Varian Chem Elute™ 1010 column which was rinsed with 4-6 mL of ethyl acetate (gravity filtration) to elute the crude product. The eluent was concentrated then dissolved in 15 mL of tetrahydrofuran. Di-tert-butyl dicarbonate (0.64 mL, 2.8 mmol), triethylamine (518 microliters, 3.7 mmol) and 15 mg of 4-(dimethylamino)pyridine were stirred for approximately 18 hours. The reaction was quenched with 5 mL 1N HCl and stirred vigorously. The reaction mixture was passed through a Varian Chem Elute™ 1010 column which was then rinsed with ethyl acetate. The eluent was concentrated onto basic alumina and purified by silica gel column chromatography (0 to 100% ethyl acetate in hexanes) to give 1,1-dimethylethyl 2,3-dihydro-1H-inden-2-yl[(4-{[4-({[(1,1-dimethylethyl)oxy]carbonyl}amino)-3-nitrophenyl]oxy}phenyl)methyl]carbamate. (M+1) 576.2, 3.47 min (LC/MS method A)

Step 4: 1,1-dimethylethyl[2-amino-4-({4-[(2,3-dihydro-1H-inden-2-yl{[(1,1-dimethylethyl)oxy]carbonyl}amino)methyl]phenyl}oxy)phenyl]carbamate Preparation

Step 5: 1,1-dimethylethyl 2,3-dihydro-1H-inden-2-yl [(4-{[4-({[(1,1-dimethylethyl)oxy]carbonyl}amino)-3-(formylamino)phenyl]oxy}phenyl)methyl]carbamate Preparation

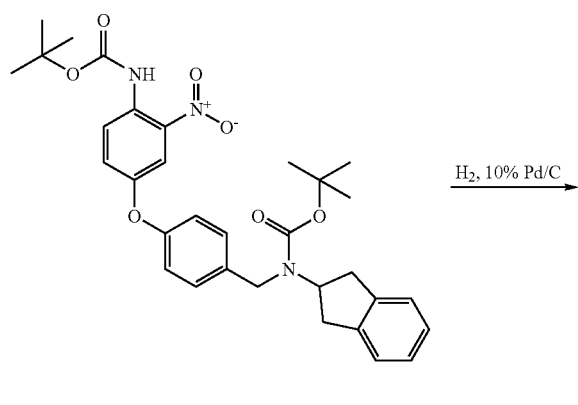

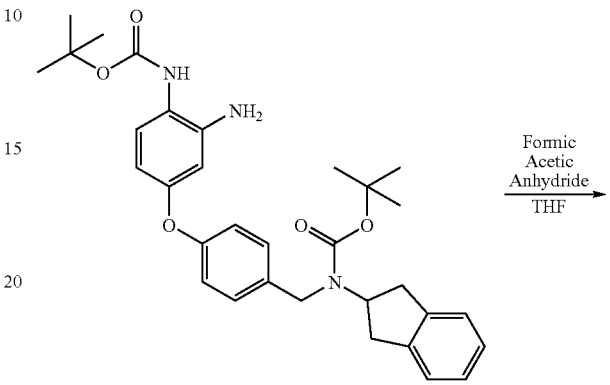

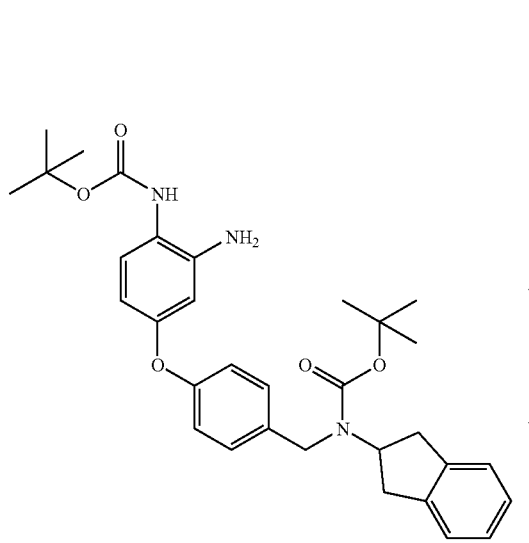

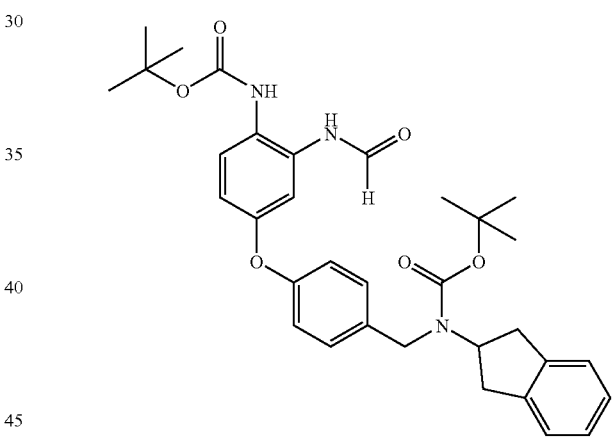

An ethyl acetate solution of 1,1-dimethylethyl 2,3-dihydro-1H-inden-2-yl[(4-{[4-({[(1,1-dimethylethyl)oxy]carbonyl}amino)-3-nitrophenyl]oxy}phenyl)methyl]carbamate (647 mg, 1.12 mmol) was hydrogenated under an atmosphere of hydrogen over approximately 50 mg of 10% Pd/carbon (wet, degussa type) for approximately 18 hours. The catalyst was filtered away, and the filtrate was concentrated. The reaction was purified by silica gel column chromatography (0 to 100% ethyl acetate in hexanes) to give 1,1-dimethylethyl[2-amino-4-({4-[(2,3-dihydro-1H-inden-2-yl{[(1,1-dimethylethyl)oxy]carbonyl}amino)methyl]phenyl}oxy)phenyl]carbamate. (M+1) 546.3, 3.15 min (LC/MS method A)

Formic acetic anhydride was prepared by adding 96% formic acid (1.24 ml, 32.2 mmol) to acetic anhydride (1.52 ml, 16.1 mmol) and stirring for 1 hour. (Ref: Org. Process Research & Development, 2000, 4, p. 567-570). Formic acetic anhydride (0.16 ml, 0.87 mmol) was added to a solution of 1,1-dimethylethyl[2-amino-4-({4-[(2,3-dihydro-1H-inden-2-yl{[(1,1-dimethylethyl)oxy]carbonyl}amino)methyl]phenyl}oxy)phenyl]carbamate (430 mg, 0.79 mmol) in 20 mL of tetrahydrofuran. The reaction mixture was stirred for 30 minutes then quenched with 2 mL of 1N NaOH and stirred vigorously. The reaction was passed through a Varian Chem Elute™ 1010 tube that was pretreated for five minutes with 2 mL of 1N NaOH. The tube was eluted with ethyl acetate. The eluent was dried over MgSO$_4$ and concentrated to give 1,1-dimethylethyl 2,3-dihydro-1H-inden-2-yl[(4-{[4-({[(1,1-dimethylethyl)oxy]carbonyl}amino)-3-(formylamino)phenyl]oxy}phenyl)methyl]carbamate. (M-1) 572.0, 2.93 min (LC/MS method B)

Step 6: N-{[4-(1H-benzimidazol-5-yloxy)phenyl]methyl}-2,3-dihydro-1H-inden-2-amine dihydrochloride (Example No. 26) Preparation

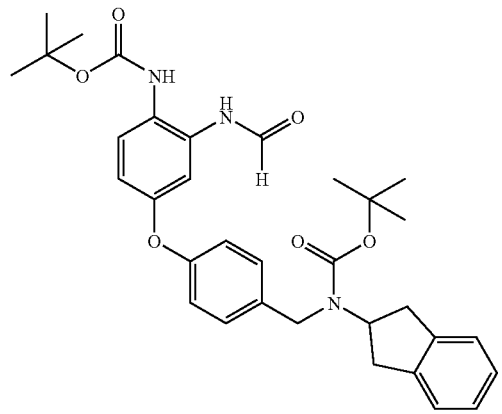

1,1-Dimethylethyl 2,3-dihydro-1H-inden-2-yl[(4-{[4-({[(1,1-dimethylethyl)oxy]carbonyl}amino)-3-(formylamino)phenyl]oxy}phenyl)methyl]carbamate (365 mg, 0.637 mmol) was dissolved in 20 mL of methylene chloride and stirred with 4 mL trifluoroacetic acid for approximately 18 hours. The reaction was concentrated and purified using preparative HPLC. Pure fractions were combined, diluted with ethyl acetate and washed with 1N NaOH. The aqueous layer was extracted with ethyl acetate. The organic layers were combined, dried over MgSO$_4$ and concentrated. The residue was dissolved in ethyl acetate. 4N HCl in dioxane was added and N-{[4-(1H-benzimidazol-5-yloxy) phenyl]methyl}-2,3-dihydro-1H-inden-2-amine dihydrochloride was collected by filtration as a white precipitate. The solid was dissolved in methanol, concentrated onto basic alumina and purified by column chromatography using an ISCO™ amine functionalized silica column. (dichloromethane to 5% methanol). The purified material was dissolved in minimal methanol. HCl (4N in dioxane) was added to the solution which was concentrated to give N-{[4-(1H-benzimidazol-5-yloxy)phenyl]methyl}-2,3-dihydro-1H-inden-2-amine dihydrochloride. (Example No. 26)

General Method 5

Preparation of Benzimidazole Compounds Where A is $CH_2$ and Containing a $R^3$ Substitution

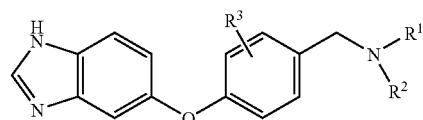

Representative Example

Preparation of N-{[4-(1H-benzimidazol-5-yloxy)-3-(methyloxy) phenyl]methyl}-2,3-dihydro-1H-inden-2-amine bis(trifluoroacetate) (Example No. 86)

Step 1: 4-[(4-amino-3-nitrophenyl)oxy]-3-(methyloxy)benzaldehyde Preparation

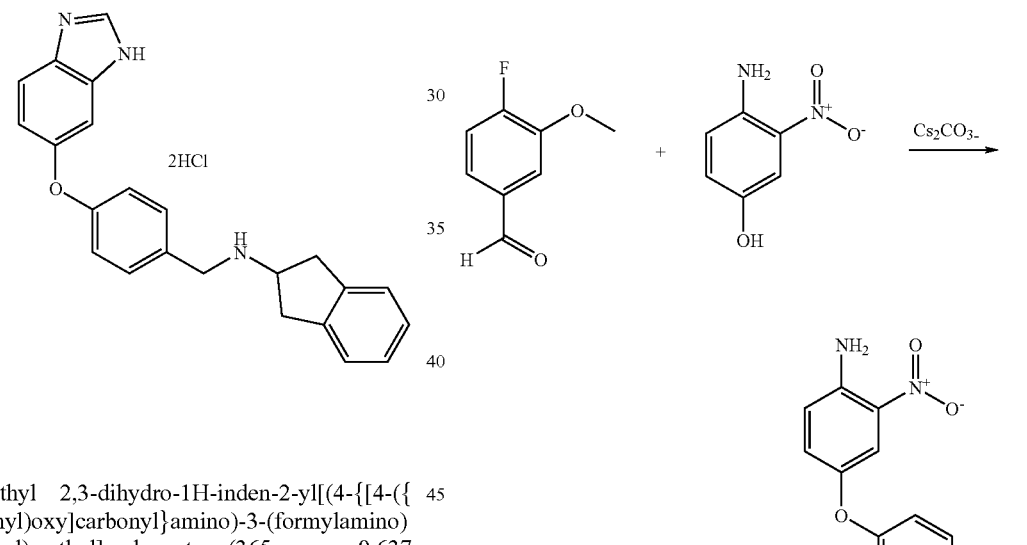

4-Amino-3-nitrophenol (2 g, 13 mmol), 4-fluoro-3-(methyloxy)benzaldehyde (2 g, 13 mmol) and Cs$_2$CO$_3$ (5.1 g, 15.6 mmol) were stirred in dimethylformamide at 100 degrees Centigrade for approximately 18 hours. The reaction was filtered through an Alltech 75 mL Extract-Clean™ filter column packed with glass wool and eluted with ethyl acetate. The eluent was stirred with 5 mL of water then passed through a Varian Chem Elute™ 1010 column which was rinsed with 4-6 mL of ethyl acetate (gravity filtration). The eluent was dried over MgSO$_4$, concentrated onto basic alumina and purified by silica gel column chromatography (hexanes/ethyl acetate gradient) to give 4-[(4-amino-3-nitrophenyl)oxy]-3-(methyloxy)benzaldehyde. (M+1) 289.0, 2.26 min (LC/MS method A)

Step 2: 4-{[4-(1,3-dioxolan-2-yl)-2-(methyloxy)phenyl]oxy}-2-nitroaniline Preparation

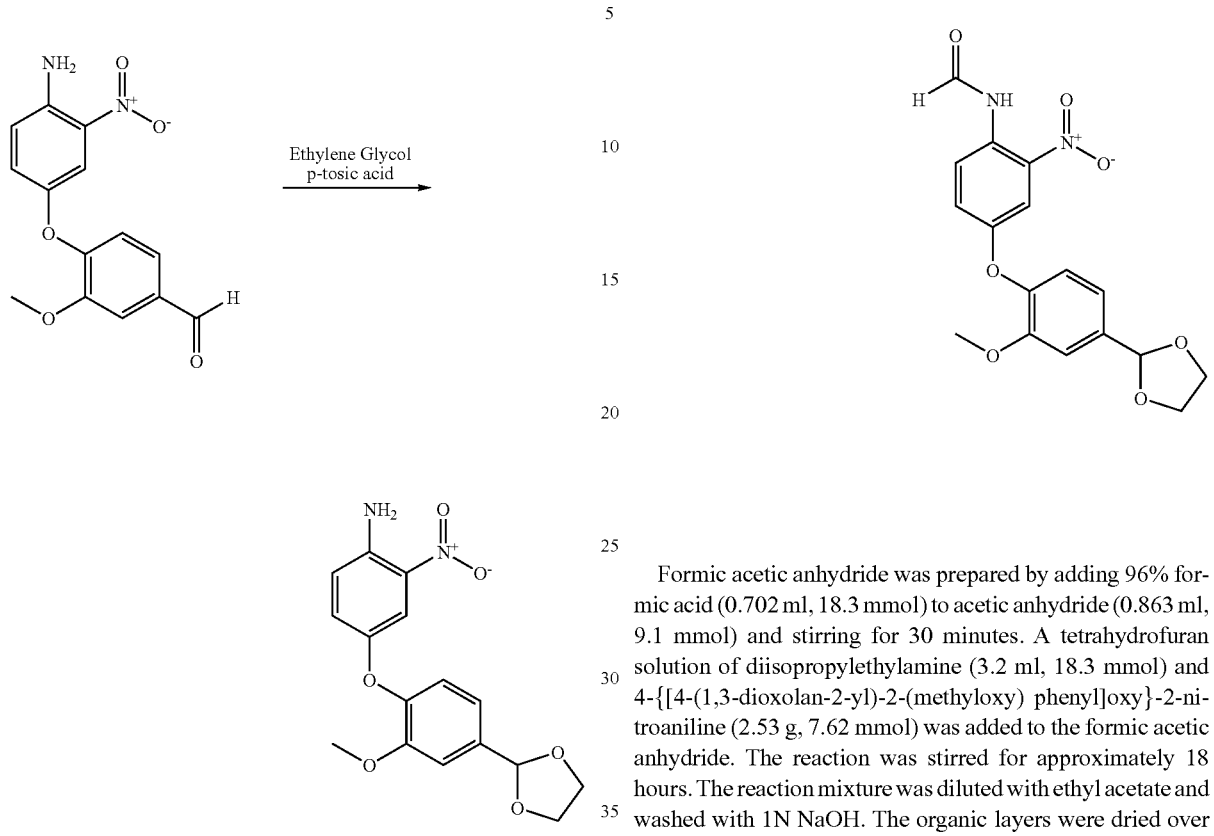

4-[(4-amino-3-nitrophenyl)oxy]-3-(methyloxy)benzaldehyde (2.42 g, 8.4 mmol), ethyleneglycol (4 ml) and p-toluenesulfonic acid (50 mg) in 50 mL of toluene was heated at 125 degrees Centigrade with a Dean-Stark trap for approximately 18 hours. The reaction mixture was diluted with ethyl acetate and washed twice with saturated $NaHCO_3$. The aqueous layers were extracted with ethyl acetate. The organic layers were combined, dried over $MgSO_4$ and concentrated to give 4-{[4-(1,3-dioxolan-2-yl)-2-(methyloxy) phenyl]oxy}-2-nitroaniline. (M+1) 332.9, 2.13 min (LC/MS method B)

Step 3: (4-{[4-(1,3-dioxolan-2-yl)-2-(methyloxy) phenyl]oxy}-2-nitrophenyl) formamide Formic acetic anhydride was prepared by adding 96% formic acid (0.702 ml, 18.3 mmol) to acetic anhydride (0.863 ml, 9.1 mmol) and stirring for 30 minutes. A tetrahydrofuran solution of diisopropylethylamine (3.2 ml, 18.3 mmol) and 4-{[4-(1,3-dioxolan-2-yl)-2-(methyloxy) phenyl]oxy}-2-nitroaniline (2.53 g, 7.62 mmol) was added to the formic acetic anhydride. The reaction was stirred for approximately 18 hours. The reaction mixture was diluted with ethyl acetate and washed with 1N NaOH. The organic layers were dried over $MgSO_4$ and concentrated. The residue was purified by silica gel column chromatography to give (4-{[4-(1,3-dioxolan-2-yl)-2-(methyloxy)phenyl]oxy}-2-nitrophenyl) formamide. (M+1) 360.8, 2.31 min (LC/MS method B)

Step 4: (2-amino-4-{[4-(1,3-dioxolan-2-yl)-2-(methyloxy)phenyl]oxy}phenyl)formamide

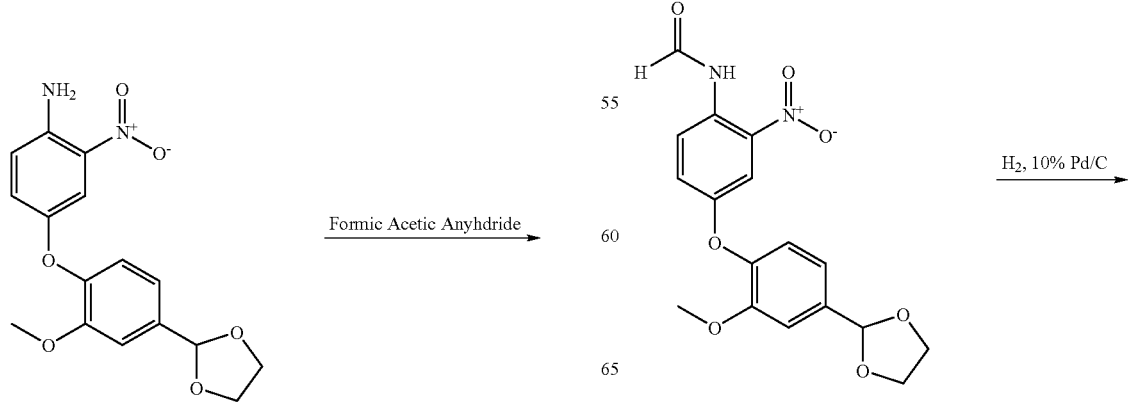

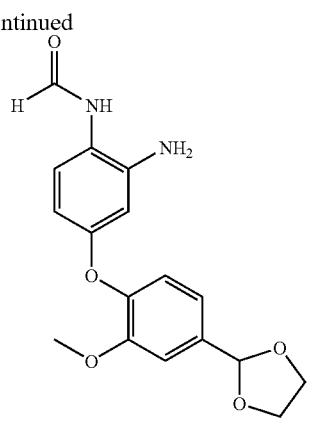

(4-{[4-(1,3-Dioxolan-2-yl)-2-(methyloxy)phenyl]oxy}-2-nitrophenyl)formamide (430 mg) was hydrogenated in approximately 75 mL of ethyl acetate under an atmosphere of hydrogen over 100 mg of 10% Pd on carbon (wet, degussa type) for 3 days. The catalyst was filtered away and the filtrate was concentrated to give (2-amino-4-{[4-(1,3-dioxolan-2-yl)-2-(methyloxy) phenyl]oxy}phenyl)formamide, which was used without further purification. (M+1) 330.9, 1.79 min (LC/MS method B)

Step 5: Preparation of a mixture of 4-(1H-benzimidazol-5-yloxy)-3-(methyloxy)benzaldehyde and 5-{[4-[bis(methyloxy)methyl]-2-(methyloxy)phenyl]oxy}-1H-benzimidazole

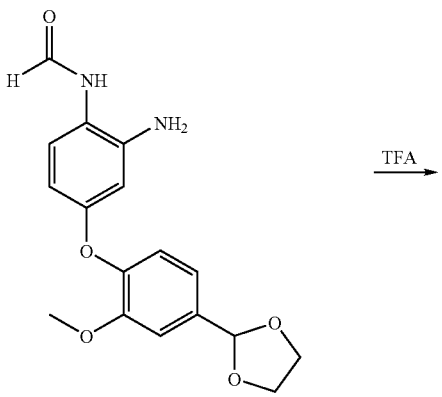

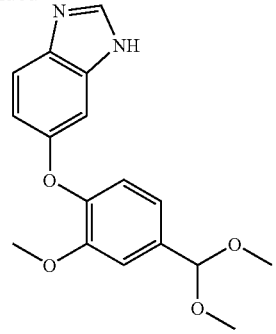

(2-Amino-4-{[4-(1,3-dioxolan-2-yl)-2-(methyloxy)phenyl]oxy}phenyl)formamide (408 mg) was stirred in 10 mL of dichloromethane and 2 mL of trifluoroacetic acid for 2 hours. The reaction mixture was concentrated. The reaction was not complete so the residue was dissolved in neat trifluoroacetic acid and stirred at 45 degrees centigrade for approximately 18 hours. The reaction mixture was concentrated and purified by silica gel column chromatography (gradient of dichloromethane to 10% 2N NH₃ in methanol/dichloromethane) to give a mixture of 4-(1H-benzimidazol-5-yloxy)-3-(methyloxy)benzaldehyde and 5-{[4-[bis(methyloxy)methyl]-2-(methyloxy)phenyl]oxy}-1H-benzimidazole which was carried on to the next step. (M+1) 269.0, 1.21 min, (M+1) 315.1, 1.50 min (LC/MS method A)

Step 6: N-{[4-(1H-benzimidazol-5-yloxy)-3-(methyloxy)phenyl]methyl}-2,3-dihydro-1H-inden-2-amine bis(trifluoroacetate) (Example No. 86)

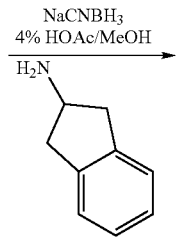

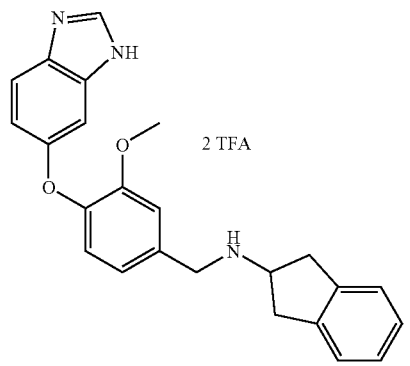

N-{[4-(1H-Benzimidazol-5-yloxy)-3-(methyloxy)phenyl]methyl}-2,3-dihydro-1H-inden-2-amine was prepared using a mixture of 4-(1H-benzimidazol-5-yloxy)-3-(methyloxy)benzaldehyde and 5-{[4-[bis(methyloxy)methyl]-2-(methyloxy)phenyl]oxy}-1H-benzimidazole and the procedure of General method 1, step 5 where 2-aminoindane is the amine.

General Method 6

Preparation of Benzimidazole Compounds Containing a R³ Substitution, and where A is CH₂

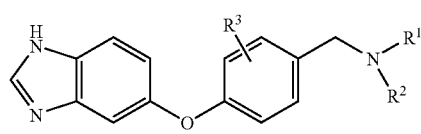

Representative Example

Preparation of N-{[4-(1H-benzimidazol-5-yloxy)-3-chlorophenyl]methyl}-2,3-dihydro-1H-inden-2-amine trifluoroacetate (Example No. 77).

Step 1: 4-[(4-amino-3-nitrophenyl)oxy]-3-chlorobenzaldehyde Preparation

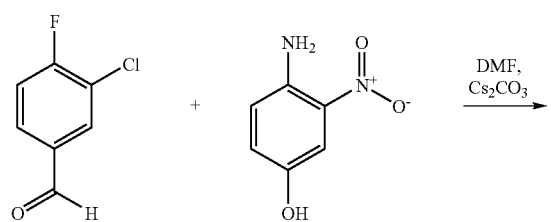

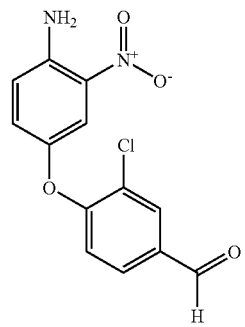

4-[(4-Amino-3-nitrophenyl)oxy]-3-chlorobenzaldehyde was prepared from 3-chloro-4-fluorobenzaldehyde (and 4-amino-3-nitrophenol using the procedure of method 5 step 1. (M-1) 291.1, 2.59 min (LC/MS method A)

Step 2: 4-{[2-Chloro-4-(1,3-dioxolan-2-yl)phenyl]oxy}-2-nitroaniline

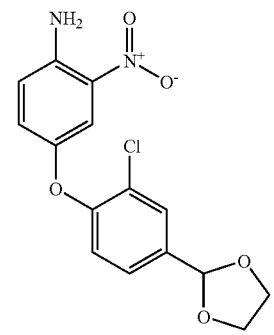

4-[(4-Amino-3-nitrophenyl)oxy]-3-chlorobenzaldehyde (1.16 g, 5.3 mmol), ethylene glycol (5 ml) and p-toluenesulfonic acid (50 mg) in 150 mL of toluene was heated at 120 degrees centigrade with a Dean-Stark trap for 24 hours. The reaction mixture was diluted with ethyl acetate and washed twice with 1N NaOH. The organic layer was dried over MgSO₄ and concentrated to give 4-{[2-chloro-4-(1,3-dioxolan-2-yl)phenyl]oxy}-2-nitroaniline. (M+1) 336.9, 2.60 min (LC/MS method B)

Step 3: 4-{[2-Chloro-4-(1,3-dioxolan-2-yl)phenyl]oxy}-1,2-benzenediamine

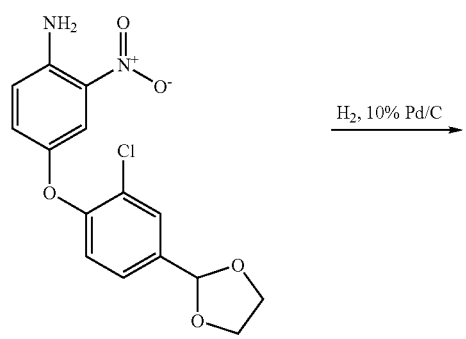

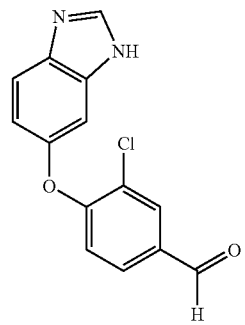

4-{[2-Chloro-4-(1,3-dioxolan-2-yl)phenyl]oxy}-2-nitroaniline (1.41 g) was dissolved in 100 mL of ethyl acetate and hydrogenated over 100 mg of 10% Pd/carbon (wet, Degussa type) under balloon of $H_2$ gas. After 24 hours, the reaction was filtered through Celite and concentrated to give 4-{[2-chloro-4-(1,3-dioxolan-2-yl)phenyl]oxy}-1,2-benzenediamine which was used without further purification. (M+1) 306.9, 1.57 min (LC/MS method B)

Step 4: 4-(1H-benzimidazol-5-yloxy)-3-chlorobenzaldehyde

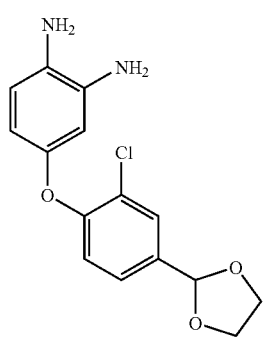

Crude 4-{[2-chloro-4-(1,3-dioxolan-2-yl)phenyl]oxy}-1,2-benzenediamine was heated to reflux in 5 mL of trimethyl orthoformate for 2 hours. The reaction mixture was then concentrated and purified by preparative HPLC, with concomiment loss of the dioxolane protecting group. The HPLC fractions were combined and diluted with 1N NaOH, extracted with ethyl acetate, dried over $MgSO_4$ and concentrated to give 4-(1H-benzimidazol-5-yloxy)-3-chlorobenzaldehyde. (M+1) 272.9, 1.65 min (LC/MS method B)

Step 5: N-{[4-(1H-benzimidazol-5-yloxy)-3-chlorophenyl]methyl}-2,3-dihydro-1H-inden-2-amine trifluoroacetate Preparation. (Example No. 77)

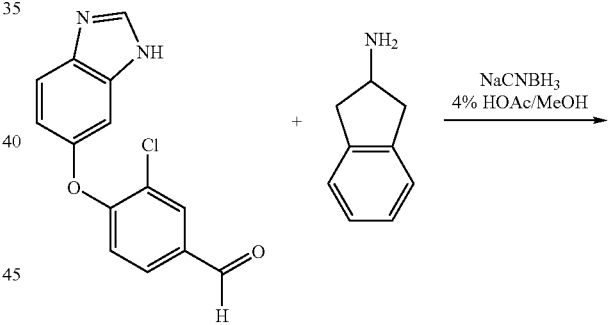

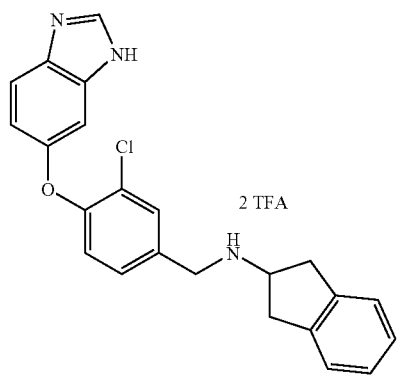

Final compounds were prepared using the appropriate aldehyde and amine using the procedure of General method 1, step 5.

General Method 7

Preparation of Benzimidazole Compounds where A is CHCH$_3$

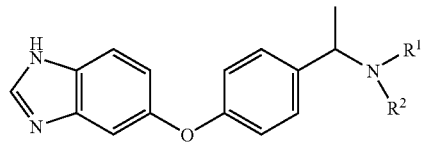

Representative Example

Preparation of {1-[4-(1H-benzimidazol-5-yloxy)phenyl]ethyl}(cyclohexylmethyl)amine bis(trifluoroacetate) (Example No. 72).

Step 1: 1-{4-[(4-Amino-3-nitrophenyl)oxy]phenyl}ethanone Preparation

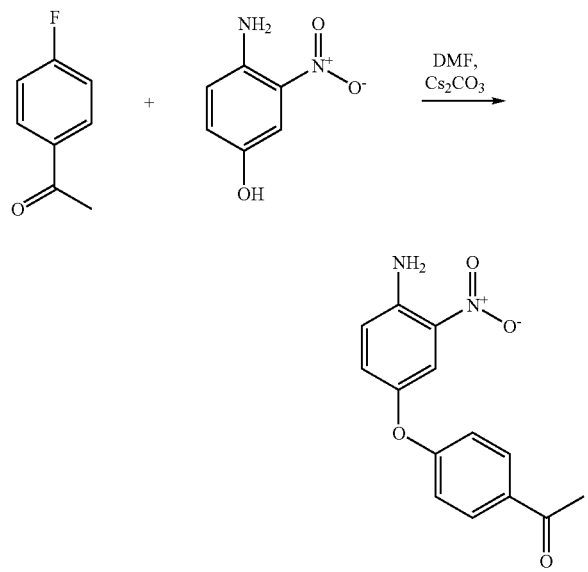

1-(4-Fluorophenyl)ethanone (1.79 g, 12.9 mmol), 4-amino-3-nitrophenol (2 g, 12.9 mmol) and Cs$_2$CO$_3$ (4.65 g, 14.3 mmol) were stirred in 50 mL of dimethylformamide at 80 degrees Centigrade for 24 hours. The solids were filtered away. The filtrate was diluted with ethyl acetate and washed with water and brine three times each. The aqueous layers were back extracted twice with ethyl acetate. The organic layers were combined, dried over MgSO$_4$ and concentrated onto basic alumina. The crude product was purified by silica gel column chromatography (hexanes to ethyl acetate gradient) to give 1-{4-[(4-amino-3-nitrophenyl)oxy]phenyl}ethanone. (M+1) 272.9, 2.42 min (LC/MS method B)

Step 2: 1-{4-[(3,4-Diaminophenyl)oxy]phenyl}ethanol Preparation

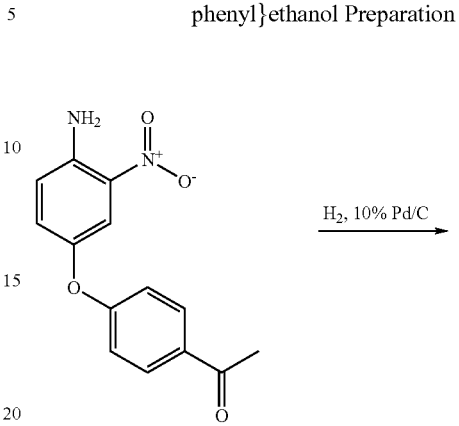

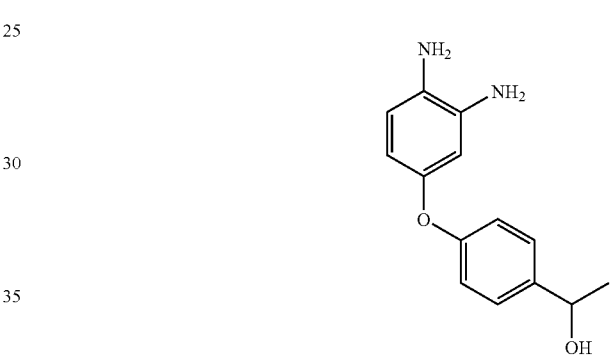

1-{4-[(4-amino-3-nitrophenyl)oxy]phenyl}ethanone (437 mg) was dissolved in 1:1 ethyl acetate: methanol and hydrogenated over 500 mg of 10% Pd/carbon (wet, Degussa type) under an atmosphere of H$_2$ gas. After 24 hours, the reaction was filtered through Celite and concentrated to give crude 1-{4-[(3,4-diaminophenyl)oxy]phenyl}ethanol which was used without further purification. (M+1) 245.2, 1.05 min (LC/MS method A)

Step 3: 1-[4-(1H-Benzimidazol-5-yloxy)phenyl]ethanol Preparation

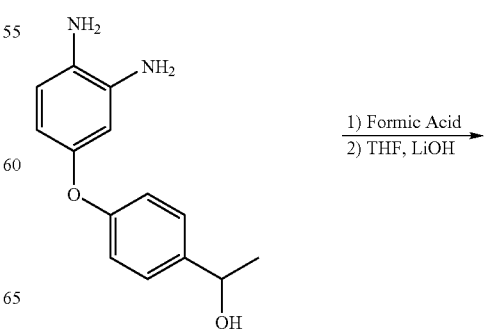

-continued

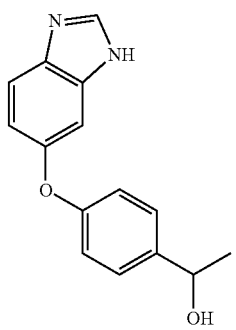

Crude 1-{4-[(3,4-diaminophenyl)oxy]phenyl}ethanol was dissolved in 10 mL of tetrahydrofuran and 5 mL of 88% formic acid and heated at 100 degrees Centigrade for 2 hours. The reaction mixture was concentrated. The residue was dissolved in ethyl acetate and saturated NaHCO$_3$. The organic layer was separated and washed twice with saturated NaHCO$_3$. The organic layer was dried over MgSO$_4$ and concentrated. The residue was dissolved in 10 mL of THF and heated at 100 degrees centigrade with 5 mL of aqueous 10% LiOH for 2 hours. The reaction mixture was diluted with water and extracted three times with ethyl acetate. The organic layers were combined, dried over MgSO$_4$ and concentrated to give crude 1-[4-(1H-benzimidazol-5-yloxy)phenyl]ethanol, which was carried on crude to the next step without further purification. (M+1) 239.0, 1.39 min (LC/MS method B)

Step 4:
1-[4-(1H-benzimidazol-5-yloxy)phenyl]ethanone Preparation

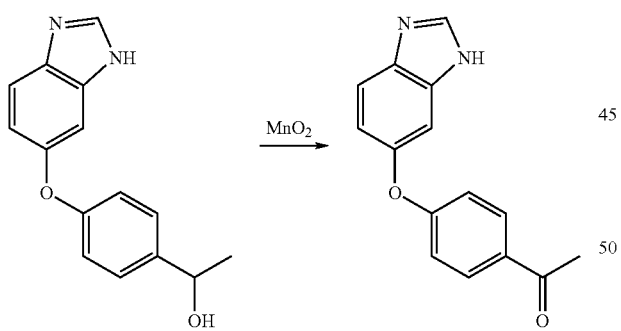

Crude 1-[4-(1H-benzimidazol-5-yloxy)phenyl]ethanol was dissolved in 75 mL of 1:1 ethanol:chloroform and stirred with MnO$_2$ (1.4 g, 10 equivalents based on step 2 starting material) at 80 degrees Centigrade for approximately 18 hours. A second 1.4 g of MnO$_2$ was added and the reaction was heated for an additional 24 hours. A third 1.4 g of MnO$_2$ was added and the reaction was heated for an additional 24 hours. The reaction was filtered through celite and concentrated onto basic alumina. The crude product was purified by silica gel column chromatography to give 1-[4-(1H-benzimidazol-5-yloxy)phenyl]ethanone and an impurity that was carried forward to the next step. (M+1) 253.0, 1.41 min (LC/MS method B).

Step 5: {1-[4-(1H-benzimidazol-5-yloxy)phenyl]ethyl}(cyclohexylmethyl)amine bis(trifluoroacetate) Preparation. (Example No. 72)

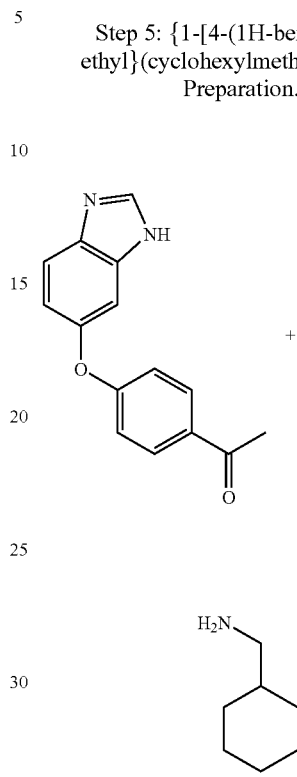

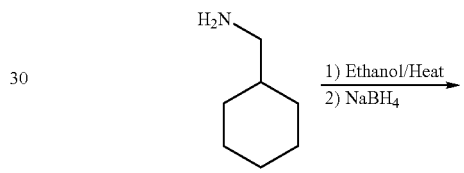

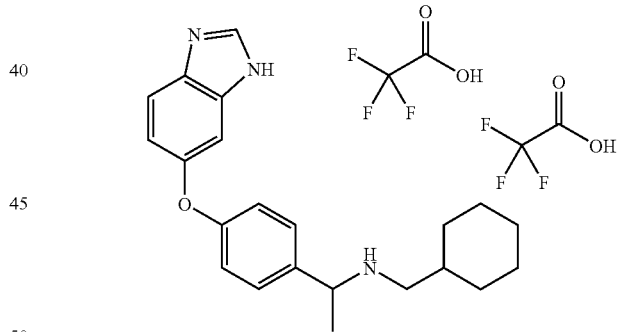

1-[4-(1H-benzimidazol-5-yloxy)phenyl]ethanone (35 mg including impurity) was heated with excess (cyclohexylmethyl)amine (0.084 ml) in ethanol at 80 degrees Centigrade for the azeotropic removal of water. When the reaction had gone to dryness, additional ethanol was added. This was done a total of three times. The residue after the final reduction to dryness was dissolved in 25 mL of ethanol. NaBH$_4$ (21 mg, 0.56 mmol) was added and the reaction stirred. The reaction mixture was concentrated, diluted with 1N NaOH and ethyl acetate and stirred vigorously. The organic layer was added to a Varian Chem Elute™ 1001 column which was rinsed with ethyl acetate (gravity filtration) to elute the crude product. The eluent was concentrated and purified by preparative HPLC to give {1-[4-(1H-benzimidazol-5-yloxy)phenyl]ethyl}(cyclohexylmethyl)amine bis(trifluoroacetate).

General Method 8

Preparation of Benzimidazole Compounds Containing R⁴ Substitution and where A is CH₂

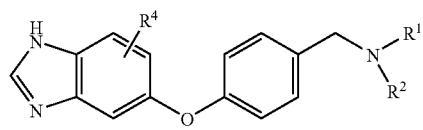

Representative Example

N-({4-[(4,6-difluoro-1H-benzimidazol-5-yl)oxy]phenyl}methyl)-2,3-dihydro-1H-inden-2-amine bis(trifluoroacetate) Preparation. (Example No. 88)

Step 1: 4-[(3-Amino-2,6-difluoro-4-nitrophenyl)oxy]benzaldehyde Preparation

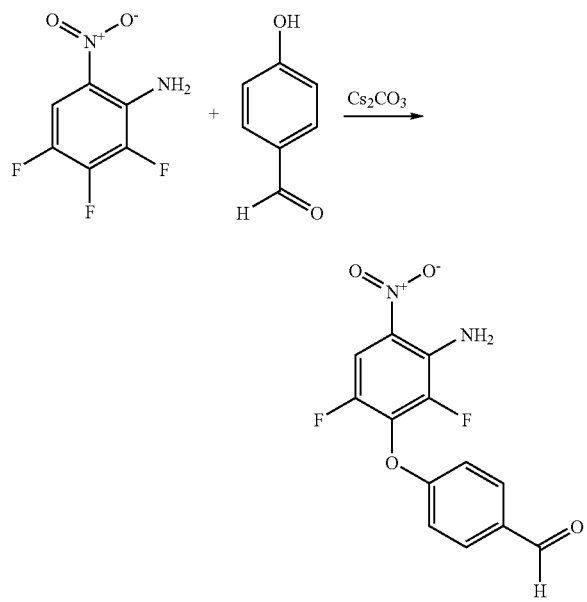

2,3,4-Trifluoro-6-nitroaniline (5 g, 26 mmol), 4-hydroxybenzaldehyde (3.5 g, 28.6 mmol) and Cs₂CO₃ (10.5 g, 32.6 mmol) were stirred in 150 mL of dimethylformamide at 65 degrees Centigrade for approximately 18 hours. The reaction mixture was concentrated and the residue was dissolved in ethyl acetate and water. The aqueous layer was extracted three times with ethyl acetate. The organic layers were combined, washed five times with brine, dried over Mg₂SO₄ and concentrated onto basic alumina. The residue was purified by silica gel column chromatography (hexane to ethyl acetate gradient) to give 4-[(3-amino-2,6-difluoro-4-nitrophenyl)oxy]benzaldehyde. 1H NMR (400 MHz, DMSO-d₆) delta ppm 7.29 (d, J=8.8 Hz, 2 H) 7.46 (s., 2 H) 7.93 (d, J=8.8 Hz, 2 H) 7.98 (dd, J=11.0, 1.7 Hz, 1 H) 9.93 (s., 1 H)

Step 2: 1,1-Dimethylethyl({4-[(3-amino-2,6-difluoro-4-nitrophenyl)oxy]phenyl}methyl)2,3-dihydro-1H-inden-2-ylcarbamate Preparation

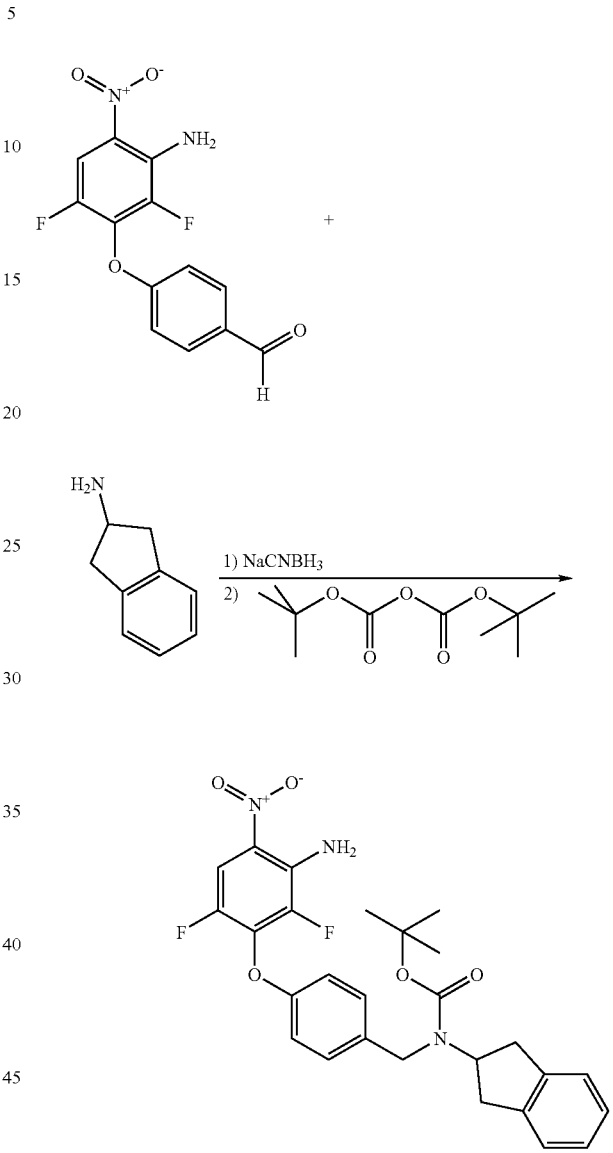

4-[(3-Amino-2,6-difluoro-4-nitrophenyl)oxy]benzaldehyde (1 g, 3.4 mmol), 2-aminoindane(543 mg, 4.1 mmol) and sodium cyanoborohydride (276 mg, 4.1 mmol) were stirred in 4% acetic acid in methanol for approximately 18 hours and concentrated. The residue was dissolved in ethyl acetate and 1N NaOH. The organic layer was washed twice with 1N NaOH. The organic layer was then vigorously stirred with 50 mL of 1N NaHCO₃ and di-tert-butyl dicarbonate (890 mg, 4.08 mmol) and stirred for approximately 18 hours. An additional 150 mg of di-tert-butyl dicarbonate was added and the reaction was stirred for an additional 2 hours. An additional 150 mg of di-tert-butyl dicarbonate was added and the reaction was stirred for an additional hour. The organic layer was separated and washed once with 1N NaOH, and twice with brine. The organic layer was dried over MgSO₄ and concentrated. The residue was purified by silica gel column chromatography (hexane to ethyl acete gradient) to give 1,1- dimethylethyl({4-[(3-amino-2,6-difluoro-4-nitrophenyl)oxy] phenyl} methyl)2,3-dihydro-1H-inden-2-ylcarbamate. (M+H-Boc) 412.2, 3.27 min (LC/MS method B)

Step 3: 1,1-Dimethylethyl({4-[(3,4-diamino-2,6-difluorophenyl)oxy]phenyl}methyl)2,3-dihydro-1H-inden-2-ylcarbamate Preparation

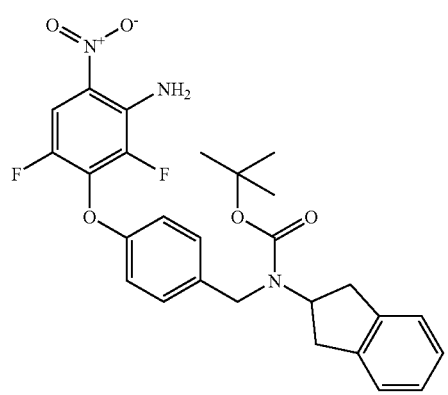

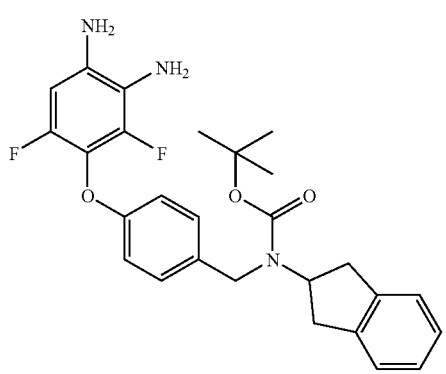

1,1-dimethylethyl({4-[(3-amino-2,6-difluoro-4-nitrophenyl)oxy]phenyl}methyl)2,3-dihydro-1H-inden-2-ylcarbamate (114 mg) was dissolved in ethyl acetate and hydrogenated over 10% Pd on carbon (wet, degussa type) with Parr hydrogenator at 45 psi. The catalyst was removed by filtration through celite. The filtrate was concentrated to give [2-amino-4-({4-[(2,3-dihydro-1H-inden-2-ylamino)methyl]phenyl}oxy)-3,5-difluorophenyl]amine which was used without further purification.

Step 4: N-({4-[(4,6-Difluoro-1H-benzimidazol-5-yl)oxy]phenyl}methyl)-2,3-dihydro-1H-inden-2-amine bis(trifluoroacetate) Preparation. (Example No. 88)

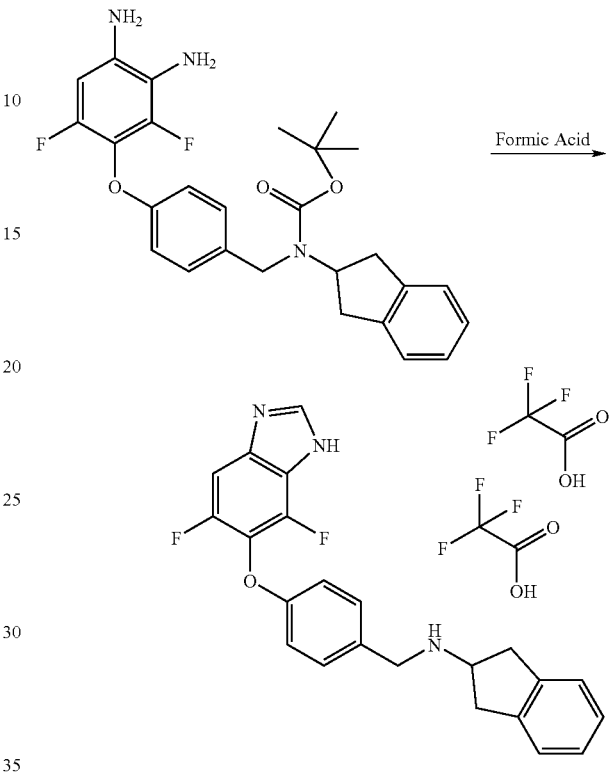

1,1-dimethylethyl({4-[(3,4-diamino-2,6-difluorophenyl)oxy]phenyl}methyl)2,3-dihydro-1H-inden-2-ylcarbamate (crude material from step 3) was dissolved in 10 mL of 96% formic acid and heated at 100 degrees Centigrade for 4 days. The reaction mixture was concentrated and purified by preparative HPLC to give N-({4-[(4,6-difluoro-1H-benzimidazol-5-yl)oxy]phenyl}methyl)-2,3-dihydro-1H-inden-2-amine bis(trifluoroacetate).

General Method 9

Preparation of Benzimidazole Compounds Where X or Z is NCH₃ and A=CH₂

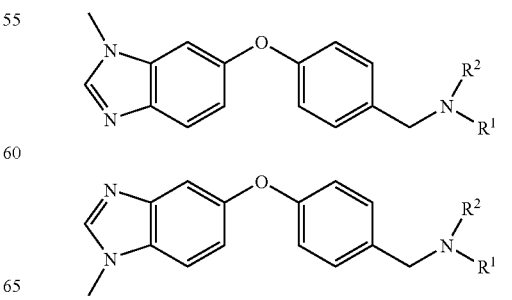

Representative Examples (4,4-dimethylcyclohexyl)({4-[(1-methyl-1H-benzimidazol-6-yl)oxy]phenyl}methyl)amine hydrochloride (Example No. 70) (4,4-dimethylcyclohexyl)({4-[(1-methyl-1H-benzimidazol-5-yl)oxy]phenyl}methyl)amine Hydrochloride (Example No. 71).

Step 1: Preparation of 1,1-dimethylethyl{[4-(1H-benzimidazol-5-yloxy)phenyl]methyl}(4,4-dimethylcyclohexyl)carbamate

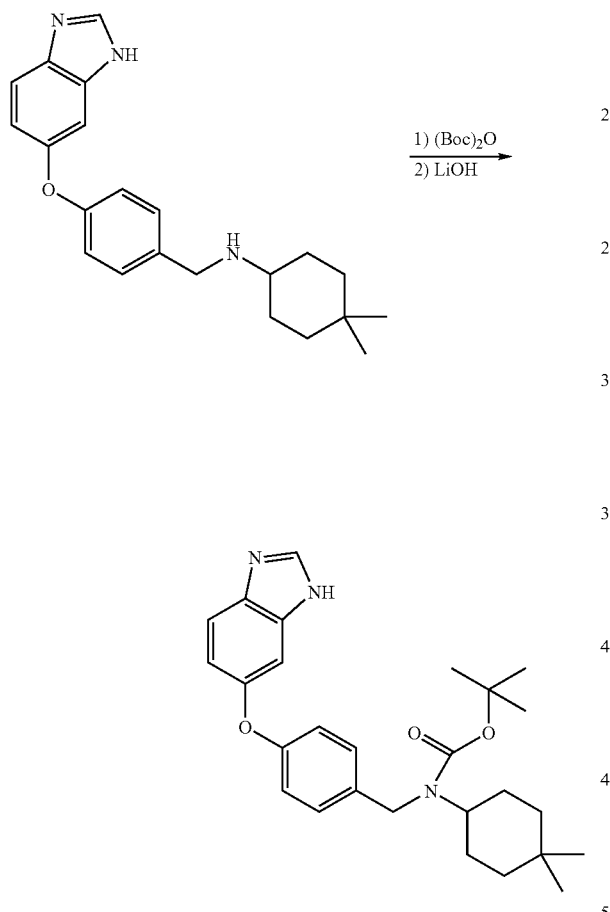

Crude N-{[4-(1H-benzimidazol-5-yloxy)phenyl]methyl}-4,4-dimethylcyclohexanamine (Example 2), (prepared using General Method 1) was dissolved in ethyl acetate and stirred with di-tert-butyl dicarbonate (403 mg, 1.85 mmol, 1.1 equivalents based on starting with 1.68 mmol of aldehyde in step 5 of General Method 1) and saturated aqueous NaHCO$_3$. After 1 hour the organic layer was separated and the aqueous layer was extracted twice with ethyl acetate. The organic layers were combined, washed with brine, dried over MgSO$_4$ and concentrated. The residue was dissolved in tetrahydrofuran and heated at 90 degrees Centigrade with 1N aqueous LiOH for 2 hours. After allowing the reaction to cool to room temperature, the reaction was diluted with water, extracted twice with ethyl acetate, dried over MgSO$_4$ and concentrated. The residue was purified by silica gel column chromatography (CH$_2$Cl$_2$ to 10% methanol (2% NH$_3$) in CH$_2$Cl$_2$) to give 1,1-dimethylethyl {[4-(1H-benzimidazol-5-yloxy)phenyl]methyl}(4,4-dimethylcyclohexyl)carbamate.
(M-H) 448.2, 2.82 min, (LC/MS method B)

Step 2: Preparation of (4,4-dimethylcyclohexyl)({4-[(1-methyl-1H-benzimidazol-6-yl)oxy]phenyl}methyl)amine hydrochloride (Example No. 70) and (4,4-dimethylcyclohexyl)({4-[(1-methyl-1H-benzimidazol-5-yl)oxy]phenyl}methyl)amine Hydrochloride (Example No. 71)

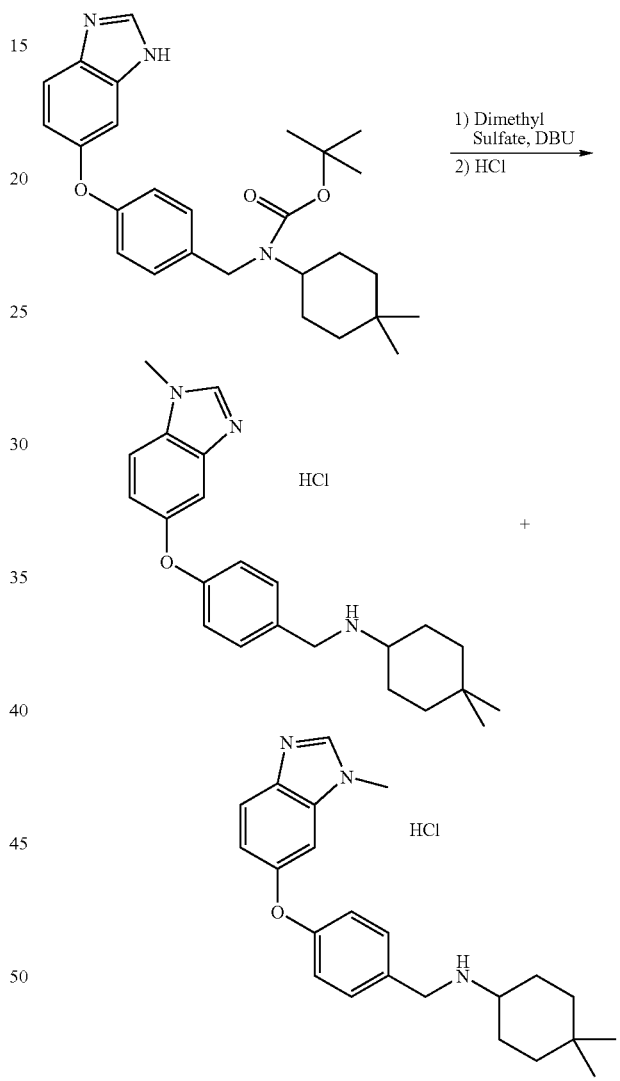

1,1-Dimethylethyl {[4-(1H-benzimidazol-5-yloxy)phenyl]methyl}(4,4-dimethylcyclohexyl)carbamate (389 mg, 0.87 mmol), dimethyl sulfate (0.166 mL, 1.7 mmol) and 1,8-diazabicyclo[5.4.0]undec-7-ene (DBU) (0.155 mL, 1.0 mmol) were stirred in dichloromethane for approximately 18 hours. The reaction was diluted with water and extracted with dichloromethane. The organic layers were washed with 1N NaOH, dried over MgSO$_4$ and concentrated. The residue was purified by silica gel column chromatography (gradient of CH$_2$Cl$_2$ to 10% methanol (2% NH$_3$) in CH$_2$Cl$_2$) to give a mixture of 1,1-dimethylethyl (4,4-dimethylcyclohexyl)({4-[(1-methyl-1H-benzimidazol-5-yl)oxy]phenyl}methyl)carbamate and 1,1-dimethylethyl (4,4-dimethylcyclohexyl)({4-[(1-methyl-1H-benzimidazol-6-yl)oxy]phenyl}methyl)carbamate. This mixture was separated on a chiral OD column at 140 bar, 40 degrees Centigrade using 13% methanol and $CO_2$ as mobile phase. The separated isomers were each treated with 3 mL of 4N HCl in dioxane for approximately 18 hours. The separate compounds were collected by filtration as white solids. The structural identity of these 2 isomers was determined by COSY and ROESY NMR.

(4,4-dimethylcyclohexyl)({4-[(1-methyl-1H-benzimidazol-6-yl)oxy]phenyl}methyl)amine hydrochloride (Example No. 70)

(4,4-dimethylcyclohexyl)({4-[(1-methyl-1H-benzimidazol-5-yl)oxy]phenyl}methyl)amine Hydrochloride (Example No. 71)

General Method 10

Preparation of Benzimidazole Compounds where $R^4$ is $CF_3$ in the 4-Position, $R^6$ is $CF_3$ and A is $CH_2$

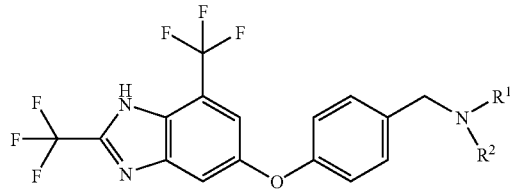

Step 1: N-[4-fluoro-2-nitro-6-(trifluoromethyl)phenyl]acetamide Preparation

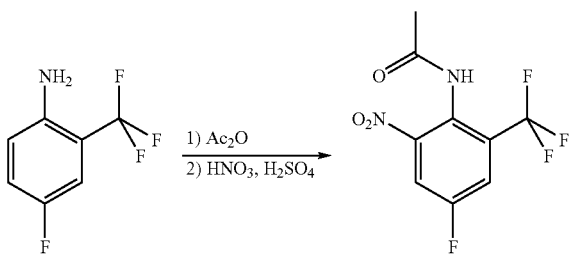

A solution of 4-fluoro-2-(trifluoromethyl)aniline (5.0 g, 27.91 mmol) in acetic anhydride (25 mL) was stirred at ambient temperature for 3 hours to produce a white needle precipitate. The reaction mixture was poured onto ice water, filtered then dried to give 6.0 g of N-[4-fluoro-2-(trifluoromethyl)phenyl]acetamide as an off-white solid which was used without further purification. The N-[4-fluoro-2-(trifluoromethyl)phenyl]acetamide (2.0 g, 9.04 mmol) was dissolved in concentrated $H_2SO_4$ (15 mL) and cooled to 0 degrees Centigrade using an ice bath. 70% $HNO_3$ (1.5 mL) was added drop wise and the reaction stirred at 0 degrees Centigrade for 30 min and then at ambient temperature for 3 hours. The reaction mixture was poured onto ice-water, filtered then dried to give 2.4 g of the desired N-[4-fluoro-2-nitro-6-(trifluoromethyl)phenyl]acetamide.

$^1$H NMR (400 MHz, $CDCl_3$) delta ppm 2.21 (s, 3 H) 7.30 (br.s, 1 H) 7.68 (dd, J=7.45; 3.05 Hz, 1 H) 7.86 (dd, J=7.2; 3.05 Hz, 1 H) (M+H) 267.1, 1.57 min (LC/MS method A)

Step 2: N-[4-[(4-formylphenyl)oxy]-2-nitro-6-(trifluoromethyl)phenyl]acetamide Preparation

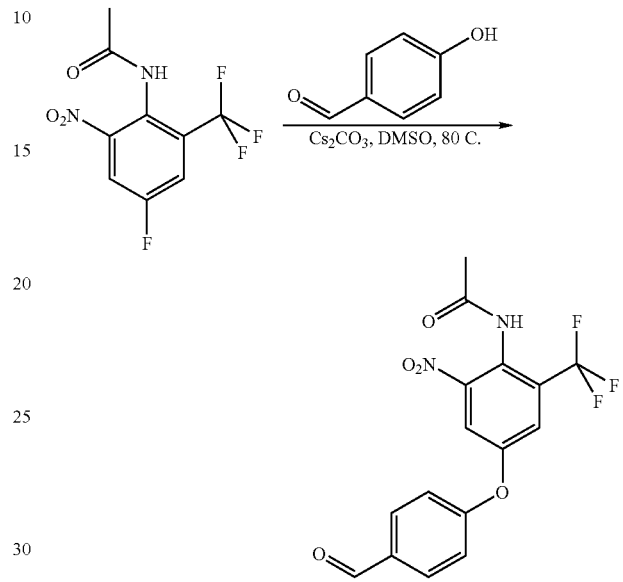

A solution of N-[4-fluoro-2-nitro-6-(trifluoromethyl)phenyl]acetamide (1.5 g, 5.63 mmol), $Cs_2CO_3$ (4.59 g, 14.09 mmol), and 4-hydroxybenzaldehyde (0.757 g, 6.20 mmol) in dimethylsulfoxide (10 mL) was heated to 80 degrees Centigrade for 2 h and then cooled. $H_2O$ was added and the organics extracted using ethyl acetate (2×50 mL). The combined organics were then washed 1× brine and then dried ($Na_2SO_4$), filtered and concentrated. Chromatography on silica gel, using 2:1 hexanes/ethyl acetate eluted N-[4-[(4-formylphenyl)oxy]-2-nitro-6-(trifluoromethyl)phenyl]acetamide as an orange solid. (0.922 g; 44% yield).

$^1$H NMR (400 MHz, $CDCl_3$) delta ppm 7.20 (m, 2 H) 7.37 (br.s, 1 H) 7.60 (d, J=2.69 Hz, 1 H) 7.72 (d, J=2.93 Hz, 1 H) 7.97 (m, 2H) 10.0 (s, 1H)

Step 3: 2,2,2-Trifluoro-N-[4-[(4-formylphenyl)oxy]-2-nitro-6-(trifluoromethyl)phenyl]acetamide Preparation

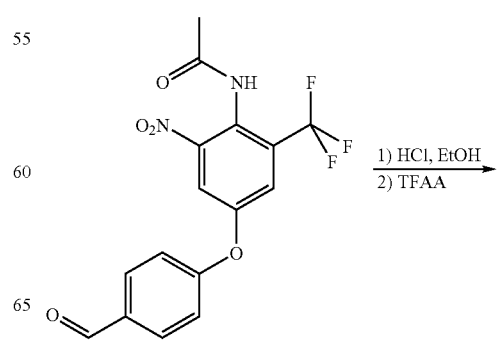

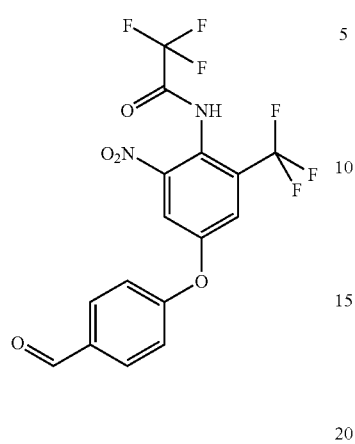

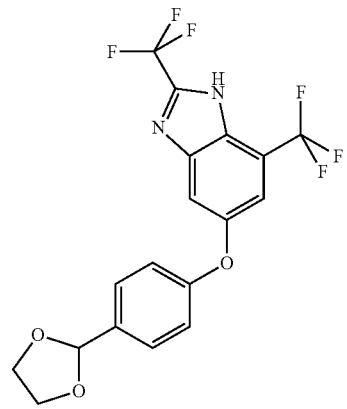

A solution of N-[4-[(4-formylphenyl)oxy]-2-nitro-6-(trifluoromethyl)phenyl]acetamide (0.750 g, 2.04 mmol) in concentrated HCl (2 mL) and ethanol (2 mL) was refluxed overnight, cooled and then slowly poured into a solution of saturated NaHCO$_3$. The organics were extracted with ethyl acetate (2×25 mL). The combined organics were washed with H$_2$O, once with brine and then dried (Na$_2$SO$_4$), filtered and concentrated. To the residue was added trifluoroacetic anhydride and the mixture stirred for 16 hours at ambient temperature. The reaction mixture was slowly poured onto cold saturated NaHCO$_3$ and extracted with ethyl acetate (2×25 mL). The combined organics were washed 1×H$_2$O, 1× brine and then dried (Na$_2$SO$_4$), filtered and concentrated. Chromatography on silica using 2:1 hexanes/ethyl acetate eluted 2,2,2-trifluoro-N-[4-[(4-formylphenyl)oxy]-2-nitro-6-(trifluoromethyl)phenyl]acetamide, 0.650 g $^1$H NMR (400 MHz, CDCl$_3$) delta ppm 6.63 (br.s, 1H) 7.05 (d, J=8.79 Hz 2H) 7.57 (d, J=2.93 Hz, 1 H) 7.89 (d, J=8.55 Hz, 2H) 8.12 (d, J=2.93 Hz, 1H) 9.95 (s, 1H)

Step 4: 5-{[4-(1,3-Dioxolan-2-yl)phenyl]oxy}-2,7-bis(trifluoromethyl)-1H-benzimidazole Preparation To a mixture of 2,2,2-trifluoro-N-[4-[(4-formylphenyl)oxy]-2-nitro-6-(trifluoromethyl)phenyl]acetamide (0.65 g, 1.54 mmol), triethyl orthoformate (0.282 mL, 1.69 mmol), and ethylene glycol (0.343 mL, 6.16 mmol) was added (butyl)$_4$NBr$_3$ (0.007 g, 0.015 mmol). The reaction was stirred at ambient temperature for 1 hour and then diluted with ethyl acetate. The organics were washed 1×NaHCO$_3$, 1× brine and then dried (Na$_2$SO$_4$), filtered and concentrated. The residue was dissolved in ethyl acetate (5 mL) and hydrogenated over 10% Palladium on carbon (0.13 g) under an atmosphere of hydrogen for 3 hours. The catalyst was removed by filtration through Celite and the filtrate concentrated. The residue was purified by silica gel column chromatography on using a gradient of 20-40% ethyl acetate:hexanes to give 5-{[4-(1,3-dioxolan-2-yl)phenyl]oxy}-2,7-bis(trifluoromethyl)-1H-benzimidazole.

(M+H) 419.1, 2.62 min (LC/MS method A)

Step 5: 4-{[2,4-Bis(trifluoromethyl)-1H-benzimidazol-6-yl]oxy}benzaldehyde Preparation

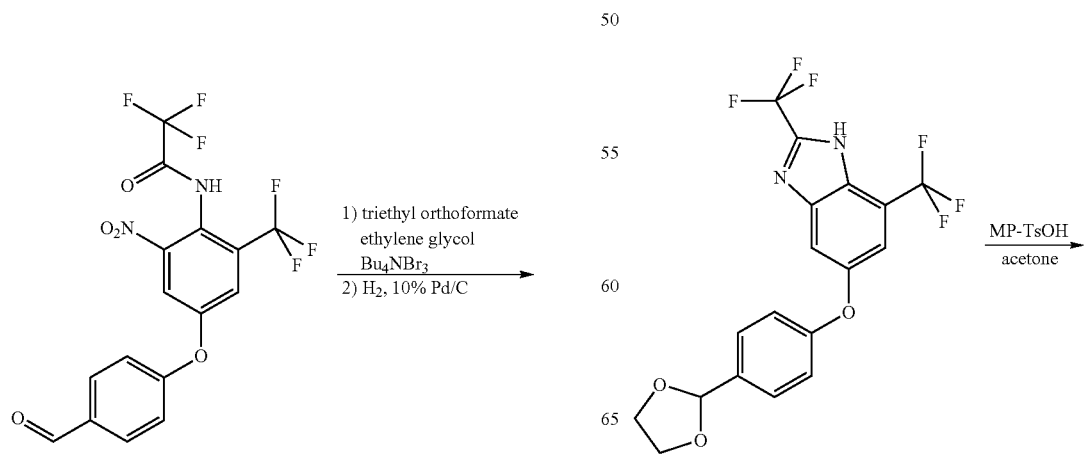

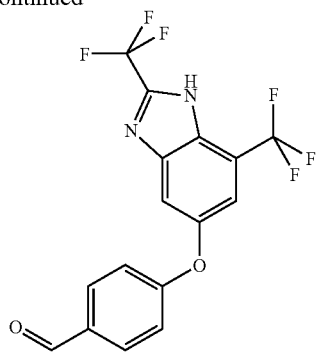

A mixture of 5-{[4-(1,3-dioxolan-2-yl)phenyl]oxy}-2,7-bis(trifluoromethyl)-1H-benzimidazole (0.260 g, 0.622 mmol) and MP-TSOH (Argonaut, macroporous polymer supported tosic acid, approximately 0.842 g, 1.24 mmol) in acetone (2 mL) was stirred for 3 h, then filtered and concentrated to give the desired 4-{[2,4-bis(trifluoromethyl)-1H-benzimidazol-6-yl]oxy}benzaldehyde which was used without further purification.

$^1$H NMR (400 MHz, CDCl$_3$) delta ppm 7.08 (d, J=8.79 Hz, 2H) 7.48 (br.s, 1H) 7.67 (br.s, 1H) 7.89 (d, J=8.55 Hz, 2H) 9.94 (s, 1H) (M+H) 375.1, 1.05 min (LC/MS method A)

Step 6: Reductive Amination to Form Final Compounds of General Method 10

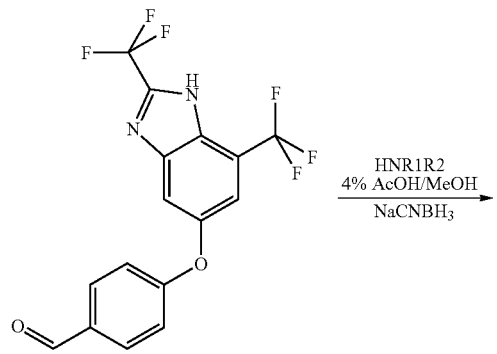

4-{[2,4-Bis(trifluoromethyl)-1H-benzimidazol-6-yl]oxy}benzaldehyde (0.103 g, 0.275 mmol) in 1 mL 4% acetic acid in methanol was treated with an amine (0.302 mmol) followed by NaCNBH$_3$ (0.012 g, 0.192 mmol). The reaction was stirred until the starting aldehyde was consumed, and the reaction was diluted with H$_2$O. This mixture was extracted with ethyl acetate. The combined organics were dried (Na$_2$SO$_4$), filtered and concentrated. Purification was accomplished by preparative HPLC and, if desired, the free-base was obtained by adjusting the pH of the collected fractions with NaHCO$_3$ until basic and extracting the organics several times with ethyl acetate. The combined organics would then be dried (Na$_2$SO$_4$), filtered and concentrated.

General Method 11

Preparation of Benzimidazole Compounds where R$^4$ is F in the 4-Position, R$^6$ is CF$_3$, and A is CH$_2$

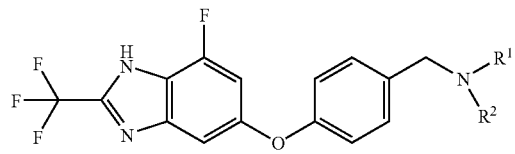

Step 1: 3,5-difluoro-2-nitroaniline Preparation

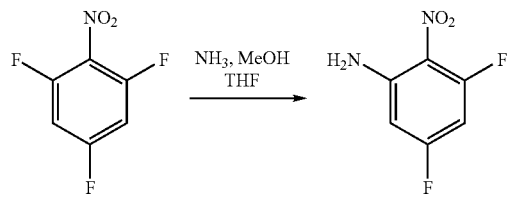

A solution of the 1,3,5-trifluoro-2-nitrobenzene (7.08 g, 39.98 mmol) in tetrahydrofuran (50 mL) was stirred at 0 degrees Centigrade while a solution of 7N ammonia in methanol (23 mL) was added. The reaction turned deep red and was stirred overnight in a sealed tube. The mixture was filtered to remove NH$_4$F and the solvent removed to give a red-orange solid which was purified by silica gel chromatography using 2:1 hexanes/ethyl acetate to give 6.27 g of 3,5-difluoro-2-nitroaniline.

(M+H) 175.1, 1.89 min (LC/MS method A)

Step 2: 4-[(3-amino-5-fluoro-4-nitrophenyl)oxy]benzaldehyde Preparation

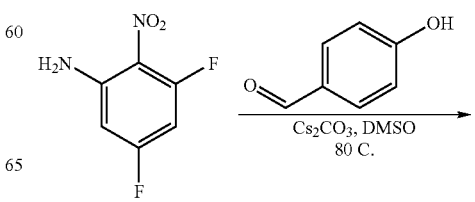

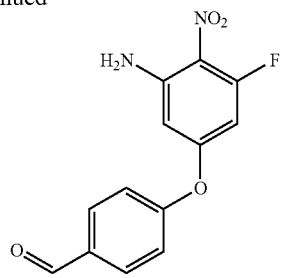

A solution of 3,5-difluoro-2-nitroaniline (0.400 g, 2.30 mmol), Cs₂CO₃ (1.87 g, 5.74 mmol), and 4-hydroxybenzaldehyde (0.309 g, 2.53 mmol) in dimethylsulfoxide (5 mL) was heated at 80 degrees Centigrade for 2 hours and then cooled. Water was added and the organics extracted using ethyl acetate (2×50 mL). The combined organics were washed once in brine and dried (Na₂SO₄), filtered and concentrated. Chromatography on silica gel using a gradient of 20%-60% ethyl acetate/hexanes eluted the product to give 0.536 g of 4-[(3-amino-5-fluoro-4-nitrophenyl)oxy]benzaldehyde as a yellow solid.

¹H NMR (400 MHz, CDCl₃) delta ppm 6.84 (d, J=8.55 Hz, 1 H) 6.97 (d, J=8.79 Hz, 2 H) 7.30 (d, J=8.55 Hz, 1 H) 7.80 (dd, J=8.79 Hz, 2 H) 8.85 (br.s, 1H) 9.82 (s,1H)

Step 3: 2,2,2-Trifluoro-N-{3-fluoro-5-[(4-formylphenyl)oxy]-2-nitrophenyl}acetamide Preparation

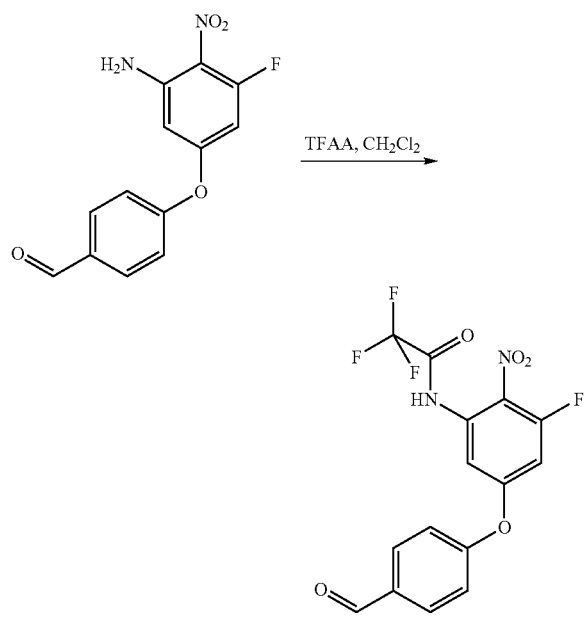

A solution of 4-[(3-amino-5-fluoro-4-nitrophenyl)oxy]benzaldehyde (1.08 g, 3.91 mmol) in a 1:1 mixture of trifluoroacetic anhydride/CH₂Cl₂ (10 mL total) was stirred at ambient temperature for 4 hours and then poured onto cold saturated NaHCO₃. The organics were extracted 2×25 mL ethyl acetate and the combined organics washed 1×H₂O, 1× brine and then dried (Na₂SO₄), filtered and concentrated. Chromatography on silica using 2:1 hexanes/ethyl acetate eluted the product to give 1.27 g of 2,2,2-trifluoro-N-{3-fluoro-5-[(4-formylphenyl)oxy]-2-nitrophenyl}acetamide.

¹H NMR (400 MHz, CDCl₃) delta ppm 6.66 (dd, J=8.55, 2.69 Hz, 1 H) 7.19 (d, J=8.55 Hz, 2 H) 7.96 (d, J=8.79 Hz, 1 H) 8.10 (dd, J=9.77, 2.69 Hz, 2 H) 9.97 (br.s, 1H) 10.0 (s, 1H) (M+Na) 395.2, 2.37 min (LC/MS method A)

Step 4: 4-{[4-Fluoro-2-(trifluoromethyl)-1H-benzimidazol-6-yl]oxy}benzaldehyde Preparation

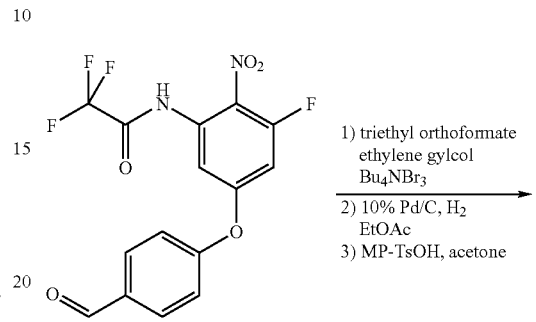

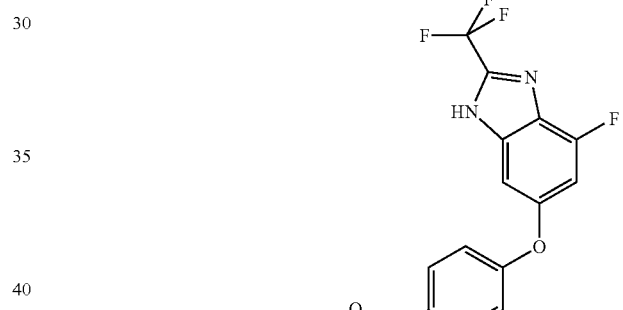

To a mixture of 2,2,2-trifluoro-N-{3-fluoro-5-[(4-formylphenyl)oxy]-2-nitrophenyl}acetamide (1.25 g, 3.36 mmol), triethyl orthoformate (0.614 mL, 3.69 mmol), and ethylene glycol (0.749 g, 13.43 mmol) was added Bu₄NBr₃ (0.016 g, 0.034 mmol). The homogeneous reaction was stirred at ambient temperature for 1 hour and then diluted with ethyl acetate. The organics were washed 1×NaHCO₃, once in brine and then dried (Na₂SO₄), filtered and concentrated with no further purification necessary. Residue (0.400 g) was re-dissolved in ethyl acetate (5 mL) and hydrogenated using 10% palladium on carbon (0.080 g) under an atmosphere of hydrogen for 16 hours. The catalyst was removed by filtration through Celite and the filtrate concentrated. The residue was re-dissolved in acetone and MP-Fosic acid resin (1.26 g, 1.92 mmol) was added. The mixture was stirred for 16 hours, filtered and the filtrate was concentrated. Chromatography on silica using 40% ethyl acetate/hexanes eluted the product to give 0.153 g of 4-{[4-fluoro-2-(trifluoromethyl)-1H-benzimidazol-6-yl]oxy}benzaldehyde as an off-white solid.

¹H NMR (400 MHz, CDCl₃) delta ppm 6.68 (dd, J=9.55, 2.69 Hz, 1 H) 7.06 (dd, J=8.57, 2.95 Hz, 1H) 7.21 (d, J=8.55 Hz, 2 H) 7.90 (m, 3 H) 9.96 (s, 1H) (M+H) 325.1, 2.46 min (LC/MS method A)

Step 5: Reductive Amination to Form Final Compounds of General Method 11

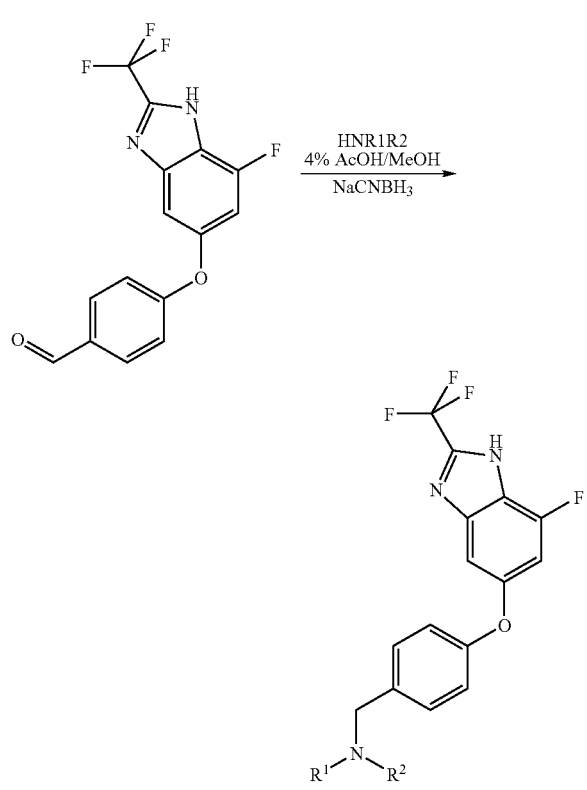

4-{[4-Fluoro-2-(trifluoromethyl)-1H-benzimidazol-6-yl]oxy}benzaldehyde (0.075 g, 0.231 mmol) in 1.5 mL 4% acetic acid in methanol was treated with an amine (0.278 mmol) followed by sodium cyanoborohydride (0.010 g, 0.162 mmol). The reaction was stirred until the starting aldehyde was consumed, and the reaction was diluted with H₂O. This mixture was extracted with ethyl acetate. The organics were combined, dried (Na₂SO₄), filtered and concentrated. Purification was accomplished by preparative HPLC and if desired the free-base was obtained by adjusting the pH of the collected fractions with NaHCO₃ until basic and extracting the organics several times with ethyl acetate. The combined organics would then be dried (Na₂SO₄), filtered and concentrated.

General Method 12

Preparation of Benzimidazole Compounds where $R^4$ is F in the 4-Position and A is $CH_2$

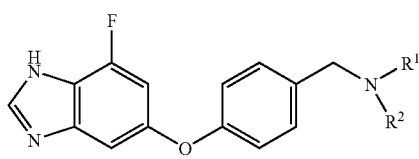

Step 1: 3,5-difluoro-2-nitroaniline Preparation

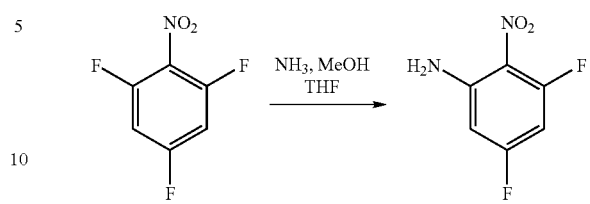

A solution of the 1,3,5-trifluoro-2-nitrobenzene (7.08 g, 39.98 mmol) in tetrahydrofuran (50 mL) was stirred at 0 degrees Centigrade while a solution of 7N ammonia in methanol (23 mL) was added. The reaction mixture was stirred overnight in a sealed tube. The mixture was filtered, and the solvent removed to give a red-orange solid which was purified by silica gel column chromatography using 2:1 hexanes/ethyl acetate to give 6.27 g of 3,5-difluoro-2-nitroaniline.

(M+H) 175.1, 1.89 min (LC/MS method A)

Step 2: {3-Fluoro-5-[(4-formylphenyl)oxy]-2-nitrophenyl}formamide Preparation

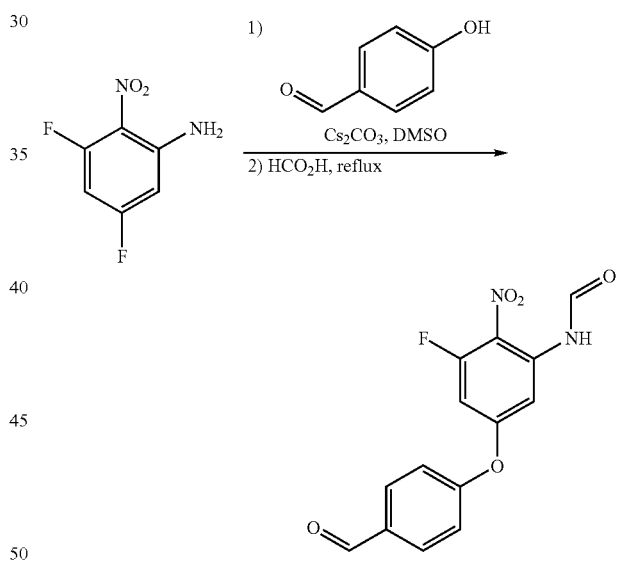

A solution of the 3,5-difluoro-2-nitroaniline (0.348 g, 2.0 mmol), Cs₂CO₃ (1.63 g, 5 mmol), and 4-hydroxybenzaldehyde (0.268 g, 2.2 mmol) in dimethylsulfoxide (2 mL) was heated to 80 degrees Centigrade for 1 hour and then cooled. Water was added and the organics extracted using ethyl acetate (2×50 mL). The combined organics were then washed once in brine and dried (Na₂SO₄), filtered and concentrated. Chromatography on silica gel (gradient of 20%-60% ethyl acetate/hexanes) eluted the product and the fractions were concentrated. The residue was refluxed in 96% formic acid (4 mL) until the reaction was complete conversion of the aniline was observed by TLC (~1.5 h) and then cooled and poured onto ice-water. The organics were extracted with ethyl acetate (2×25 mL) and the combined organics washed once in water, once in brine, dried (Na₂SO₄), filtered and concentrated to give 0.230 g of the {3-fluoro-5-[(4-formylphenyl)oxy]-2-nitrophenyl}formamide as a solid.

(M+H) 305.1, 2.15 min (LC/MS method A)

Step 3: Reductive Amination of Amines Followed by Reduction and Ring Closure to Form Final Benzimidazole Compounds of Geeral Method 12

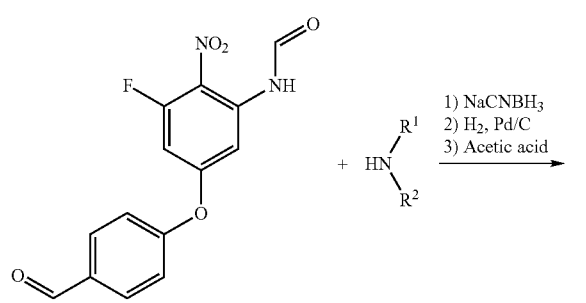

3-Fluoro-5-[(4-formylphenyl)oxy]-2-nitrophenyl}formamide (0.110 g, 0.362 mmol) in 2.0 mL 4% acetic acid in methanol was treated with an amine (0.434 mmol) followed by sodium cyanoborohydride (0.016 g, 0.253 mmol). The reaction was stirred until the starting aldehyde was consumed, and the reaction was diluted with water. This mixture was extracted with ethyl acetate. The organics were combined, dried (Na$_2$SO$_4$), filtered and concentrated. Purification was accomplished by chromatography on silica using ethyl acetate to elute the desired material and the fractions concentrated. The residue was dissolved in ethyl acetate. Triethylamine (1 mol equivalent) was added along with 10% palladium on carbon (50% water, 0.030 g) and the reaction mixture hydrogenated under an atmosphere of hydrogen for 6 hours. The reaction mixture was filtered over Celite to remove the catalyst and concentrated. The residue was taken up in glacial acetic acid (1 mL) and heated to 60 degrees Centigrade to effect ring closure to the benzimidazole. Purification of the final products was accomplished by preparative HPLC and if desired the free-base was obtained by adjusting the pH of the collected fractions with NaHCO$_3$ until basic and extracting the organics several times with ethyl acetate. The combined organics would be dried (Na$_2$SO$_4$), filtered and concentrated.

General Method 13

Preparation of Benzimidazole Compounds where R$^4$ is 5-CF$_3$

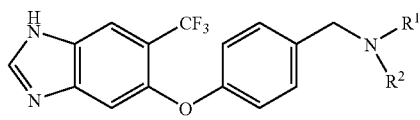

Representative Example (4,4-dimethylcyclohexyl)[(4-{[5-(trifluoromethyl)-1H-benzimidazol-6-yl]oxy}phenyl)methyl]amine trifluoroacetate (Example No. 94)

Step 1: 4-{[5-Amino-4-nitro-2-(trifluoromethyl)phenyl]oxy}benzaldehyde Preparation

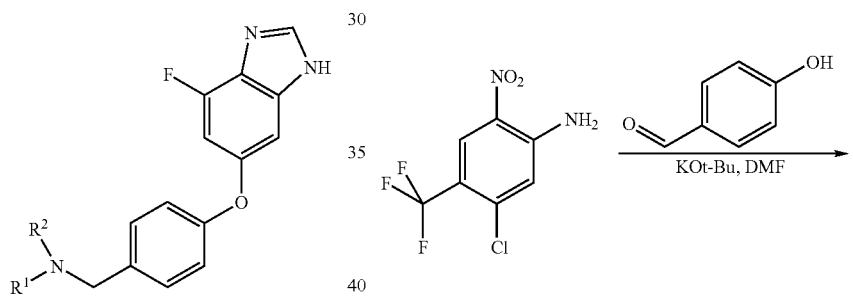

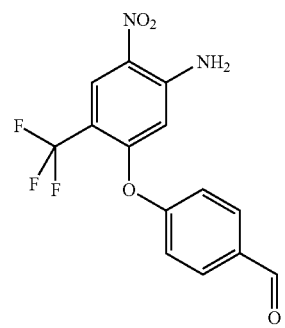

A solution of 5-chloro-2-nitro-4-(trifluoromethyl)aniline (0.240 g, 1.00 mmol), potassium t-butoxide (0.135 g, 1.2 mmol), and 4-hydroxybenzaldehyde (0.147 g, 1.2 mmol) in dimethylformamide (5 mL) was heated to 80 degrees Centigrade for 6 hours and then cooled. Water was added and the organics extracted using ethyl acetate (2×50 mL). The combined organics were then washed once in brine and then dried (Na$_2$SO$_4$), filtered and concentrated. Chromatography on silica gel using a gradient of 30%-40% ethyl acetate/hexanes eluted the product to give 0.243 g of 4-{[5-amino-4-nitro-2-(trifluoromethyl)phenyl]oxy}benzaldehyde as an yellowish solid.

(M+H) 327.1, 2.66 min (LC/MS method A)

Step 2: 1,1-Dimethylethyl[(4-{[5-amino-4-nitro-2-(trifluoromethyl)phenyl]oxy}phenyl)methyl](4,4-dimethylcyclohexyl)carbamate Preparation

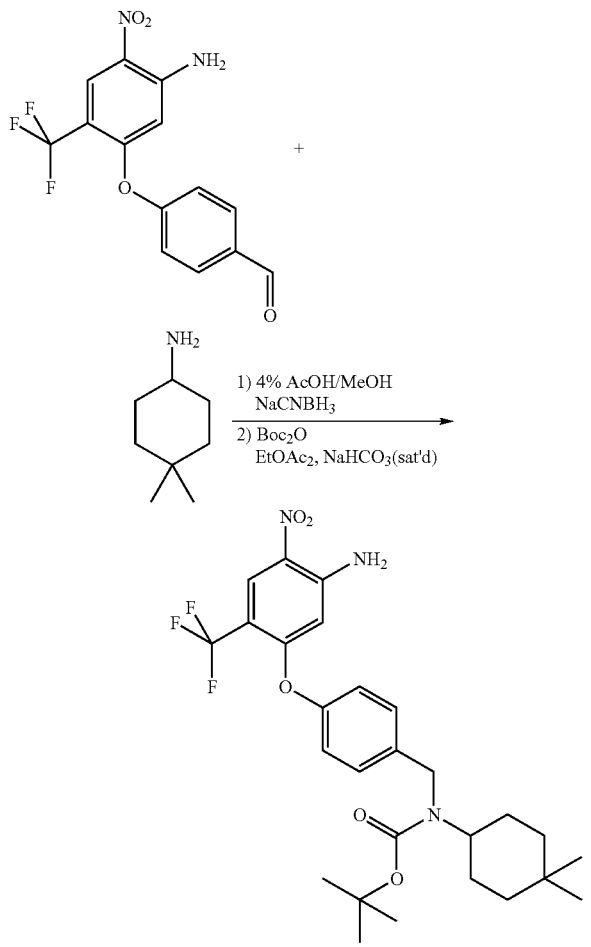

4-{[5-Amino-4-nitro-2-(trifluoromethyl)phenyl]oxy}benzaldehyde (0.167 g, 0.512 mmol) in 2.0 mL 4% acetic acid in methanol was treated with 4,4-dimethylcyclohexylamine (0.078 g, 0.614 mmol) followed by sodium cyanoborohydride (0.023 g, 0.358 mmol). The reaction was monitored by TLC and stirred until the starting aldehyde was consumed, then the reaction was diluted with water. This mixture was extracted with ethyl acetate, and the combined organics were dried ($Na_2SO_4$), filtered and concentrated. To a solution of the crude [(4-{[5-amino-4-nitro-2-(trifluoromethyl)phenyl]oxy}phenyl)methyl](4,4-dimethylcyclohexyl)amine (0.197 g, 0.450 mmol) in a 2:1 mixture of ethyl acetate/saturated $NaHCO_3$ (3 mL total) was added di-tert-butyl dicarbonate (0.108 g, 0.495 mmol) with stirring. The reaction mixture stirred for 6 hours at ambient temperature and the layers separated. The aqueous layer was extracted 1×10 mL ethyl acetate and the combined organics dried ($Na_2SO_4$), filtered and concentrated to give 1,1-dimethylethyl [(4-{[5-amino-4-nitro-2-(trifluoromethyl)phenyl]oxy}phenyl)methyl](4,4-dimethylcyclohexyl)carbamate.

$^1$H NMR (400 MHz, $CDCl_3$) delta ppm 0.86 (s, 3H) 0.88 (s, 3H) 1.29-1.60 (m, 17H) 3.50-4.00 (m, 1H) 4.33-4.49 (m, 2H) 5.98 (s, 1H) 6.28 (br.s, 2H) 7.05 (d, J=8.55 Hz, 1H) 7.31 (d, J=8.55 Hz, 2H) 8.49 (s, 1H)

Step 3 (4,4-Dimethylcyclohexyl)[(4-{[5-(trifluoromethyl)-1H-benzimidazol-6-yl]oxy}phenyl)methyl]amine trifluoroacetate (Example No. 94)

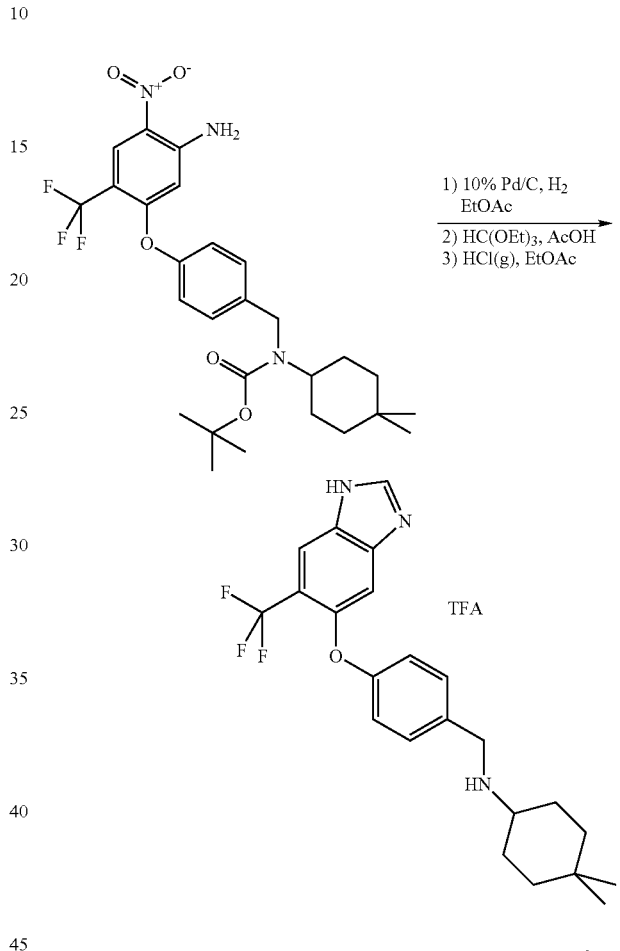

An ethyl acetate solution of the 1,1-dimethylethyl[(4-{[5-amino-4-nitro-2-(trifluoromethyl)phenyl]oxy}phenyl)methyl](4,4-dimethylcyclohexyl)carbamate (0.427 mmol) was subjected to hydrogenation using 10% palladium on carbon (50% $H_2O$, 0.050 g) under an atmosphere of hydrogen for 3 hours. The catalyst was removed by filtration through Celite and the filtrate concentrated. The residue was taken up in a 1:1 mixture of triethyl orthoformate and acetic acid (2 mL total) and refluxed for 16 h, then cooled and concentrated to give crude 1,1-dimethylethyl (4,4-dimethylcyclohexyl)[(4-{[5-(trifluoromethyl)-1H-benzimidazol-6-yl]oxy}phenyl)methyl]carbamate which was used without further purification.

(M+H) 518.2, 3.36 min (LC/MS method A).

The residue was dissolved in ethyl acetate and cooled to −70 degrees Centigrade. Gaseous HCl was bubbled through the solution until it was saturated and the reaction mixture was warmed slowly to room temperature. After 1 hour the reaction mixture was concentrated to a white solid, free-based using saturated $NaHCO_3$ and extracted 2×10 mL Ethyl Acetate, dried ($Na_2SO_4$), filtered and concentrated. Purification of the final compound was accomplished by preparative HPLC and if desired the free-base was obtained by adjusting the pH of the collected fractions with NaHCO$_3$ until basic and extracting the organics several times with ethyl acetate. The combined organics would then be dried (Na$_2$SO$_4$), filtered and concentrated.

General Method 14

Preparation of Benzimidazole Compounds where R$^4$ is Either Cl or F in the 5-Position

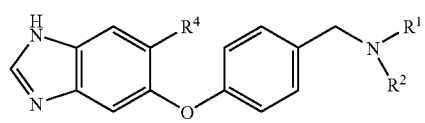

Representative Example

N-({4-[(5-fluoro-1H-benzimidazol-6-yl)oxy] phenyl}methyl)-4,4-dimethylcyclohexanamine trifluoroacetate (Example No. 96)

Step 1: 4-[(5-amino-2-fluoro-4-nitrophenyl)oxy] benzaldehyde Preparation

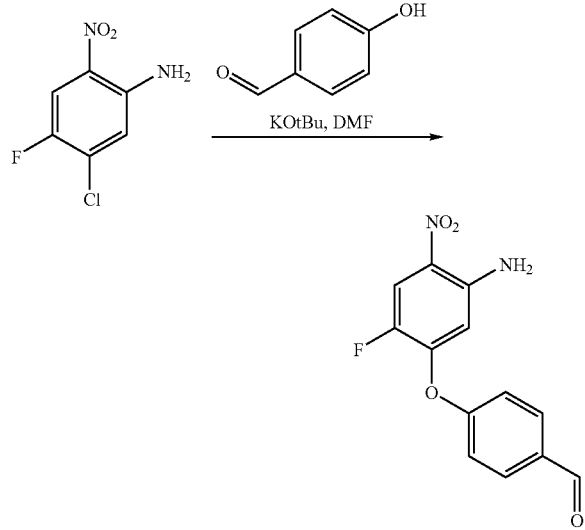

A solution of 5-chloro-4-fluoro-2-nitroaniline (0.380 g, 1.99 mmol), potassium t-butoxide (0.269 g, 2.39 mmol), and 4-hydroxybenzaldehyde (0.292 g, 2.39 mmol) in dimethylformamide (5 mL) was heated to 80 degrees Centigrade for 6 hours and then cooled. Water was added and the organics extracted using ethyl acetate (2×50 mL). The combined organics were then washed one time in brine and then dried (Na$_2$SO$_4$), filtered and concentrated. Chromatography on silica gel using a gradient of 20%-30% ethyl acetate/hexanes eluted the product to give 0.468 g of 4-[(5-amino-2-fluoro-4-nitrophenyl)oxy]benzaldehyde as an orange solid.

$^1$H NMR (400 MHz, dimethylsulfoxide-d$_6$) delta ppm 6.63 (d, J=7.57 Hz, 1H) 7.37 (d, J=8.55 Hz, 2H) 7.45 (br.s, 2H) 7.95-8.01 (m, 3 H) 9.98 (s, 1H)

Step 2: 1,1-Dimethylethyl({4-[(5-amino-2-fluoro-4-nitrophenyl)oxy]phenyl}methyl)(4,4-dimethylcyclohexyl)carbamate

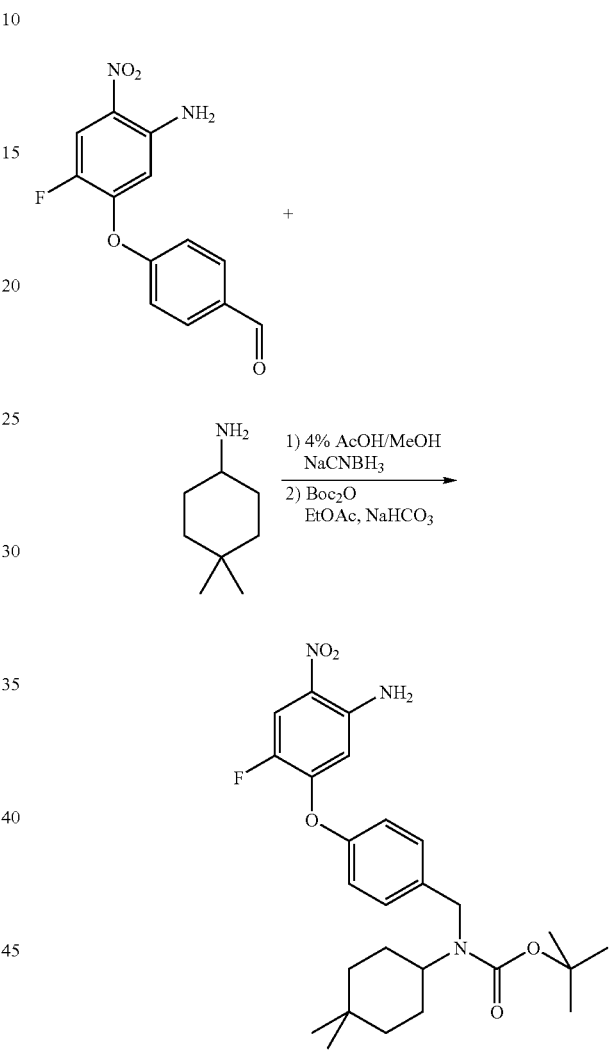

4-[(5-Amino-2-fluoro-4-nitrophenyl)oxy]benzaldehyde (0.100 g, 0.362 mmol) in 2.0 mL 4% acetic acid in methanol was treated with 4,4-dimethylcyclohexylamine (0.055 g, 0.434 mmol) followed by sodium cyanoborohydride (0.016 g, 0.253 mmol). The reaction was stirred until the starting aldehyde was consumed, and the reaction was diluted with water. This mixture was extracted with ethyl acetate. The organics were combined, dried (Na$_2$SO$_4$), filtered and concentrated. To a solution of this crude amine in a 2:1 mixture of ethyl acetate/saturated NaHCO$_3$ (3 mL total) was added di-tert-butyl dicarbonate (0.434 mmol) with stirring. The reaction mixture stirred for 6 hours at ambient temperature and the layers separated. The aqueous layer was extracted 1×10 mL ethyl acetate and the combined organics were dried (Na$_2$SO$_4$), filtered and concentrated to give 1,1-dimethylethyl ({4- [(5-amino-2-fluoro-4-nitrophenyl)oxy]

Step 3: N-({4-[(5-fluoro-1H-benzimidazol-6-yl)oxy]phenyl}methyl)-4,4-dimethylcyclohexanamine trifluoroacetate Preparation (Example No. 96)

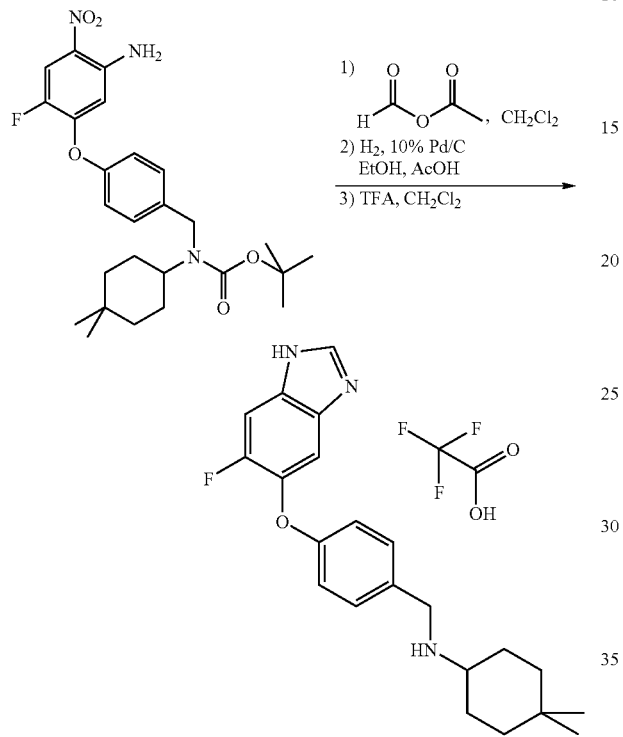

To a solution of 1,1-dimethylethyl({4-[(5-amino-2-fluoro-4-nitrophenyl)oxy]phenyl}methyl)(4,4-dimethylcyclohexyl)carbamate (0.158 g, 0.313 mmol) in CH₂Cl₂ (3 mL) was added formic acetic anhydride (1.5 mL) [prepared as described in Organic Process and Development, 4 (6), p. 569] while stirring at 0 degrees Centigrade. The reaction mixture was stirred an additional 1 hour at ambient temperature and then concentrated and used without further purification. A solution of the crude 1,1-dimethylethyl (4,4-dimethylcyclohexyl)[(4-{[2-fluoro-5-(formylamino)-4-nitrophenyl]oxy}phenyl)methyl]carbamate (0.173 g, 0.335 mmol) in ethanol (3 mL) and acetic acid (3 mL) was subjected to hydrogenation using 10% palladium on carbon (50% H₂O, 0.040 g) under an atmosphere of hydrogen(*). After 3 hours the reaction mixture was filtered through Celite and the filtrate concentrated. The residue was free-based using 1N NaOH and extracting (2×10 mL) CH₂Cl₂. The organics were dried (Na₂SO₄), filtered and concentrated. The residue was subjected to trifluoroacetic acid deprotection using 1 mL trifluoroacetic acid in CH₂Cl₂ (2 mL), and concentrated after 1 h. Purification of the final compound was accomplished by preparative HPLC to give N-({4-[(5-fluoro-1H-benzimidazol-6-yl)oxy]phenyl}methyl)-4,4-dimethylcyclohexanamine trifluoroacetate (Example No. 96)

(*) For Example No. 97, N-({4-[(5-fluoro-1H-benzimidazol-6-yl)oxy]phenyl}methyl)-2,3-dihydro1H-inden-2-amine trifluoroacetate, the hydrogenation and ring closure was accomplished in two ways. First as described above, and in a subsequent preparation as follows. The hydrogenation can be performed in ethanol as the only solvent. The subsequent ring closure can be accomplished by treatment of the dianiline (1 mmol) with trimethyl orthoformate (1.2 mmol) and Yb(OTf)₃ (0.005 mmol) as described by Limin Wang and co-workers in Synth. Commun. 34 (23) 4265-72.

General Method 15

Preparation of Benzimidazole Compounds where R⁴ is in the 5-Position, R⁶=CF₃, and A=CH₂

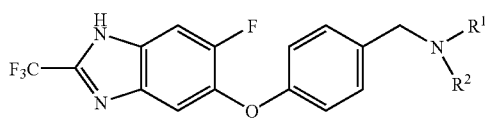

Representative Example

N-[(4-{[5-Fluoro-2-(trifluoromethyl)-1H-benzimidazol-6-yl]oxy}phenyl)methyl]-2,3-dihydro-1H-inden-2-amine trifluoroacetate (Example No. 100)

Step 1: 2,2,2-trifluoro-N-[4-fluoro-5-[(4-formylphenyl)oxy]-2-nitrophenyl]acetamide Preparation

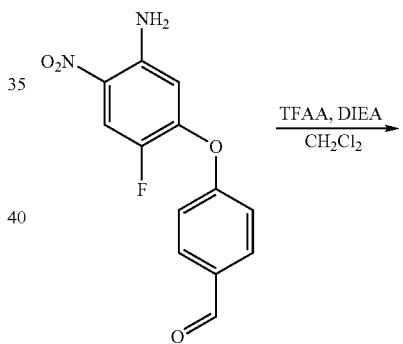

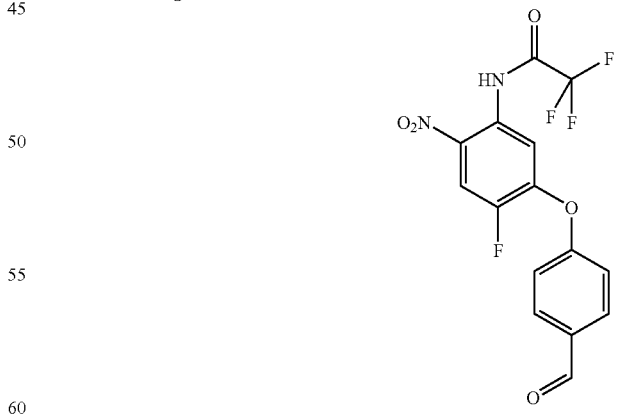

A solution of the 4-[(5-amino-2-fluoro-4-nitrophenyl)oxy]benzaldehyde (previously described synthesis in General Method 14 Step 1) (0.275 g, 0.996 mmol) and N,N-diisopropylethylamine (0.208 mL, 1.19 mmol) in CH₂Cl₂ (2 mL) was stirred for 2 hours and then water (5 mL) was added. The layers were separated and the aqueous layer was extracted with CH₂Cl₂. The combined organics were washed (1×10 mL) 10% HCl, (1×10 mL) NaHCO₃, once in brine, then dried (Na₂SO₄) filtered and concentrated to give 2,2,2-trifluoro-N-{4-fluoro-5-[(4-formylphenyl)oxy]-2-nitrophenyl}acetamide. No further purification was necessary.

¹H NMR (400 MHz, CDCl₃) delta ppm 7.23 (d, J=8.55 Hz, 2 H) 7.99 (d, J=8.79 Hz, 2 H) 8.23 (d, J=10.25 Hz, 1 H) 8.49 (d, J=7.32 Hz, 1 H) 10.0 (s, 1H) 11.48 (br.s, 1H) (M+H) 373.1, 2.58 min (LC/MS method A)

Step 2: ({4-[(5-Amino-2-fluoro-4-nitrophenyl)oxy]phenyl}methyl)2,3-dihydro-1H-inden-2-ylamine Preparation

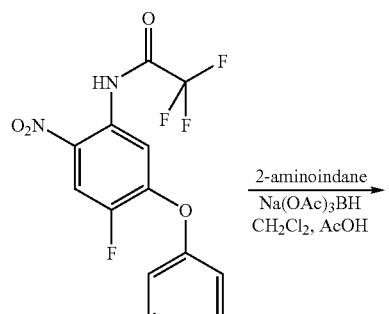

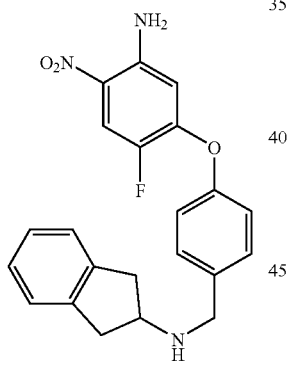

A solution of 2,2,2-trifluoro-N-{4-fluoro-5-[(4-formylphenyl)oxy]-2-nitrophenyl}acetamide (0.300 g, 0.806 mmol), 2-aminoindane (0.161 g, 1.21 mmol), and acetic acid (0.5 mL) in CH₂Cl₂ (3 mL) was stirred for 30 min and then Na(OAc)₃BH (0.205 g, 0.967 mmol) was added slowly over 2 min. The reaction mixture stirred for 1 hour at ambient temperature and then H₂O (3 mL) was added. The layers were separated and the aqueous layer extracted one additional time with CH₂Cl₂. The combined organics were washed 1× brine, then dried (Na₂SO₄), filtered and concentrated to give ({4-[(5-Amino-2-fluoro-4-nitrophenyl)oxy]phenyl}methyl)2,3-dihydro-1H-inden-2-ylamine. No further purification was necessary.

¹H NMR (400 MHz, CDCl₃) delta ppm 2.92-2.97 (m, 2H) 3.22-3.27 (m, 2H) 3.72-3.83 (m, 1H) 3.94 (s, 2H) 6.00 (d, J=7.32 Hz, 1 H) 6.22 (br.s, 2H) 7.07-7.09 (m, 2 H) 7.14-7.21 (m, 4H) 7.44 (d, J=8.3 Hz, 2 H) 7.92 (d, J=11.23 Hz, 1 H) (M+H) 394.2, 1.88 min (LC/MS method A)

Step 3: N-[(4-{[5-Fluoro-2-(trifluoromethyl)-1H-benzimidazol-6-yl]oxy}phenyl)methyl]-2,3-dihydro-1H-inden-2-amine trifluoroacetate (Example No. 100)

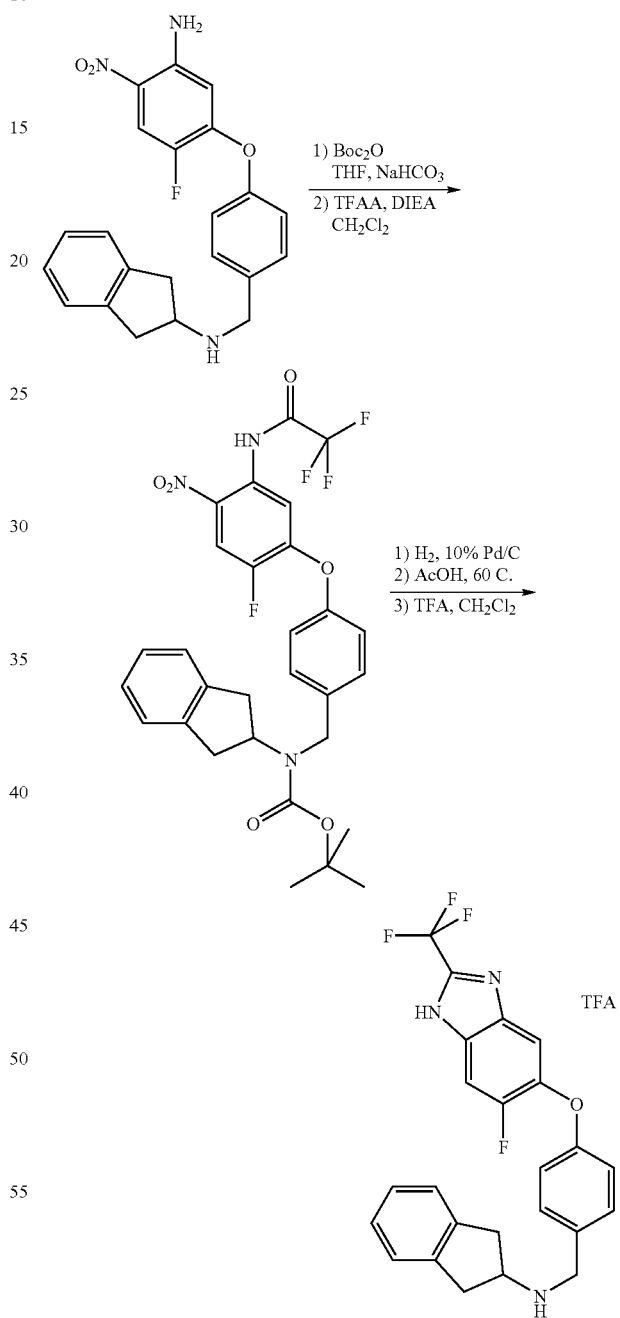

To a solution of ({4-[(5-amino-2-fluoro-4-nitrophenyl)oxy]phenyl}methyl)2,3-dihydro-1H-inden-2-ylamine (0.272 g, 0.691 mmol) in tetrahydrofuran (3 mL) and saturated NaHCO₃ (1 mL) was added di-tert-butyl dicarbonate (0.158 g, 0.726 mmol) in one portion. The reaction mixture was stirred for 2 hours and the layers separated. The aqueous layer was extracted (1×5 mL) diethyl ether and the combined organics washed 1× brine, then dried (Na$_2$SO$_4$), filtered and concentrated. The residue was dissolved in CH$_2$Cl$_2$ (3 mL) and N,N-diisopropylethylamine (0.145 mL, 0.830 mmol) was added followed by trifluoroacetic anhydride (0.100 mL, 0.726 mmol). The reaction mixture stirred for 2 hours and then H$_2$O (4 mL) was added. The layers were separated and the aqueous layer extracted 1×5 mL CH$_2$Cl$_2$ and the combined organics washed one time in brine, then dried (Na$_2$SO$_4$), filtered and concentrated. The resulting 1,1-dimethylethyl 2,3-dihydro-1H-inden-2-yl{[4-({2-fluoro-4-nitro-5-[(trifluoroacetyl)amino]phenyl}oxy)phenyl]methyl}carbamate was used without further purification. (M+H) 590.6, 3.21 min (LC/MS method A).

To an ethanol (3 mL) solution of the crude 1,1-dimethylethyl 2,3-dihydro-1H-inden-2-yl{[4-({2-fluoro-4-nitro-5-[(trifluoroacetyl)amino]phenyl}oxy)phenyl]methyl}carbamate (0.375 g, 0.636 mmol) was added 10% palladium on carbon (0.076 g) and the reaction mixture was subjected to hydrogenation under an atmosphere of hydrogen. The reaction mixture was stirred for 4 hours and the catalyst removed by filtration through Celite. The filtrate was concentrated and the residue re-dissolved in glacial acetic acid (3 mL) and heated to 60 degrees Centigrade for 1 hour, cooled, concentrated and azeotroped several times with toluene/CH$_2$Cl$_2$. The residue was dissolved in CH$_2$Cl$_2$ and trifluoroacetic acid added. The reaction mixture was stirred for 16 hours and then concentrated. Purification of the final compound was accomplished by preparative HPLC to afford N-[(4-{[5-Fluoro-2-(trifluoromethyl)-1H-benzimidazol-6-yl]oxy}phenyl)methyl]-2,3-dihydro-1H-inden-2-amine trifluoroacetate (Example No. 100).

General Method 16

Preparation of 2-Substituted Benzimidazole Compounds where A is CH$_2$ and Y is CR$^6$

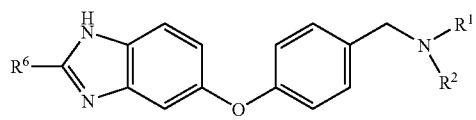

Step 1: Preparation of 4-[(4-Amino-3-nitrophenyl)oxy]benzaldehyde

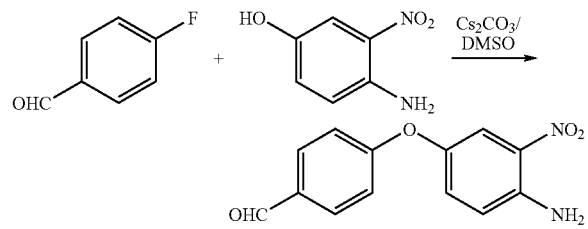

A mixture of 4-amino-3-nitrophenol (1.54 g; 10.0 mmol), 4-fluorobenzaldehyde (1.05 mL; 10.0 mmol) and Cs$_2$CO$_3$ (3.91 g; 12.0 mmol) in anhydrous dimethylsulfoxide (10 mL) was heated at 80 degrees Centigrade, under nitrogen. An additional portion of 4-fluorobenzaldehyde (0.050 mL; 0.50 mmol) was added after 1 hour and heating was continued. After 2 hours the mixture was cooled, poured into water and extracted three times with ethyl acetate. Combined organics were washed (H$_2$O, brine), dried over Na$_2$SO$_4$, filtered and concentrated in vacuo. The residue was purified by flash chromatography (ethyl acetate/hexanes), affording 2.56 g of 4-[(4-Amino-3-nitrophenyl)oxy]benzaldehyde as an orange solid. 1H NMR (400 MHz, CDCl$_3$) delta ppm 6.11 (br. s, 2H), 6.90 (d, J=9.1 Hz, 1H), 7.04 (m, 2H), 7.20 (dd, J=9.0, 2.8 Hz, 1H), 7.86 (m, 2H), 7.89 (d, J=2.7 Hz, 1H), 9.93 (s, 1H) ppm. (M+H) 259, 2.33 min (LC/MS method A).

Step 2: Preparation of 1,1-Dimethylethyl({4-[(4-amino-3-nitrophenyl)oxy]phenyl}methyl)(4,4-dimethylcyclohexyl)carbamate

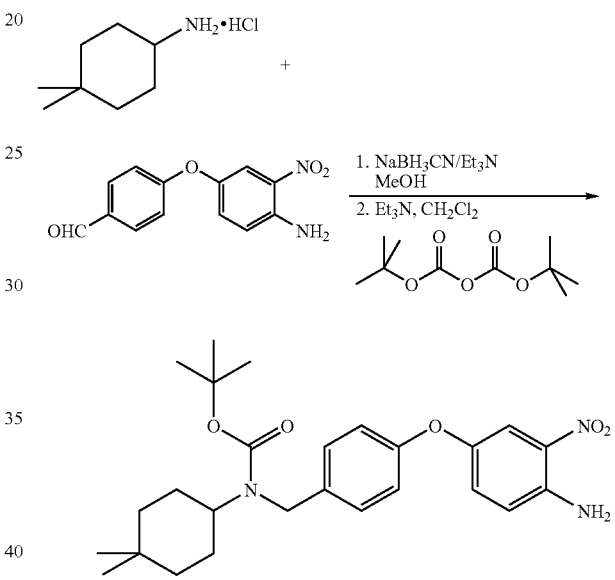

To a solution of 4,4-dimethylcyclohexylamine hydrochloride (0.911 g; 5.56 mmol), 4-[(4-amino-3-nitrophenyl)oxy]benzaldehyde (1.304 g; 5.05 mmol) and triethylamine (0.77 mL; 5.5 mmol) in methanol (50 mL) at room temperature was added NaBH$_3$CN (0.317 g; 5.05 mmol) in one portion. The mixture was stirred 16 hours at room temperature and additional portions of 4,4-dimethylcyclohexylamine hydrochloride (0.083 g; 0.51 mmol), triethylamine (0.08 mL; 0.6 mmol) and NaBH$_3$CN (0.035 g; 0.56 mmol) were added. Stirring was continued 6 hours and volatiles were removed in vacuo. The residue was dissolved in CH$_2$Cl$_2$ (25 mL), triethylamine (0.70 mL; 5.1 mmol) and di-tert-butyl dicarbonate (1.10 g; 5.05 mmol) were added. The mixture was stirred 14 hours at room temp, concentrated onto a minimal amount of silica gel and purified by silica gel flash chromatography (ethyl acetate/hexanes), affording 1.62 g of 1,1-dimethylethyl({4-[(4-amino-3-nitrophenyl)oxy]phenyl}methyl)(4,4-dimethylcyclohexyl)carbamate as an orange foam.

1H NMR (400 MHz, CDCl$_3$) delta ppm 0.86 (s, 3H), 0.88 (s, 3H), 1.14-1.71 (br. overlapping m, 17 H), 3.97 (br s, 1H), 4.35 (br. s, 2H), 5.98 (br. s, 2H), 6.82 (d, J=9 Hz, 1H), 6.90 (m, 2H), 7.17 (dd, J=9.0, 2.8 Hz, 1H), 7.21 (m, 2H, partially overlapping 7.17), 7.73 (partially resolved d, J≈2.3 Hz, 1H) ppm. (M+H) 470, (M+Na) 492, 3.35 min (LC/MS method A).

Step 3: Acylation of 1,1-Dimethylethyl({4-[(4-amino-3-nitrophenyl)oxy]phenyl}methyl)(4,4-dimethylcyclohexyl)carbamate to Form Nitroanilide Intermediates

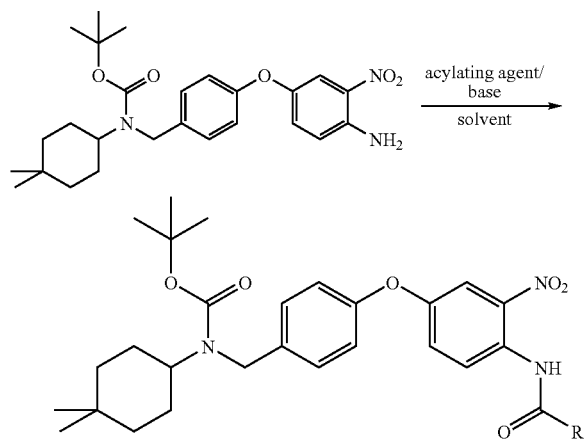

Representative Example 1,1-Dimethylethyl[(4-{[4-(acetylamino)-3-nitrophenyl]oxy}phenyl)methyl](4,4-dimethylcyclohexyl)carbamate (R=CH₃)

To a solution of 1,1-dimethylethyl({4-[(4-amino-3-nitrophenyl)oxy]phenyl}methyl)(4,4-dimethylcyclohexyl)carbamate (0.115 g; 0.244 mmol) and triethylamine (0.040 mL; 0.27 mmol) in CH₂Cl₂ (2.5 mL) was added acetyl chloride (0.020 mL; 0.27 mmol) and the mixture was stirred at room temp. After 16 hours an additional portion of acetyl chloride (0.010 mL), and 4-(dimethylamino)pyridine (3 mg) were added, and stirring continued an additional 2 hours. The whole was concentrated onto a small amount of silica gel and purified by silica gel flash chromatography (ethyl acetate/hexanes), affording 0.103 g of 1-dimethylethyl[(4-{[4-(acetylamino)-3-nitrophenyl]oxy}phenyl)methyl](4,4-dimethylcyclohexyl)carbamate as a yellow gum. ¹H NMR (400 MHz, CDCl₃) delta ppm 0.87 (s, 3H), 0.89 (s, 3H), 1.14-1.74 (br. overlapping m, 17 H), 3.40-4.09 (br. m, 1H), 4.37 (br. s, 2H), 6.96 (m, 2H), 7.27 (br. m, 2H, overlapping solvent), 7.32 (dd, J=9.3, 2.9 Hz, 1H), 7.74 (d, J=2.9 Hz, 1H), 8.69 (d, J=9.3 Hz, 1H), 10.12 (br. s, 1H). (M-H) 510, 3.20 min (LC/MS method A).

Other Nitroanilide Intermediates were Prepared as Follows:

To a solution of 1,1-dimethylethyl({4-[(4-amino-3-nitrophenyl)oxy]phenyl}methyl)(4,4-dimethylcyclohexyl)carbamate (0.125 g; 0.267 mmol) in tetrahydrofuran (2 mL) at room temperature was added pyridine (mL; 0.53 mmol) and an acylating agent (acid chloride or acid anhydride; 0.40 mmol). The mixture was heated at 70 degrees Centigrade (septum-sealed vials) overnight. The mixture was cooled, diluted with ethyl acetate, washed separately (with H₂O, saturated Na₂CO₃, brine), dried over Na₂SO₄, filtered, concentrated and purified by flash chromatography (ethyl acetate/hexanes), affording pure nitroanilide intermediate. Nitroanilide intermediates prepared in this fashion were:

1,1-Dimethylethyl (4,4-dimethylcyclohexyl)[(4-{[3-nitro-4-(propanoylamino)phenyl]oxy}phenyl)methyl]carbamate (R=Et). (M-H) 524, 3.27 min (LC/MS method A).

1,1-Dimethylethyl (4,4-dimethylcyclohexyl){[4-({3-nitro-4-[(trifluoroacetyl)amino]phenyl}oxy)phenyl]methyl}carbamate (R=CF₃). (M-H) 564, 3.30 min (LC/MS method A).

1,1-Dimethylethyl (4,4-dimethylcyclohexyl){[4-({3-nitro-4-[(phenylcarbonyl)amino]phenyl}oxy)phenyl]methyl}carbamate (R=Ph). (M-H) 572, 3.42 min (LC/MS method A).

Step 4: Nitro Group Reduction and Ring Closure to Form 2-Substituted Benzimidazoles

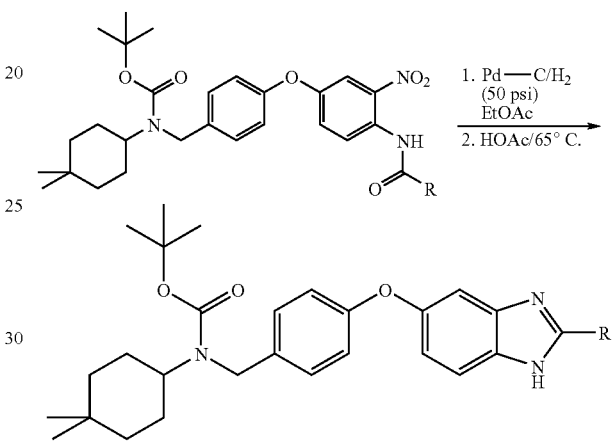

To a solution of nitroanilide intermediate in ethyl acetate (5 mL) was added Pd-carbon (10 wt % (dry basis), wet, DeGussa type E101; ca. 0.10 equiv Pd) and the slurry was hydrogenated using a Parr hydrogenator (50 psi H₂) until complete reduction of starting material was observed (as judged by LC/MS). Catalyst was removed by filtration (either a Celite® pad, or 0.45 μm PTFE membrane filter), the filtrate was concentrated and the residue was dissolved in acetic acid (2-3 mL). The resulting solution was heated at 65 degrees Centigrade until complete conversion of anilino-anilide intermediate to benzimidazole was observed (as judged by LC/MS). The mixture was concentrated in vacuo, re-dissolved in toluene and concentrated in vacuo, affording 2-substituted benzimidazole, which was either carried directly through step 5 below, or purified by chromatography if necessary. 2-Substituted benzimidazoles prepared in this fashion were:

1,1-Dimethylethyl (4,4-dimethylcyclohexyl)({4-[(2-methyl-1H-benzimidazol-5-yl)oxy]phenyl}methyl)carbamate (R=CH₃). Used directly in step 5 without purification. (M+H) 464, 2.55 min (LC/MS method A).

1,1-Dimethylethyl (4,4-dimethylcyclohexyl)({4-[(2-ethyl-1H-benzimidazol-5-yl)oxy]phenyl}methyl)carbamate (R=Et). Purified by RP-HPLC (C₁₈ column, MeCN/H₂O/0.1% TFA) prior to step 5. (M+H) 478, 2.59 min (LC/MS method A).

1,1-Dimethylethyl (4,4-dimethylcyclohexyl)[(4-{[2-(trifluoromethyl)-1H-benzimidazol-5-yl]oxy}phenyl)methyl]carbamate (R=CF₃). Used directly in step 5 without purification. (M-H) 516, 3.29 min (LC/MS method A).

1,1-Dimethylethyl (4,4-dimethylcyclohexyl)({4-[(2-phenyl-1H-benzimidazol-5-yl)oxy]phenyl}methyl)carbamate (R=Ph). Purified by flash chromatography (ethyl acetate/hexanes) prior to step 5. (M+H) 526, 3.12 min (LC/MS method A).

Step 5: Removal of tert-Butoxycarbonyl Protecting Group to Form Final Compounds of Formula 1

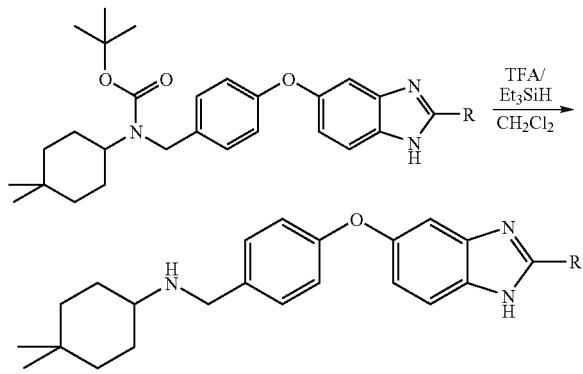

To a solution of tert-butoxycarbonyl-protected intermediate (step 4 above) and (ethyl)$_3$SiH ($\geqq$2.5 equiv) in CH$_2$Cl$_2$ (5 mL) was added TFA (1 mL) in one portion. The mixture was stirred 1 hour at room temp and concentrated in vacuo, affording pure final compound (as TFA salt).

Preparation of Additional Amines

Preparation of 4,4-dimethylcyclohexylamine hydrochloride

Prepared similarly to the procedure in Thomas P. Johnston, George S. McCaleb, Pamela S. Opliger, W. Russell Laster and John A. Montgomery. J. Med. Chem., 14 (7), 600-614, 1971.

Step 1: 4,4-Dimethylcyclohexanone 4,4-Dimethyl-2-cyclohexene-1-one[Aldrich] (5.5 g) was dissolved in 50 ml of ethyl acetate. The solution, along with 0.25 g of 10% Palladium on Carbon (Degussa type E101), was hydrogenated under 15 psi for 3 h at room temperature. The mixture was passed through a Celite® pad to remove the catalyst and then was concentrated to dryness in vacuum. The desired 4,4-dimethylcyclohexanone was obtained as a colorless solid (5.56 g). 1H NMR (400 MHz, CDCl$_3$) delta ppm 1.07 (s, 6H), 1.65 (t, J=7 Hz, 4H), 2.35 (t, J=7 Hz, 4H).

Step 2: 4,4-dimethylcyclohexanone oxime

To a solution of 4,4-dimethylcyclohexanone (3.0 g, 0.024 mole) and hydroxylamine hydrochloride (2.2 g, 0.031 mole) in a mixture of ethanol (15 mL) and water (20 mL) at room temperature was added dropwise a solution of sodium carbonate (3.3 g, 0.031 mole) in water (10 mL). The mixture was heated at reflux for 3 hours, cooled to room temperature and concentrated in vacuo to remove the ethanol. The aqueous residue was extracted several times with ethyl acetate. The organic extracts were dried (MgSO$_4$), filtered and concentrated in vacuo to give 3.0 g (88%) of the desired 4,4-dimethylcyclohexanone oxime as a white solid. This was used without further purification.

1H NMR (400 MHz, DMSO-d$_6$) delta ppm 0.93 (s, 6H), 1.28 (t, J=6.6 Hz, 2H), 1.35 (t, J=6.6 Hz, 2H), 2.11 (t, J=6.6 Hz, 2H), 2.36 (t, J=6.6 Hz, 2H), 10.12 (s, 1H).

Step 3: 4,4-dimethylcyclohexylamine hydrochloride

A mixture of 4,4-dimethylcyclohexanone oxime (3.0 g, 0.021 mole) and Raney 2800 Nickel (0.8 g, slurry in water) in ethanol (100 mL) was hydrogenated on a Parr hydrogenation apparatus at 50 psi. After hydrogen absorption ceased the mixture was filtered through Celite®. To the filtrate was added 50 mL of 1N HCl in diethyl ether. The mixture was concentrated in vacuo. The residue was triturated with diethyl ether, filtered, washed with diethyl ether and air dried to give 2.60 g (76%) of the desired 4,4-dimethylcyclohexylamine hydrochloride as a white solid. 1H NMR (400 MHz, DMSO-d$_6$) delta ppm 0.86 (s, 3H), 0.87 (s, 3H), 1.19 (m, 2H), 1.36 (m, 2H), 1.48 (m, 2H), 1.70 (m, 2H), 2.87 (m, 1H), 7.93 (br. s, 3H).

Synthesis of 5,6-difluoro-2,3-dihydro-1H-inden-2-amine hydrochloride

Step 1: 3-(3,4-Difluorophenyl)propanoyl Chloride Preparation

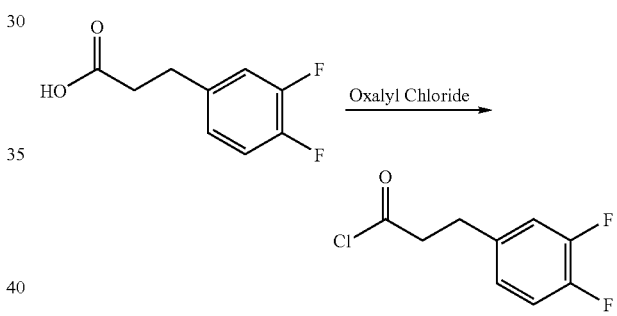

To a dichloromethane solution (200 mL) containing 3,4-difluorophenyl propionic acid (30.45 g, 163.6 mmol) and 2 drops of dimethylformamide was added oxalyl chloride (41.4 g, 327.1 mmol) over 20 min. The resulting solution was stirred for 24 hours at which time the solvent was removed in vacuo. The residual oil was then evaporated with toluene (~100 mL) yielding 33.4 g of 3-(3,4-difluorophenyl)propanoyl chloride as a yellow liquid, which was taken directly into the next step.

Step 2: 5,6-Difluoro-2,3-dihydro-1H-inden-1-one

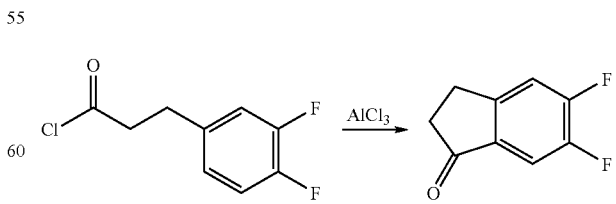

To a carbon disulfide solution (300 mL) containing AlCl$_3$ (76.4 g, 572.6 mmol) at 0° C. was added a carbon disulfide solution (120 mL) of 3-(3,4-difluorophenyl)propanoyl chloride (33.4 g, 163.6 mmol) over 10 min. The solution was stirred for 30 min at 0° C. and heated to reflux for 4 hours. Upon cooling to room temperature the solution was carefully poured onto crushed ice. The carbon disulfide layer was separated and the aqueous layer extracted with ethyl acetate. The combined organic layers were dried over MgSO$_4$ and the solvent removed in vacuo. The residual solid was purified by silica gel column chromatography (5-10% ethyl acetate/hexanes) yielding 19.3 g (114.9 mmol, 70% yield) of 5,6-difluoro-2,3-dihydro-1H-inden-1-one as a white solid. 1H NMR (400 MHz, CDCl$_3$) delta ppm 7.50 (t, 1H, J=8.0 Hz), 7.24 (t, 1H, J=6.6 Hz), 3.09 (t, 2H, J=5.5 Hz), 2.72-2.69 (m, 2H).

Step 3: 5,6-Difluoro-1H-indene-1,2(3H)-dione 2-oxime

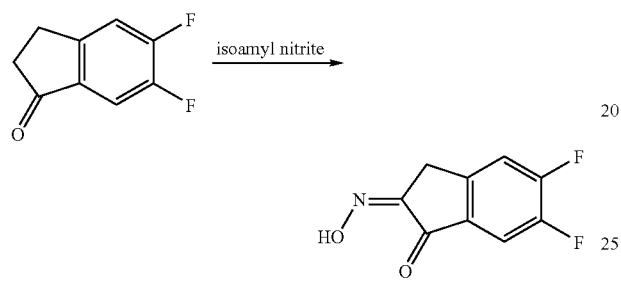

To a methanol solution (90 mL) containing 5,6-difluoro-2,3-dihydro-1H-inden-1-one (4.60 g, 27.4 mmol) at 40 degrees Centigrade, was added isoamyl nitrite (4.17 g, 35.6 mmol) followed by concentrated HCl (2.7 mL). Upon heating for 45 min the solution was allowed to cool to room temperature and water was added. The resulting precipitate was collected via vacuum filtration. The solid was rinsed thoroughly with water yielding 3.97 g (20.2 mmol, 74% yield) of 5,6-difluoro-1H-indene-1,2(3H)-dione 2-oxime as a light orange solid. The crude solid was taken directly into the next step.

Step 4: 5,6-Difluoro-2,3-dihydro-1H-inden-2-amine hydrochloride

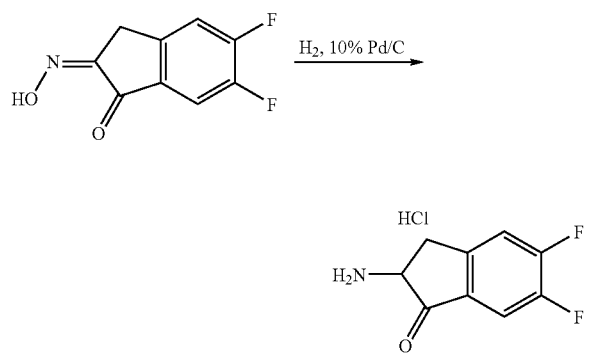

To an acetic acid solution (100 mL) containing 5,6-difluoro-1H-indene-1,2(3H)-dione 2-oxime (3.97 g, 20.2 mmol) in a Parr bottle was added 8 mL of concentrated HCl followed by 10% Pd/C (1.07 g). The solution was hydrogenated at 50 psi for 24 hours on a Parr hydrogenator. The heterogeneous solution was filtered through a bed of Celite with the celite being rinsed thoroughly with chloroform. The solvent was then removed in vacuo and the residual dark oil dissolved in water. The aqueous solution was then made basic with solid K$_2$CO$_3$. The organics were extracted with chloroform three times followed by drying over MgSO$_4$. The solvent was removed in vacuo and the residual amber oil purified by column chromatography (10% MeOH/CH$_2$Cl$_2$) yielding 1.06 g (6.26 mmol) of 5,6-difluoro-2,3-dihydro-1H-inden-2-amine as a brown oil. 1H NMR (400 MHz, CDCl$_3$) delta 6.95 (t, 2H, J=8.9 Hz), 3.83 (m, 1H), 3.10 (dd, 2H, J=15.8, 6.8 Hz), 2.60 (dd, 2H, J=15.8 & 5.0 Hz) ppm; (M+1) 170.1, 0.68 min (LC/MS method A). The oil was dissolved in diethyl ether (~5 mL) and 4.0 mL of a 4.0 M dioxane solution of HCl (16.0 mmol) was added. The resulting precipitate was triturated with diethyl ether and collected by vacuum filtration yielding 795 mg (3.87 mmol, 19% yield) of 5,6-difluoro-2,3-dihydro-1H-inden-2-amine hydrochloride as an off-white solid.

Synthesis of 2-amino-2,3-dihydro-1H-indene-5-carbonitrile hydrochloride

Step 1: 1,1-Dimethylethyl (5-bromo-2,3-dihydro-1H-inden-2-yl)carbamate.

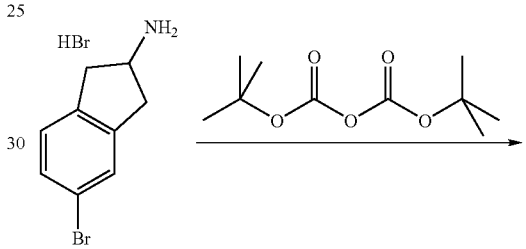

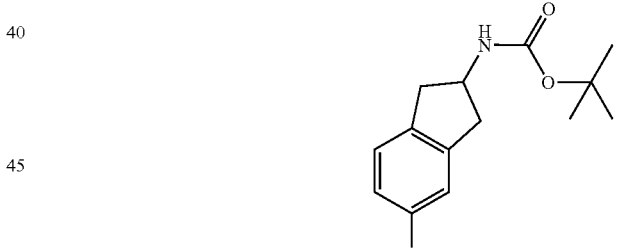

To a slurry of (5-bromo-2,3-dihydro-1H-inden-2-yl)amine hydrobromide (5.61 g; 19.1 mmol; prepared according to Prashad, M; Hu, B.; Har, D.; Repic, O.; Blacklock, T.; Acemoglub, M. Adv. Synth. Catal. 2001, 343 (5), 461) in CH$_2$Cl$_2$ (40 mL) was added triethylamine (5.8 mL, 42 mmol) in one portion. The mixture was stirred 15 min and then di-tert-butyl dicarbonate (4.58 g; 21 mmol) was added in one portion. After 2 hours the reaction mixture was adsorbed onto a minimal amount of silica gel and purified by silica gel flash chromatography (ethyl acetate/hexanes), affording 5.94 g of 1,1-dimethylethyl (5-bromo-2,3-dihydro-1H-inden-2-yl) carbamate as a colorless solid. 1H NMR (400 MHz, DMSO-d$_6$) delta ppm 1.39 (s, 9H), 2.73 (m, 2H), 3.08 (m, 2H), 4.20 (app. sext, J=7.0 Hz, 1H), 7.14 (d, J=8.2 Hz, 1H), 7.19 (br. d, J=6.8 Hz, 1H), 7.30 (partially resolved dd, J=8.0, ~1.9 Hz, 1H), 7.38 (m, 1H).

Step 2: 1,1-Dimethylethyl (5-cyano-2,3-dihydro-1H-inden-2-yl)carbamate

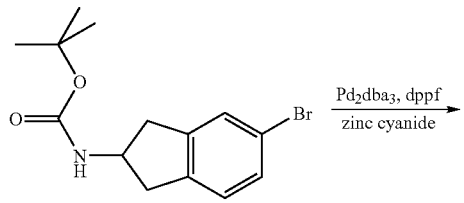

A flask containing 1,1-dimethylethyl (5-bromo-2,3-dihydro-1H-inden-2-yl)carbamate (3.0 g, 9.26 mmol) from the preceding step, diphenylphosphinoferrocene (645 mg, 1.16 mmol), $Pd_2 dba_3$ (532 mg, 0.58 mmol), zinc cyanide (1.50 g, 12.8 mmol) and water in 50 mL dimethylformamide was degassed four times under nitrogen and allowed to stir at 110° C. for 21 hours. Upon cooling the reaction was quenched with saturated $NH_4Cl$ and the organics were taken up in ethyl acetate. The organic layer was washed with water (3x), sat. NaCl and dried over $MgSO_4$. The solvent was removed in vacuo and the residual orange-yellow oil was purified by silica gel column chromatography (15-40% ethyl acetate/hexanes) yielding 1.85 g (7.18 mmol, 78% yield) of the 1,1-dimethylethyl (5-cyano-2,3-dihydro-1H-inden-2-yl)carbamate as an off-white solid. 1H NMR (400 MHz, $CDCl_3$) delta 7.47 (s, 1H), 7.45 (d, 1H, J=7.9 Hz), 7.28 (d, 1H, J=7.7 Hz), 4.69 (br.s), 1H), 4.47 (s(br), 1H), 3.33-3.25 (m, 2H), 2.86-2.80 (m, 2H), 2.79 (s, 9H) ppm. (M+1) 259.1, 2.46 min (LC/MS method A).

Step 3: 2-Amino-2,3-dihydro-1H-indene-5-carbonitrile hydrochloride

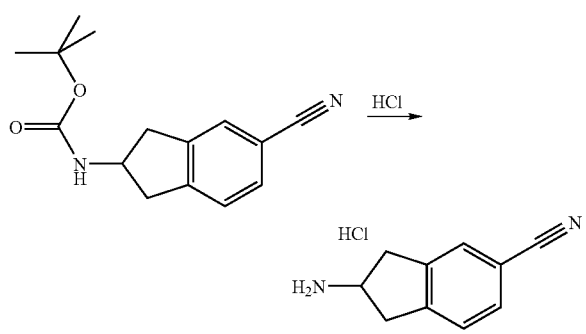

To a dioxane solution (30 mL) containing 1,1-dimethylethyl (5-cyano-2,3-dihydro-1H-inden-2-yl)carbamate (1.85 g, 7.18 mmol) was added 18 mL of a 4.0 M dioxane solution of HCl (72.0 mmol) at room temperature. The resulting solution was stirred for approximately 18 hr at which time the heterogeneous solution was diluted with diethyl ether. The solid was collected by vacuum filtration and then rinsed thoroughly with diethyl ether yielding 1.33 g (6.84 mmol, 95% yield) of 2-amino-2,3-dihydro-1H-indene-5-carbonitrile hydrochloride as a tan solid. 1H NMR (400 MHz, $CD_3OD$) delta ppm 7.65 (s, 1H), 7.59 (d, 1H, J=7.9 Hz), 7.46 (d, 1H, J=7.9 Hz), 4.14 (m, 1H), 3.51-3.43 (m, 2H), 3.10-3.04 (m, 1H).

Preparation of (2R)-and (2S)-5-fluoro-2,3-dihydro-1H-inden-2-amine hydrochloride

Step 1: 5-Fluoro-2,3-dihydro-1H-inden-2-amine

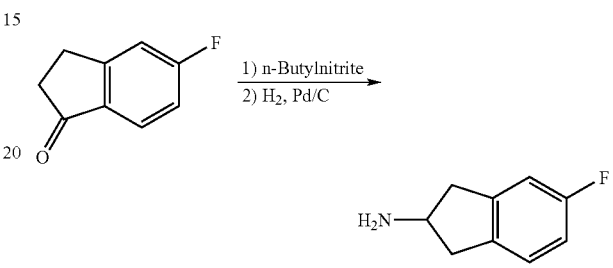

To a solution 5-fluoro-2,3-dihydro-1H-inden-1-one (10.0 g; 66.7 mmol) in methanol at 40 degrees Centigrade was added n-butylnitrite (13.2 mL; 113 mmol) dropwise over 3 minutes, followed by concentrated HCl (10 mL), dropwise at such a rate that the internal temp was maintained below 55 degrees Centigrade. The mixture was stirred 30 min and concentrated in vacuo. The residue was diluted with ethyl acetate and saturated $NaHCO_3$, filtered and the layers were separated. The aqueous layer was extracted with ethyl acetate (×1), combined organics were washed ($H_2O$, brine), dried over $Na_2SO_4$, filtered and concentrated in vacuo. The residue was purified by flash chromatography (ethyl acetate/hexanes), affording 7.59 g of the keto-oxime intermediate as an orange solid. This solid was dissolved in acetic acid/$H_2SO_4$ (250 mL/12.5 mL), Pd-carbon was added (4.5 g; 10 wt % (dry basis), wet, DeGussa type E101) and the mixture was hydrogenated using a Parr hydrogenator (50 psi $H_2$) for approximately 18 h. The mixture was filtered through Celite ($H_2O$ wash) and partially concentrated to an aqueous mixture. The mixture was adjusted to pH 11 (1 N NaOH) and extracted with $CHCl_3$ (×5).

Combined organics were washed (brine), dried over $Na_2SO_4$, filtered and concentrated in vacuo, affording 5.79 g 5-fluoro-2,3-dihydro-1H-inden-2-amine as an amber oil which was used without further purification. 1H NMR (400 MHz, DMSO-$d_6$) delta ppm 1.69 (br. s, 2H), 2.53 (m, 2H, overlapping solvent), 2.99 (m, 2H), 3.69 (quint, J=6.2 Hz, 1H), 6.89 (partially resolved ddd, J=9.8, ~7.7, 2.5 Hz, 1H), 6.99 (partially resolved dd, J=9.3, ~2.3 Hz, 1H), 7.16 (partially resolved dd, J=8.3, 5.6 Hz, 1H).

Step 2: rac-(5-Fluoro-2,3-dihydro-1H-inden-2-yl)benzyl carbamate

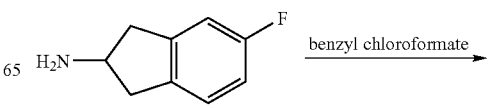

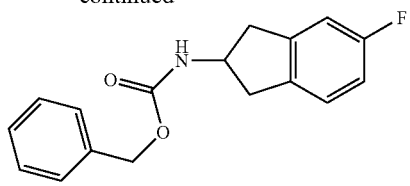

To a mixture of 5-fluoro-2,3-dihydro-1H-inden-2-amine (5.79 g; 38.3 mmol; step 1 above) and saturated $Na_2CO_3$ (200 mL) at room temp was added benzyl chloroformate (6.9 mL; 46 mmol). The mixture was stirred 1 h at room temp and extracted with ethyl acetate (×3). Combined organics were washed ($H_2O$, brine), dried over $Na_2SO_4$, filtered and concentrated in vacuo. The residue was purified by flash chromatography (ethyl acetate/hexanes), affording 8.33 g of rac-(5-fluoro-2,3-dihydro-1H-inden-2-yl)benzyl carbamate as an off-white solid. 1H NMR (400 MHz, DMSO-$d_6$) delta ppm 2.77 (m, 2H), 3.12 (m, 2H), 4.29 (app. sext, J=7.1 Hz, 1H), 5.02 (s, 2H), 6.94 (m, 1H), 7.03 (partially resolved dd, J=9.2, ~2.4 Hz, 1H), 7.19 (partially resolved dd, J=8.2, 5.5 Hz, 1 H), 7.28-7.40 (m, 5H), 7.64 (d, J=6.8 Hz, 1H).

Step 3: Resolution of rac-(5-Fluoro-2,3-dihydro-1H-inden-2-yl)benzyl carbamate into [(2S)-5-fluoro-2,3-dihydro-1H-inden-2-yl]benzyl carbamate and [(2R)-5-fluoro-2,3-dihydro-1H-inden-2-yl]benzyl carbamate rac-(5-Fluoro-2,3-dihydro-1H-inden-2-yl)benzyl carbamate was separated into individual enantiomers by supercritical fluid chromatography using an AD-H prep column (30 mm ID ×25 mm, 5 micrometer particle size), methanol/$CO_2$ (17/83) at 140 bar, 90 g/min total flow, 33 degrees Centigrade. Chromatographic peaks were detected at 215 nm. Absolute configuration assignments for the enantiomers obtained above were made by comparison of experimentally measured vibrational circular dichroism (VCD) spectra (c=0.036 gm/ml; $CDCl_3$) with the VCD spectrum calculated for [(2S)-5-fluoro-2,3-dihydro-1H-inden-2-yl]benzyl carbamate. The earlier-eluting enantiomer from the chiral separation described above was found to have VCD bands of the same relative sign as the (S)-configuration model used for ab initio calculations, and thus assigned the (S)-configuration. In contrast, the latter-eluting enantiomer was found to was found to have VCD bands of the opposite relative sign as the (S)-configuration model used for ab initio calculations, and thus assigned the (R)-configuration.

Step 4: (S)-and (R)-5-fluoro-2,3-dihydro-1H-inden-2-amine hydrochloride

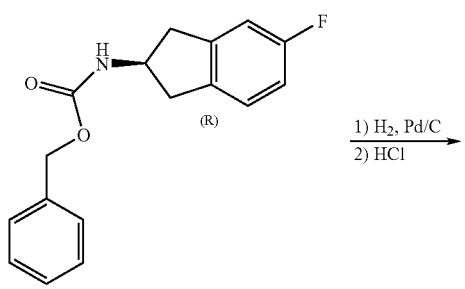

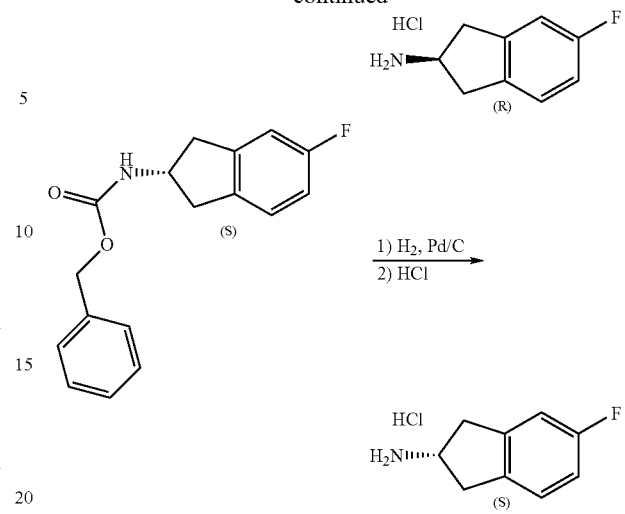

Representative Example (S)-5-fluoro-2,3-dihydro-1H-inden-2-amine hydrochloride

To a solution of [(2S)-5-fluoro-2,3-dihydro-1H-inden-2-yl]benzyl carbamate (2.26 g; 7.93 mmol) in ethyl acetate/ethanol (40 mL each) was added Pd—C (0.85 g; 10 wt % (dry basis), wet, DeGussa type E101). The mixture was stirred under an atmosphere of $H_2$ for 5 hours and catalyst was removed by filtration through a 0.45 micrometer PTFE membrane filter. HCl (5 mL of a 4N solution in dioxane) was added to the filtrate and the whole was concentrated to dryness, affording 1.41 g (S)-5-fluoro-2,3-dihydro-1H-inden-2-amine hydrochloride as a tan solid. 1H NMR (400 MHz, DMSO-$d_6$) delta ppm 2.97 (m, 2H), 3.24 (m, 2H), 4.00 (m, 1), 7.01 (m, 1H), 7.13 (partially resolved dd, J=9.2, ~2.4 Hz, 1H), 7.28 (dd, J=8.4, 5.4 Hz, 1H), 8.40 (br. s, 2H). (M+H) 152, 0.73 min (LC/MS method C).

(R)-5-Fluoro-2,3-dihydro-1H-inden-2-amine hydrochloride

This compound was prepared in an identical fashion to (S)-5-fluoro-2,3-dihydro-1H-inden-2-amine hydrochloride, and exhibited an identical $^1H$ NMR spectrum and LC/MS retention time.

Preparation of [5-(methyloxy)-2,3-dihydro-1H-inden-2-yl]amine hydrochloride

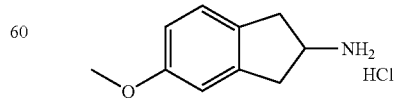

Prepared similar to the procedure of Susanne R. Haadsma-Svensson, Kerry A. Cleek, Dac M. Dinh, J. Neil Duncan, Christopher L. Haber, Rita M. Huff, Mary E. Lajiness, Nanette F. Nichols, Martin W. Smith, Kjell A. Svensson, Matt J. Zaya, Arvid Carlsson, and Chiu-Hong Lin *J. Med. Chem.* 44, (26) 4716-4732.

Step 1: (2Z)-5-(methyloxy)-1H-indene-1,2(3H)-dione 2-oxime Preparation

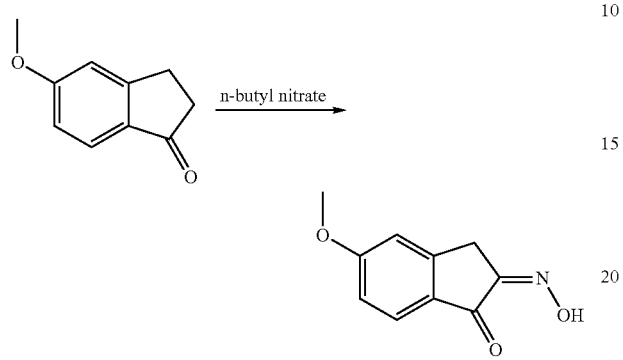

To a solution of 5-(methyloxy)-2,3-dihydro-1H-inden-1-one (1.0 g, 6.2 mmol) in methanol (15 mL) at 40 degrees Centigrade was added n-butyl nitrite (0.8 mL, 6.25 mmol) followed by concentrated HCl (0.6 mL). The reaction was stirred for 30 min during which time a precipitate formed, collected, dried and used without further purification.

$^1$H NMR (400 MHz, DMSO-$d_6$) delta ppm 3.60 (br.s, 2H) 3.86 (s, 3H) 6.99 (dd, J=8.54, 2.2 Hz, 1H) 7.12 (d, J=1.71 Hz, 1H) 7.66 (d, J=8.55 Hz, 1 H) 12.45 (s, 1H)

Step 2: [5-(methyloxy)-2,3-dihydro-1H-inden-2-yl]amine hydrochloride Preparation

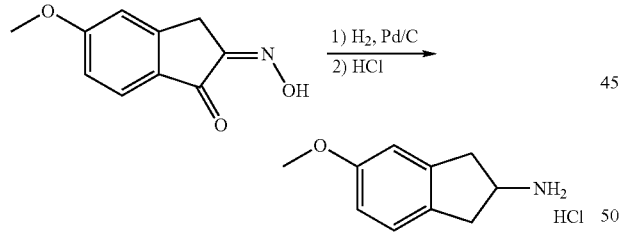

To a solution of the (2Z)-5-(methyloxy)-1H-indene-1,2 (3H)-dione 2-oxime (0.96 g, 5.02 mmol) in glacial acetic acid (25 mL) and concentrated H$_2$SO$_4$ (2 mL) was added 10% palladium on carbon (50% H$_2$O, 0.200 g). This mixture was hydrogenated on a Parr apparatus at 50 psi for 7 hours, then filtered over Celite to remove the catalyst and washed 2×10 mL methanol and concentrated to remove the acetic acid, basified to pH 12 at which point a solid formed and extracted with CH$_2$Cl$_2$ (2×100 mL). The combined organics were dried (Na$_2$SO$_4$) and concentrated to one half volume. Gaseous HCl was bubbled through the remaining solution for a approximately one minute and the resulting mixture concentrated after standing 15 minutes at ambient temperature to give 0.906 g of [5-(methyloxy)-2,3-dihydro-1H-inden-2-yl]amine hydrochloride.

$^1$H NMR (400 MHz, DMSO-$d_6$) delta ppm 2.84-2.98 (m, 2H) 3.09-3.24 (m, 2H) 3.75 (s, 3H) 3.92 (br.s, 1H) 6.73 (dd, J=8.3, 2.44 Hz, 1H) 6.83 (d, J=2.2 Hz, 1H) 7.13 (d, J=8.06 Hz, 1 H) 8.40 (br.s, 2H)

Preparation of [4-(methyloxy)-2,3-dihydro-1H-inden-2-yl]amine hydrochloride

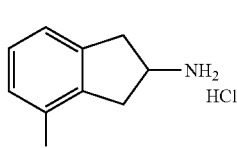

This compound was prepared in the same manner as [5-(methyloxy)-2,3-dihydro-1H-inden-2-yl]amine hydrochloride from 4-(methyloxy)-2,3-dihydro-1H-inden-1-one.

$^1$H NMR (400 MHz, DMSO-$d_6$) delta ppm 2.84-2.98 (m, 2H) 3.10-3.27 (m, 2H) 3.75 (s, 3H) 3.95 (br.s, 1H) 6.79 (d, J=8.06 Hz, 1H) 6.84 (d, J=7.32 Hz, 1H) 7.16 (t, J=7.81 Hz, 1 H) 8.31 (br.s, 2H)

Preparation of [5,6-bis(methyloxy)-2,3-dihydro-1H-inden-2-yl]amine hydrochloride

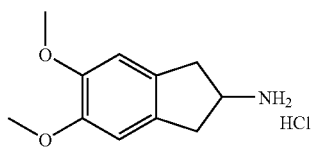

This compound was prepared in the same manner as [5-(methyloxy)-2,3-dihydro-1H-inden-2-yl]amine hydrochloride from 5,6-bis(methyloxy)-2,3-dihydro-1H-inden-1-one.

$^1$H NMR (400 MHz, DMSO-$d_6$) delta ppm 2.84-2.98 (m, 2H) 3.10-3.27 (m, 2H) 3.75 (s, 3H) 3.95 (br.s, 1H) 6.79 (d, J=8.06 Hz, 1H) 6.84 (d, J=7.32 Hz, 1H) 7.16 (t, J=7.81 Hz, 1 H) 8.31 (br.s, 2H)

Preparation of (2-methyl-2,3-dihydro-1H-inden-2-yl)amine hydrochloride

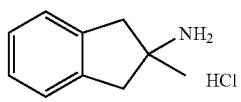

Step 1: Methyl 2-methyl-1-oxo-2,3-dihydro-1H-indene-2-carboxylate Preparation

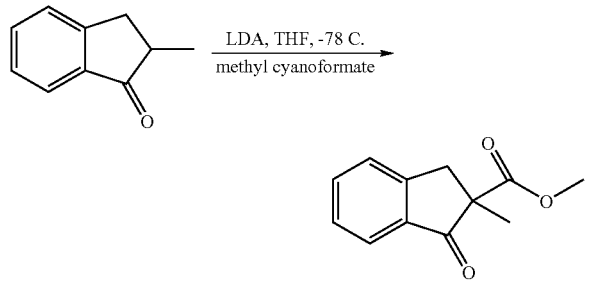

To a flask cooled at 0 degrees Centigrade containing diisopropylamine (2.06 mL, 14.58 mmol) in tetrahydrofuran (14 mL) was added dropwise over 15 minutes a solution of n-butyl lithium (5.55 mL of 2.5 M in hexanes, 14.58 mmol). This mixture was stirred for 30 min. A second flask containing the 2-methyl-1-indanone (2.03 g, 13.89 mmol) in tetrahydrofuran (10 mL) was cooled to −78 degrees Centigrade under $N_2$. The freshly prepared lithium diisopropylethylamide was cooled to −78 degrees centigrade and added drop wise via cannula. The orangish mixture became somewhat heterogeneous over 30 minutes and then neat methyl cyanoformate (1.32 mL, 16.66 mmol) was added and the reaction mixture stirred an additional 40 minutes while allowing the reaction to warm to −20 degrees centigrade. The reaction was quenched with saturated aqueous $NH_4Cl$ solution and the organics extracted 2×25 mL diethyl ether, washed one time in brine, then dried ($Na_2SO_4$), filtered and concentrated to give methyl 2-methyl-1-oxo-2,3-dihydro-1H-indene-2-carboxylate. No further purification was necessary.

$^1$H NMR (400 MHz, $CDCl_3$) delta ppm 1.52 (s, 3H) 3.00 (d, J=17.32 Hz, 1 H) 3.67-3.73 (m, 4H) 7.41 (t, J=7.57 Hz, 1 H) 7.47 (m, 1H) 7.63 (m, 1 H) 7.79 (d, J=7.57 Hz, 1 H)

Step 2: Methyl 2-methyl-2,3-dihydro-1H-indene-2-carboxylate

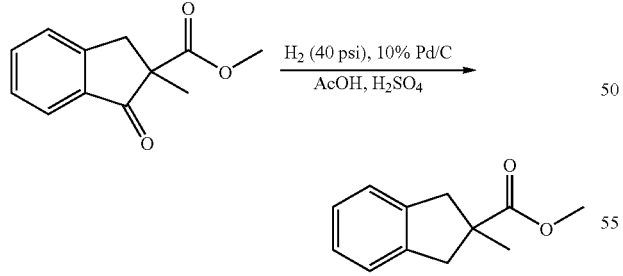

A solution of the methyl 2-methyl-1-oxo-2,3-dihydro-1H-indene-2-carboxylate (2.04 g, 9.99 mmol) in glacial acetic acid (22 mL) and concentrated $H_2SO_4$ (2 mL) was hydrogenated on a Parr apparatus under 50 psi of hydrogen using 10% palladium on carbon (50% $H_2O$, 0.200 g) as the catalyst. After 4 hours the reaction was filtered to remove the catalyst and washed 2× methanol, then concentrated to remove most of the acetic acid. The residue was neutralized using saturated $Na_2CO_3$ and the organics extracted twice with 25 mL ethyl acetate, then the combined organics washed with brine, dried ($Na_2SO_4$), filtered and concentrated to 2.0 g of methyl 2-methyl-2,3-dihydro-1H-indene-2-carboxylate.

$^1$H NMR (400 MHz, $CDCl_3$) delta ppm 1.35 (s, 3H) 2.81 (d, J=15.63 Hz, 2 H) 3.47 (d, J =15.63 Hz, 2 H) 3.71 (s, 3H) 7.12-7.23 (m, 4H)

Step 3: 2-Methyl-2,3-dihydro-1H-indene-2-carboxylic acid

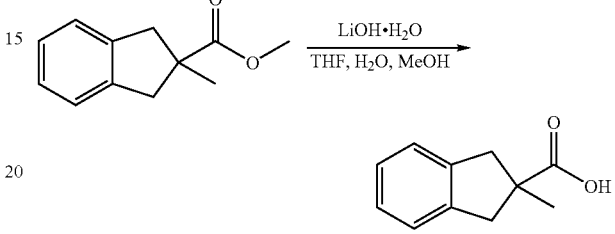

To a tetrahydrofuran/$H_2O$/methanol (4 mL/1 mL/1 mL) solution of the methyl 2-methyl-2,3-dihydro-1H-indene-2-carboxylate (1.80 g, 9.46 mmol) was added lithium hydroxide monohydrate (1.19 g, 28.39 mmol). The reaction mixture stirred at ambient temperature for 4 hours and then the mixture was acidified to pH 3 using 1N HCl. The organics were extracted twice with 25 mL diethyl ether, the combined organics were washed with brine and then dried ($Na_2SO_4$), filtered and concentrated to as 2-Methyl-2,3-dihydro-1H-indene-2-carboxylic acid a white solid.

$^1$H NMR (400 MHz, $CDCl_3$) delta ppm 1.39 (s, 3H) 2.83 (d, J=15.87 Hz, 2 H) 3.50 (d, J=15.87 Hz, 2 H) 7.12-7.23 (m, 4H)

Step 4: Phenylmethyl (2-methyl-2,3-dihydro-1H-inden-2-yl)carbamate

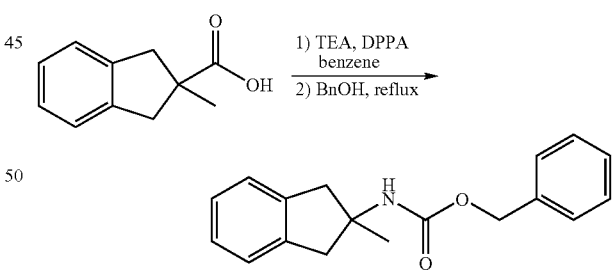

To a solution 2-methyl-2,3-dihydro-1H-indene-2-carboxylic acid (0.200 g, 1.14 mmol) and triethylamine (0.166 mL, 1.19 mmol) in 2 mL of benzene at to 0 degrees Centigrade was added diphenyl phosphorylazide (0.257 g, 1.19 mmol). The reaction mixture was stirred for 15 minutes and benzyl alcohol (0.123 mL, 1.19 mmol) was added and the reaction was heated to reflux for 16 hours, then cooled and 10% HCl was added. The organics were extracted 2×25 mL ethyl acetate, then washed 1× brine, dried ($Na_2SO_4$), filtered and concentrated. The residue was chromatographed on silica using 5:1 hexanes/ethyl acetate to give 0.271 g of the phenylmethyl (2-methyl-2,3-dihydro-1H-inden-2-yl)carbamate.

¹H NMR (400 MHz, CDCl₃) delta ppm 1.55 (s, 3H) 2.98 (d, J=15.87 Hz, 2 H) 3.28 (d, J=15.87 Hz, 2 H) 7.12-7.18 (m, 4H) 7.29-7.37 (m, 5H)

Step 5: (2-Methyl-2,3-dihydro-1H-inden-2-yl)amine hydrochloride

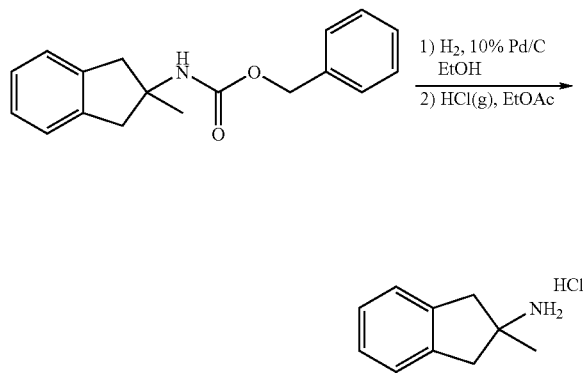

A Parr vessel containing the phenylmethyl (2-methyl-2,3-dihydro-1H-inden-2-yl)carbamate (0.271 g, 0.963 mmol) and 10% palladium on carbon (50% H₂O, 0.050 g) in ethanol (2 mL) was charged and evacuated several times with hydrogen before maintaining a final pressure of 40 psi while shaking for 4 hours. The catalyst was removed by filtration over Celite® and the filtrate concentrated to an oil. The residue was dissolved in ethyl acetate cooled to −70 degrees Centigrade and gaseous HCl was bubbled through the solution until saturated. The reaction mixture stirred for 1 hour and then concentrated to give 0.175 g of (2-methyl-2,3-dihydro-1H-inden-2-yl)amine hydrochloride as a white solid.

¹H NMR (400 MHz, methanol-d₄) delta ppm 1.56 (s, 3H) 3.17 (br.s, 4H) 7.19-7.29 (m, 4H)

Preparation of 3,3-dimethylcyclohexylamine hydrochloride

Step 1: 3,3-Dimethylcyclohexanone oxime

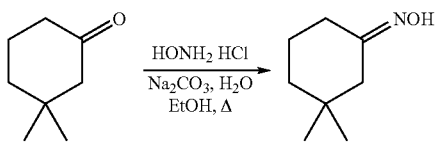

To a mixture of 3,3-dimethylcyclohexanone (4.0 g, 0.032 mol) and hydroxylamine hydrochloride (2.9 g, 0.041 mol) in ethanol (20 mL) was added dropwise a solution of sodium carbonate (4.3 g, 0.041 mol) in water (25 mL). The mixture was heated at reflux for 3 hours. The mixture was concentrated in vacuo to remove the ethanol and the aqueous residue was extracted with ethyl acetate. The organic phase was dried (MgSO₄), filtered and concentrated in vacuo to give 3,3-dimethylcyclohexanone oxime as a yellow oil. This material was used without further purification.

Step 2: (3,3-dimethylcyclohexyl)amine hydrochloride

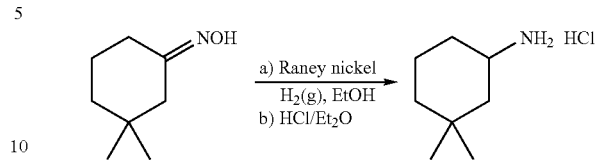

A mixture of 3,3-dimethylcyclohexanone oxime (4.41 g, 0.031 mol) and Raney nickel in water (1.0 g) in ethanol (100 mL) was placed on a Parr hydrogenation apparatus. After 11 days, the reaction mixture was filtered through celite. To the filtrate was added 1.0N HCl in ethyl ether (50 mL) and the mixture was concentrated in vacuo. The residue was triturated with ethyl ether, filtered, washed with ethyl ether and dried to give (3,3-dimethylcyclohexyl)amine hydrochloride as a white solid. ¹H NMR (400 MHz, DMSO-d₆) delta ppm: 0.85 (s, 3 H); 0.90 (s, 3 H); 0.97-1.16 (m, 3 H); 1.29 (br d, 1 H); 1.34-1.46 (m, 1H); 1.53-1.63 (m, 2H); 1.90 (br d, 1H); 3.05 (m, 1H); 7.99 (br s, 3H).

[(1S)-3,3-dimethylcyclohexyl]amine Hydrochloride and [(1R)-3,3-dimethylcyclohexyl]amine Hydrochloride Step 1: Phenylmethyl (3,3-dimethylcyclohexyl)carbamate

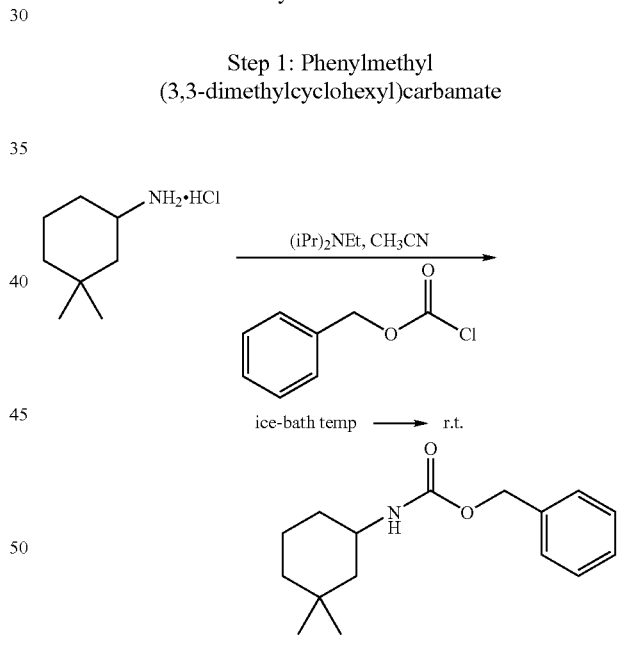

To a solution of (3,3-dimethylcyclohexyl)amine hydrochloride (10.0 g, 0.06 mol) and N,N-diisopropylethylamine (15.8 g, 0.12 mol) in acetonitrile (125 mL) chilled in an ice bath was added dropwise a solution of benzylchloroformate (11.4 g, 0.067 mol) in acetonitrile (25 mL). The mixture was stirred and allowed to come to ambient temperature overnight. The reaction mixture was concentrated in vacuo and the residue was partitioned between ethyl acetate and 5% aqueous citric acid solution. The organic phase was washed with saturated aqueous sodium chloride solution and dried over sodium sulfate. The mixture was filtered, silica gel was added to the residue and the mixture was concentrated in vacuo. The residue was purified by column chromatography using dichloromethane/hexanes (4:1) as eluent to give 11.2 g (70%) of phenylmethyl (3,3-dimethylcyclohexyl) carbamate as a colorless oil. $^1$H NMR (400 MHz, DMSO-d$_6$) delta ppm: 0.85 (s, 6H); 0.92-1.02 (m, 3 H); 1.25 (d, 1 H); 1.36-1.52 (m, 3 H); 1.76 (br d, 1 H); 3.36-3.44 (m, 1H); 4.96 (s, 2H); 7.10 (d, 1H); 7.27-7.36 (m, 5H).

Step 2: Phenylmethyl[(1S)-3,3-dimethylcyclohexyl] carbamate and Phenylmethyl[(1R)-3,3-dimethylcyclohexyl]carbamate Phenylmethyl (3,3-dimethylcyclohexyl)carbamate (11.2 g) was separated by supercritical fluid chromatography (SFC) on a Chiralpak AS column (30 mm). The flow rate was 75 gr/min. CO$_2$ and 4 mL/min. ethanol. The pressure was 140 bar and the temperature was 40° C. The enantiomer eluting at 4.41 min. was combined and concentrated in vacuo to give 3.98 g of a colorless oil. Analytical SFC showed this enantiomer to be >99% pure. Ab Initio vibrational circular dichroism determined this to be the S-enantiomer. $[\alpha]_D=-17.2°$ (c=0.01, methanol), optical rotation was obtained at 25 degrees centigrade. $^1$H NMR (400 MHz, DMSO-d$_6$) delta ppm: 0.85 (s, 6H); 0.93-1.01 (m, 3 H); 1.25 (d, 1 H); 1.33-1.52 (m, 3 H); 1.75 (br d, 1 H); 3.35-3.44 (m, 1H); 4.96 (s, 2H); 7.08 (d, 1H); 7.25-7.35 (m, 5H). (M+1) 262, 2.8 min. (LC/MS Method A).

The enantiomer eluting at 5.51 min. was combined and concentrated in vacuo to give 3.57 g of a colorless oil. Analytical SFC showed this enantiomer to be >96% pure. Ab Initio vibrational circular dichroism determined this to be the R-enantiomer. $[\alpha]_D=+16.3°$ (c=0.011, MeOH), optical rotation was obtained at 25 degrees centigrade. $^1$H NMR (400 MHz, DMSO-d$_6$) delta ppm: 0.85 (s, 6H); 0.92-1.01 (m, 3 H); 1.25 (d, 1 H); 1.33-1.52 (m, 3 H); 1.75 (br d, 1 H); 3.36-3.44 (m, 1H); 4.96 (s, 2H); 7.08 (d, 1H); 7.26-7.35 (m, 5H). (M+1) 262, 2.86 min. (LC/MS Method B).

Step 3: [(1S)-3,3-dimethylcyclohexyl]amine Hydrochloride

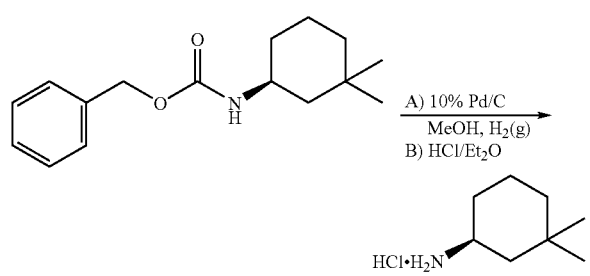

Phenylmethyl[(1S)-3,3-dimethylcyclohexyl]carbamate (1.0 g, 0.004 mol) and 10% Pd/C (0.15 g) in 10 mL of MeOH was placed under a balloon of H$_2$ for 24 hours. The catalyst was removed by filtration through Celite®. To the filtrate was added 1N HCl in ethyl ether (2.5 mL) and the mixture was left at room temperature overnight. The mixture was concentrated in vacuo. The residue was triturated with ethyl ether. The resulting solid was filtered, washed with ethyl ether and dried in vacuo to give 0.41 g (66%) of [(1S)-3,3-dimethylcyclohexyl]amine hydrochloride as a white solid. $^1$H NMR (400 MHz, DMSO-d$_6$) delta ppm: 0.89 (s, 3H); 0.93 (s, 3H); 1.00-1.17 (m, 3H); 1.33 (br d, 1H); 1.38-1.49 (br q, 1H); 1.58-1.63 (m, 2H); 1.92 (br d, 1H); 3.06-3.14 (m, 1H); 7.86 (s, 3H).

Step 4: [(1R)-3,3-dimethylcyclohexyl]amine Hydrochloride

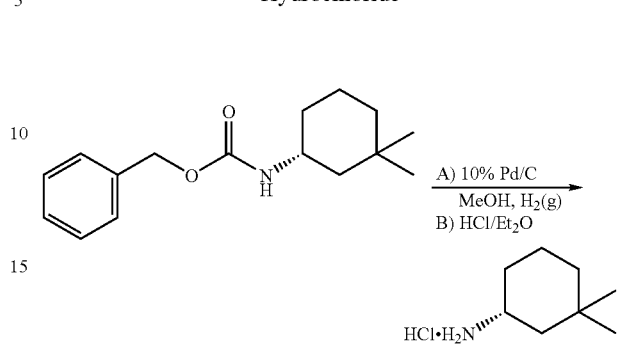

Phenylmethyl[(1R)-3,3-dimethylcyclohexyl]carbamate (1.0 g, 0.004 mol) and 10% Pd/C (0.15 g) in 10 mL of MeOH was placed under a balloon of H$_2$ for 20 hours. The catalyst was removed by filtration through Celite®. To the filtrate was added 1N HCl in ethyl ether (3.0 mL) and the mixture was concentrated in vacuo. The residue was triturated with ethyl ether containing 1N ethereal hydrogen chloride (0.5 mL). The resulting solid was filtered, washed with ethyl ether and dried in vacuo to give 0.56 g (90%) of [(1R)-3,3-dimethylcyclohexyl]amine hydrochloride as a white solid. $^1$H NMR (400 MHz, DMSO-d$_6$) delta ppm: 0.85 (s, 3H); 0.90 (s, 3H); 0.96-1.14 (m, 3H); 1.29 (br d, 1H); 1.35-1.45 (br q, 1H); 1.53-1.61 (m, 2H); 1.89 (br d, 1H); 3.02-3.09 (m, 1H); 7.88 (s, 3H).

Test Methods

LC-MS Method A (Standard Electrospray Method): Mass Spectrometry is used to confirm peak identity with electrospray+/−ionization scanning from 100-1000 m/z and DAD from 220-400 nm. Phenomenex Luna column 4.6 mm by 2 cm, particle size 3 um, ambient temperature. Solvent flow at 2 ml/min. Gradient begins at 10% MeOH and goes linearly to 100% MeOH in 3 minutes, holds 100% MeOH for 1 minute, making total chromatogram time 4 minutes. 2 ul sample injection. Aqueous mobile phase contains 0.1% v/v Formic Acid and MeOH contains 0.075% v/v Formic Acid.

LC-MS Method B (Standard APCI Method): Mass Spectrometry is used to confirm peak identity with APCI+/−ionization scanning from 100-1000 m/z and DAD from 220-400 nm. Phenomenex Luna column 4.6 mm by 2 cm, particle size 3 um, ambient temperature. Solvent flow at 2 ml/min. Gradient begins at 10% MeOH and goes linearly to 100% MeOH in 3 minutes, holds 100% MeOH for 1 minute, making total chromatogram time 4 minutes. 2 ul sample injection. Aqueous mobile phase contains 0.1% v/v Formic Acid and MeOH contains 0.075% v/v Formic Acid.

LC-MS Method C (Polar Electrospray Method): Mass Spectrometry is used to confirm peak identity with electrospray+/−ionization scanning from 100-1000 m/z with DAD from 220-400 nm. Phenomenex Luna column 4.6 mm by 2 cm, particle size 3 um, ambient temperature. Solvent flow at 2 ml/min. Gradient begins at 2% MeOH and goes linearly to 26% MeOH in 1 minute. Gradient then changes linearly from 26% to 100% from time 1 minute to time 3 minutes, holds 100% MeOH for 1 minute, making total chromatogram time 4 minutes. 2 ul sample injection. Aqueous mobile phase contains 0.1% v/v Formic Acid and MeOH contains 0.075% v/v Formic Acid.

LC-MS Method D (Basic Electrospray Method): Mass Spectrometry is used to confirm peak identity with electrospray+/−ionization scanning from 100-1000 m/z with DAD from 220-400 nm. Phenomenex Luna column 4.6 mm by 2 cm, particle size 3 um, ambient temperature. Solvent flow at 2 ml/min. Gradient begins at 10% MeOH and goes linearly to 100% MeOH in 3 minutes, holds 100% MeOH for 1 minute, making total chromatogram time 4 minutes. 2 ul sample injection. Aqueous mobile phase contains 0.1% v/v Ammonium Hydroxide to pH 10, and MeOH contains no Ammonium Hydroxide.

LC-MS Method E (Polar APCI Method): Mass Spectrometry is used to confirm peak identity with APCI+/−ionization scanning from 100-1000 m/z and DAD from 220-400 nm. Phenomenex Luna column 4.6 mm by 2 cm, particle size 3 um, ambient temperature. Solvent flow at 2 ml/min. Gradient begins at 2% MeOH and goes linearly to 26% MeOH in 1 minute. Gradient then changes linearly from 26% to 100% from time 1 minute to time 3 minutes, holds 100% MeOH for 1 minute, making total chromatogram time 4 minutes. 2 ul sample injection. Aqueous mobile phase contains 0.1% v/v Formic Acid and MeOH contains 0.075% v/v Formic Acid.

LC-MS Method F (Standard Electrospray Fast Mass Spec Method): Electrospray+ionization scanning from 100-800 m/z with DAD sum from 220-400 nm. Waters Acquity UPLC column 2.1 mm by 5 cm, particle size 1.7 um, temperature at 40 degrees C. Solvent flow at 1 ml/min. Gradient begins at 6% ACN and goes linearly to 70% ACN in 0.57 minute; gradient then goes linearly to 99% ACN from 0.57 minute to 1.06 minute, holds 99% ACN until 1.5 minute, making total chromatogram time 1.5 minutes. 1.5 ul sample injection. Aqueous mobile phase contains 0.1% v/v Formic Acid and ACN contains trace v/v Formic Acid.

The compounds of this invention have functional antagonist activity at least one of the opioid receptors with a $pIC_{50} > 5$ (10 micromolar).

| Ex. | Structure | Name and Characterization Data | Method/Comments |
|---|---|---|---|
| 1 | 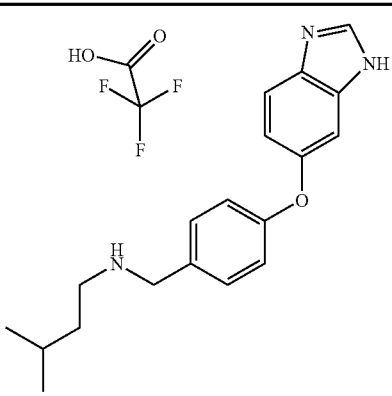 | N-{[4-(1H-benzimidazol-5-yloxy)phenyl]methyl}-3-methyl-1-butanamine trifluoroacetate<br>$^1$H NMR(400 MHz, DMSO-D6) Delta ppm 0.86(d, J = 6.6 Hz, 6 H) 1.47(m, 2 H) 1.59 (m, 1 H) 2.91(m, 2 H) 4.11(m, 2 H) 7.05 (d, J = 8.5 Hz, 2 H) 7.10(dd, J = 8.8, 2.2 Hz, 1 H) 7.33(d, J = 2.4 Hz, 1 H) 7.47(d, J = 8.8 Hz, 2 H) 7.75(d, J = 8.8 Hz, 1 H) 8.66(m, 2 H) 8.89(s, 1 H)<br>(M + 1) 310.2, 1.06 min (LC/MS method B) | Method 1<br>Note 1 |
| 2 | 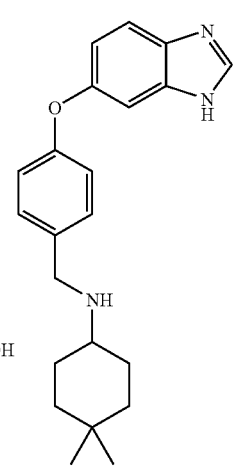 | N-{[4-(1H-benzimidazol-5-yloxy)phenyl]methyl}-4,4-dimethylcyclohexanamine trifluoroacetate<br>$^1$H NMR(400 MHz, DMSO-D6) Delta ppm 0.88(m, 6 H) 1.18(m, 2 H) 1.46(m, 4 H) 1.89(m, 2 H) 2.95(m, 1 H) 4.13(m, 2 H) 7.07(m, 3 H) 7.32(d, J = 2.2 Hz, 1 H) 7.48 (d, J = 8.5 Hz, 2 H) 7.73(d, J = 9.0 Hz, 1 H) 8.61(m, 2 H) 8.85(s, 1 H)<br>(M + 1) 350.3, 1.31 min(LC/MS method B) | Method 1<br>Note 1 |

| Ex. | Structure | Name and Characterization Data | Method/ Comments |
|---|---|---|---|
| 3 | 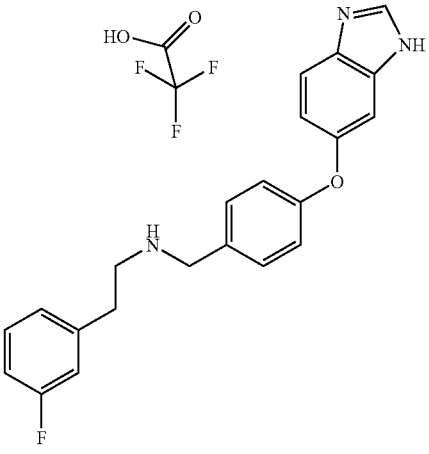 | N-{[4-(1H-benzimidazol-5-yloxy)phenyl]methyl}-2-(3-fluorophenyl)ethanamine trifluoroacetate<br>$^1$H NMR(400 MHz, DMSO-D6) Delta ppm 2.94(m, 2 H) 3.18(m, 2 H) 4.15(m, 2 H) 7.10(m, 6 H) 7.37(m, 2 H) 7.48(d, J = 8.8 Hz, 2 H) 7.78(d, J = 8.8 Hz, 1 H) 8.90(m, 2 H) 9.04(s, 1 H)<br>(M + 1) 362.2, 1.14 min(LC/MS method B) | Method 1 |
| 4 | 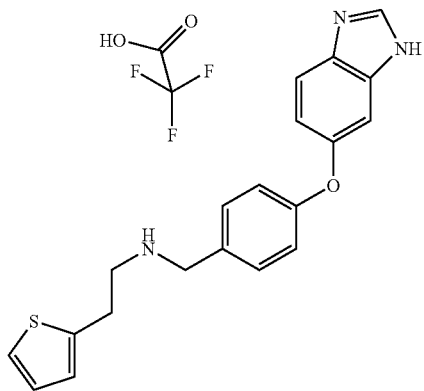 | N-{[4-(1H-benzimidazol-5-yloxy)phenyl]methyl}-2-(2-thienyl)ethanamine trifluoroacetate<br>$^1$H NMR(400 MHz, DMSO-D6) Delta ppm 3.16(m, 4 H) 4.16(m, 2 H) 6.95(m, 1 H) 6.98(m, 1 H) 7.06(d, J = 8.5 Hz, 2 H) 7.11(dd, J = 8.8, 2.2 Hz, 1 H) 7.34(d, J = 2.2 Hz, 1 H) 7.41(dd, J = 5.1, 1.2 Hz, 1 H) 7.48(d, J = 8.8 Hz, 2 H) 7.75(d, J = 8.8 Hz, 1 H) 8.91(m, 3 H)<br>(M + 1) 350.2, 0.98 min(LC/MS method B) | Method 1 |
| 5 | 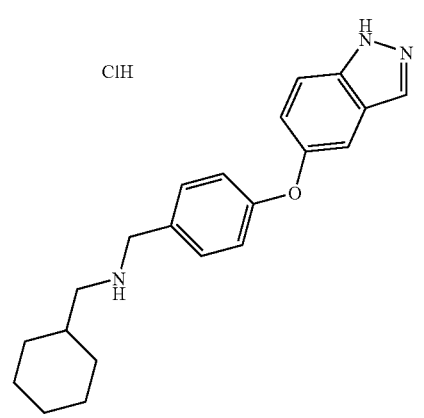 | (cyclohexylmethyl){[4-(1H-indazol-5-yloxy)phenyl]methyl}amine hydrochloride<br>$^1$H NMR(400 MHz, DMSO-d$_6$) Delta ppm 0.84-0.95(m, 2 H) 1.09-1.23(m, 3 H) 1.54-1.75(m, 6 H) 2.67-2.74(m, 2 H) 4.06(t, J = 5.9, 5.4 Hz, 3 H) 6.97(d, J = 8.5 Hz, 2 H) 7.09(dd, J = 9.3, 2.7 Hz, 1 H) 7.37(d, J = 2.2 Hz, 1 H) 7.47(d, J = 8.5 Hz, 2 H) 7.58(d, J = 9.3 Hz, 1 H) 8.02(m, 1 H) 8.76(brs, 2 H)<br>(M + 1) 336.3, 1.79 min(LC/MS method 2) | Method 2 |

-continued

| Ex. | Structure | Name and Characterization Data | Method/ Comments |
|---|---|---|---|
| 6 | 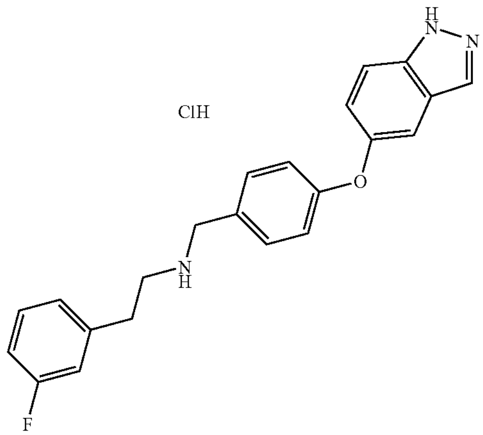 | [2-(3-fluorophenyl)ethyl]{[4-(1H-indazol-5-yloxy)phenyl]methyl}amine hydrochloride<br>¹H NMR(400 MHz, DMSO-d$_6$) Delta ppm 2.94-2.99(m, 2 H) 3.11-3.18(m, 2 H) 4.11(s, 2 H) 6.98(d, J = 8.5 Hz, 2 H) 7.05-7.13(m, 4 H) 7.33-7.39(m, 2 H) 7.47 (d, J = 8.5 Hz, 2 H) 7.58(d, J = 8.8 Hz, 1 H) 8.01(s, 1 H) 9.03(brs, 2 H) 13.15(s, 1 H)<br>(M + 1) 362.3, 1.74 min(LC/MS method A) | Method 2 |
| 7 | 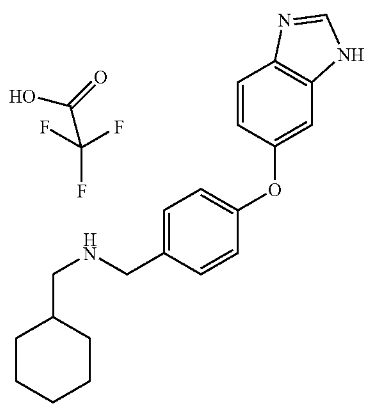 | {[4-(1H-benzimidazol-5-yloxy)phenyl]methyl}(cyclohexylmethyl)amine trifluoroacetate<br>1H NMR(400 MHz, DMSO-d$_6$) Delta ppm 0.91(m, 2 H) 1.16(m, 3 H) 1.65(m, 6 H) 2.74(m, 2 H) 4.10(m, 2 H) 7.05(d, J = 8.7 Hz, 2 H) 7.11(dd, J = 8.7, 2.1 Hz, 1 H) 7.33(d, J = 2.3 Hz, 1 H) 7.48(d, J = 8.6 Hz, 2 H) 7.75(d, J = 8.9 Hz, 1 H) 8.63(brs, 2 H) 8.91(s, 1 H)<br>(M + 1) 336.3, 1.12 min(LC/MS method A) | Method 1 Note 1 |
| 8 | 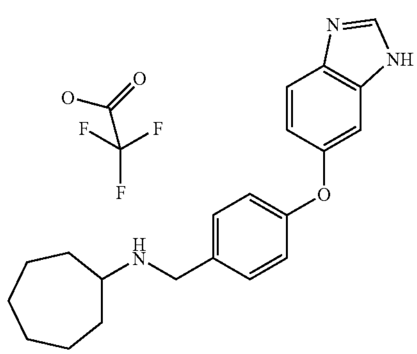 | N-{[4-(1H-benzimidazol-5-yloxy)phenyl]methyl}cycloheptanamine trifluoroacetate<br>1H NMR(400 MHz, DMSO-d$_6$) Delta ppm 1.49(m, 8 H) 1.68(m, 2 H) 2.06(m, 2 H) 3.16(m, 1 H) 4.13(m, 2 H) 7.06(d, J = 8.7 Hz, 2 H) 7.09(dd, J = 8.9, 2.3 Hz, 1 H) 7.32(d, J = 2.0 Hz, 1 H) 7.49(d, J = 8.9 Hz, 2 H) 7.75(d, J = 8.9 Hz, 1 H) 8.58(brs, 2 H) 8.88(s, 1 H)<br>(M + 1) 336.3, 1.09 min(LC/MS method A) | Method 1 Note 2 |
| 9 | 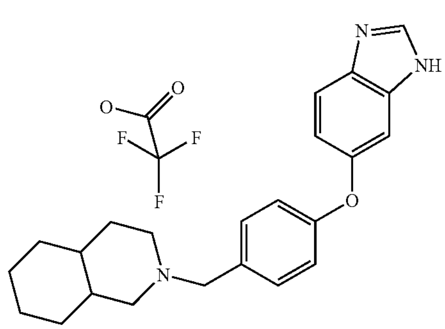 | 2-{[4-(1H-benzimidazol--yloxy)phenyl]methyl}decahydroisoquinoline trifluoroacetate<br>1H NMR(400 MHz, DMSO-d$_6$) Delta ppm 1.22(m, 3 H) 1.56(m, 6 H) 1.94(m, 2 H) 2.93(m, 2 H) 3.11(m, 1 H) 3.22(m, 1 H) 3.33(m, 1 H) 4.26(m, 2 H) 7.07(d, J = 8.7 Hz, 2 H) 7.16(dd, J = 8.7, 2.1 Hz, 1 H) 7.39(m, 1 H) 7.48(m, 2 H) 7.77(d, J = 8.9 Hz, 1 H) 8.98(s, 1 H) 9.32(brs, 1 H)<br>(M + 1) 362.3, 1.12 min(LC/MS method A) | Method 1 |

-continued

| Ex. | Structure | Name and Characterization Data | Method/Comments |
|---|---|---|---|
| 10 | 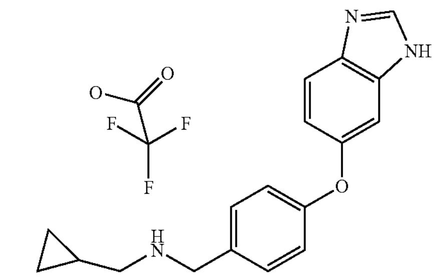 | {[4-(1H-benzimidazol-5-yloxy)phenyl]methyl}(cyclopropylmethyl)amine trifluoroacetate<br>1H NMR(400 MHz, DMSO-$d_6$) Delta ppm 0.33(m, 2 H) 0.57(m, 2 H) 1.02(m, 1 H) 2.81(m, 2 H) 4.12(m, 2 H) 7.05(d, J = 8.7 Hz, 2 H) 7.10(dd, J = 8.7, 2.3 Hz, 1 H) 7.33(d, J = 2.3 Hz, 1 H) 7.48(d, J = 8.6 Hz, 2 H) 7.74(d, J = 8.7 Hz, 1 H) 8.80(brs, 2 H) 8.87(s, 1 H)<br>(M + 1) 294.2, 1.05 min (LC/MS method C) | Method 1 |
| 11 | 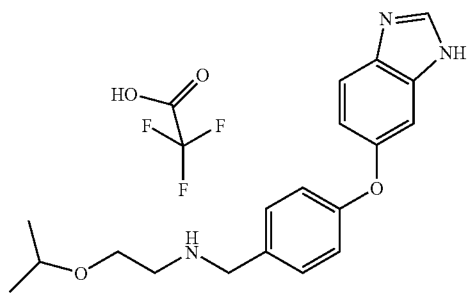 | N{[4-(1H-benzimidazol-5-yloxy)phenyl]methyl}-2-[(1-methylethyl)oxy]ethanamine trifluoroacetate<br>1H NMR(400 MHz, DMSO-$d_6$) Delta ppm 1.10(d, J = 6.1 Hz, 6 H) 3.04(m, 2 H) 3.58 (m, 3 H) 4.13(m, 2 H) 7.05(d, J = 8.6 Hz, 2 H) 7.10(dd, J = 8.7, 2.3 Hz, 1 H) 7.33(d, J = 2.3 Hz, 1 H) 7.48(d, J = 8.6 Hz, 2 H) 7.75(d, J = 8.7 Hz, 1 H) 8.77(brs, 2 H) 8.90(s, 1 H)<br>(M + 1) 326.2, 0.82 min(LC/MS method A) | Method 1 |
| 12 | 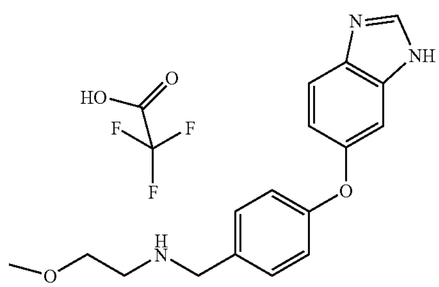 | N-{[4-(1H-benzimidazol-5-yloxy)phenyl]methyl}-2-(methyloxy)ethanamine trifluoroacetate<br>1H NMR(400 MHz, DMSO-$d_6$) Delta ppm 3.07(m, 2 H) 3.28(s, 3 H) 3.56(m, 2 H) 4.12(m, 2 H) 7.05(d, J = 8.7 Hz, 2 H) 7.12 (dd, J = 8.7, 2.3 Hz, 1 H) 7.35(d, J = 2.1 Hz, 1 H) 7.49(d, J = 8.7 Hz, 2 H) 7.76(d, J = 8.7 Hz, 1 H) 8.88(brs, 2 H) 8.97(s, 1 H)<br>(M + 1) 298.2, 0.95 min(LC/MS method C) | Method 1 |
| 13 | 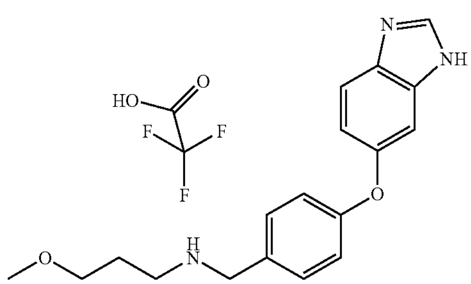 | N-{[4-(1H-benzimidazol-5-yloxy)phenyl]methyl}-3-(methyloxy)-1-propanamine trifluoroacetate<br>1H NMR(400 MHz, DMSO-$d_6$) Delta ppm 1.83(m, 2 H) 2.95(m, 2 H) 3.21(s, 3 H) 3.36(t, J = 5.9 Hz, 2 H) 4.12(m, 2 H) 7.06 (d, J = 8.7 Hz, 2 H) 7.11(dd, J = 8.9, 2.3 Hz, 1 H) 7.34(d, J = 2.0 Hz, 1 H) 7.47(d, J = 8.7 Hz, 2 H) 7.75(d, J = 8.7 Hz, 1 H) 8.69(brs, 2 H) 8.91(s, 1 H)<br>(M + 1) 312.2, 1.07 min (LC/MS method C) | Method 1 |
| 14 | 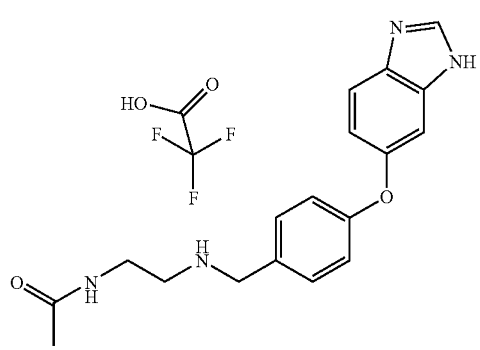 | N-[2-({[4-(1H-benzimidazol-5-yloxy)phenyl]methyl}amino)ethyl]acetamide trifluoroacetate<br>1H NMR(400 MHz, DMSO-$d_6$) Delta ppm 1.82(s, 3 H) 2.95(m, 2 H) 3.32(m, 2 H) 4.13(m, 2 H) 7.06(d, J = 8.6 Hz, 2 H) 7.12 (dd, J = 8.9, 2.3 Hz, 1 H) 7.34(d, J = 1.8 Hz, 1 H) 7.48(d, J = 8.7 Hz, 2 H) 7.76(d, J = 8.6 Hz, 1 H) 8.08(dt, J = 5.9 Hz, 1 H) 8.74(brs, 2 H) 8.96(s, 1 H)<br>(M + 1) 325.2, 0.93 min (LC/MS method C) | Method 1 |

| Ex. | Structure | Name and Characterization Data | Method/Comments |
|---|---|---|---|
| 15 | 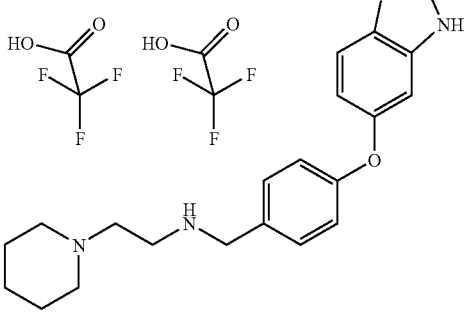 | N-{[4-(1H-benzimidazol-5-yloxy)phenyl]methyl}-2-(1-piperidinyl)ethanamine bis(trifluoroacetate)<br>1H NMR(400 MHz, DMSO-$d_6$) Delta ppm 1.51(m, 4 H) 1.81(m, 2 H) 2.95(m, 2 H) 3.34(m, 4 H) 3.45(m, 2 H) 4.17(m, 2 H) 7.06(m, 3 H) 7.33(d, J = 2.3 Hz, 1 H) 7.47 (d, J = 8.6 Hz, 2 H) 7.74(d, J = 8.9 Hz, 1 H) 8.81(brs, 1 H) 9.07(brs, 2 H) 9.39(s, 1 H)<br>(M + 1) 351.2, 1.84 min(LC/MS method D) | Method 1 |
| 16 | 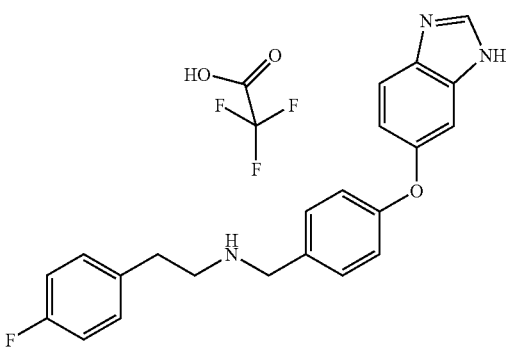 | N-{[4-(1H-benzimidazol-5-yloxy)phenyl]methyl}-2-(4-fluorophenyl)ethanamine trifluoroacetate<br>1H NMR(400 MHz, DMSO-$d_6$) Delta ppm 2.91(m, 2 H) 3.14(m, 2 H) 4.15(m, 2 H) 7.06(d, J = 8.7 Hz, 2 H) 7.10(dd, J = 8.9, 2.3 Hz, 1 H) 7.16(m, 2 H) 7.28(m, 2 H) 7.33(d, J = 2.1 Hz, 1 H) 7.48(d, J = 8.7 Hz, 2 H) 7.74(d, J = 8.9 Hz, 1 H) 8.87(m, 3 H)<br>(M + 1) 362.2, 1.14 min(LC/MS method A) | Method 1<br>Note 3 |
| 17 | 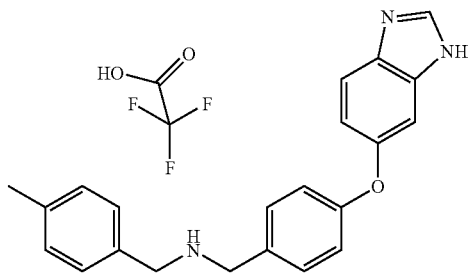 | {[4-(1H-benzimidazol-5-yloxy)phenyl]methyl}[(4-methylphenyl)methyl]amine trifluoroacetate<br>1H NMR(400 MHz, DMSO-$d_6$) Delta ppm 2.30(s, 3 H) 4.11(m, 4 H) 7.05(d, J = 8.7 Hz, 2 H) 7.11(dd, J = 8.7, 2.3 Hz, 1 H) 7.24(d, J = 7.8 Hz, 2 H) 7.34(m, 3 H) 7.47 (d, J = 8.7 Hz, 2 H) 7.75(d, J = 8.7 Hz, 1 H) 8.91(s, 1 H) 9.14(brs, 2 H)<br>(M + 1) 344.2, 1.18 min(LC/MS method A) | Method 1 |
| 18 | 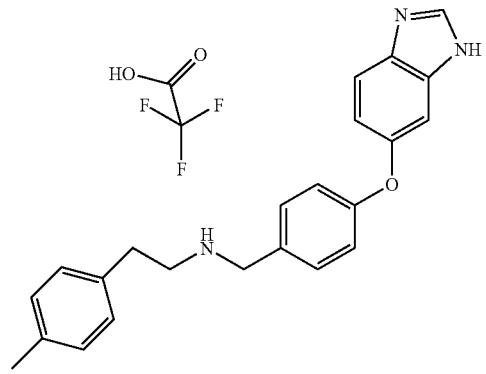 | N-{[4-(1H-benzimidazol-5-yloxy)phenyl]methyl}-2-(4-methylphenyl)ethanamine trifluoroacetate<br>1H NMR(400 MHz, DMSO-$d_6$) Delta ppm 2.26(s, 3 H) 2.86(m, 2 H) 3.11(m, 2 H) 4.14(m, 2 H) 7.05(d, J = 8.7 Hz, 2 H) 7.11 (m, 5 H) 7.32(d, J = 2.1 Hz, 1 H) 7.47(d, J = 8.7 Hz, 2 H) 7.73(d, J = 8.7 Hz, 1 H) 8.80(brs, 3 H)<br>(M + 1) 358.2, 1.29 min(LC/MS method A) | Method 1 |

| Ex. | Structure | Name and Characterization Data | Method/ Comments |
|---|---|---|---|
| 19 | 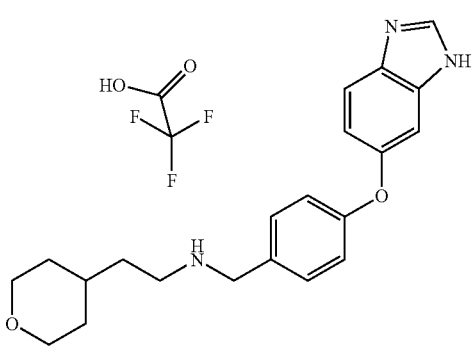 | N-{[4-(1H-benzimidazol-5-yloxy)phenyl]methyl}-2-(tetrahydro-2H-pyran-4-yl)ethanamine trifluoroacetate<br>1H NMR(400 MHz, DMSO-$d_6$) Delta ppm 1.13(m, 2 H) 1.53(m, 5 H) 2.94(m, 2 H) 3.24(m, 2 H) 3.81(dd, J = 11.2, 3.7 Hz, 2 H) 4.11(m, 2 H) 7.06(d, J = 8.6 Hz, 2 H) 7.11(dd, J = 8.9, 2.3 Hz, 1 H) 7.34(d, J = 2.3 Hz, 1 H) 7.47(d, J = 8.7 Hz, 2 H) 7.76(d, J = 8.9 Hz, 1 H) 8.70(brs, 2 H) 8.95(s, 1 H)<br>(M + 1) 352.2, 0.82 min(LC/MS method A) | Method 1 |
| 20 | 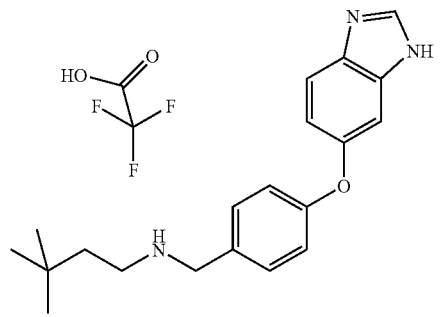 | N-{[4-(1H-benzimidazol-5-yloxy)phenyl]methyl}-3,3-dimethyl-1-butanamine trifluoroacetate<br>1H NMR(400 MHz, DMSO-$d_6$) Delta ppm 0.87(s, 9 H) 1.49(m, 2 H) 2.93(m, 2 H) 4.12(m, 2 H) 7.05(m, 3 H) 7.30(d, J = 2.1 Hz, 1 H) 7.47(d, J = 8.6 Hz, 2 H) 7.72(d, J = 8.7 Hz, 1 H) 8.60(brs, 2 H) 8.77(brs, 1 H)<br>(M + 1) 324.3, 1.14 min(LC/MS method A) | Method 1 |
| 21 | 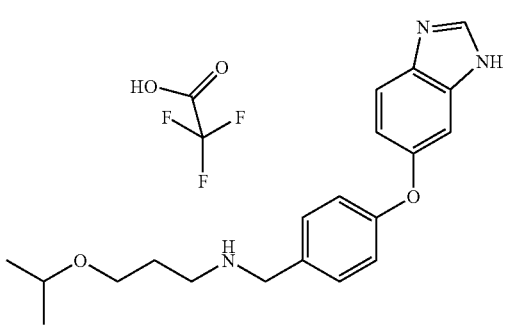 | N-{[4-(1H-benzimidazol-5-yloxy)phenyl]methyl}-3-[(1-methylethyl)oxy]-1-propanamine trifluoroacetate<br>1H NMR(400 MHz, DMSO-$d_6$) Delta ppm 1.05(d, J = 6.1 Hz, 6 H) 1.79(m, 2 H) 2.95 (m, 2 H) 3.39(m, 2 H) 3.50(m, 1 H) 4.13 (m, 2 H) 7.06(d, J = 8.7 Hz, 2 H) 7.11(dd, J = 8.7, 2.3 Hz, 1 H) 7.34(d, J = 2.3 Hz, 1 H) 7.47(d, J = 8.7 Hz, 2 H) 7.76(d, J = 8.7 Hz, 1 H) 8.69(brs, 2 H) 8.94(s, 1 H)<br>(M + 1) 340.2, 0.94 min(LC/MS method A) | Method 1 |
| 22 | 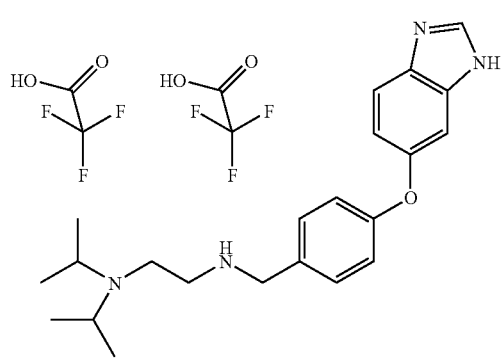 | N-{[4-(1H-benzimidazol-5-yloxy)phenyl]methyl}-N,N-bis(1-methylethyl)-1,2-ethanediamine bis(trifluoroacetate)<br>1H NMR(400 MHz, DMSO-$d_6$) Delta ppm 1.25(m, 12 H) 3.27(m, 4 H) 3.68(m, 2 H) 4.22(m, 2 H) 7.06(m, 3 H) 7.32(d, J = 2.1 Hz, 1 H) 7.47(d, J = 8.7 Hz, 2 H) 7.72(d, J = 9.1 Hz, 1 H) 8.76(brs, 1 H) 9.09(brs, 3 H)<br>(M + 1) 367.3, 0.55 min(LC/MS method C) | Method 1 |

| Ex. | Structure | Name and Characterization Data | Method/Comments |
|---|---|---|---|
| 23 | 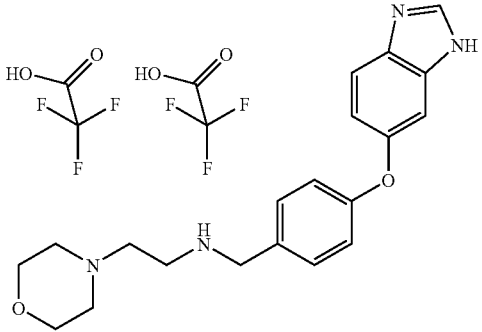 | N-{[4-(1H-benzimidazol-5-yloxy)phenyl]methyl}-2-(4-morpholinyl)ethanamine bis(trifluoroacetate)<br>1H NMR(400 MHz, DMSO-$d_6$) Delta ppm 2.95(m, 6 H) 3.22(m, 2 H) 3.71(m, 4 H) 4.16(brs, 2 H) 7.07(d, J = 8.8 Hz, 2 H) 7.13(dd, J = 8.8, 2.2 Hz, 1 H) 7.36(d, J = 2.2 Hz, 1 H) 7.49(d, J = 8.8 Hz, 2 H) 7.78(d, J = 8.8 Hz, 1 H) 9.02(s, 1 H)<br>(M + 1) 353.1, 0.1.36 min(LC/MS method D) | Method 1 |
| 24 | 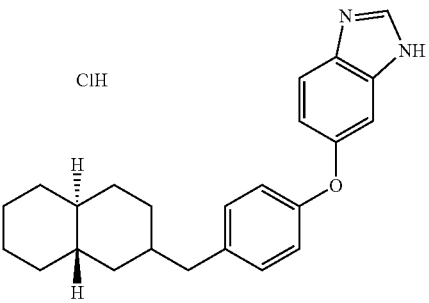 | (4aS,8aR)-2-{4-(1H-benzimidazol-5-yloxy)phenyl]methyl}decahydroisoquinoline hydrochloride<br>1H NMR(400 MHz, DMSO-$d_6$) delta ppm 0.89(m, 2 H) 1.16(m, 3 H) 1.59(m, 7 H) 2.56(m, 1 H) 2.85(m, 1 H) 3.09(m, 1 H) 3.28(m, 1 H) 4.20(d, J = 5.1 Hz, 2 H) 7.09 (d, J = 8.1 Hz, 2 H) 7.30(m, 1 H) 7.43(m, 1 H) 7.63(d, J = 8.5 Hz, 2 H) 7.87(d, J = 9.0 Hz, 1 H) 9.49(m, 1 H)<br>(M + 1) 262.1, 1.23 min(LC/MS method B) | Method 1<br>Note 4 |
| 25 | 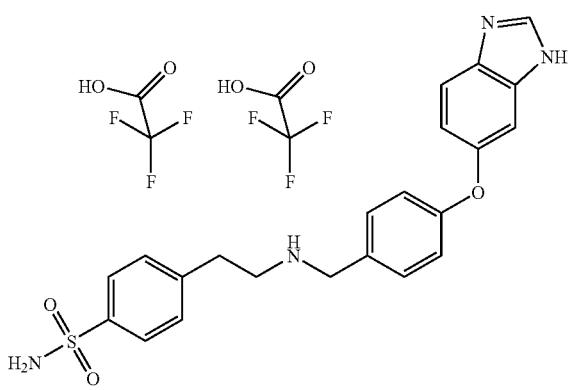 | 4-[2-({[4-(1H-benzimidazol-5-yloxy)phenyl]methyl}amino)ethyl]benzenesulfonamide bis(trifluoroacetate)<br>1H NMR(400 MHz, DMSO-$d_6$) delta ppm 3.00(m, 2 H) 3.20(m, 2 H) 4.16(m, 2 H) 7.06(d, J = 8.7 Hz, 2 H) 7.10(dd, J = 8.7, 2.3 Hz, 1 H) 7.34(m, 3 H) 7.43(d, J = 8.4 Hz, 2 H) 7.48(d, J = 8.7 Hz, 2 H) 7.76(m, 3 H) 8.91(m, 2 H)<br>(M + 1) 423.1, 0.84 min(LC/MS method E) | Method 1 |
| 26 | 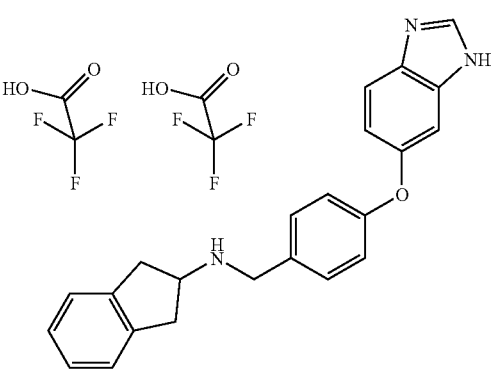 | N-{[4-(1H-benzimidazol-5-yloxy)phenyl]methyl}-2,3-dihydro-1H-inden-2-amine bis(trifluoroacetate)<br>1H NMR(400 MHz, DMSO-$d_6$) delta ppm 3.11(m, 2 H) 3.32(m, 2 H) 4.05(m, 1 H) 4.21(m, 2 H) 7.08(m, 3 H) 7.20(m, 2 H) 7.26(m, 2 H) 7.32(d, J = 2.1 Hz, 1 H) 7.53 (d, J = 8.7 Hz, 2 H) 7.74(d, J = 8.7 Hz, 1 H) 8.85(m, 1 H) 9.10(m, 2 H)<br>(M + 1) 356.2, 1.04 min(LC/MS method B) | Method 1<br>Method 4 |

-continued

| Ex. | Structure | Name and Characterization Data | Method/Comments |
|---|---|---|---|
| 27 | 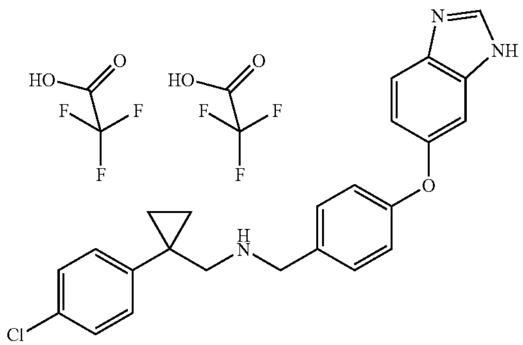 | {[4-(1H-5-benzimidazol-5-yloxy)phenyl]methyl}{[1-(4-chlorophenyl)cyclopropyl]methyl}amine bis(trifluoroacetate)<br>1H NMR(400 MHz, DMSO-$d_6$) delta ppm 0.96(m, 4 H) 4.05(m, 2 H) 7.03(d, J = 8.7 Hz, 2 H) 7.12(dd, J = 8.7, 2.3 Hz, 1 H) 7.34(d, J = 1.8 Hz, 1 H) 7.38(m, 3 H) 7.42 (d, J = 8.7 Hz, 2 H) 7.77(d, J = 8.7 Hz, 1 H) 8.72(br. s., 2 H) 9.01(m, 1 H)<br>(M + 1) 404.1, 1.45 min(LC/MS method B) | Method 1 |
| 28 | 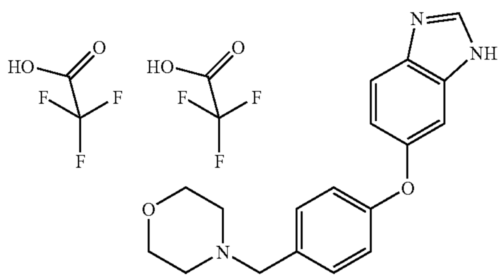 | 5-{[4-(4-morpholinylmethyl)phenyl]oxy}-1H-benzimidazole bis(trifluoroacetate)<br>1H NMR(400 MHz, DMSO-$d_6$) delta ppm 3.16(m, 6 H) 3.62(m, 2 H) 3.94(m, 2 H) 7.08(d, J = 8.7 Hz, 2 H) 7.17(dd, J = 8.7, 2.3 Hz, 1 H) 7.39(d, J = 2.0 Hz, 1 H) 7.49 (d, J = 8.7 Hz, 2 H) 7.79(d, J = 8.9 Hz, 1 H) 9.04(m, 1 H)<br>(M + 1) 310.1, 0.96 min(LC/MS method E) | Method 1 |
| 29 | 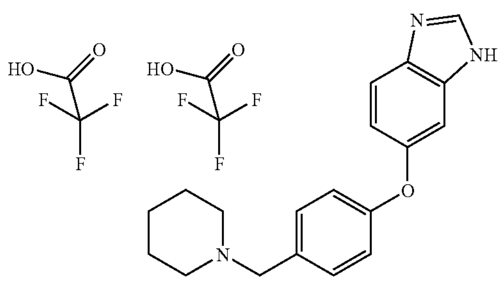 | 5-{[4-(1-piperidinylmethyl)phenyl]oxy}-1H-benzimidazole bis(trifluoroacetate)<br>1H NMR(400 MHz, DMSO-$d_6$) delta ppm 1.33(m, 1 H) 1.62(m, 3 H) 1.80(m, 2 H) 2.83(m, 2 H) 3.31(m, 2 H) 4.24(m, 2 H) 7.07(d, J = 8.7 Hz, 2 H) 7.18(dd, J = 8.7, 2.1 Hz, 1 H) 7.41(d, J = 2.3 Hz, 1 H) 7.48 (d, J = 8.7 Hz, 2 H) 7.79(d, J = 8.9 Hz, 1 H) 9.08(m, 1 H) 9.42(br. s., 1 H)<br>(M + 1) 308.1, 1.03 min(LC/MS method E) | Method 1 |
| 30 | 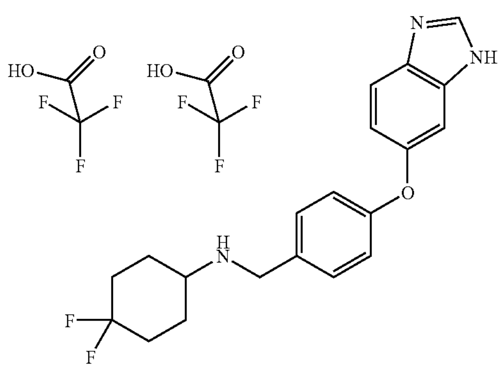 | N-{[4-(1H-benzimidazol-5-yloxy)phenyl]methyl}-4,4-difluorocyclohexanamine bis(trifluoroacetate)<br>1H NMR(400 MHz, DMSO-$d_6$) delta ppm 1.61(m, 2 H) 1.91(m, 2 H) 2.12(m, 3 H) 3.23(m, 2 H) 4.16(m, 2 H) 7.06(d, J = 8.6 Hz, 3 H) 7.31(d, J = 2.1 Hz, 1 H) 7.49(d, J = 8.7 Hz, 2 H) 7.72(d, J = 8.7 Hz, 1 H) 8.77(m, 2 H)<br>(M + 1) 358.0, 0.68 min(LC/MS method E) | Method 1 |
| 31 | 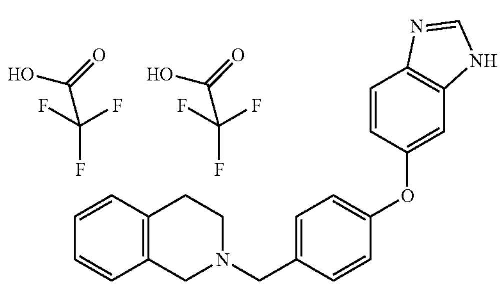 | 2-{[4-(1H-benzimidazol-5-yloxy)phenyl]methyl}-1,2,3,4-tetrahydroisoquinoline bis(trifluoroacetate)<br>1H NMR(400 MHz, DMSO-$d_6$) delta ppm 3.09(m, 2 H) 3.34(m, 1 H) 3.65(m, 1 H) 4.34(m, 2 H) 4.45(m, 2 H) 7.11(d, J = 8.7 Hz, 5 H) 7.24(m, 5 H) 7.43(d, J = 2.3 Hz, 1 H) 7.55(d, J = 8.7 Hz, 2 H) 7.81(d, J = 8.9 Hz, 1 H) 9.12(m, 1 H)<br>(M + 1) 356.0, 0.89 min(LC/MS method B) | Method 1 |

-continued

| Ex. | Structure | Name and Characterization Data | Method/Comments |
|---|---|---|---|
| 32 | 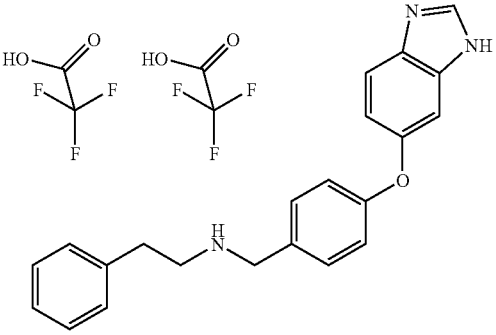 | N-{[4-(1H-benzimidazol-5-yloxy)phenyl]methyl}-2-phenylethanamine bis(trifluoroacetate)<br>1H NMR(400 MHz, DMSO-$d_6$) delta ppm 2.92(m, 2 H) 3.14(m, 2 H) 4.15(m, 2 H) 7.07(m, 3 H) 7.24(m, 3 H) 7.33(m, 3 H) 7.48(d, J = 8.7 Hz, 2 H) 7.74(d, J = 8.9 Hz, 1 H) 8.86(m, 3 H)<br>(M + 1) 344.1, 1.00 min(LC/MS method B) | Method 1 |
| 33 | 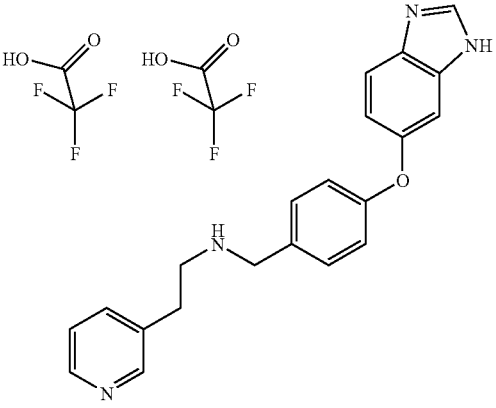 | N-{[4-(1H-benzimidazol-5-yloxy)phenyl]methyl}-2-(3-pyridinyl)ethanamine bis(trifluoroacetate)<br>1H NMR(400 MHz, DMSO-$d_6$) delta ppm 2.99(m, 2 H) 3.22(m, 2 H) 4.16(m, 2 H) 7.07(m, 2 H) 7.15(m, 1 H) 7.36(m, 1 H) 7.49(m, 3 H) 7.78(m, 1 H) 7.84(m, 1 H) 8.54(m, 2 H) 8.90(m, 2 H) 9.06(br. s., 1 H) | Method 1 |
| 34 | 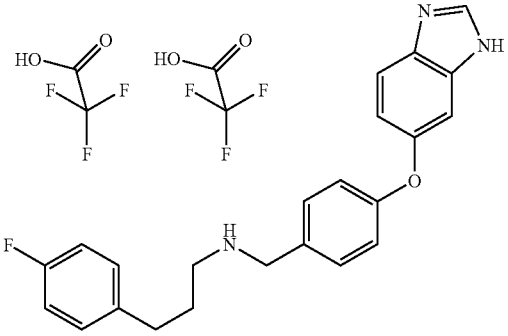 | N-{[4-(1H-benzimidazol-5-yloxy)phenyl]methyl}-3-(4-fluorophenyl)-1-propanamine bis(trifluoroacetate)<br>1H NMR(400 MHz, DMSO-$d_6$) delta ppm 1.87(m, 2 H) 2.62(m, 2 H) 2.88(m, 2 H) 4.11(m, 2 H) 7.05(m, 2 H) 7.11(m, 3 H) 7.22(m, 2 H) 7.34(d, J = 2.3 Hz, 1 H) 7.46 (d, J = 8.7 Hz, 2 H) 7.76(d, J = 8.9 Hz, 1 H) 8.72(m, 2 H) 8.93(m, 1 H)<br>(M + 1) 376.1, 1.24 min(LC/MS method B) | Method 1 |
| 35 | 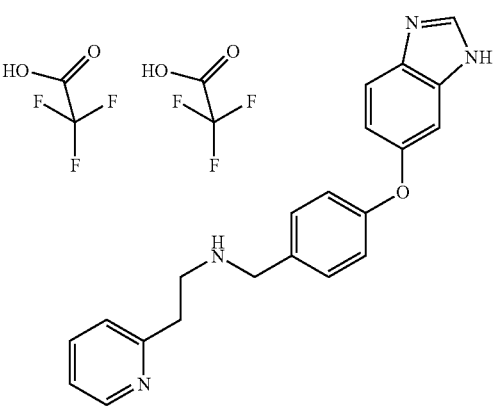 | N-{[4-(1H-benzimidazol-5-yloxy)phenyl]methyl}-2-(2-pyridinyl)ethanamine bis(trifluoroacetate)<br>1H NMR(400 MHz, DMSO-$d_6$) delta ppm 3.12(m, 2 H) 3.31(m, 2 H) 4.20(m, 2 H) 7.08(d, J = 8.4 Hz, 2 H) 7.19(m, 1 H) 7.32 (m, 2 H) 7.39(m, 1 H) 7.51(d, J = 8.4 Hz, 2 H) 7.80(m, 2 H) 8.51(d, J = 4.5 Hz, 1 H) 8.95(br. s., 2 H) 9.20(m, 1 H)<br>(M + 1) 345.2, 0.99 min(LC/MS method E) | Method 1 |

| Ex. | Structure | Name and Characterization Data | Method/Comments |
|---|---|---|---|
| 36 | 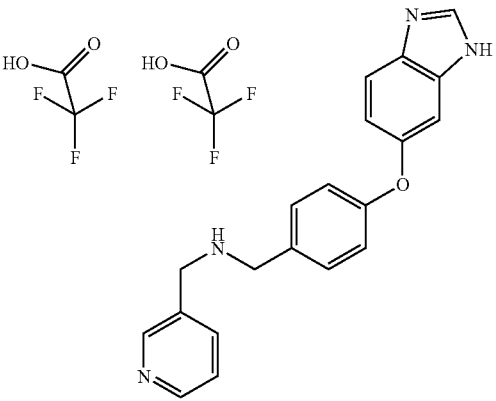 | {[4-(1H-benzimidazol-5-yloxy)phenyl]methyl}(3-pyridinylmethyl)amine bis(trifluoroacetate)<br>1H NMR(400 MHz, DMSO-d$_6$) delta ppm 4.22(m, 4 H) 7.08(d, J = 8.4 Hz, 2 H) 7.18 (d, J = 8.6 Hz, 1 H) 7.38(m, 1 H) 7.49(m, 3 H) 7.81(d, J = 8.9 Hz, 1 H) 7.93(d, J = 7.7 Hz, 1 H) 8.61(d, J = 4.8 Hz, 1 H) 8.67(m, 1 H) 9.20(m, 1 H) 9.29(br. s., 2 H).<br>(M + 1) 331.2, 0.81 min(LC/MS method E) | Method 1 |
| 37 | 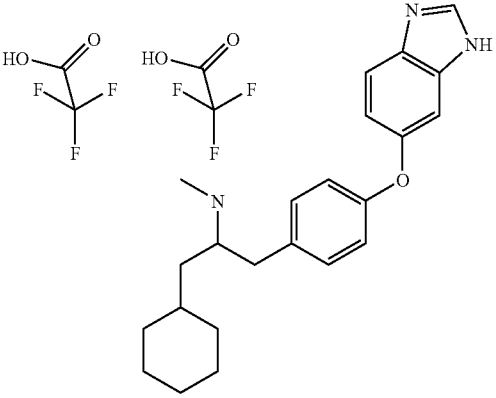 | N-{[4-(1H-benzimidazol-5-yloxy)phenyl]methyl}-N-(cyclohexylmethyl)ethanamine bis(trifluoroacetate)<br>1H NMR(400 MHz, DMSO-d$_6$) delta ppm 0.86(m, 2 H) 1.12(m, 2 H) 1.24(t, J = 7.1 Hz, 3 H) 1.65(m, 6 H) 2.83(m, 2 H) 3.09 (m, 2 H) 4.29(m, 2 H) 7.08(d, J = 8.7 Hz, 2 H) 7.15(dd, J = 8.9, 2.3 Hz, 1 H) 7.39(d, J = 2.3 Hz, 1 H) 7.52(d, J = 8.9 Hz, 2 H) 7.78(d, J = 8.7 Hz, 1 H) 8.92(br. s., 1 H) 9.02(m, 1 H)<br>(M + 1) 364.1, 1.23 min(LC/MS method B) | Method 1 |
| 38 | 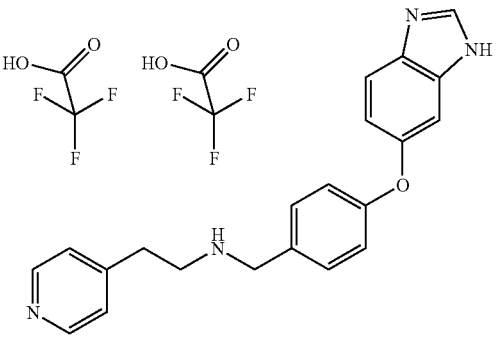 | N-{[4-(1H-benzimidazol-5-yloxy)phenyl]methyl}-2-(4-pyridinyl)ethanamine bis(trifluoroacetate)<br>1H NMR(400 MHz, DMSO-d$_6$) delta ppm 3.03-3.10(m, 2 H) 3.22-3.32(m, 2 H) 4.14-4.21(m, 2 H) 7.08(d, J = 8.74 Hz, 2 H) 7.17(dd, J = 8.74, 2.14 Hz, 1 H) 7.38 (d, J = 2.32 Hz, 1 H) 7.49(d, J = 8.74 Hz, 2 H) 7.54(d, J = 6.24 Hz, 2 H) 7.80(d, J = 8.92 Hz, 1 H) 8.65(d, J = 6.24 Hz, 2 H) 8.99(br. s., 2 H) 9.13(s, 1 H)<br>(M + 1) 345.1, 0.56 min(LC/MS method C) | Method 1 |
| 39 | 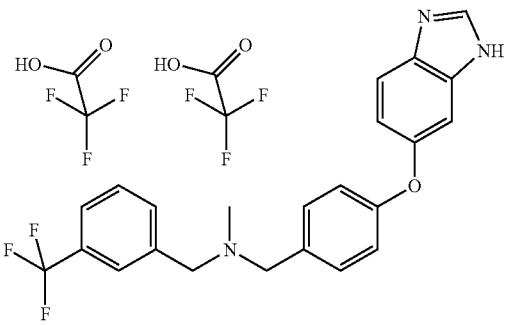 | {[4-(1H-benzimidazol-5-yloxy)phenyl]methyl}methyl{[3-(trifluoromethyl)phenyl]methyl}amine bis(trifluoroacetate)<br>1H NMR(400 MHz, DMSO-d$_6$) delta ppm 2.53(s, 3 H) 4.19-4.37(m, 2 H) 4.38-4.61(m, 2 H) 7.07(d, J = 8.74 Hz, 2 H) 7.14(dd, J = 8.92, 2.32 Hz, 1 H) 7.39(d, J = 2.32 Hz, 1 H) 7.51(d, J = 8.74 Hz, 2 H) 7.67-7.73(m, 1 H) 7.77(d, J = 8.92 Hz, 1 H) 7.79-7.85(m, 2 H) 7.91-7.95(m, 1 H) 8.97(br. s., 1 H)<br>(M + 1) 412.1, 1.27 min(LC/MS method B) | Method 1 |

| Ex. | Structure | Name and Characterization Data | Method/ Comments |
|---|---|---|---|
| 40 | 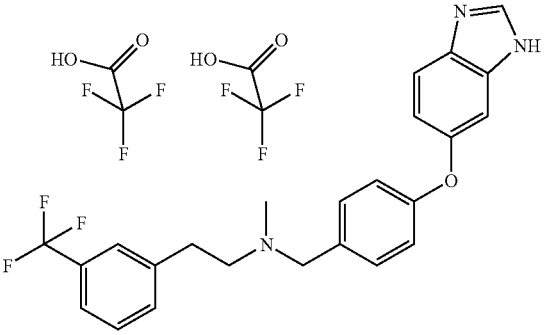 | N-{[4-(1H-benzimidazol-5-yloxy)phenyl]methyl}-N-methyl-2-[3-(trifluoromethyl)phenyl]ethanamine bis(trifluoroacetate) 1H NMR(400 MHz, DMSO-$d_6$) delta ppm 2.73(s., 3 H) 3.07-3.19(m, 6 H) 3.24-3.46(m, 2 H) 4.17-4.51(m, 2 H) 7.08(d, J = 8.74 Hz, 2 H) 7.15(dd, J = 8.92, 2.32 Hz, 1 H) 7.39(d, J = 2.32 Hz, 1 H) 7.52(d, J = 8.74 Hz, 2 H) 7.57-7.65(m, 3 H) 7.66-7.69(m, 1 H) 7.77(d, J = 8.74 Hz, 1 H) 8.97(s., 1 H) 9.78(br. s., 1 H) (M + 1) 426.1, 1.39 min(LC/MS method B) | Method 1 |
| 41 | 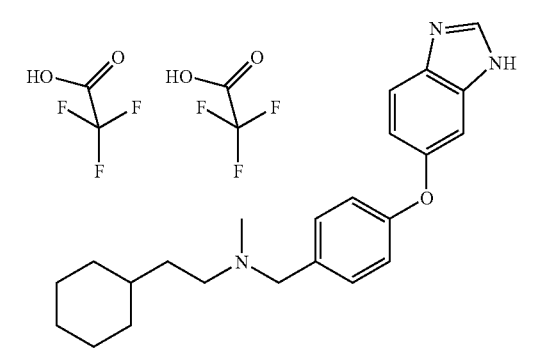 | N-{[4-(1H-benzimidazol-5-yloxy)phenyl]methyl}-2-cyclohexyl-N-methylethanamine bis(trifluoroacetate) 1H NMR(400 MHz, DMSO-$d_6$) delta ppm 0.82-0.95(m, 3 H) 1.06-1.30(m, 5 H) 1.49-1.68(m, 7 H) 2.63(d, J = 4.46 Hz, 3 H) 2.91-3.04(m, 2 H) 3.06-3.16(m, 2 H) 4.11-4.39(m, 2 H) 7.06(d, J = 8.74 Hz, 2 H) 7.12(dd, J = 8.74, 2.32 Hz, 1 H) 7.37(d, J = 1.96 Hz, 1 H) 7.48(d, J = 8.74 Hz, 2 H) 7.75(d, J = 8.74 Hz, 1 H) 8.89(br. s., 1 H) 9.39(br. s, 1 H) (M + 1) 364.2, 1.37 min (LC/MS method B) | Method 1 |
| 42 | 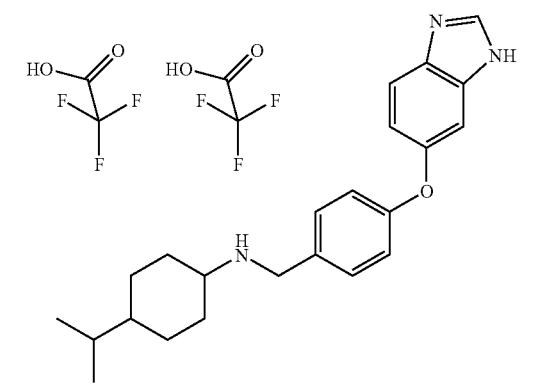 | N-{[4-(1H-benzimidazol-5-yloxy)phenyl]methyl}-4-(1-methylethyl)cyclohexanamine bis(trifluoroacetate) 1H NMR(400 MHz, DMSO-$d_6$) delta ppm 0.82(s., 6 H) 0.92-1.04(m, 3 H) 1.24-1.34(m, 2 H) 1.35-1.45(m, 1 H) 1.71-1.80(m, 2 H) 2.08-2.16(m, 2 H) 2.89-3.01(m, 2 H) 4.09-4.16(m, 2 H) 7.02-7.09(m, 3 H) 7.31(d, J = 2.32 Hz, 1 H) 7.47(d, J = 8.74 Hz, 2 H) 7.73(d, J = 8.92 Hz, 1 H) 8.61(br.s., 2 H) 8.80(br. s., 1 H (M + 1) 364.1, 1.47 min(LC/MS method B) | Method 1 |
| 43 | 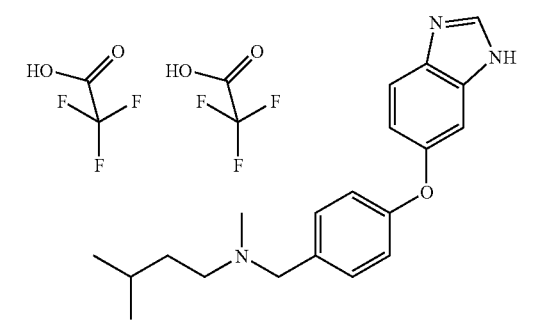 | N-{[4-(1H-benzimidazol-5-yloxy)phenyl]methyl}-N,3-dimethyl-1-butanamine bis(trifluoroacetate) 1H NMR(400 MHz, DMSO-$d_6$) delta ppm 0.83-0.90(m, 6 H) 1.49-1.61(m, 3 H) 2.64(d, J = 3.92 Hz, 3 H) 2.93-3.14(m, 2 H) 4.13-4.39(m, 2 H) 7.08(d, J = 8.74 Hz, 2 H) 7.17(dd, J = 8.74, 2.32 Hz, 2 H) 7.39(d, J = 1.78 Hz, 1 H) 7.50(d, J = 8.74 Hz, 2 H) 7.79(d, J = 8.92 Hz, 1 H) 9.05(s., 1 H) 9.51(br. s., 1 H) (M + 1) 324.1, 0.9 min(LC/MS method B) | Method 1 |

| Ex. | Structure | Name and Characterization Data | Method/Comments |
|---|---|---|---|
| 44 | 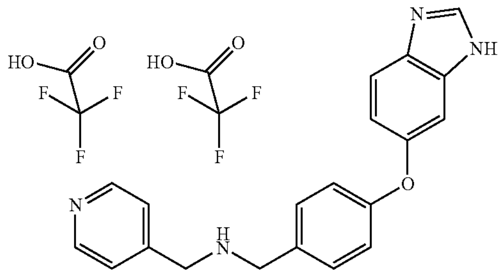 | {[4-(1H-benzimidazol-5-yloxy)phenyl]methyl}(4-pyridinylmethyl)amine bis(trifluoroacetate)<br>1H NMR(400 MHz, DMSO-$d_6$) delta ppm 4.18-4.24(m, 2 H) 4.24-4.31(m, 2 H) 7.05(d, J = 8.76 Hz, 2 H) 7.14(d, J = 9.10 Hz, 1 H) 7.35(s., 1 H) 7.40-7.45(m, 1 H) 7.46(d, J = 7.90 Hz, 1 H) 7.51(d, J = 8.41 Hz, 2 H) 7.77(d, J = 8.93 Hz, 1 H) 7.84-7.91(m, 1 H) 8.63(d, J = 4.46 Hz, 1 H) 9.01(s., 1 H) 9.41(br. s., 2 H)<br>(M + 1) 331.1, 0.69 min(LC/MS method E) | Method 1 |
| 45 | 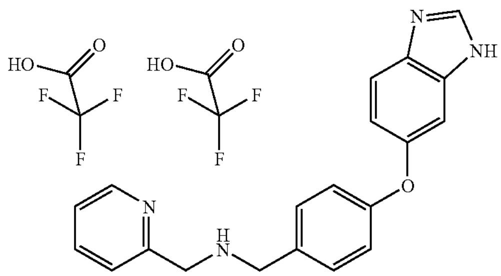 | {[4-(1H-benzimidazol-5-yloxy)phenyl]methyl}(2-pyridinylmethyl)amine bis(trifluoroacetate)<br>1H NMR(400 MHz, DMSO-$d_6$) delta ppm 4.18-4.22(m, 2 H) 4.22-4.28(m, 2 H) 7.07(d, J = 8.76 Hz, 2 H) 7.17(dd, J = 8.93, 2.40 Hz, 1 H) 7.37(d, J = 2.23 Hz, 1 H) 7.46-7.54(m, 4 H) 7.80(d, J = 8.76 Hz, 1 H) 8.63-8.68(m, 2 H) 9.13(s., 1 H) 9.37 (br. s., 2 H)<br>(M + 1) 331.0, 1.13 min(LC/MS method E) | Method 1 |
| 46 | 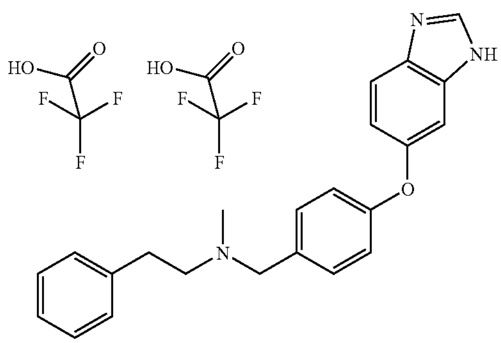 | N-{[4-(1H-benzimidazol-5-yloxy)phenyl]methyl}-N-methyl-2-phenylethanamine bis(trifluoroacetate)<br>1H NMR(400 MHz, DMSO-$d_6$) delta ppm 2.73(s., 3 H) 2.92-3.10(m, 2 H) 3.16-3.40(m, 2 H) 4.18-4.48(m, 2 H) 7.08(d, J = 8.41 Hz, 2 H) 7.15-7.19(m, 1 H) 7.21-7.28 (m, 3 H) 7.29-7.36(m, 2 H) 7.39-7.42 (m, 1 H) 7.52(d, J = 8.58 Hz, 2 H) 7.78(d, J = 8.93 Hz, 1 H) 9.04(s., 1 H) 9.78(br. s., 1 H)<br>(M + 1) 358.1, 104 min(LC/MS method B) | Method 1 |
| 47 | 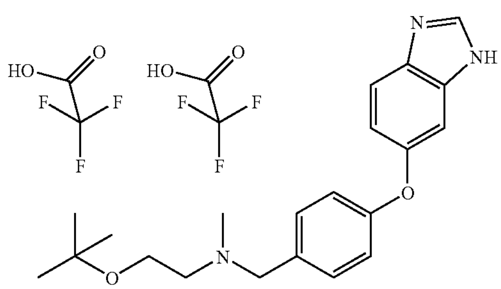 | N-{[4-(1H-benzimidazol-5-yloxy)phenyl]methyl}-2-[(1,1-dimethylethyl)oxy]-N-methylethanamine bis(trifluoroacetate)<br>1H NMR(400 MHz, DMSO-$d_6$) delta ppm 1.14(s, 9 H) 2.71(s., 3 H) 3.05-3.26(m, 2 H) 3.58-3.66(m, 2 H) 4.19-4.38(m, 2 H) 7.07(d, J = 8.58 Hz, 2 H) 7.11-7.17 (m, 1 H) 7.36-7.39(m, 1 H) 7.50(d, J = 8.41 Hz, 2 H) 7.77(d, J = 8.93 Hz, 1 H) 8.96(s., 1 H) 9.34(br. s., 1 H)<br>(M + 1) 354.1, 1.00 min(LC/MS method B) | Method 1 |
| 48 | 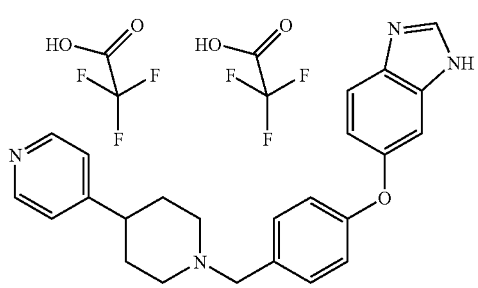 | 5-[(4-{[4-(4-pyridinyl)-1-piperidinyl]methyl}phenyl)oxy]-1H-benzimidaozle bis(trifluoroacetate)<br>1H NMR(400 MHz, DMSO-$d_6$) delta ppm 1.78-1.93(m, 2 H) 2.02-2.11(m, 2 H) 2.92-3.10(m, 3 H) 3.49(d, J = 12.02 Hz, 2 H) 4.30-4.36(m, 2 H) 7.09(d, J = 8.58 Hz, 2 H) 7.20(d, J = 9.10 Hz, 1 H) 7.43(s., 1 H) 7.50-7.56(m, 4 H) 7.80(d, J = 8.93 Hz, 1 H) 8.66(d, J = 5.49 Hz, 2 H) 9.11(s., 1 H) 9.68(br. s., 1 H) | Method 1 |

| Ex. | Structure | Name and Characterization Data | Method/Comments |
|---|---|---|---|
| 49 | 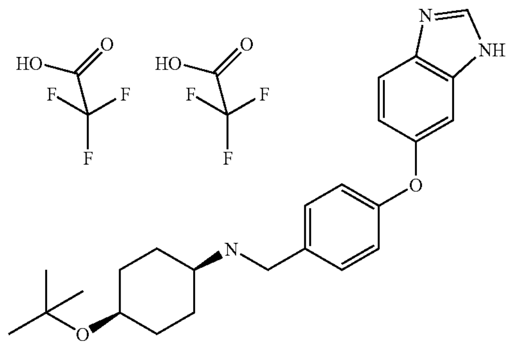 | N-{[4-(1H-benzimidazol-5-yloxy)phenyl]methyl}-4-[(1,1-dimethylethyl)oxy]-Nmethylcyclohexanamine bis(trifluoroacetate)(Cis isomer)<br>1H NMR(400 MHz, DMSO-$d_6$) delta ppm 0.95-1.18(m, 3 H) 1.48-1.59(m, 1 H) 1.68-1.76(m, 4 H) 2.70-2.78(m, 2 H) 3.26-3.37(m, 1 H) 4.07-4.12(m, 2 H) 7.05(d, J = 6.67 Hz, 2 H) 7.12(dd, J = 8.81, 2.26 Hz, 1 H) 7.35(d, J = 1.76 Hz, 1 H) 7.48(d, J = 8.81 Hz, 2 H) 7.77(d, J = 8.93 Hz, 1 H) 8.65(br. s., 2 H) 8.98(s., 1 H)<br>(M + 1) 408.1, 1.42 min(LC/MS method B) | Method 1 |
| 50 | 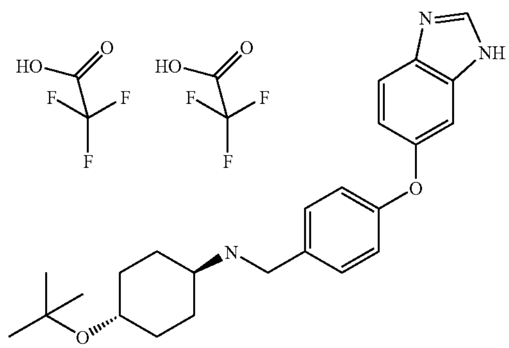 | N-{[4-(1H-benzimidazol-5-yloxy)phenyl]methyl}-4-[(1,1-dimethylethyl)oxy]-N-methylcyclohexanamine bis(trifluoroacetate)(Trans isomer)<br>1H NMR(400 MHz, DMSO-$d_6$) delta ppm 1.09(s., 9 H) 1.29-1.51(m, 7 H) 1.64-1.73(m, 1 H) 2.76-2.83(m, 2 H) 3.62-3.68(m, 1 H) 4.08-4.13(m, 2 H) 7.06(d, J = 8.81 Hz, 2 H) 7.13(dd J = 8.81, 2.26 Hz, 1 H) 7.36(d, J = 1.89 Hz, 1 H) 7.49(d, J = 8.81 Hz, 2 H) 7.77(d, J = 8.81 Hz, 1 H) 8.65(br. s., 2 H) 9.01(s., 1 H)<br>(M + 1) 408.1, 1.51 min(LC/MS method B) | Method 1 |
| 51 | 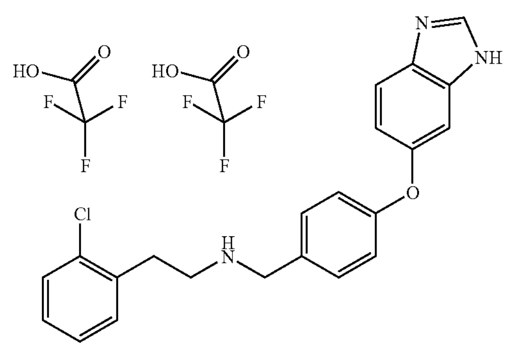 | N-{[4-(1H-benzimidazol-5-yloxy)phenyl]methyl}-2-(2-chlorophenyl)ethanamine bis(trifluoroacetate)<br>1H NMR(400 MHz, DMSO-$d_6$) delta ppm 3.01-3.09(m, 2 H) 3.09-3.18(m, 2 H) 4.15-4.21(m, 2 H) 7.03-7.11(m, 3 H) 7.28-7.38(m, 4 H) 7.44-7.52(m, 3 H) 7.73(d, J = 8.55 Hz, 1 H) 8.82(br. s., 1 H) 8.93(br. s., 2 H)<br>(M + 1) 377.9, 1.27 min(LC/MS method B) | Method 1 |
| 52 | 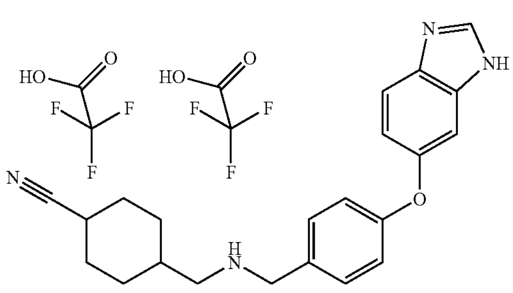 | 4-[({[4-(1H-benzimidazol-5-yloxy)phenyl]methyl}amino)methyl]cyclohexanecarbonitrile bis(trifluoroacetate)(mixture of Cis and Trans)<br>1H NMR(400 MHz, DMSO-$d_6$) delta ppm 0.74(m, 0.5 H) 0.93(m, 0.5 H) 1.41(m, 1 H) 1.65(m, 2 H) 1.92(m, 0.5 H) 2.73(m, 0.5 H) 2.83(m, 0.5 H) 3.05(m, 0.5 H) 3.47(m, 0.5 H) 3.48(m, 0.5 H) 4.23(m, 1 H) 4.44(m, 1 H) 7.06(m, 2 H) 7.16(d, J = 9.3 Hz, 1 H) 7.40(m, 1 H) 7.54(m, 2 H) 7.79(m, 1 H) 9.05(s., 1 H) 9.32(m, 0.5 H)<br>(M + 1) 361.1, 1.28 min(LC/MS method B) | Method 1 |

-continued

| Ex. | Structure | Name and Characterization Data | Method/Comments |
|---|---|---|---|
| 53 | 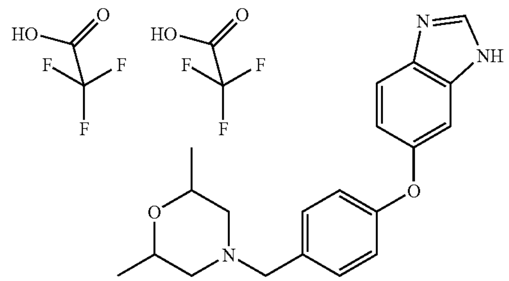 | 5-({4-[(2,6-dimethyl-4-morpholinyl)methyl]phenyl}oxy)-1H-benzimidazole bis(trifluoroacetate)<br>1H NMR(400 MHz, DMSO-$d_6$) delta ppm 1.10(d, J = 6.42 Hz, 6 H) 2.60-2.69(m, 2 H) 3.23-3.29(m, 2 H) 3.72-3.82(m, 2 H) 4.24-4.30(m, 2 H) 7.05-7.10(m, 2 H) 7.16-7.20(m, 1 H) 7.41(d, J = 2.32 Hz, 1 H) 7.46-7.53(m 2 H) 7.80(d, J = 8.74 Hz, 1 H) 9.05-9.11(m, 1 H)<br>(M + 1) 338, 1.21 min(LC/MS ethod B) | Method 1 |
| 54 | 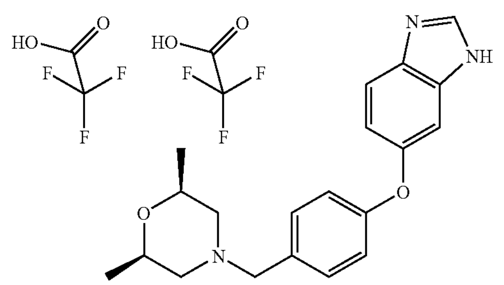 | 5-[(4-{[(2R,6S)-2,6-dimethyl-4-morpholinyl]methyl}phenyl)oxy]-1H-benzimidazole bis(trifluoroacetate)<br>1H NMR(400 MHz, DMSO-$d_6$) delta ppm 1.11(d, J = 6.24 Hz, 6 H) 2.60-2.69(m, 2 H) 3.26(d, J = 11.95 Hz, 2 H) 3.71-3.82 (m, 2 H) 4.27(s., 2 H) 7.07(d, J = 8.74 Hz, 2 H) 7.15(dd, J = 8.74, 2.14 Hz, 1 H) 7.39 (d, J = 1.78 Hz, 1 H) 7.48(d, J = 8.74 Hz, 2 H) 7.77(d, J = 8.92 Hz, 1 H) 8.97(s., 1 H)<br>(M + 1) 338.0, 1.05 min(LC/MS method B) | Method 1 |
| 55 | 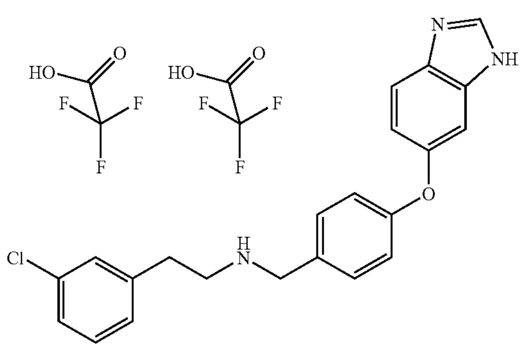 | N-{[4-(1H-benzimidazol-5-yloxy)phenyl]methyl}-2-(3-chlorophenyl)ethanamine bis(trifluoroacetate)<br>1H NMR(400 MHz, DMSO-$d_6$) delta ppm 2.90-2.97(m, 2 H) 3.13-3.22(m, 2 H) 4.11-4.19(m, 2 H) 7.06(d, J = 8.74 Hz, 2 H) 7.13(dd, J = 8.92, 2.32 Hz, 1 H) 7.19-7.24(m, 1 H) 7.29-7.39(m, 4 H) 7.48(d, J = 8.74 Hz, 2 H) 7.77(d, J = 8.74 Hz, 1 H) 8.92(br. s., 2 H) 8.98(s., 1 H)<br>(M + 1) 377.9, 1.28 min(LC/MS method B) | Method 1 |
| 56 | 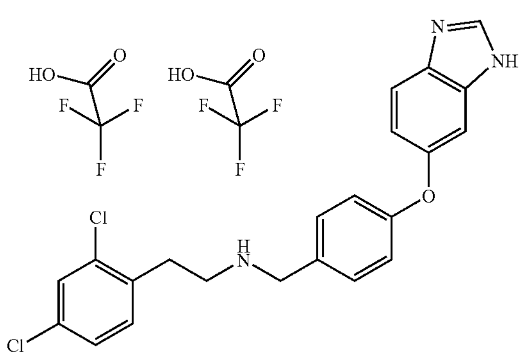 | N-{[4-(1H-benzimidazol-5-yloxy)phenyl]methyl}-2-(2,4-dichlorophenyl)ethanamine bis(trifluoroacetate)<br>1H NMR(400 MHz, DMSO-$d_6$) delta ppm 3.01-3.07(m, 2 H) 3.09-3.18(m, 2 H) 4.15-4.20(m, 2 H) 7.05(d, J = 8.74 Hz, 2 H) 7.08(dd, J = 8.56, 2.14 Hz, 1 H) 7.32 (d, J = 1.96 Hz, 1 H) 7.39(d, J = 8.20 Hz, 1 H) 7.43(dd J = 8.20, 1.96 Hz, 1 H) 7.49 (d, J = 8.74 Hz, 2 H) 7.64(d, J = 2.14 Hz, 1 H) 7.73(d, J = 8.74 Hz, 1 H) 8.83(br. s., 1 H) 8.91(br. s., 2 H)<br>(M + 1) 411.9, 1.51 min(LC/MS method B) | Method 1 |

| Ex. | Structure | Name and Characterization Data | Method/ Comments |
|---|---|---|---|
| 57 | 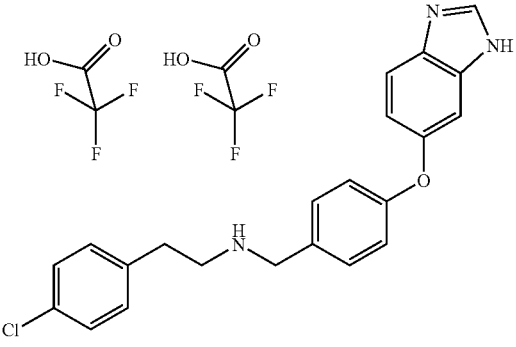 | N-{[4-(1H-benzimidazol-5-yloxy)phenyl]methyl}-2-(4-chlorophenyl)ethanamine bis(trifluoroacetate) 1H NMR(400 MHz, DMSO-$d_6$) delta ppm 2.88-2.94(m, 2 H) 3.10-3.19(m, 2 H) 4.11-4.17(m, 2 H) 7.05(d, J = 8.56 Hz, 2 H) 7.10(dd, J = 8.74, 2.32 Hz, 1 H) 7.27 (d, J = 8.38 Hz, 2 H) 7.33(d, J = 2.14 Hz, 1 H) 7.39(d, J = 8.38 Hz, 2 H) 7.47(d, J = 8.74 Hz, 2 H) 7.74(d, J = 8.92 Hz, 1 H) 8.81-8.91(m, 3 H) (M + 1) 377.9, 1.29 min(LC/MS method B) | Method 1 |
| 58 | 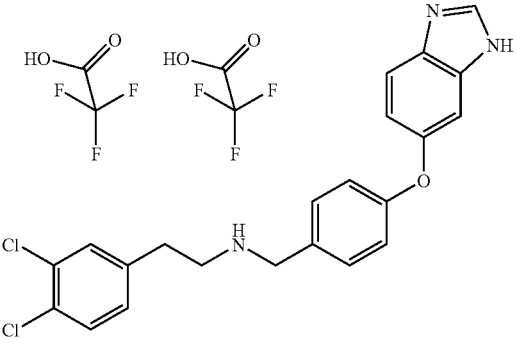 | N-{[4-(1H-benzimidazol-5-yloxy)phenyl]methyl}-2-(3,4-dichlorophenyl)ethanamine bis(trifluoroacetate) 1H NMR(400 MHz, DMSO-$d_6$) delta ppm 2.90-2.96(m, 2 H) 3.15-3.23(m, 2 H) 4.10-4.16(m, 2 H) 7.03-7.10(m, 3 H) 7.26(dd, J = 8.20, 1.96 Hz, 1 H) 7.32(d, J = 1.96 Hz, 1 H) 7.46(d, J = 8.74 Hz, 2 H) 7.57(d, J = 1.96 Hz, 1 H) 7.60(d, J = 8.20 Hz, 1 H) 7.73(d, J = 8.74 Hz, 1 H) 8.76-8.84 (m, 3 H) (M + 1) 411.9, 1.49 min(LC/MS method B) | Method 1 |
| 59 | 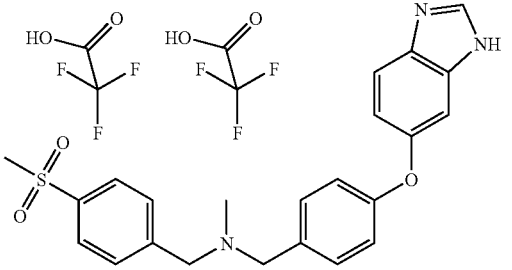 | {[4-(1H-benzimidazol-5-yloxy)phenyl]methyl}{[4-(methylsulfonyl)phenyl]methyl}amine bis(trifluoroacetate) 1H NMR(400 MHz, DMSO-$d_6$) delta ppm 3.14(s., 3 H) 3.24(s., 3 H) 4.18-4.53(m, 4 H) 7.06(d, J = 6.78 Hz, 2 H) 7.13(dd, J = 8.74, 2.32 Hz, 1 H) 7.37(d, J = 1.96 Hz, 1 H) 7.50(d, J = 8.74 Hz, 2 H) 7.74-7.80 (m, 3 H) 8.01(d, J = 8.56 Hz, 2 H) 8.91(br. s., 1 H) (M + 1) 421.9, 0.75 min(LC/MS method B) | Method 1 |
| 60 | 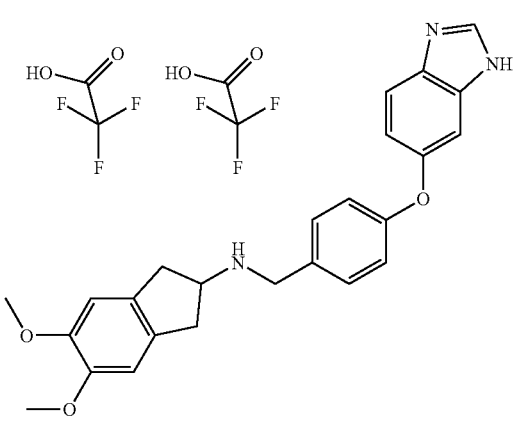 | N-{[4-(1H-benzimidazol-5-yloxy)phenyl]methyl}-5,6-bis(methyloxy)-2,3-dihydro-1H-inden-2-amine bis(trifluoroacetate) 1H NMR(400 MHz, DMSO-$d_6$) delta ppm 2.96-3.07(m, 2 H) 3.18-3.28(m, 2 H) 3.70(s., 6 H) 3.97-4.06(m, 1 H) 4.16-4.22 (m, 2 H) 6.85(s., 2 H) 7.04-7.12 (m, 3 H) 7.32(d, J = 1.95 Hz, 1 H) 7.52(d, J = 8.55 Hz, 2 H) 7.73(d, J = 8.55 Hz, 1 H) 8.85(s., 1 H) 9.07(br. s., 2 H) (M + 1) 416.1, 1.13 min(LC/MS method B) | Method 1 |

| Ex. | Structure | Name and Characterization Data | Method/ Comments |
|---|---|---|---|
| 61 | 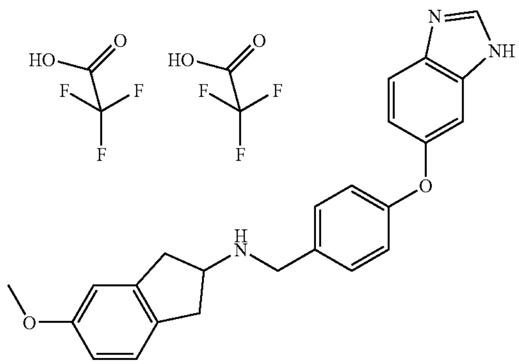 | N-{[4-(1H-benzimidazol-5-yloxy)phenyl]methyl}-5-(methyloxy)-2,3-dihydro-1H-inden-2-amine bis(trifluoroacetate)<br>1H NMR(400 MHz, DMSO-$d_6$) delta ppm 2.97-3.10(m, 2 H) 3.17-3.31(m, 2 H) 3.70(s., 3 H) 3.98-4.08(m, 1 H) 4.15-4.24(m, 2 H) 6.76(dd, J = 7.08, 2.44 Hz, 1 H) 6.83-6.85(m, 1 H) 7.03-7.11(m, 3 H) 7.15(d, J = 8.30 Hz, 1 H) 7.32(d, J = 1.71 Hz, 1 H) 7.52(d, J = 8.79 Hz, 2 H) 7.74(d, J = 8.55 Hz, 1 H) 8.84(s., 1 H) 9.08(br. s., 2 H)<br>(M + 1) 386.2, 1.23 min(LC/MS method B) | Method 1 |
| 62 | 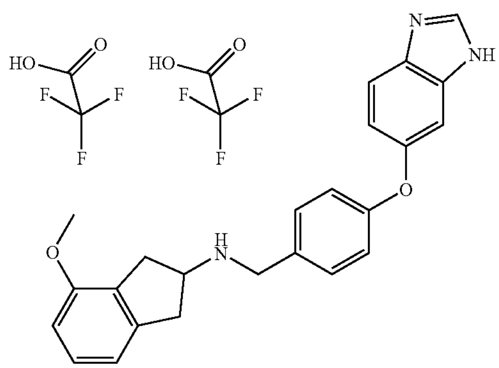 | N-{[4-(1H-benzimidazol-5-yloxy)phenyl]methyl}-4-(methyloxy)-2,3-dihydro-1H-inden-2-amine bis(trifluoroacetate)<br>1H NMR(400 MHz, DMSO-$d_6$) delta ppm 2.93-3.14(m, 2 H) 3.20-3.35(m, 2 H) 3.77(s., 3 H) 3.99-4.08(m, 1 H) 4.17-4.25(m, 2 H) 6.80-6.87(m, 2 H) 7.03-7.11(m, 3 H) 7.16-7.22(m, 1 H) 7.32(d, J = 1.22 Hz, 1 H) 7.53(d, J = 8.30 Hz, 2 H) 7.74(d, J = 8.79 Hz, 1 H) 8.86(s., 1 H) 9.08(br. s., 2 H)<br>(M + 1) 386.1, 1.25 min(LC/MS method B) | Method 1 |
| 63 | 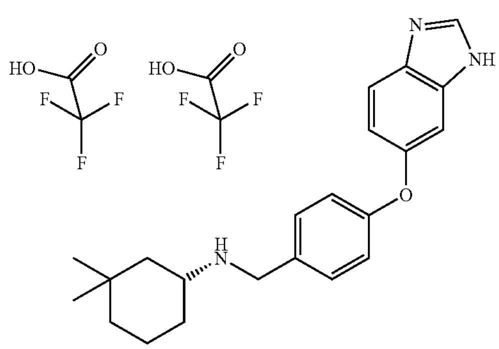 | {[4-(1H-benzimidazol-5-yloxy)phenyl]methyl}[(1R)-3,3-dimethylcyclohexyl]amine bis(trifluoroacetate)<br>1H NMR(400 MHz, DMSO-$d_6$) delta ppm 0.86(s., 3 H) 0.94(s., 3 H) 1.01-1.21(m, 3 H) 1.27-1.44(m, 2 H) 1.57-1.67(m, 1 H) 1.76-1.84(m, 1 H) 2.05-2.12(m, 1 H) 3.12-3.22(m, 1 ) 4.09-4.17(m, 2 H) 7.03-7.12(m, 3 H) 7.30-7.34(m, 1 H) 7.48(d, J = 8.30 Hz, 2 H) 7.74(d, J = 9.03 Hz, 1 H) 8.51-8.68(m, 2 H) 8.89 (s., 1 H)<br>(M + 1) 350.1, 1.32 min(LC/MS method B) | Method 1 |
| 64 | 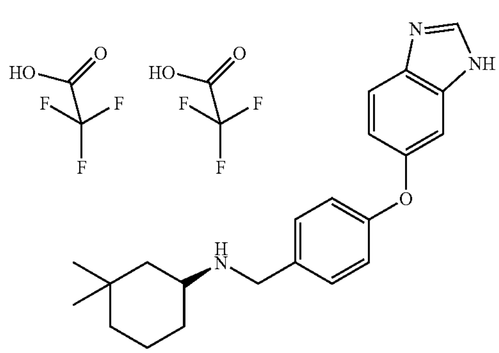 | {[4-(1H-benzimidazol-5-yloxy)phenyl]methyl}[(1S)-3,3-dimethylcyclohexyl]amine bis(trifluoroacetate)<br>1H NMR(400 MHz, DMSO-$d_6$) delta ppm 0.86(s., 3 H) 0.95(s., 3 H) 1.01-1.22(m, 3 H) 1.27-1.47(m, 2 H) 1.58-1.68(m, 1 H) 1.75-1.85(m, 1 H) 2.03-2.13(m, 1 H) 3.14-3.22(m, 1 H) 4.10-4.17(m, 2 H) 7.02-7.11(m, 3 H) 7.32(d, J = 2.20 Hz, 1 H) 7.49(d, J = 8.55 Hz, 2 H) 7.74(d, J = 8.79 Hz, 1 H) 8.48-8.66(m, 2 H) 8.86 (s., 1 H)<br>(M + 1) 350.2, 1.29 min(LC/MS method B) | Method 1 |

| Ex. | Structure | Name and Characterization Data | Method/Comments |
|---|---|---|---|
| 65 | 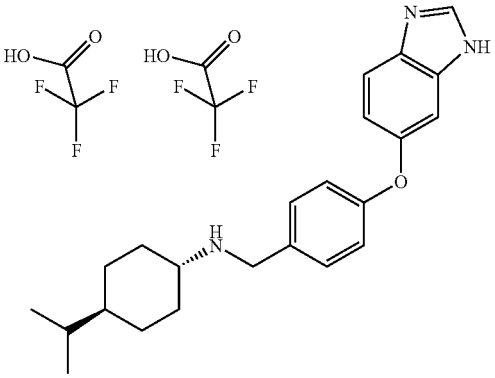 | trans-N-{[4-(1H-benzimidazol-5-yloxy)phenyl]methyl}-4-(1-methylethyl)cyclohexanamine bis(trifluoroacetate)<br>1H NMR(400 MHz, DMSO-$d_6$) delta ppm 0.82(d, J = 6.84 Hz, 6 H) 0.91-1.03(m, 3 H) 1.24-1.45(m, 3 H) 1.71-1.80(m, 2 H) 2.08-2.16(m, 2 H) 2.89-3.00(m, 1 H) 4.09-4.16(m, 2 H) 7.06(d, J = 8.79 Hz, 2 H) 7.11(dd, J = 8.79, 1.95 Hz, 1 H) 7.33(d, J = 2.20 Hz, 1 H) 7.49(d, J = 8.55 Hz, 2 H) 7.76(d, J = 8.79 Hz, 1 H) 8.66-8.76(m, 1 H) 8.95(s., 1 H)<br>(M + 1) 364.1, 1.59 min(LC/MS method B) | Method 1 |
| 66 | 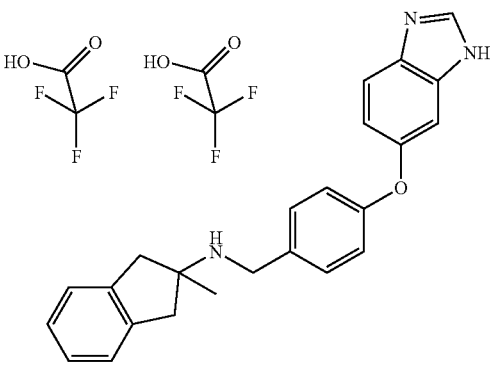 | N-{[4-(1H-benzimidazol-5-yloxy)phenyl]methyl}-2-methyl-2,3-dihydro-1H-inden-2-amine bis(trifluoroacetate)<br>1H NMR(400 MHz, DMSO-$d_6$) delta ppm 1.48(s., 3 H) 3.03(d, J = 16.11 Hz, 2 H) 3.37(d, J = 16.36 Hz, 2 H) 4.15-4.21(m, 2 H) 7.05-7.14(m, 3 H) 7.18-7.23(m, 2 H) 7.23-7.28(m, 2 H) 7.33-7.35(m, 1 H) 7.55(d, J = 8.79 Hz, 2 H) 7.77(d, J = 8.79 Hz, 1 H) 8.97(s., 1 H) 9.14-9.26 (m, 2 H)<br>(M + 1) 370.1, 1.17 min(LC/MS method B) | Method 1 |
| 66 | 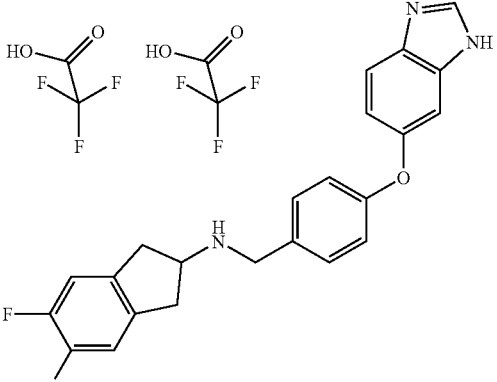 | N-{[4-(1H-benzimidazol-5-yloxy)phenyl]methyl}-5,6-difluoro-2,3-dihydro-1H-inden-2-amine bis(trifluoroacetate)<br>1H NMR(400 MHz, DMSO-$d_6$) delta ppm 3.04-3.13(m, 2 H) 3.25-3.34(m, 2 H) 4.05-4.12(m, 1 H) 4.17-4.22(m 2 H) 7.02-7.11(m, 3 H) 7.29-7.39(m, 3 H) 7.50(d, J = 8.79 Hz, 2 H) 7.74(d, J = 8.79 Hz, 1 H) 8.85(s., 1 H) 9.09(br. s., 2 H)<br>(M + 1) 392.2, 1.18 min(LC/MS method A) | Method 1 |
| 67 | 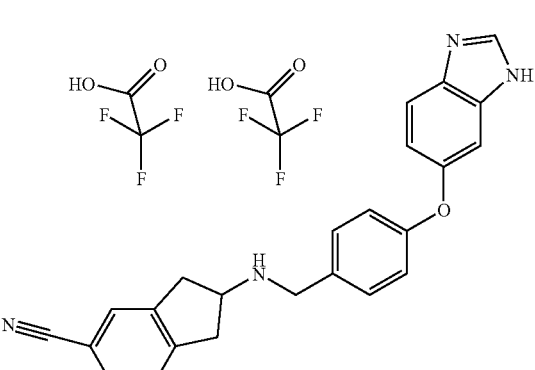 | 2-({[4-(1H-benzimidazol-5-yloxy)phenyl]methyl}amino)-2,3-dihydro-1H-indene-5-carbonitrile bis(trifluoroacetate)<br>1H NMR(400 MHz, DMSO-$d_6$) delta ppm 3.14-3.26(m, 2 H) 3.33-3.45(m, 2 H) 4.05-4.14(m, 1 H) 4.17-4.24(m, 2 H) 7.03-7.12(m, 3 H) 7.31-7.34(m, 1 H) 7.46-7.53(m, 3 H) 7.67(d, J = 8.06 Hz, 1 H) 7.73-7.77(m, 2 H) 8.92(s., 1 H) 9.10 (br. s., 2 H)<br>(M + 1) 381.1, 1.02 min(LC/MS method B) | Method 1 |

-continued

| Ex. | Structure | Name and Characterization Data | Method/Comments |
|---|---|---|---|
| 68 | 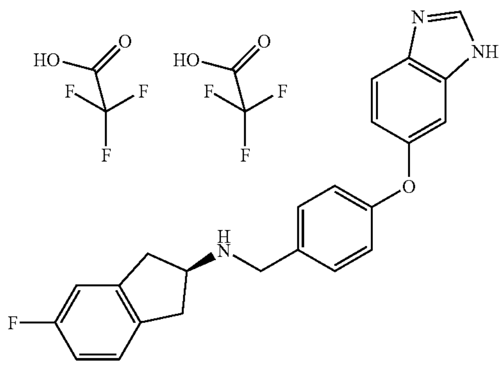 | {[4-(1H-benzimidazol-5-yloxy)phenyl]methyl}[(2S)-5-fluoro-2,3-dihydro-1H-inden-2-yl]amine bis(trifluoroacetate)e) 1H NMR(400 MHz, DMSO-$d_6$) delta ppm 3.01-3.18(m, 7 H) 3.23-3.36(m, 2 H) 4.00-4.12(m, 1 H) 4.14-4.24(m, 2 H) 6.96-7.04(m, 1 H) 7.05-7.14(m, 3 H) 7.17(dd, J = 8.79, 2.20 Hz, 1 H) 7.24-7.31(m, 1 H) 7.36-7.40(m, 1 H) 7.53(d, J = 8.79 Hz, 2 H) 7.80(d, J = 8.79 Hz, 3 H) 9.15(s., 1 H) 9.26(br. s., 2 H) (M + 1) 374.0, 1.19 min(LC/MS method B) | Method 1 |
| 69 | 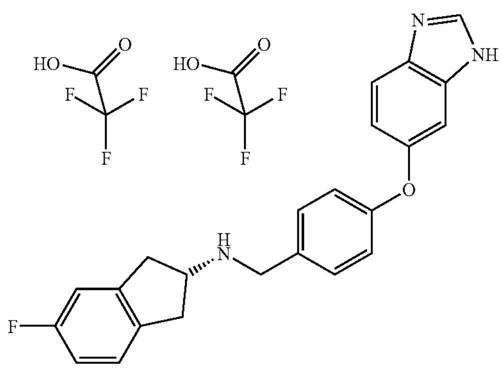 | {[4-(1H-benzimidazol-5-yloxy)phenyl]methyl}[(2R)-5-fluoro-2,3-dihydro-1H-inden-2-yl]amine bis(trifluoroacetate) 1H NMR(400 MHz, DMSO-$d_6$) delta ppm 3.02-3.19(m, 2 H) 3.22-3.36(m, 2 H) 4.03-4.11(m, 1 H) 4.16-4.24(m, 2 H) 6.96-7.03(m, 1 H) 7.05-7.13(m, 3 H) 7.14-7.21(m, 1 H) 7.23-7.31(m, 1 H) 7.36-7.40(m, 1 H) 7.52(d, J = 8.55 Hz, 2 H) 7.81(d, J = 8.79 Hz, 1 H) 9.19(s., 1 H) 9.29(br. s., 2 H) (M + 1) 374.0, 1.19 min(LC/MS method B) | Method 1 |
| 70 | 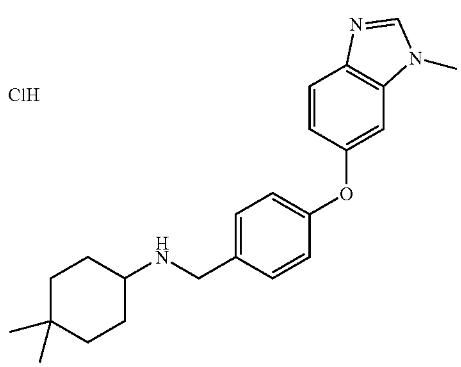 | (4,4-dimethylcyclohexyl)({4-[(1-methyl-1H-benzimidazol-6-yl)oxy]phenyl}methyl)amine hydrochloride 1H NMR(400 MHz, DMSO-$d_6$) delta ppm 0.88(s., 6 H) 1.10-1.22(m, 2 H) 1.37-1.44(m, 2 H) 1.51-1.65(m, 2 H) 1.86-1.94(m, 2 H) 2.86-2.96(m, 1 H) 3.91 (s., 3 H) 4.08-4.15(m, 2 H) 7.06(d, J = 8.55 Hz, 2 H) 7.13-7.18(m, 1 H) 7.52-7.59(m, 3 H) 7.81(d, J = 9.03 Hz, 1 H) 8.96(br. s., 2 H) 9.10(br. s., 1 H)(M + 1) 364.2, 1.35 min(LC/MS method B) | Method 9 |
| 71 | 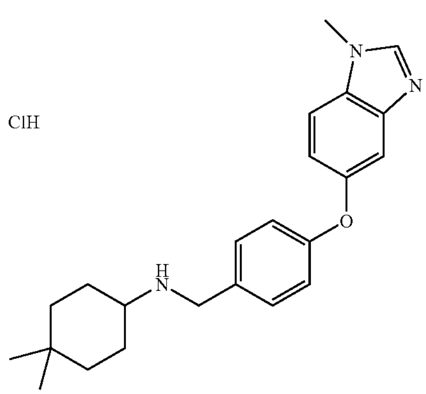 | (4,4-dimethylcyclohexyl)({4-[(1-methyl-1H-benzimidazol-5-yl)oxy]phenyl}methyl)amine hydrochloride 1H NMR(400 MHz, DMSO-$d_6$) delta ppm 0.88(s., 6 H) 1.11-1.22(m, 2 H) 1.37-1.44(m, 2 H) 1.54-1.66(m, 2 H) 1.85-1.94(m, 2 H) 2.88-2.97(m, 1 H) 3.99 (s., 3 H) 4.10-4.15(m, 2 H) 7.08(d, J = 8.55 Hz, 2 H) 7.24-7.29(m, 1 H) 7.36 (d, J = 2.20 Hz, 1 H) 7.57(d, J = 8.79 Hz, 2 H) 7.90(d, J = 8.79 Hz, 1 H) 8.99(br. s., 1 H) 9.18(br. s., 1 H) (M + 1) 364.2, 1.36 min(LC/MS method B) | Method 9 |

| Ex. | Structure | Name and Characterization Data | Method/ Comments |
|---|---|---|---|
| 72 | 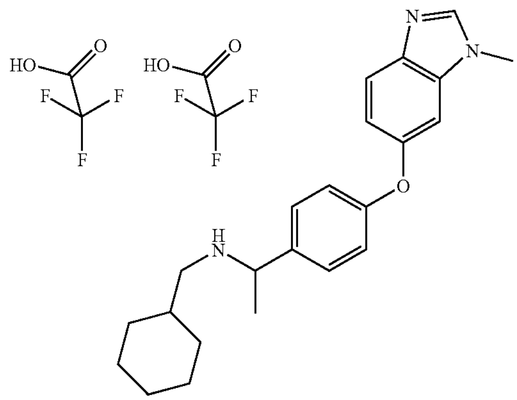 | {1-[4-(1H-benzimidazol-5-yloxy)phenyl]methyl}(cyclohexylmethyl)amine bis(trifluoroacetate) 1H NMR(400 MHz, DMSO-$d_6$) delta ppm 0.77-0.94(m, 2 H) 1.01-1.22(m, 3 H) 1.52(d, J = 6.84 Hz, 3 H) 1.52-1.72(m, 5 H) 2.36-2.47(m, 1 H) 2.63-2.75(m, 1 H) 4.30-4.39(m, 1 H) 7.06(d, J = 8.55 Hz, 2 H) 7.11(dd, J = 8.79, 2.44 Hz, 1 H) 7.34(d, J = 2.20 Hz, 1 H) 7.49(d, J = 8.79 Hz, 2 H) 7.75(d, J = 9.03 Hz, 1 H) 8.55(br. s., 1 H) 8.74(br. s., 1 H) 8.90(s., 1 H) (M + 1) 350.1, 1.29 min(LC/MS method B) | Method 7 |
| 73 | 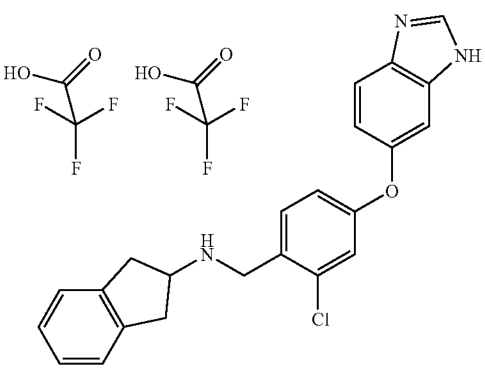 | N-{[4-(1H-benzimidazol-5-yloxy)-2-chlorophenyl]methyl}-2,3-dihydro-1H-inden-2-amine bis(trifluoroacetate) 1H NMR(400 MHz, DMSO-$d_6$) delta ppm 3.08-3.15(m, 2 H) 3.33-3.42(m, 2 H) 4.10-4.19(m, 1 H) 4.28-4.33(m, 2 H) 7.04-7.11(m, 2 H) 7.14-7.17(m, 1 H) 7.18-7.23(m, 2 H) 7.24-7.29(m, 2 H) 7.38-7.41(m, 1 H) 7.63(d, J = 8.55 Hz, 1 H) 7.71-7.76(m, 1 H) 8.73(br. s., 1 H) 9.11-9.18(m, 2 H) (M + 1) 389.9, 1.37 min(LC/MS method B) | Method 3 Note 5 Method 6 Note 6 |
| 74 | 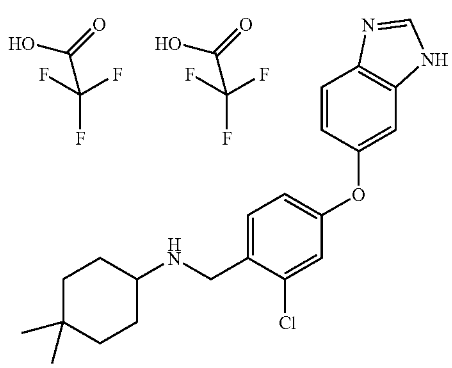 | N-{[4-(1H-benzimidazol-5-yloxy)-2-chlorophenyl]methyl}-4,4-dimethylcyclohexanamine bis(trifluoroacetate) 1H NMR(400 MHz, DMSO-$d_6$) delta ppm 0.88(s., 6 H) 1.13-1.26(m, 2 H) 1.37-1.46(m, 2 H) 1.46-1.60(m, 2 H) 1.88-1.96(m, 2 H) 2.99-3.10(m, 1 H) 4.19-4.26(m, 2 H) 7.02-7.11(m, 2 H) 7.15(d, J = 2.44 Hz, 1 H) 7.40(d, J = 2.20 Hz, 1 H) 7.59(d, J = 8.79 Hz, 1 H) 7.75(d, J = 8.79 Hz, 1 H) 8.67(br. s., 2 H) 8.77(s., 1 H) (M + 1) 389.4, 1.55 min(LC/MS method B) | Method 6 Note 6 |
| 75 | 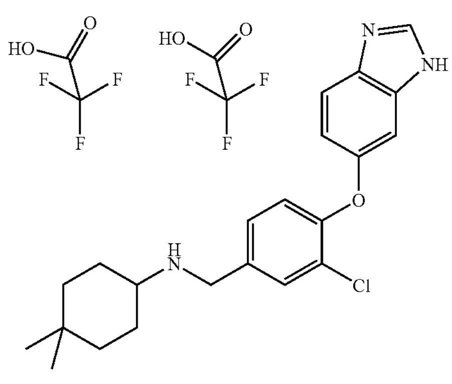 | N-{[4-(1H-benzimidazol-5-yloxy)-3-clorophenyl]methyl}-4,4-dimethylcyclohexanamine bis(trifluoroacetate) 1H NMR(400 MHz, DMSO-$d_6$) delta ppm 0.89(s., 6 H) 1.14-1.24(m, 2 H) 1.37-1.46(m, 2 H) 1.44-1.56(m, 2 H) 1.85-1.94(m, 2 H) 2.94-3.03(m, 1 H) 4.13-4.20(m, 2 H) 7.05-7.10(m, 2 H) 7.24-7.28(m, 1 H) 7.40-7.46(m, 1 H) 7.74(d, J = 8.79 Hz, 1 H) 7.76-7.78(m, 1 H) 8.67(br. s., 2 H) 8.82(s., 1 H) (M + 1) 383.9, 1.49 min(LC/MS method B) | Method 6 |

-continued

| Ex. | Structure | Name and Characterization Data | Method/Comments |
|---|---|---|---|
| 76 | 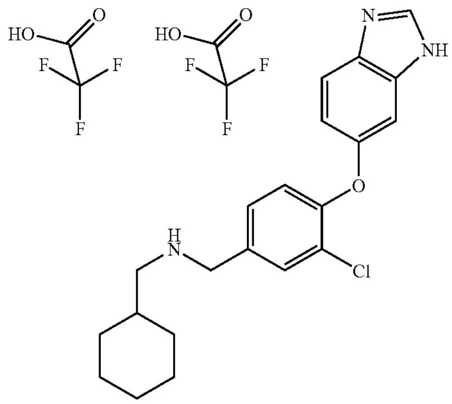 | {[4-(1H-benzimidazol-5-yloxy)-3-chlorophenyl]methyl}(cyclohexylmethyl)amine bis(trifluoroacetate)<br>1H NMR(400 MHz, DMSO-$d_6$) delta ppm 0.86-0.99(m, 2 H) 1.08-1.26(m, 3 H) 1.57-1.76(m, 5 H) 2.72-2.80(m, 2 H) 4.10-4.16(m, 2 H) 7.05-7.10(m, 2 H) 7.27(d, J = 1.71 Hz, 1 H) 7.42(dd, J = 9.03, 1.95 Hz, 1 H) 7.71-7.79(m, 2 H) 8.68 (br. s., 2 H) 8.86(s, 1 H)<br>(M + 1) 370.0, 1.35 min(LC/MS method B) | Method 6 |
| 77 | 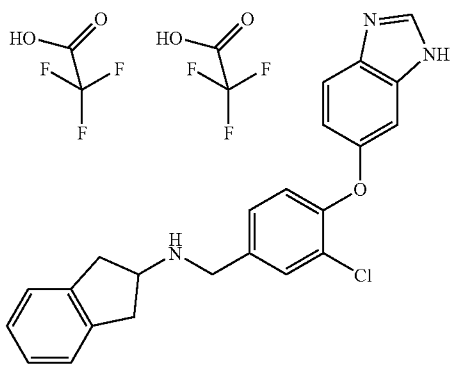 | N-{[4-(1H-benzimidazol-5-yloxy)-3-chlorophenyl]methyl}-2,3-dihydro-1H-inden-2-amine bis(trifluoroacetate)<br>1H NMR(400 MHz, DMSO-$d_6$) delta ppm 3.07-3.16(m, 2 H) 3.28-3.37(m, 2 H) 4.01-4.11(m, 1 H) 4.21-4.28(m, 2 H) 7.04-7.11(m, 2 H) 7.16-7.23(m, 2 H) 7.24-7.31(m, 3 H) 7.47(d, J = 8.55 Hz, 1 H) 7.74(d, J = 9.03 Hz, 1 H) 7.81-7.84 (m, 1 H) 8.84(s., 1 H) 9.15(br. s., 2 H)<br>(M + 1) 389.9, 1.31 min(LC/MS method B) | Method 6 |
| 78 | 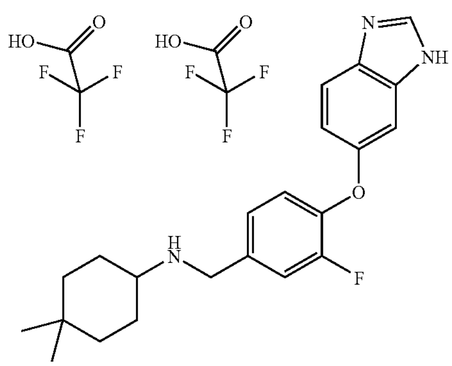 | N-{[4-(1H-benzimidazol-5-yloxy)-3-fluorophenyl]methyl}-4,4-dimethylcyclohexanamine bis(trifluoroacetate)<br>1H NMR(400 MHz, DMSO-$d_6$) delta ppm 0.89(s, 6 H) 1.15-1.25(m, 2 H) 1.38-1.46(m, 2 H) 1.44-1.57(m, 2 H) 1.85-1.93(m, 2 H) 2.93-3.01(m, 1 H) 4.13-4.21(m, 2 H) 7.10(dd, J = 8.79, 2.44 Hz, 1 H) 7.15-7.21(m, 1 H) 7.27-7.33(m, 2 H) 7.56(dd, J = 11.72, 1.71 Hz, 1 H) 7.73 (d, J = 8.79 Hz, 1 H) 8.67-8.78(m, 2 H) 8.86(br. s., 1 H)<br>(M + 1) 368.1, 1.35 min(LC/MS method B) | Method 3 |
| 79 | 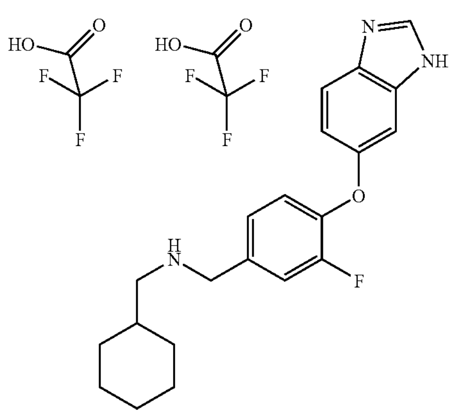 | {[4-(1H-benzimidazol-5-yloxy)-3-fluorophenyl]meth-yl}(cyclohexylmethyl)amine bis(trifluoroacetate)<br>1H NMR(400 MHz, DMSO-$d_6$) delta ppm 0.86-0.98(m, 2 H) 1.05-1.25(m, 3 H) 1.55-1.76(m, 6 H) 2.74-2.80(m, 2 H) 4.11-4.16(m, 2 H) 7.12(dd, J = 8.79, 2.44 Hz, 1 H) 7.17(dd, J = 8.55 Hz, 1 H) 7.27-7.33(m, 2 H) 7.56(dd, J = 11.47, 1.71 Hz, 1 H) 7.74(d, J = 8.79 Hz, 1 H) 8.65-8.80(m, 2 H) 8.91(s., 1 H)<br>(M + 1) 354.2, 1.24 min(LC/MS method B) | Method 3 |

| Ex. | Structure | Name and Characterization Data | Method/Comments |
|---|---|---|---|
| 80 | 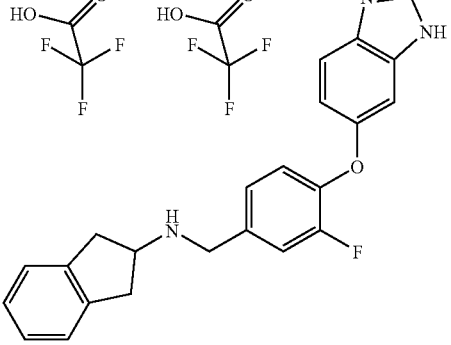 | N-{[4-(1H-benzimidazol-5-yloxy)-3-fluorophenyl]methyl}-2,3-dihydro-1H-inden-2-amine bis(trifluoroacetate)<br>1H NMR(400 MHz, DMSO-$d_6$) delta ppm 3.09-3.16(m, 2 H) 3.28-3.37(m, 2 H) 4.02-4.10(m, 1 H) 4.23-4.28(m, 2 H) 7.10(dd, J = 9.03, 2.44 Hz, 1 H) 7.15-7.23(m, 3 H) 7.24-7.30(m, 3 H) 7.33-7.38(m, 1 H) 7.61(dd, J = 11.48, 1.95 Hz, 1 H) 7.73(d, J = 8.79 Hz, 1 H) 8.85(s., 1 H) 9.12-9.26(m, 2 H)<br>(M + 1) 374.1, 1.35 min (LC/MS method B) | Method 3 |
| 81 | 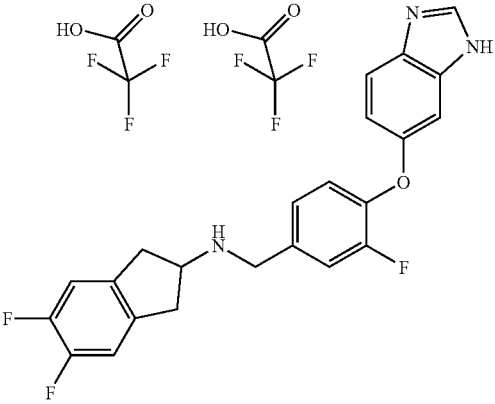 | N-{[4-(1H-benzimidazol-5-yloxy)-3-fluorophenyl]methyl}-5,6-difluoro-2,3-dihydro-1H-inden-2-amine bis(trifluoroacetate)<br>1H NMR(400 MHz, DMSO-$d_6$) delta ppm 3.04-3.15(m, 2 H) 3.26-3.35(m, 2 H) 4.06-4.14(m, 1 H) 4.20-4.26(m, 2 H) 7.11(dd, J = 9.03, 2.44 Hz, 1 H) 7.18(dd, J = 8.55 Hz, 1 H) 7.26-7.40(m, 4 H) 7.56-7.63(m 1 H) 7.72(d, J = 8.55 Hz, 1 H) 8.87(br. s., 1 H) 9.17(br.s, 2 H)<br>(M + 1) 410.2, 1.20 min(LC/MS method A) | Method 3 |
| 82 | 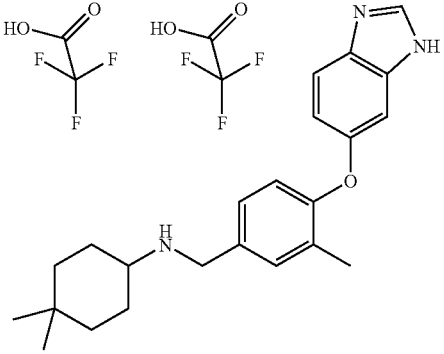 | N-{[4-(1H-benzimidazol-5-yloxy)-3-methylphenyl]methyl}-4,4-dimethylcyclohexanamine bis(trifluoroacetate)<br>1H NMR(400 MHz, DMSO-$d_6$) delta ppm 0.88(s., 6 H) 1.14-1.24(m, 2 H) 1.38-1.45(m, 2 H) 1.46-1.59(m 2 H) 1.86-1.94(m, 2 H) 2.22(s., 3 H) 2.92-3.01 (m, 1 H) 4.09-4.15(m, 2 H) 6.91(d, J = 8.30 Hz, 1 H) 7.06(dd, J = 8.79, 2.20 Hz, 1 H) 7.16(d, J = 1.95 Hz, 1 H) 7.31 (dd, J = 8.30, 2.20 Hz, 1 H) 7.45(d, J = 1.71 Hz, 1 H) 7.73(d, J = 9.03 Hz, 1 H) 8.62-8.73(m, 2 H) 8.94(s., 1H)<br>(M + 1) 364.2, 1.48 min(LC/MS method B) | Method 3 |
| 83 | 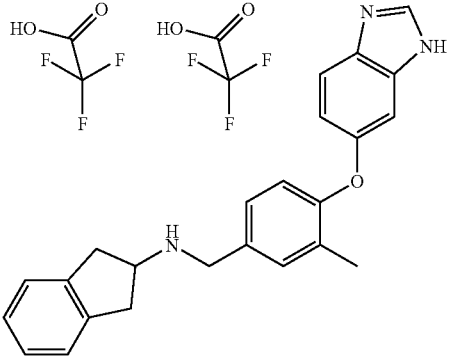 | N-{[4-(1H-benzimidazol-5-yloxy)-3-methylphenyl]methyl}-2,3-dihydro-1H-inden-2-amine bis(trifluoroacetate)<br>1H NMR(400 MHz, DMSO-$d_6$) delta ppm 2.24(s., 3 H) 3.07-3.16(m, 2 H) 3.30-3.37(m, 2 H) 4.00-4.08(m, 1 H) 4.17-4.23(m, 2 H) 6.92(d, J = 8.30 Hz, 1 H) 7.07(dd, J = 8.79, 2.20 Hz, 1 H) 7.16-7.22(m, 3 H) 7.24-7.29(m, 2 H) 7.33-7.38(m, 1 H) 7.49-7.52(m, 1 H) 7.74(d, J = 9.03 Hz, 1 H) 8.95(s., 1 H) 9.11-9.24 (m, 2 H)<br>(M + 1) 370.2, 1.33 min (LC/MS method B) | Method 3 |

| Ex. | Structure | Name and Characterization Data | Method/ Comments |
|---|---|---|---|
| 84 | 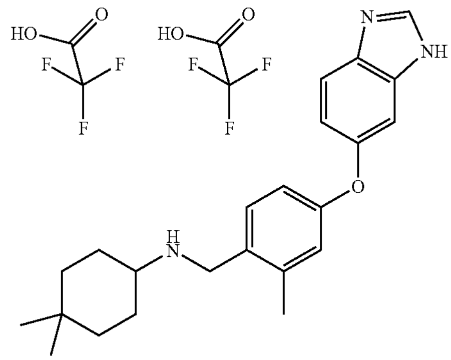 | N-{[4-(1H-benzimidazol-5-yloxy)-2-methylphenyl]methyl}-4,4-dimethylcyclohexanamine bis(trifluoroacetate) 1H NMR(400 MHz, DMSO-d$_6$) delta ppm 0.89(s., 6 H) 1.15-1.25(m, 2 H) 1.39-1.47(m, 2 H) 1.48-1.60(m, 2 H) 1.89-1.97(m, 2 H) 2.32(s., 3 H) 3.03-3.11 (m, 1 H) 4.09-4.14(m, 2 H) 6.88-6.93 (m, 2 H) 7.07(dd, J = 8.55, 2.20 Hz, 1 H) 7.30(d, J = 1.95 Hz, 1 H) 7.41(d, J =7.81 Hz, 1 H) 7.73(d, J = 8.79 Hz, 1 H) 8.51(br. s., 2 H) 8.85(s., 1 H) (M + 1) 364.2, 1.43 min(LC/MS method B) | Method 3 |
| 85 | 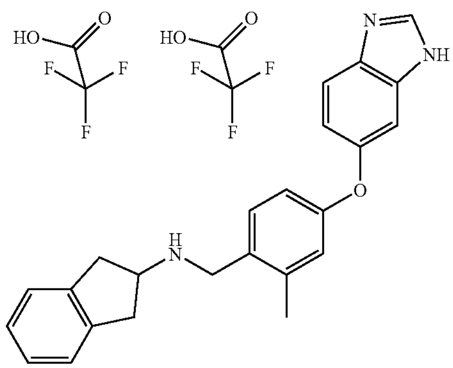 | N-{[4-(1H-benzimidazol-5-yloxy)-2-methylphenyl]methyl}-2,3-dihydro-1H-inden-2-amine bis(trifluoroacetate) 1H NMR(400 MHz, DMSO-d$_6$) delta ppm 2.35(s., 3 H) 3.08-3.16(m, 2 H) 3.32-3.41(m, 2 H) 4.12-4.23(m, 3 H) 6.88-6.94(m, 2 H) 7.09(dd, J = 8.55, 2.20 Hz, 1 H) 7.18-7.22(m, 2 H) 7.24-7.29(m, 2 H) 7.32(d, J = 2.20 Hz, 1 H) 7.46(d, J = 8.30 Hz, 1 H) 7.75(d, J = 8.79 Hz, 1 H) 8.91(s., 1 H) 9.04(br. s., 2 H) (M + 1) 370.2, 1.28 min(LC/MS method B) | Method 3 |
| 86 | 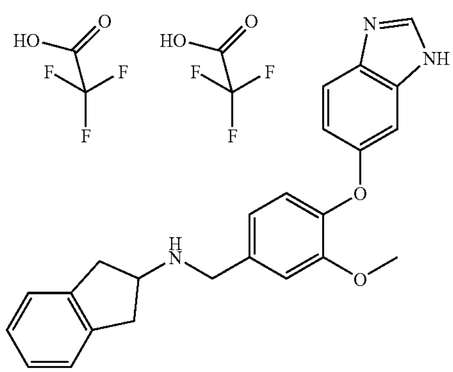 | N-{[4-(1H-benzimidazol-5-yloxy)-3-(methyloxy)phenyl]methyl}-2,3-dihydro-1H-inden-2-amine bis(trifluoroacetate) 1H NMR(400 MHz, DMSO-d$_6$) delta ppm 3.10-3.19(m, 2 H) 3.29-3.39(m, 2 H) 3.77(s., 3 H) 4.03-4.13(m, 1 H) 4.22-4.28(m, 2 H) 7.05-7.16(m, 4 H) 7.18-7.23(m, 2 H) 7.24-7.30(m, 2 H) 7.38-7.42(m, 1 H) 7.72(d, J = 8.79 Hz, 1 H) 9.09(s., 1 H) 9.20(br. s., 2 H) (M + 1) 386.1, 1.13 min(LC/MS method B) | Method 3 Method 5 |
| 87 | 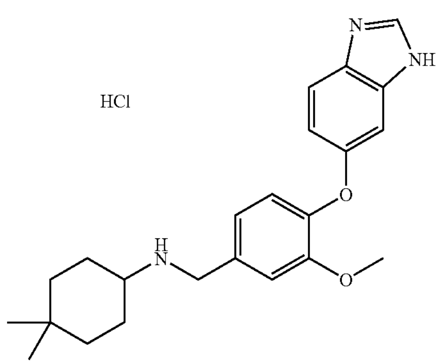 | N-{[4-(1H-benzimidazol-5-yloxy)-3-(methyloxy)phenyl]methyl}-4,4-dimethylcyclohexanamine hydrochloride 1H NMR(400 MHz, DMSO-d$_6$) delta ppm 0.89(s., 6 H) 1.14-1.24(m, 2 H) 1.39-1.46(m, 2 H) 1.52-1.67(m, 2 H) 1.90-1.97(m, 2 H) 2.92-3.00(m, 1 H) 3.76 (s., 3 H) 4.13-4.19(m, 2 H) 7.05-7.16 (m, 4 H) 7.48-7.52(m, 1 H) 7.71-7.75 (m, 1 H) 9.00(br. s., 2 H) 9.12(br. s., 1 H) (M + 1) 380.1, 1.28 min(LC/MS method B) | Method 5 Note 7 Method 3 |

| Ex. | Structure | Name and Characterization Data | Method/Comments |
|---|---|---|---|
| 88 | 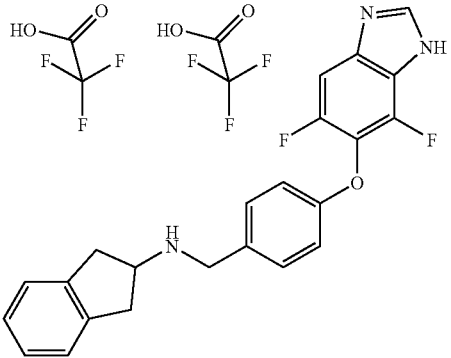 | N-({4-[(4,6-difluoro-1H-benzimidazol-5-yl)oxy]phenyl}methyl)-2,3-dihydro-1H-inden-2-amine<br>1H NMR(400 MHz, DMSO-d$_6$) delta ppm 3.03-3.14(m, 2 H) 3.26-3.37(m, 2 H) 4.00-4.09(m, 1 H) 4.14-4.22(m, 2 H) 7.02(d, J = 8.79 Hz, 2 H) 7.16-7.21(m, 2 H) 7.23-7.29(m, 2 H) 7.45-7.54(m, 3 H) 8.36(s., 1 H) 9.01(br. s., 2 H) (M + 1) 392.4, 0.57 min(LC/MS method F) | Method 8 |
| 89 | 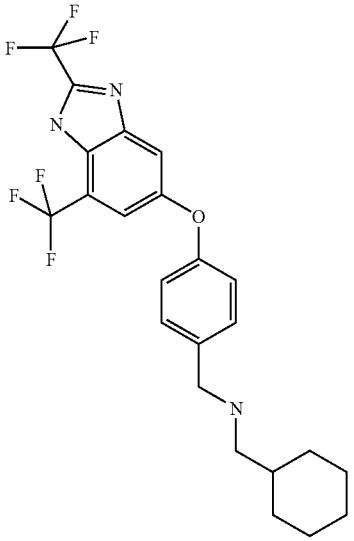 | [(4-{[2,4-bis(trifluoromethyl)-1H-benzimidazol-6-yl]oxy}phenyl)methyl](cyclohexylmethyl)amine<br>$^1$H NMR(400 MHz, DMSO-d$_6$) delta ppm 0.68-1.37(m, 7 H) 1.53-1.75(m, 4 H) 2.76 (br.s, 2 H) 4.12(br.s, 2 H) 7.14(d, J = 8.30 Hz, 2 H) 7.35-7.40(m, 1 H) 7.48-7.57(m, 3 H) 8.58 (br.s, 2 H) (M + H) 472.25, 2.12 min(LC/MS method A) | Method 10 |
| 90 | 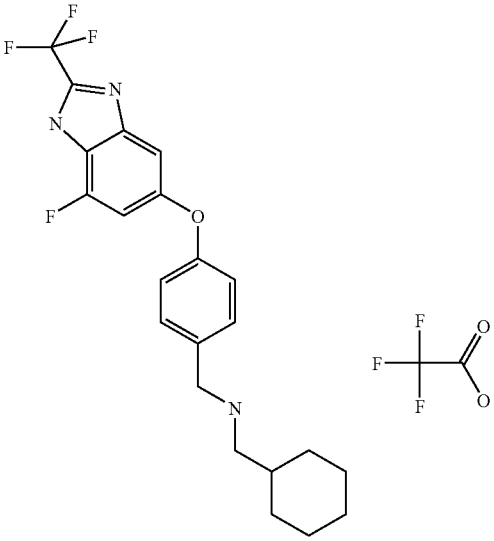 | (cyclohexylmethyl)[(4-{[4-fluoro-2-(trifluoromethyl)-1H-benzimidazol-6-yl]oxy}phenyl)methyl]amine trifluoroacetate<br>$^1$H NMR(400 MHz, DMSO-d$_6$) delta ppm 0.79-1.27(m, 7 H) 1.53-1.75(m, 4 H) 2.75 (br.s, 2 H) 4.12(br.s, 2 H) 6.64-6.71(m, 1 H) 7.08-7.31(m, 3 H) 7.46-7.56(m, 2 H) 8.58(br.s, 2 H) (M + H) 422.26, 1.91 min (LC/MS method A) | Method 11 |

| Ex. | Structure | Name and Characterization Data | Method/Comments |
|---|---|---|---|
| 91 | 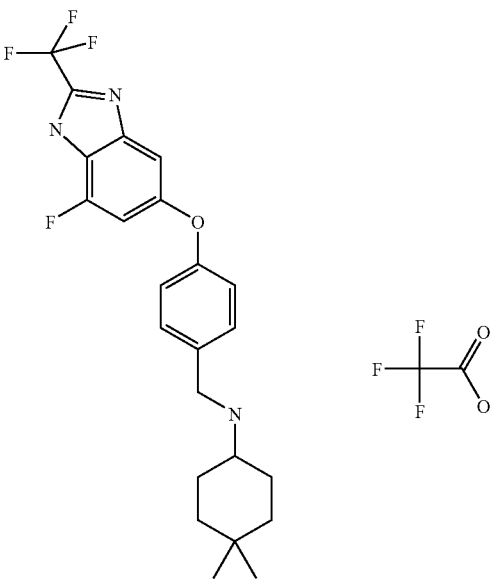 | N-[(4-{[4-fluoro-2-(trifluoromethyl)-1H-benzimidazol-6-yl]oxy}phenyl)methyl]-4,4-dimethylcyclohexanamine trifluoroacetate <br> $^1$H NMR(400 MHz, DMSO-d$_6$) delta ppm 0.75-0.96(m, 6 H) 1.08-1.25(m, 2 H) 1.32-1.61(m, 4 H) 1.81-1.98(m, 2 H) 2.87-3.02 (m, 1 H) 4.16(br.s, 2 H) 6.61-6.74(m, 1 H) 7.07-7.34(m, 3 H) 7.46-7.63(m, 2 H) 8.71(br.s, 2 H) (M + H) 436.24, 2.05 min (LC/MS method A) | Method 11 |
| 92 | 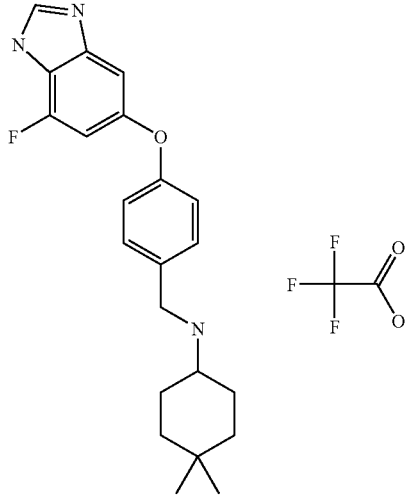 | N-({4-[(4-fluoro-1H-benzimidazol-6-yl)oxy]phenyl}methyl)-4,4-dimethylcyclohexanamine trifluoroacetate <br> $^1$H NMR(400 MHz, DMSO-d$_6$) delta ppm 0.87(s, 3 H) 0.88(s, 3 H) 1.13-1.25(m, 2 H) 1.36-1.56(m, 4 H) 1.85-1.93(m, 2 H) 2.89-3.01(m, 1 H) 4.14(br.s, 2 H) 6.61(dd, J = 10.99, 1.95 Hz, 1 H) 7.11(d, J = 8.55 Hz, 2 H) 7.23 (dd, J = 8.79, 2.20 Hz, 1 H) 7.48(d, J = 8.79 Hz, 2 H) 8.27(br.s, 1 H) 8.59(br.s, 2 H) (M + H) 368.25, 1.68 min(LC/MS method A) | Method 12 |
| 93 | 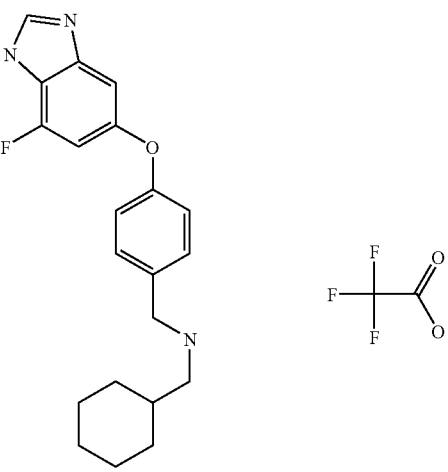 | (cyclohexylmethyl)({4-[(4-fluoro-1H-benzimidazol-6-yl)oxy]phenyl}methyl)amine trifluoroacetate <br> $^1$H NMR(400 MHz, DMSO-d$_6$) delta ppm 0.80-1.25(m, 6 H) 1.52-1.77(m, 5 H) 1.85-1.93(m, 2 H) 2.69-2.80(m, 2 H) 4.11 (br.s, 2 H) 6.62(dd, J = 10.99, 2.20 Hz, 1 H) 7.11 (d, J = 8.55 Hz, 2 H) 7.23(dd, J = 8.79, 2.20 Hz, 1 H) 7.49(d, J = 8.79 Hz, 2 H) 8.34(br.s, 1 H) 8.62(br.s, 2 H) (M + H) 354.18, 1.61 min(LC/MS method A) | Method 12 |

| Ex. | Structure | Name and Characterization Data | Method/Comments |
|---|---|---|---|
| 94 | 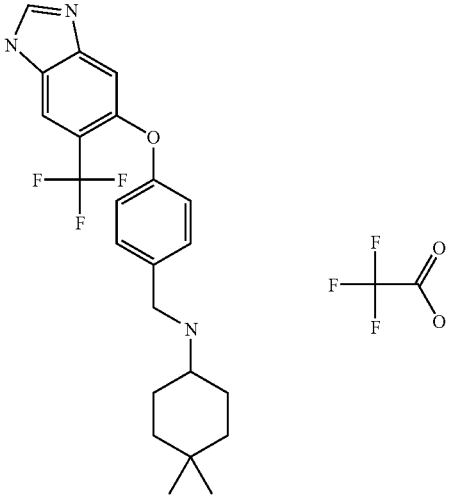 | (4,4-dimethylcyclohexyl)[(4-{[5-(trifluoromethyl)-1H-benzimidazol-6-yl]oxy}phenyl)methyl]amine trifluoroacetate<br>$^1$H NMR(400 MHz, DMSO-$d_6$) delta ppm 0.92(s, 6 H) 1.18-1.27(m, 2 H) 1.42-1.59 (m, 4 H) 1.88-1.97(m, 2 H) 2.92-3.06 (m, 1 H) 4.17(br.s, 2 H) 7.10(d, J = 7.31 Hz, 2 H) 7.33(s, 1 H) 7.52(d, J = 7.67 Hz, 2 H) 8.09(s, 1 H) 8.56(br.s, 1 H) 8.68(br.s, 2 H) (M + H) 418.19, 1.98 min(LC/MS method A) | Method 13 |
| 95 | 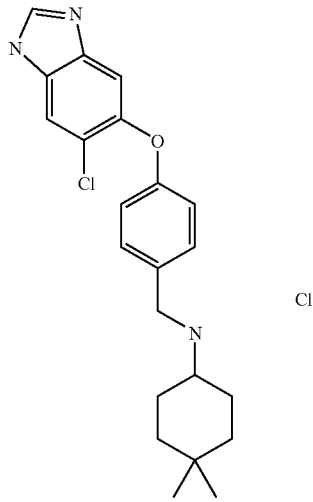 | N-({4-[(5-chloro-1H-benzimidazol-6-yl)oxy]phenyl}methyl)-4,4-dimethylcyclohexanamine hydrochloride<br>$^1$H NMR(400 MHz, DMSO-$d_6$) delta ppm 0.87(s, 6 H) 1.19-1.27(m, 2 H) 1.34-1.44 (m, 2 H) 1.53-1.67(m, 2 H) 1.83-1.93(m, 2 H) 2.81-2.95 (m, 1 H) 4.10(br.s, 2 H) 7.00(d, J = 8.55 Hz, 2 H) 7.52(s, 1 H) 7.57(d, J = 8.55 Hz, 2 H) 8.06(s, 1 H) 8.65(br.s, 1 H) 8.86(br.s, 2 H) (M + H) 384.03, 1.67 min(LC/MS method A) | Method 14 |
| 96 | 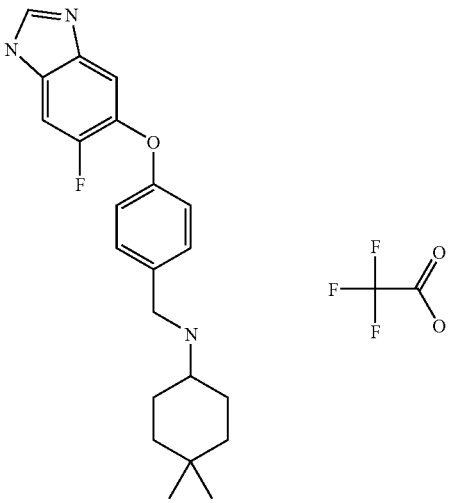 | N-({4-[(5-fluoro-1H-benzimidazol-6-yl)oxy]phenyl}methyl)-4,4-dimethylcyclohexanamine trifluoroacetate<br>$^1$H NMR(400 MHz, DMSO-$d_6$) delta ppm 0.87(s, 3 H) 0.88(s, 3 H) 1.13-1.23(m, 2 H) 1.36-1.56(m, 4 H) 1.84-1.93(m, 2 H) 2.89-3.01(m, 1 H) 4.12(br.s, 2 H) 7.01(d, J = 8.54 Hz, 2 H) 7.45(d, J = 8.55 Hz, 2 H) 7.53(d, J = 7.32 Hz, 1 H) 7.72(d, J = 10.74 Hz, 1 H) 8.56-8.69(m, 3 H) (M + H) 368.13, 1.56 min(LC/MS method A) | Method 14 |

| Ex. | Structure | Name and Characterization Data | Method/ Comments |
|---|---|---|---|
| 97 | 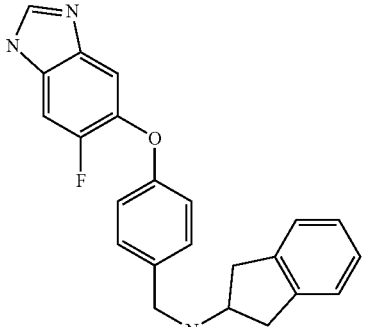 | N-({4-[(5-fluoro-1H-benzimidazol-6-yl)oxy]phenyl}methyl)-2,3-dihydro-1H-inden-2-amine trifluoroacetate<br>$^1$H NMR(400 MHz, DMSO-$d_6$) delta ppm 3.10(dd, J = 16.36, 6.84, 2 H) 3.31(dd, J = 16.48, 7.93, 2 H) 3.96-4.10(m, 1 H) 4.19(br.s, 2 H)<br>7.01(d, J = 8.54 Hz, 2 H) 7.14-7.30(m, 4 H) 7.44-7.56(m, 3 H) 7.70(d, J = 10.74 Hz, 1 H) 8.57(s, 1 H) 9.07(br.s, 2 H) (M + H) 374.15, 1.30 min(LC/MS method )A | Method 14 |
| 98 | 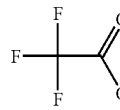 | N-({4-[(5-chloro-1H-benzimidazol-6-yl)oxy]phenyl}methyl)-2-cyclohexylethanamine trifluoroacetate<br>$^1$H NMR(400 MHz, DMSO-$d_6$) delta ppm 0.80-0.93(m, 2 H) 1.06-1.33(m, 4 H) 1.42-1.68(m, 7 H) 2.86-2.97(m, 2 H) 4.08(br.s, 2 H)<br>6.94(d, J = 8.55 Hz, 2 H) 7.44(d, J = 8.79 Hz, 2 H) 7.48(s, 1 H) 7.92(s, 1 H) 8.57-8.74(m, 3 H) (M + H) 384.2, 1.80 min (LC/MS method A) | Method 14 |
| 99 | 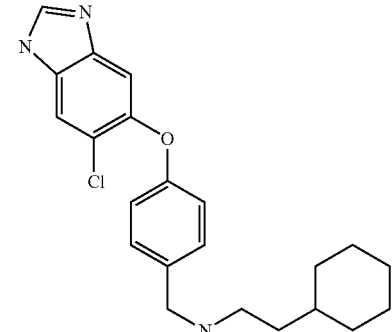 | N-({4-[(5-chloro-1H-benzimidazol-6-yl)oxy]phenyl}methyl)-2,3-dihydro-1H-inden-2-amine trifluoroacetate<br>$^1$H NMR(400 MHz, DMSO-$d_6$) delta ppm 3.10(dd, J = 16.60, 6.60, 2 H) 3.31(dd, J = 16.48, 7.93, 2 H) 3.96-4.10(m, 1 H) 4.19(br.s, 2 H)<br>6.95(d, J = 8.79 Hz, 2 H) 7.18-7.26(m, 4 H) 7.45-7.51(m, 3 H) 7.87(s, 1 H) 8.46(s, 1 H) 9.07(br.s, 2 H) (M + H) 389.1, 1.54 min (LC/MS method A) | Method 14 |

-continued

| Ex. | Structure | Name and Characterization Data | Method/ Comments |
|---|---|---|---|
| 100 | 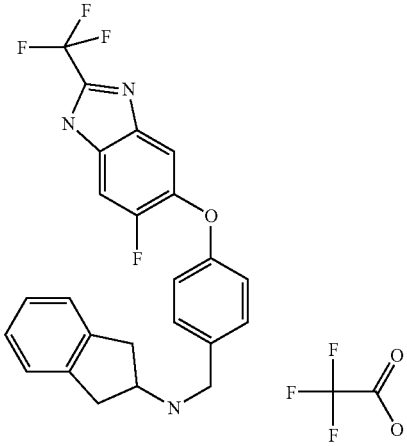 | N-[(4-{[5-floro-2-(trifluoromethyl)-1H-benzimidazol-6-yl]oxy}phenyl)methyl]-2,3-dihydro-1H-inden-2-amine trifluoroacetate <br> $^1$H NMR(400 MHz, methanol-d$_4$) delta ppm 3.15(dd, J = 16.60, 6.59, 2 H) 3.46 (dd, J = 16.48, 7.93, 2 H) 4.05-4.17(m, 1 H) 4.27(br.s, 2 H) 7.03-7.07(m, 2 H) 7.14-7.30(m, 4 H) 7.46-7.53(m, 3 H) 7.59(d, J = 10.25 Hz, 1 H) (M + H) 442.26, 1.94 min (LC/MS method A) | Method 15 |
| 101 | 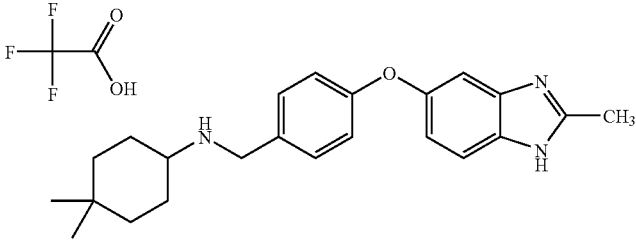 | (4,4-dimethylcyclohexyl)({4-[(2-methyl-1H-benzimidazol-5-yl)oxy]phenyl}methyl)amine trifluoroacetate <br> 1H NMR(400 MHz, DMSO-d$_6$) delta ppm 0.90(s, 6 H), 1.19(m, 2 H), 1.43(m, 2 H), 1.55(m, 2 H), 1.91(m, 2 H), 2.77(s, 3 H), 2.95(m, 1 H), 4.15(m, 2 H), 7.07(m, 2 H), 7.18(partially resolved dd, J = 8.9, ~2.2 Hz, 1 H), 7.40(m, 1 H), 7.52(m, 2 H), 7.79 (partially resolved dd, J = 8.8, ~1.2 Hz, 1 H), 8.86(br. s, 2 H) <br> (M − H) 362, 1.22 min(LC/MS method A) | Method 16 |
| 102 | 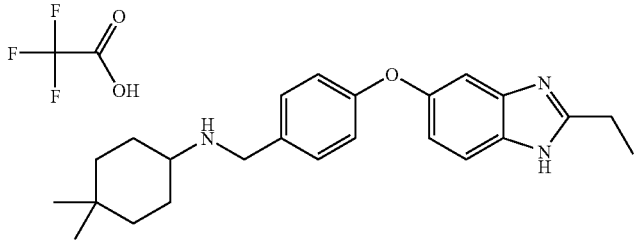 | N-({4-[(2-ethyl-1H-benzimidazol-5-yl)oxy]phenyl}methyl)-4,4-dimethylcyclohexanamine trifluoroacetate <br> 1H NMR(400 MHz, DMSO-d$_6$) delta ppm 0.90(s, 6 H), 1.19(m, 2 H), 1.40(t, J = 7.6 Hz, 3 H, partially overlapping 1.43), 1.43 (m, 2 H), 1.55(m, 2 H), 1.91(m, 2 H), 2.95 (m, 1 H), 3.11(q, J = 7.6 Hz, 2 H), 4.15 (m, 2 H), 7.06(m, 2 H), 7.18(partially resolved dd, J = 8.8, ~2.1 Hz, 1 H), 7.40 (m, 1 H), 7.52(m, 2 H), 7.79(partially resolved dd, J = 8.8, ~1.4 Hz, 1 H), 8.87 (br. s, 2 H) <br> (M − H) 376, 1.31 min(LC/MS method A) | Method 16 |
| 103 | 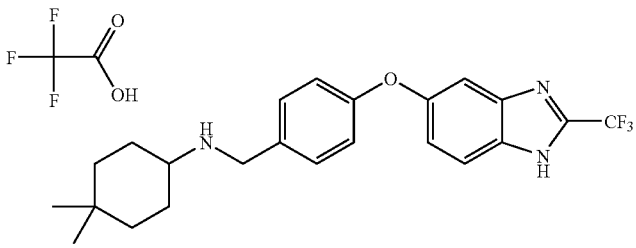 | (4,4-dimethylcyclohexyl)[(4-{[2-(trifluoromethyl)-1H-benzimidazol-5-yl]oxy}phenyl)methyl]amine trifluoroacetate <br> 1H NMR(400 MHz, DMSO-d$_6$) delta ppm 0.90(s, 6 H), 1.19(m, 2 H), 1.43(m, 2 H), 1.54(m, 2 H), 1.91(m, 2 H), 2.96(m, 1 H), 4.14(m, 2 H), 7.05(m, 2 H), 7.11(d, J = 8.8 Hz, 1 H), 7.32(s, 1 H), 7.50(m, 2 H) 7.77(d, J = 8.8, 1 H), 8.75(br. s, 2 H) <br> (M − H) 416, 1.99 min(LC/MS method A) | Method 16 |
| 104 | 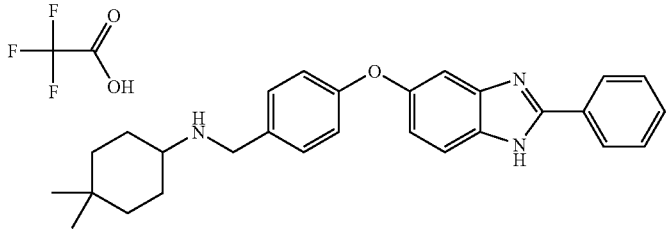 | (4,4-dimethylcyclohexyl)({4-[(2-phenyl-1H-benzimidazol-5-yl)oxy]phenyl}methyl)amine trifluoroacetate <br> 1H NMR(400 MHz, DMSO-d$_6$) delta ppm 0.90(s, 6 H), 1.20(m, 2 H), 1.43(m, 2 H), 1.54(m, 2 H), 1.91(m, 2 H), 2.96(m, 1 H), 4.15(m, 2 H), 7.07(overlapping m, 3 H), 7.32(m, 1 H), 7.50(m, 2 H), 7.57-7.65 (m, 3 H), 7.74(partially resolved dd, J = 8.8, ~2.1 Hz, 1 H), 8.17(m, 2 H), 8.78(br. s, 2 H) <br> (M − H) 424, 1.88 min(LC/MS method A) | Method 16 |

Note 1: In one preparation of Examples Nos. 1 and 2 the oxidation of step 4 of General Method 1 was accomplished by swern oxidation as follows.

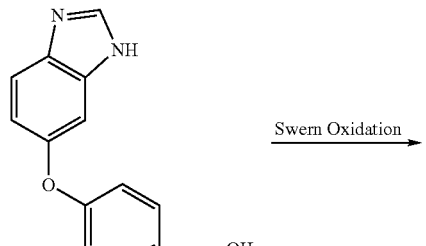

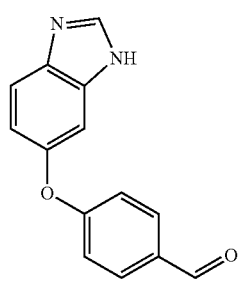

Representative Example

Preparation of N-{[4-(1H-benzimidazol-5-yloxy)phenyl]methyl}cycloheptanamine bis(trifluoroacetate) (Example No. 8)

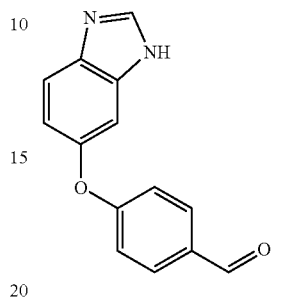

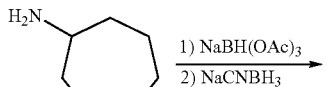

DMSO (dimethylsulfoxide) (0.415 mL, 5.37 mmol) was added drop wise to a solution of oxalyl chloride (0.293 mL, 335 mmol) in 25 mL of $CH_2Cl_2$ at −78 degrees Centigrade and stirred for 30 minutes. A solution of [4-(1H-benzimidazol-5-yloxy)phenyl]methanol (0.644 g, 2.69 mmol) in 20 mL $CH_2Cl_2$ and 10 ml of DMSO was added to the reaction drop wise and stirred at −78 degrees Centigrade for 30 minutes. Triethylamine (1.5 mL, 10.7 mmol) was added and the reaction was allowed to warm to room temperature and stirred for one hour. The reaction mixture was diluted with water and extracted with $CH_2Cl_2$, dried over $MgSO_4$ and concentrated. The crude residue was re-subjected to the reaction conditions using twice the amount of each reagent, followed by stirring at room temperature overnight. The reaction mixture was diluted with water and extracted with $CH_2Cl_2$, dried over $MgSO_4$ and concentrated. The crude 4-(1H-benzimidazol-5-yloxy)benzaldehyde was carried to the next step without further purification.

Note 2: For Examples Nos. 7 and 8, the reductive amination of General Method 1 step 5 was accomplished by sodium triacetoxyborohydride followed by $NaCNBH_3$ as set forth below.

4-(1H-Benzimidazol-5-yloxy)benzaldehyde (200 mg, 0.839 mmol), cycloheptylamine (0.214 mL, 1.68 mmol) and sodium triacetoxyborohydride (534 mg, 2.52 mmol) were shaken in 10 mL of 1,2 dichloromethane for approximately 18 hours. Two drops of acetic acid and excess NaCNBH3 were added and the reaction stirred at room temperature overnight. The reaction was concentrated and the residue was dissolved in ethyl acetate and 1N NaOH. The organic layer was added to a Varian Chem Elute™ 1001 column which was rinsed with 4-6 ml of ethyl acetate (gravity filtration) to elute the crude product. The eluent was concentrated. The residue was dissolved in 1.5-2 ml of methanol and approximately 150 μl of trifluoroacetic acid and purified using preparative HPLC to give of N-{[4-(1H-benzimidazol-5-yloxy)phenyl]methyl}cycloheptanamine bis(trifluoroacetate) (Example No. 8).

Note 3: N-{[4-(1H-Benzimidazol-5-yloxy)phenyl]methyl}-2-(4-fluorophenyl)ethanamine dihydrochloride (Example No. 16) was prepared using General Method 4, but was not pure. The compound was dissolved in ethyl acetate and stirred with di-tert-butyl dicarbonate (1 equivalent) and saturated $NaHCO_3$ for 30 minutes. The organic layer was separated, washed with saturated $NaHCO_3$ and concentrated. The residue was purified by preparative HPLC. The pure fractions were diluted with ethyl acetate, washed with 1N NaOH, dried over MgSO₄ and concentrated. The residue was dissolved in 25 mL of CH₂Cl₂ and stirred for approximately 18 hours with 2 mL 4N HCl in dioxane then concentrated. The residue was dissolved in methanol and concentrated to give N-{[4-(1H-benzimidazol-5-yloxy)phenyl]methyl}-2-(4-fluorophenyl)ethanamine dihydrochloride (Example No. 16) as a white powder.

Note 4: The reductive amination of method 1 step 5 was performed by shaking 4-(1H-benzimidazol-5-yloxy)benzaldehyde (60 mg, 0.25 mmol), trans-decahydroisoquinoline (53 mg, 0.38 mmol), and excess Argonaut MP triacetoxyborohydride resin in THF. The reaction did not go to completion, so NaCNBH₃ (100 mg) was added. The reaction mixture was filtered and the filtrate was diluted with water, made basic with 10N NaOH, extracted twice with ethyl acetate and concentrated. The crude product was purified by preparative HPLC to give Example No. 24.

Note 5: When prepared by General Method 3, Example No. 73 was purified by column chromatography using an Isco amine functionalized silica column (0-10% methanol/CH₂Cl₂ gradient). This material was then purified by preparative HPLC to give pure N-{[4-(1H-benzimidazol-5-yloxy)-2-chlorophenyl]methyl}-2,3-dihydro-1H-inden-2-amine bis(trifluoroacetate) (Example No. 73).

Note 6: In the cases of Examples Nos. 73 and 74, the product of General Method 6, step 4 needed an additional step (below) to remove the acetal protecting group.

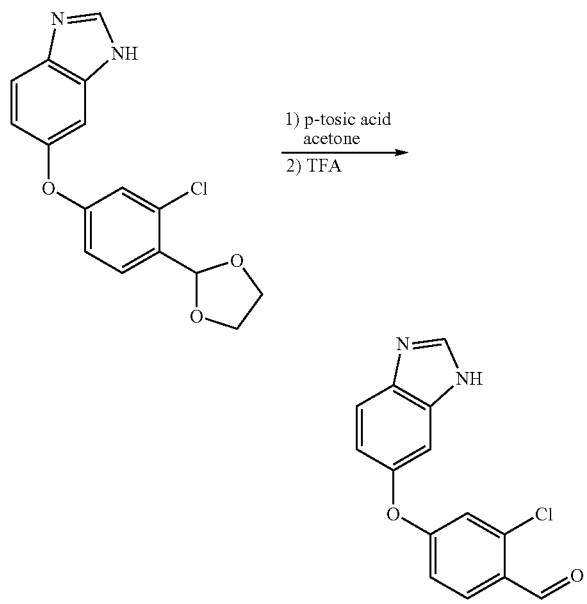

5-{[3-Chloro-4-(1,3-dioxolan-2-yl)phenyl]oxy}-1H-benzimidazole (1.41 g) was dissolved in approximately 15 mL of acetone and heated at reflux over 3 days with 25 mg of p-tosic acid. An additional 50 mg of p-tosic acid was added and the reaction was heated at 80 degrees Centigrade for an additional 6 hours. The reaction was allowed to cool to room temperature, diluted with water and ethyl acetate, made basic with 10 N NaOH and extracted twice with ethyl acetate. The organic layer was washed with brine and 1N NaOH, dried over MgSO₄ and concentrated. The residue was dissolved and stirred in neat trifluoroacetic acid overnight. The reaction was concentrated and purified by silica gel column chromatography (0-10% gradient of methanolic 2N NH₃/CH₂Cl₂). The fractions were concentrated and the residue was purified by preparative HPLC to give 4-(1H-benzimidazol-5-yloxy)-2-chlorobenzaldehyde, which was ultimately used to prepare Examples Nos. 73 and 74.

Note 7: When prepared by General Method 5, Example No. 87 was purified by preparative HPLC using a Luna C18 column and a 10-50% acetonitrile in water gradient. Solvents contained 0.1% formic acid.

What is claimed is:
1. A compound of Formula 1

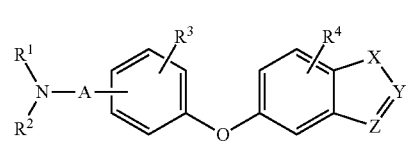

Formula 1 wherein
R¹ is selected from the group consisting of hydrogen, $C_{1-12}$ alkyl, $C_{3-10}$ cycloalkyl, arylalkyl, heterocyclyl, heterocycloalkyl, heteroarylalkyl, cycloalkenyl, $C_{2-12}$ fluoroalkyl, $C_{3-10}$ alkoxy, and heteroalkyl, with the proviso that the carbon atoms that are bonded to the nitrogen are not aromatic or carbonyl;
R² is selected from the group consisting of $C_{3-12}$ alkyl, $C_{3-10}$ cycloalkyl, arylalkyl, heterocyclyl, heterocycloalkyl, heteroarylalkyl, cycloalkenyl, $C_{3-12}$ fluoroalkyl, $C_{3-10}$ alkoxy, and heteroalkyl, with the proviso that the carbon atoms that are bonded to the nitrogen are not aromatic or carbonyl;
R¹ and R² may optionally be joined to form a ring;
A is attached in the meta or para position with respect to the diarylether linker and is a $C_{1-3}$ alkylene;
R³ and R⁴ are each independently selected from the group consisting of —H, —F, —Cl, —Br, —OH, —O$C_{1-3}$ alkyl, —$C_{1-3}$ fluoroalkyl, and —$C_{1-3}$ alkyl;
X, Y, and Z are each independently selected from the group consisting of —N, —NH, —CH, —O, —S, —NR⁵, and —CR⁶, wherein R⁵ and R⁶ are each independently a $C_{1-6}$ alkyl or a fluoroalkyl; and
a pharmaceutically acceptable salt thereof.

2. The compound of claim 1 wherein A is a methylene attached in the para position with respect to the diarylether linker.

3. The compound of claim 2 wherein R¹ is hydrogen; R² is selected from the group consisting of arylmethyl, arylethyl, $C_{4-10}$ alkyl, cycloalkenyl, cycloalkyl, heteroalkyl, heteroaryl methyl, heteroarylethyl, heterocyclylmethyl, and heterocyclylethyl; R³ and R⁴ are each independently selected from the group consisting of H, methyl, and F.

4. The compound of claim 3 wherein either X or Z is —NH with the other being —CH or —N; and wherein Y is —CH or —N.

5. The compound of claim 1 wherein the compound of Formula 1 is selected from the group consisting of N—{[4—(1H-benzimidazol-5-yloxy)phenyl]methyl}-3-methyl-1-butanamine trifluoroacetate;
N—{[4—(1H-benzimidazol-5-yloxy)phenyl]methyl}-4,4-dimethylcyclohexanamine trifluoroacetate;
N—{[4—(1H-benzimidazol-5-yloxy)phenyl]methyl}-2-(3-fluorophenyl) ethanamine trifluoroacetate;
N—{[4—(1H-benzimidazol-5-yloxy)phenyl]methyl}-2-(2-thienyl)ethanamine trifluoroacetate;
{[4—(1H-benzimidazol-5-yloxy)phenyl]methyl}cyclohexylmethyl)amine trifluoroacetate;

N—{[4—(1H-benzimidazol-5-yloxy)phenyl]methyl}cycloheptanamine trifluoroacetate;

N—{[4—(1H-benzimidazol-5-yloxy)phenyl]methyl}-2-(tetrahydro-2H-pyran-4-yl) ethanamine trifluoroacetate;

(Cyclohexylmethyl){[4-(1H-indazol-5-yloxy)phenyl]methyl}amine hydrochloride; and

[2-(3-fluorophenyl)ethyl]{[4-(1H-indazol-5-yloxy)phenyl]methyl}amine hydrochloride.

6. A pharmaceutical composition comprising (i) a compound of claim 1, or a pharmaceutically acceptable salt thereof and (ii) at least one carrier.

7. A method of treatment of a condition selected from the group consisting of obesity, diabetes, hypertension, depression, anxiety, drug addiction, and substance addiction comprising administering to a mammal a therapeutically effective amount of a pharmaceutical composition comprising (i) a compound of claim 1, or a pharmaceutically acceptable salt thereof and (ii) at least one carrier.

8. The method of claim 7 wherein the mammal is a human.

9. A method of treatment of a condition selected from the group consisting of obesity, diabetes, hypertension, depression, anxiety, drug addiction, and substance addiction comprising administering to a mammal a therapeutically effective amount of a compound of claim 1, or a pharmaceutically acceptable salt thereof.

10. The method of claim 9 wherein the mammal is a human.

11. The method of claim 7 wherein said treatment is for the condition of obesity.

12. A compound of claim 1, or a pharmaceutically acceptable salt thereof in combination with at least one other species for treating obesity wherein said other species for treating obesity is an agent or drug selected from the group of consisting of human ciliary neurotropic factor, a CB-1 antagonist or inverse agonist, a neurotransmitter reuptake inhibitor, a lipase inhibitor, an MC4R agonist, a 5-HT2c agonist, a ghrelin receptor antagonist, a CCK-A receptor agonist, an NPY Y1 antagonist, $PYY^3_{-36}$, and a PPAR activator.

13. A process for the preparation of a pharmaceutical formulation comprising admixing a compound of claim 1 or a salt thereof, with one or more pharmaceutical excipients.

* * * * *